United States Patent
Paige et al.

(10) Patent No.: US 8,841,077 B2
(45) Date of Patent: Sep. 23, 2014

(54) BIOMARKERS FOR AMYOTROPHIC LATERAL SCLEROSIS AND METHODS USING THE SAME

(75) Inventors: Lisa A. Paige, Hillsborough, NC (US); Matthew W. Mitchell, Durham, NC (US); Anne Evans, Durham, NC (US); Don Harvan, Durham, NC (US); Kay A. Lawton, Raleigh, NC (US); Robert Brown, Needham, MA (US); Merit Cudkowicz, Newton, MA (US)

(73) Assignees: Massachusetts General Hospital, Boston, MA (US); Metabolon, Inc., Durham, NC (US)

( * ) Notice: Subject to any disclaimer, the term of this patent is extended or adjusted under 35 U.S.C. 154(b) by 1048 days.

(21) Appl. No.: 11/711,518

(22) Filed: Feb. 27, 2007

(65) Prior Publication Data

US 2007/0298998 A1 Dec. 27, 2007

Related U.S. Application Data

(60) Provisional application No. 60/777,338, filed on Feb. 28, 2006, provisional application No. 60/789,392, filed on Apr. 5, 2006, provisional application No. 60/851,144, filed on Oct. 12, 2006.

(51) Int. Cl.
| | | |
|---|---|---|
| *G01N 33/48* | (2006.01) | |
| *G01N 33/49* | (2006.01) | |
| *G01N 33/53* | (2006.01) | |
| *G01N 24/00* | (2006.01) | |
| *G01N 33/68* | (2006.01) | |

(52) U.S. Cl.
CPC .... *G01N 33/6896* (2013.01); *G01N 2800/2835* (2013.01); *G01N 2800/28* (2013.01); *G01N 2800/56* (2013.01); *G01N 2500/10* (2013.01)
USPC .............................. 435/7.1; 436/173; 436/73

(58) Field of Classification Search
None
See application file for complete search history.

(56) References Cited

U.S. PATENT DOCUMENTS

| | | |
|---|---|---|
| 7,005,255 B2 | 2/2006 | Kaddurah-Daouk et al. |
| 2005/0014132 A1 | 1/2005 | Kaddurah-Daouk et al. |
| 2005/0266467 A1 | 12/2005 | Roy |
| 2006/0134677 A1 | 6/2006 | Kaddurah-Daouk et al. |
| 2006/0134678 A1 | 6/2006 | Kaddurah-Daouk et al. |
| 2007/0026389 A1 | 2/2007 | Kaddurah-Daouk et al. |
| 2007/0072203 A1 | 3/2007 | Kaddurah-Daouk et al. |

OTHER PUBLICATIONS

Cudkowicz et al NeuroRx 1: 273-283, 2004.*
Turner et al. Lancet Neurol 8: 94-109, 2009.*
Belsh, Neurol 53: S26-S30; 1999.*
Rowland et al. New Engl J Med 344: 1688-1700, 2001.*
Felice et al. J Neurol Sc 160 (Suppl) S30-S32, 1998.*
Crenn et al. Clin Nut 27: 328-339, 2008.*
Camu et al. Acta Neurol Scand 88: 51-55, 1993.*
Berlet et al (Z. Neurol. 201: 310-325, 1972).*
Benkert et al (Anal Chem 72: 916-921, 2000).*
Van Kan et al., "Association between CYP1A2 activity and riluzole clearance in patients with amyotrophic lateral sclerosis," British Journal of Clinical Pharmacology, vol. 59, No. 3, pp. 310-313 (2004).
Supplementary European Search Report for European Application No. EP 07 75 1735; Date of Completion: Mar. 11, 2009.
Heafield, M. et al., "Plasma cysteine and sulphate levels in patients with motor neurone, Parkinson's and Alzheimer's disease", Neuroscience Letter, 110 (1-2), (1990), 216-220, XP024362783.
Kaddurah-Daouk et al., "Metabolomics: A New Approach Towards Identifying Biomarkers and therapeutic targets in CNS disorders" (2005), Springer US, XP002517451, 45-61, URL: http://www.springerlink.com/content/n07546698137w7g7/fulltext.pdf.
Nagata, H. et al., "Heavy metal concentrations in blood cells in patients with amyotrophic lateral sclerosis", Journal of Neurological Sciences, 67(2), (1985), 173-178, XP024297821.
Rozen et al., Metabolomic analysis and signatures in motor neuron disease, Metabolomics, 1(2), 2005, 101-108, XP002517450.

* cited by examiner

*Primary Examiner* — Daniel E Kolker
*Assistant Examiner* — Aditi Dutt
(74) *Attorney, Agent, or Firm* — Brinks Gilson & Lione

(57) ABSTRACT

The present invention provides various biomarkers of amyotrophic lateral sclerosis (ALS). The present invention also provides various methods of using the biomarkers, including methods for diagnosis of ALS, methods of determining predisposition to ALS, methods of monitoring progression/regression of ALS, methods of assessing efficacy of compositions for treating ALS, methods of screening compositions for activity in modulating biomarkers of ALS, methods of treating ALS, as well as other methods based on biomarkers of ALS.

10 Claims, 1 Drawing Sheet

Importance Plot, ALS vs. Control
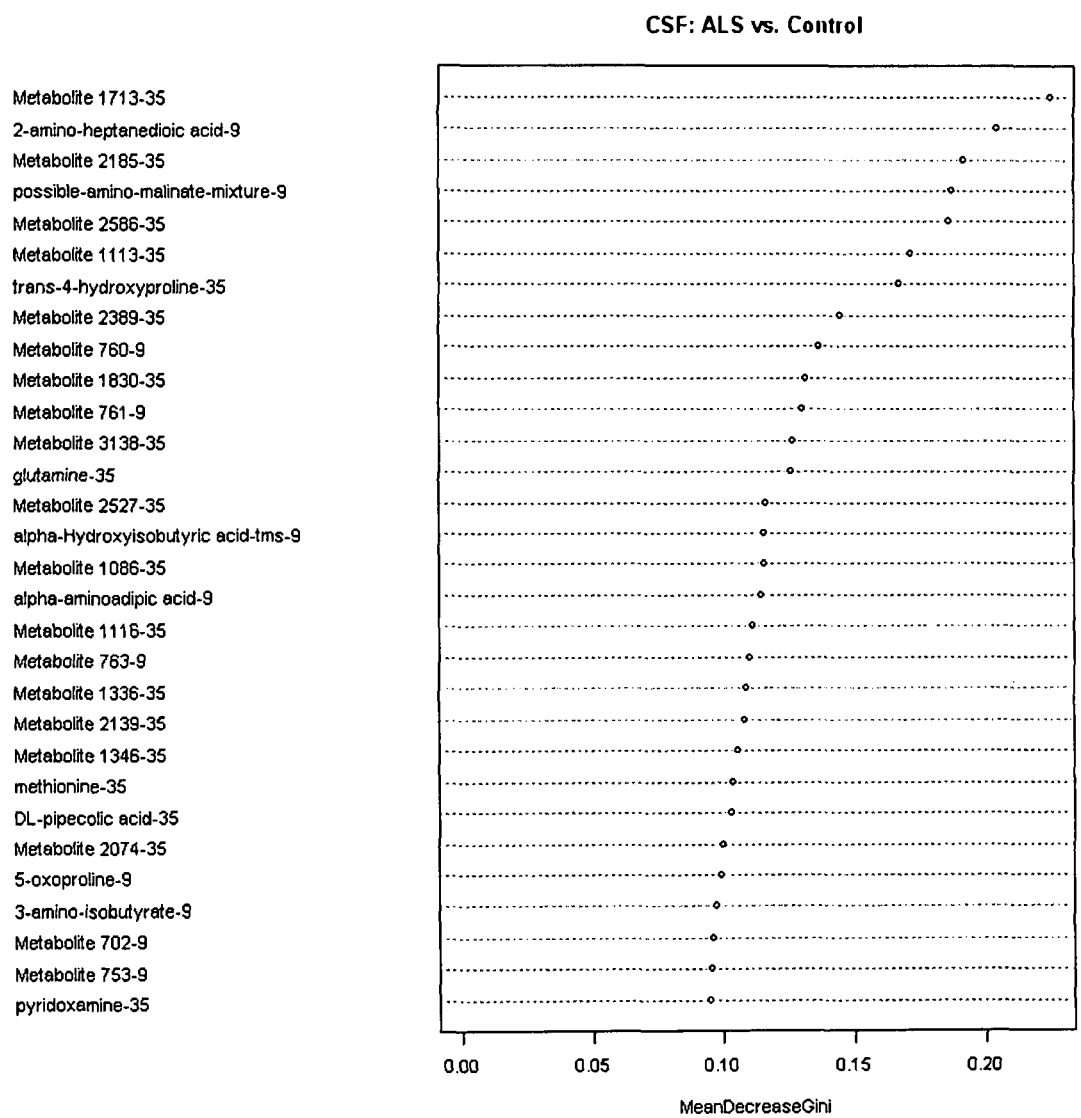

BIOMARKERS FOR AMYOTROPHIC LATERAL SCLEROSIS AND METHODS USING THE SAME

CROSS-REFERENCE TO RELATED APPLICATIONS

This application claims the benefit of U.S. Provisional Application No. 60/777,338, filed Feb. 28, 2006, U.S. Provisional Application No. 60/789,392, filed Apr. 5, 2006, and U.S. Provisional Application No. 60/851,144, filed Oct. 12, 2006; the entire contents of these applications are hereby incorporated herein by reference.

STATEMENT REGARDING FEDERALLY SPONSORED RESEARCH

This invention was made, in part, with Government support under Grant No. 1 R43 ES013646-01 from the National Institutes of Health. The U.S. Government may have certain rights in this invention.

FIELD

The invention generally relates to biomarkers for amyotrophic lateral sclerosis and methods based on the same biomarkers.

BACKGROUND

Amyotrophic lateral sclerosis (ALS), also known as Lou Gehrig's Disease, is a fatal neurological disease that rapidly attacks and destroys the nerve cells that are responsible for voluntary movement. The destruction of the neurons in the brain and spinal cord that control movement eventually progresses to the point that all voluntary motor control is lost. Death typically occurs from respiratory failure within 3-5 years of disease onset.

Approximately 20,000 people in the United States have ALS, and 5,000 people are diagnosed with ALS each year. ALS is common worldwide, affecting people of all races and ethnic backgrounds. The average age of onset of ALS is between 40 and 60 years of age, but ALS can strike both younger and older men and women. In 90-95% of ALS cases, the disease is apparently random (known as sporadic ALS (SALS)). In such SALS cases, there is no family history of the disease and no clearly associated risk factors. In 5-10% of ALS cases there is an inherited genetic link (known as familial ALS (FALS)).

SUMMARY

In one aspect, a method of diagnosing whether a subject has amyotrophic lateral sclerosis (ALS) is provided. The method comprises:
  analyzing a biological sample from a subject to determine the level(s) of one or more biomarkers for amyotrophic lateral sclerosis in the sample, wherein the one or more biomarkers are selected from (a) one or more biomarkers listed in Tables 3, 4, 5, 6, 7, and 8, (b) one or more xenobiotics, (c) one or more metabolites of xenobiotics, and (d) combinations thereof; and
  comparing the level(s) of the one or more biomarkers in the sample to ALS-positive and/or ALS-negative reference levels of the one or more biomarkers in order to diagnose whether the subject has amyotrophic lateral sclerosis.

In another aspect, a method of determining whether a subject is predisposed to developing amyotrophic lateral sclerosis (ALS) is provided, comprising:
  analyzing a biological sample from a subject to determine the level(s) of one or more biomarkers for amyotrophic lateral sclerosis in the sample, wherein the one or more biomarkers are selected from (a) one or more biomarkers listed in Tables 3, 4, 5, 6, 7, and 8, (b) one or more xenobiotics, (c) one or more metabolites of xenobiotics, and (d) combinations thereof; and
  comparing the level(s) of the one or more biomarkers in the sample to ALS-positive and/or ALS-negative reference levels of the one or more biomarkers in order to determine whether the subject is predisposed to developing amyotrophic lateral sclerosis.

In yet another aspect, a method of monitoring progression/regression of amyotrophic lateral sclerosis (ALS) in a subject is provided. The method comprises:
  analyzing a first biological sample from a subject to determine the level(s) of one or more biomarkers for amyotrophic lateral sclerosis in the sample, wherein the first sample is obtained from the subject at a first time point and the one or more biomarkers are selected from (a) one or more biomarkers listed in Tables 3, 4, 5, 6, 7, 8, 16, 17, and 18, (b) one or more xenobiotics, (c) one or more metabolites of xenobiotics, and (d) combinations thereof;
  analyzing a second biological sample from a subject to determine the level(s) of the one or more biomarkers, wherein the second sample is obtained from the subject at a second time point; and
  comparing the level(s) of one or more biomarkers in the first sample to the level(s) of the one or more biomarkers in the second sample in order to monitor the progression/regression of ALS in the subject.

In a further aspect, a method of assessing the efficacy of a composition for treating amyotrophic lateral sclerosis (ALS) is provided. The method comprises:
  analyzing, from a subject having amyotrophic lateral sclerosis and currently or previously being treated with a composition, a biological sample to determine the level(s) of one or more biomarkers for ALS selected from (a) one or more biomarkers listed in Tables 3, 4, 5, 6, 7, 8, 16, 17, and 18, (b) one or more xenobiotics, (c) one or more metabolites of xenobiotics, and (d) combinations thereof; and
  comparing the level(s) of the one or more biomarkers in the sample to (a) levels of the one or more biomarkers in a previously-taken biological sample from the subject, wherein the previously-taken biological sample was obtained from the subject before being treated with the composition, (b) ALS-positive reference levels of the one or more biomarkers, (c) ALS-negative reference levels of the one or more biomarkers, (d) ALS-progression-positive reference levels of the one or more biomarkers, and/or (e) ALS-regression-positive reference levels of the one or more biomarkers.

In yet a further aspect, a method for assessing the efficacy of a composition in treating amyotrophic lateral sclerosis (ALS) is provided comprising:
  analyzing a first biological sample from a subject to determine the level(s) of one or more biomarkers for ALS, the first sample obtained from the subject at a first time point wherein the one or more biomarkers are selected from (a) one or more biomarkers listed in Tables 3, 4, 5, 6, 7, 8, 16, 17, and 18, (b) one or more xenobiotics, (c) one or more metabolites of xenobiotics, and (d) combinations thereof;

administering the composition to the subject;

analyzing a second biological sample from the subject to determine the level(s) of the one or more biomarkers, the second sample obtained from the subject at a second time point after administration of the composition;

comparing the level(s) of one or more biomarkers in the first sample to the level(s) of the one or more biomarkers in the second sample in order to assess the efficacy of the composition for treating amyotrophic lateral sclerosis.

In another aspect, a method of assessing the relative efficacy of two or more compositions for treating amyotrophic lateral sclerosis (ALS) is provided. The method comprises:

analyzing, from a first subject having ALS and currently or previously being treated with a first composition, a first biological sample to determine the level(s) of one or more biomarkers selected from (a) one or more biomarkers listed in Tables 3, 4, 5, 6, 7, 8, 16, 17, and 18, (b) one or more xenobiotics, (c) one or more metabolites of xenobiotics, and (d) combinations thereof;

analyzing, from a second subject having ALS and currently or previously being treated with a second composition, a second biological sample to determine the level(s) of the one or more biomarkers; and comparing the level(s) of one or more biomarkers in the first sample to the level(s) of the one or more biomarkers in the second sample in order to assess the relative efficacy of the first and second compositions for treating amyotrophic lateral sclerosis.

In yet another aspect, a method for screening a composition for activity in modulating one or more biomarkers of amyotrophic lateral sclerosis is provided comprising:

contacting one or more cells with a composition;

analyzing at least a portion of the one or more cells or a biological sample associated with the cells to determine the level(s) of one or more biomarkers of amyotrophic lateral sclerosis selected from (a) one or more biomarkers listed in Tables 3, 4, 5, 6, 7, and 8, (b) one or more xenobiotics, (c) one or more metabolites of xenobiotics, and (d) combinations thereof; and comparing the level(s) of the one or more biomarkers with predetermined standard levels for the biomarkers to determine whether the composition modulated the level(s) of the one or more biomarkers.

In a further aspect, a method for identifying a potential drug target for amyotrophic lateral sclerosis (ALS) is provided. The method comprises:

identifying one or more biochemical pathways associated with one or more biomarkers for ALS, wherein the one or more biomarkers are selected from (a) one or more biomarkers listed in Tables 3, 4, 5, 6, 7, and 8, (b) one or more xenobiotics, (c) one or more metabolites of xenobiotics, and (d) combinations thereof; and identifying a protein affecting at least one of the one or more identified biochemical pathways, the protein being a potential drug target for amyotrophic lateral sclerosis.

In another aspect, a method for treating a subject having amyotrophic lateral sclerosis (ALS) is provided. The method comprises administering to the subject an effective amount of one or more biomarkers selected from Tables 3, 4, 5, 6, 7, and 8 that are decreased in subjects having ALS as compared to subjects not having ALS.

In yet a further aspect, a method of distinguishing whether a subject has amyotrophic lateral sclerosis (ALS) or has peripheral neuropathy or myopathy is provided. The method comprises:

analyzing a biological sample from a subject to determine the level(s) of one or more biomarkers for amyotrophic lateral sclerosis in the sample, wherein the one or more biomarkers comprise one or more xenobiotics, metabolites of xenobiotics, and/or biomarkers listed in Tables 14 and 15; and comparing the level(s) of the one or more biomarkers in the sample to ALS-positive and/or ALS-negative reference levels of the one or more biomarkers in order to determine whether a subject has ALS or has peripheral neuropathy or myopathy.

BRIEF DESCRIPTION OF THE DRAWINGS

FIG. 1 is an importance plot for a random forest analysis as explained in Example 1 below.

DETAILED DESCRIPTION

The present invention relates to biomarkers of amyotrophic lateral sclerosis, methods for diagnosis of ALS, methods of determining predisposition to ALS, methods of monitoring progression/regression of ALS, methods of assessing efficacy of compositions for treating ALS, methods of screening compositions for activity in modulating biomarkers of ALS, methods of treating ALS, as well as other methods based on biomarkers of ALS. Prior to describing this invention in further detail, however, the following terms will first be defined.

Definitions

"Biomarker" means a compound, preferably a xenobiotic or a metabolite, that is differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (i.e., a p-value less than 0.05 and/or a q-value of less than 0.10 as determined using either Welch's T-test or Wilcoxon's rank-sum Test).

The "level" of one or more biomarkers means the absolute or relative amount or concentration of the biomarker in the sample.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, blood, blood plasma, urine, or cerebral spinal fluid (CSF).

"Subject" means any animal, but is preferably a mammal, such as, for example, a human, monkey, mouse, or rabbit.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, an "ALS-positive reference level" of a biomarker means a level of a biomarker that is indicative of a positive diagnosis of ALS in a subject, and an "ALS-negative reference level" of a biomarker means a level of a biomarker that is indicative of a negative diagnosis of ALS in a subject. As another example, an "ALS-progression-positive reference level" of a biomarker means a level of a biomarker that is indicative of progression of ALS in a subject, and an "ALS-regression-positive reference level" of a biomarker means a level of a biomarker that is indicative of regression of ALS in a subject. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., LC-MS, GC-MS, etc.), where the levels of biomarkers may differ based on the specific technique that is used.

"Metabolite", or "small molecule", means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell.

"Xenobiotic" means a chemical foreign to a given organism (i.e., not produced in vivo). Xenobiotics include, but are not limited to, drugs, pesticides, and carcinogens. The metabolism of xenobiotics occurs in two phases. Phase I enzymes include Cytochrome P450 enzymes and Phase II enzymes include UDP-glucuronosyltransferases and glutathione S-transferases.

"Phase I metabolite of a xenobiotic" means the product of phase I metabolism of a xenobiotic. For example, paraxanthine (i.e., 1-7-dimethylxanthine), theophylline, and theobromine are Phase I metabolites of caffeine.

"Metabolic profile", or "small molecule profile", means a complete or partial inventory of small molecules within a targeted cell, tissue, organ, organism, or fraction thereof (e.g., cellular compartment). The inventory may include the quantity and/or type of small molecules present. The "small molecule profile" may be determined using a single technique or multiple different techniques.

"Non-biomarker compound" means a compound that is not differentially present in a biological sample from a subject or a group of subjects having a first phenotype (e.g., having a first disease) as compared to a biological sample from a subject or group of subjects having a second phenotype (e.g., not having the first disease). Such non-biomarker compounds may, however, be biomarkers in a biological sample from a subject or a group of subjects having a third phenotype (e.g., having a second disease) as compared to the first phenotype (e.g., having the first disease) or the second phenotype (e.g., not having the first disease).

"Metabolome" means all of the small molecules present in a given organism.

A "neurodegenerative disease" includes, but is not limited to, amyotrophic lateral sclerosis, multiple sclerosis, Huntington's Disease, Alzheimer's Disease, and Parkinson's Disease.

I. Biomarkers

The ALS biomarkers described herein were discovered using metabolomic profiling techniques. Such metabolomic profiling techniques are described in more detail in the Examples set forth below as well as in U.S. Pat. No. 7,005,255 and U.S. patent application Ser. Nos. 11/357,732, 10/695,265 (Publication No. 2005/0014132), Ser. No. 11/301,077 (Publication No. 2006/0134676), Ser. No. 11/301,078 (Publication No. 2006/0134677), Ser. No. 11/301,079 (Publication No. 2006/0134678), and Ser. No. 11/405,033, the entire contents of which are hereby incorporated herein by reference.

Generally, metabolic profiles were determined for biological samples from human subjects diagnosed with ALS as well as from one or more other groups of human subjects (e.g., healthy control subjects not diagnosed with ALS). The metabolic profile for ALS was compared to the metabolic profile for biological samples from the one or more other groups of subjects. Those molecules differentially present, including those molecules differentially present at a level that is statistically significant, in the metabolic profile of ALS samples as compared to another group (e.g., healthy control subjects not diagnosed with ALS) were identified as biomarkers to distinguish those groups.

The biomarkers are discussed in more detail herein. The biomarkers that were discovered correspond with the following group(s):

Biomarkers for distinguishing ALS vs. control subjects not diagnosed with ALS (see Tables 3, 4, 5, 6, 7, 8, and 9);
Biomarkers for distinguishing subjects having ALS vs. subjects having peripheral neuropathy (see Table 14);
Biomarkers for distinguishing subjects having ALS vs. subjects having myopathy (see Table 15);

Biomarkers for distinguishing early stage ALS vs. later stages of ALS (i.e., biomarkers for distinguishing progression/regression of ALS) (see Tables 16, 17, and 18);

Non-biomarker compounds associated with the compared groups were also identified. The non-biomarker compounds that were discovered correspond with the following group(s):

Non-biomarker compounds present at the same levels between ALS and control subjects not diagnosed with ALS (see Tables 3, 4, 5, 6, 7, 8, 16, 17, and 18).

Although the identities of some of the biomarkers and non-biomarker compounds are not known at this time, such identities are not necessary for the identification of the biomarkers or non-biomarker compounds in biological samples from subjects, as the "unnamed" compounds have been sufficiently characterized by analytical techniques to allow such identification. The analytical characterization of all such "unnamed" compounds is listed in the Examples. Such "unnamed" biomarkers and non-biomarker compounds are designated herein using the nomenclature "Metabolite" followed by a specific metabolite number.

In addition, where the identity of a previously "unnamed" metabolite has been determined, the actual metabolite identity is followed by the nomenclature of "previously Metabolite-xxxx" (e.g. Lactate (previously: Metabolite-2694)-35), or the "Metabolite" number is followed by the nomenclature "retired" and the actual metabolite identity (e.g. Metabolite-1713 retired: n-acetyl-L-aspartic acid).

Finally, where the potential identity of a compound is proposed for an "unnamed" metabolite and such identity has not been confirmed, the nomenclature of "possible" (along with the potential compound identity) follows the "Metabolite" number. Such proposed identity should not be considered as limiting the analytical characterization of the otherwise "unnamed" compounds.

II. Xenobiotics and Xenobiotic Metabolites as Biomarkers

In addition to the biomarkers listed above, it has been determined that xenobiotics (including, but not limited to, caffeine) and the metabolites of xenobiotics are biomarkers for ALS.

Without being limited by theory, it is believed that at least one factor in the etiology of ALS (especially sporadic ALS) is an imbalance in the metabolism of xenobiotics in the body due to higher Phase I enzyme activity relative to Phase II enzyme activity (i.e., (1) higher than normal Phase I enzyme activity coupled with normal Phase II enzyme activity, (2) normal Phase I enzyme activity coupled with under active Phase II enzyme activity, or (3) higher than normal Phase I enzyme activity coupled with under active Phase II enzyme activity). Such an imbalance may result in more toxins and free radicals (produced by Phase I enzymes) being present in the body, which may lead to onset and progression of ALS, especially SALS. Thus, xenobiotics and their corresponding metabolites may be used as biomarkers for various methods described herein (including, e.g., distinguishing ALS versus normal subjects as well as distinguishing ALS versus subjects having a neurodegenerative disease similar to ALS).

An example of a xenobiotic and corresponding metabolites that may be used as biomarkers for ALS is caffeine and its corresponding metabolites. As shown in Examples 4-7, caffeine and the Phase I metabolites of caffeine (e.g., paraxanthine (i.e., 1-7-dimethylxanthine), theophylline, and theobromine) may be used as biomarkers to distinguish subjects having ALS from normal subjects not having ALS and to distinguish subjects having ALS from subjects having other neurodegenerative diseases with symptoms similar to ALS (e.g., myopathy, neuropathy). As explained below, the level of caffeine and the caffeine metabolites (i.e., paraxanthine/1,7-dimethylxanthine, theophylline, theobromine) have been shown to be lower in plasma from ALS patients compared to healthy control subjects and the levels of caffeine and paraxanthine can be used to distinguish between ALS and diseases (e.g. myopathy, PN) with symptoms that resemble those of ALS. Such biomarkers may therefore be useful in ALS diagnosis.

Lower levels of caffeine and caffeine metabolites (i.e. paraxanthine/1,7-dimethylxanthine, theobromine, theophylline) were measured in plasma from ALS patients compared to levels in plasma from control subjects (see Table 9 and Example 4). It is believed that the lower levels of caffeine and caffeine metabolites in ALS subjects are due to increased activity of enzymes that metabolize caffeine (e.g. liver Phase I Cytochrome P450 enzymes, which react with toxins, drugs, alcohol, paint fumes and many other substances to form compounds that are capable of being transformed to less toxic, water soluble substances by Phase II reactions in the liver) rather than lower caffeine intake in such subjects.

The activity of CYP1A2, an inducible Cytochrome P450, is reflected in how fast caffeine is removed from the body. A high rate caffeine clearance (i.e. high ratio of caffeine metabolites/caffeine) indicates that the liver is working at a high rate to clear toxic substances. Individuals with very high rates of caffeine clearance are susceptible to environmental toxins, pesticides and even car exhaust because the metabolism of these xenobiotics and toxins by the Phase I Cytochrome P450 activity generates additional toxic substances and free radicals. If the activity of the Phase II system is also high, the systems are in balance. However, if the Phase II system activity is out of balance with Phase I activity, Phase I toxins and free radicals can accumulate.

It is possible that the generation of toxins and free-radicals through rapid hepatic phase I metabolism could contribute to the onset of sporadic ALS. The levels of caffeine and caffeine metabolites are much lower in ALS subjects compared to control subjects (see Table 9 and Example 4). However, the ratios of caffeine metabolites to caffeine are higher in ALS compared to control subjects (see Table 10 and Example 5) indicating that the Phase I hepatic detoxification system in ALS patients may be working at higher than normal levels. This is unlikely to be an age effect because in a demographic study of individuals of various ages, the levels of both caffeine and the caffeine metabolite paraxanthine increase with age (see Table 11 and Example 5). Further, as shown in Table 11, the paraxanthine/caffeine ratio is lowest in the oldest age group, which is the age when ALS typically is diagnosed. Thus, the measurement of the levels of caffeine, caffeine metabolites and/or the ratio of caffeine/caffeine metabolites (i.e., caffeine metabolism/clearance) may provide valuable information useful to diagnose individuals who have ALS as well as to identify individuals who are at risk for ALS, and also implicates an overactive Cytochrome P450 system and/or other mechanisms of xenobiotic metabolism in the etiology of some cases of sporadic ALS. Therapeutics that target these enzyme systems and decrease the rate of formation of toxic substances may be able to prevent or substantially delay ALS onset.

The level of caffeine is significantly lower in plasma from patients with ALS compared to plasma from individuals with myopathy as well as in plasma from peripheral neuropathy (PN) patients (see Table 12 and Example 6). Thus, caffeine and/or caffeine metabolites are also useful biomarker(s) to distinguish ALS from illnesses that have symptoms resembling ALS, such as myopathy and PN. Further, the ratios of paraxanthine to caffeine are higher in ALS than the ratios in myopathy or PN. This supports the idea that caffeine clearance is higher in ALS than in diseases resembling ALS and provides potential useful therapeutic targets for ALS. In addition, the levels of caffeine, caffeine metabolites and/or the ratio of caffeine metabolites/caffeine are useful in diagnostic tests to distinguish ALS from these ALS "mimics".

In some embodiments of the methods described herein, at least one of the biomarkers used includes a xenobiotic and/or a metabolite of a xenobiotic (preferably a xenobiotic and a Phase I metabolite of the xenobiotic) such as, for example, caffeine and/or a metabolite of caffeine (e.g., paraxanthine, theophylline, and/or theobromine).

III. Diagnosis of ALS

The identification of biomarkers for ALS allows for the diagnosis of (or for aiding in the diagnosis of) ALS in subjects presenting one or more symptoms of ALS. A method of diagnosing (or aiding in diagnosing) whether a subject has ALS comprises (1) analyzing a biological sample from a subject to determine the level(s) of one or more biomarkers of amyotrophic lateral sclerosis in the sample and (2) comparing the level(s) of the one or more biomarkers in the sample to ALS-positive and/or ALS-negative reference levels of the one or more biomarkers in order to diagnose (or aid in the diagnosis of) whether the subject has amyotrophic lateral sclerosis. The one or more biomarkers that are used are selected from xenobiotics (e.g., caffeine), metabolites of xenobiotics (e.g., paraxanthine, theophylline, and theobromine), and/or Tables 3, 4, 5, 6, 7, and/or 8 and combinations thereof. When such a method is used to aid in the diagnosis of ALS, the results of the method may be used along with other methods (or the results thereof) useful in the clinical determination of whether a subject has ALS.

Any suitable method may be used to analyze the biological sample in order to determine the level(s) of the one or more biomarkers in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured.

The levels of one or more of the biomarkers selected from xenobiotics (e.g., caffeine), metabolites of xenobiotics (e.g., paraxanthine, theophylline, and theobromine), and/or Tables 3, 4, 5, 6, 7, and/or 8 may be determined in the methods of diagnosing and methods of aiding in diagnosing whether a subject has ALS. For example, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers selected from xenobiotics (e.g., caffeine), metabolites of xenobiotics (e.g., paraxanthine, theophylline, and theobromine), and/or Tables 3, 4, 5, 6, 7, and/or 8 or any fraction thereof, may be determined and used in such methods. Determining levels of combinations of the biomarkers may allow greater sensitivity and specificity in diagnosing ALS and aiding in the diagnosis of ALS, and may allow better differentiation of ALS from other neurodegenerative diseases that may have similar or overlapping biomarkers to ALS (as compared to a subject not having a neurodegenerative disease). For example, ratios of the levels of certain biomarkers (and non-biomarker compounds) in biological samples may allow greater sensitivity and specificity in diagnosing ALS and aiding in the diagnosis of ALS, and may allow better differentiation of ALS from other neurodegenerative diseases that may have similar or overlapping biomarkers to ALS (as compared to a subject not having a neurodegenerative disease).

One or more biomarkers that are specific for diagnosing ALS (or aiding in diagnosing ALS) in a certain type of sample (e.g., CSF sample or blood plasma sample) may also be used. For example, when the biological sample is cerebral spinal fluid, one or more biomarkers listed in Tables 3 and/or 4 may be used to diagnose (or aid in diagnosing) whether a subject has ALS. When the biological sample is blood plasma, one or more biomarkers selected from Tables 5, 6, 7 and/or 8 may be used to diagnose (or aid in diagnosing) whether a subject has ALS.

After the level(s) of the one or more biomarkers in the sample are determined, the level(s) are compared to ALS-positive and/or ALS-negative reference levels to aid in diagnosing or to diagnose whether the subject has ALS. Levels of the one or more biomarkers in a sample corresponding to the ALS-positive reference levels (e.g., levels that are the same as the reference levels, substantially the same as the reference levels, above and/or below the minimum and/or maximum of the reference levels, and/or within the range of the reference levels) are indicative of a diagnosis of ALS in the subject. Levels of the one or more biomarkers in a sample corresponding to the ALS-negative reference levels (e.g., levels that are the same as the reference levels, substantially the same as the reference levels, above and/or below the minimum and/or maximum of the reference levels, and/or within the range of the reference levels) are indicative of a diagnosis of no ALS in the subject. In addition, levels of the one or more biomarkers that are differentially present (especially at a level that is statistically significant) in the sample as compared to ALS-negative reference levels are indicative of a diagnosis of ALS in the subject. Levels of the one or more biomarkers that are differentially present (especially at a level that is statistically significant) in the sample as compared to ALS-positive reference levels are indicative of a diagnosis of no ALS in the subject. In one embodiment, when caffeine and paraxanthine and/or theophylline levels are determined in the sample, the ALS-positive and/or ALS-negative reference levels may comprise the paraxanthine/caffeine and/or the theophylline/caffeine ratios listed in Table 10.

The level(s) of the one or more biomarkers may be compared to ALS-positive and/or ALS-negative reference levels using various techniques, including a simple comparison (e.g., a manual comparison) of the level(s) of the one or more biomarkers in the biological sample to ALS-positive and/or ALS-negative reference levels. The level(s) of the one or more biomarkers in the biological sample may also be compared to ALS-positive and/or ALS-negative reference levels using one or more statistical analyses (e.g., t-test, Welch's T-test, Wilcoxon's rank sum test, random forest).

In addition, the biological samples may be analyzed to determine the level(s) of one or more non-biomarker compounds. The level(s) of such non-biomarker compounds may also allow differentiation of ALS from other neurodegenerative diseases that may have similar or overlapping biomarkers to ALS (as compared to a subject not having a neurodegenerative disease). For example, a known non-biomarker compound present in biological samples of subjects having ALS and subjects not having ALS could be monitored to verify a diagnosis of ALS as compared to a diagnosis of another neurodegenerative disease when biological samples from subjects having the other neurodegenerative disease do not have the non-biomarker compound.

IV. Methods of Determining Predisposition to ALS

The identification of biomarkers for ALS also allows for the determination of whether a subject having no symptoms of ALS is predisposed to developing ALS. A method of determining whether a subject having no symptoms of ALS is predisposed to developing amyotrophic lateral sclerosis comprises (1) analyzing a biological sample from a subject to determine the level(s) of one or more biomarkers selected from xenobiotics (e.g., caffeine), metabolites of xenobiotics (e.g., paraxanthine, theophylline, and theobromine), and/or Tables 3, 4, 5, 6, 7, and/or 8 in the sample and (2) comparing the level(s) of the one or more biomarkers in the sample to ALS-positive and/or ALS-negative reference levels of the one or more biomarkers in order to determine whether the subject is predisposed to developing amyotrophic lateral sclerosis. The results of the method may be used along with other methods (or the results thereof) useful in the clinical determination of whether a subject is predisposed to developing ALS.

As described above in connection with methods of diagnosing (or aiding in the diagnosis of) ALS, any suitable method may be used to analyze the biological sample in order to determine the level(s) of the one or more biomarkers in the sample.

As with the methods of diagnosing (or aiding in the diagnosis of) ALS described above, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers selected from xenobiotics (e.g., caffeine), metabolites of xenobiotics (e.g., paraxanthine, theophylline, and theobromine), and/or Tables 3, 4, 5, 6, 7, and/or 8 or any fraction thereof, may be determined and used in methods of determining whether a subject having no symptoms of ALS is predisposed to developing ALS.

After the level(s) of the one or more biomarkers in the sample are determined, the level(s) are compared to ALS-positive and/or ALS-negative reference levels in order to predict whether the subject is predisposed to developing amyotrophic lateral sclerosis. Levels of the one or more biomarkers in a sample corresponding to the ALS-positive reference levels (e.g., levels that are the same as the reference levels, substantially the same as the reference levels, above and/or below the minimum and/or maximum of the reference levels, and/or within the range of the reference levels) are indicative of the subject being predisposed to developing ALS. Levels of the one or more biomarkers in a sample corresponding to the ALS-negative reference levels (e.g., levels that are the same as the reference levels, substantially the same as the reference levels, above and/or below the minimum and/or maximum of the reference levels, and/or within the range of the reference levels) are indicative of the subject not being predisposed to developing ALS. In addition, levels of the one or more biomarkers that are differentially present (especially at a level that is statistically significant) in the sample as compared to ALS-negative reference levels are indicative of the subject being predisposed to developing ALS. Levels of the one or more biomarkers that are differentially present (especially at a level that is statistically significant) in the sample as compared to ALS-positive reference levels are indicative of the subject not being predisposed to developing ALS.

Furthermore, it may also be possible to determine reference levels specific to assessing whether or not a subject that does not have ALS is predisposed to developing ALS. For example, it may be possible to determine reference levels of the biomarkers for assessing different degrees of risk (e.g., low, medium, high) in a subject for developing ALS. Such reference levels could be used for comparison to the levels of the one or more biomarkers in a biological sample from a subject.

As with the methods described above, the level(s) of the one or more biomarkers may be compared to ALS-positive and/or ALS-negative reference levels using various techniques, including a simple comparison, one or more statistical analyses, and combinations thereof.

As with the methods of diagnosing (or aiding in diagnosing) whether a subject has ALS, the methods of determining whether a subject having no symptoms of ALS is predisposed to developing amyotrophic lateral sclerosis may further comprise analyzing the biological sample to determine the level(s) of one or more non-biomarker compounds.

V. Methods of Monitoring Progression/Regression of ALS

The identification of biomarkers for ALS also allows for monitoring progression/regression of ALS in a subject. A method of monitoring the progression/regression of amyotrophic lateral sclerosis in a subject comprises (1) analyzing a first biological sample from a subject to determine the level(s) of one or more biomarkers for ALS selected from xenobiotics (e.g., caffeine), metabolites of xenobiotics (e.g., paraxanthine, theophylline, and theobromine), and/or Tables 3, 4, 5, 6, 7, 8, 16, 17, and/or 18, the first sample obtained from the subject at a first time point, (2) analyzing a second biological sample from a subject to determine the level(s) of the one or more biomarkers, the second sample obtained from the subject at a second time point, and (3) comparing the level(s) of one or more biomarkers in the first sample to the level(s) of the one or more biomarkers in the second sample in order to monitor the progression/regression of ALS in the subject. The results of the method are indicative of the course of ALS (i.e., progression or regression, if any change) in the subject.

The change (if any) in the level(s) of the one or more biomarkers over time may be indicative of progression or regression of ALS in the subject. In order to characterize the course of ALS in the subject, the level(s) of the one or more biomarkers in the first sample, the level(s) of the one or more biomarkers in the second sample, and/or the results of the comparison of the levels of the biomarkers in the first and second samples may be compared to ALS-positive and/or ALS-negative reference levels of the one or more biomarkers. If the comparisons indicate that the level(s) of the one or more biomarkers are increasing or decreasing over time (e.g., in the second sample as compared to the first sample) to become more similar to the ALS-positive reference levels (or less similar to the ALS-negative reference levels), then the results are indicative of ALS progression. If the comparisons indicate that the level(s) of the one or more biomarkers are increasing or decreasing over time to become more similar to the ALS-negative reference levels (or less similar to the ALS-positive reference levels), then the results are indicative of ALS regression.

The course of ALS in the subject may also be characterized by comparing the level(s) of the one or more biomarkers in the first sample, the level(s) of the one or more biomarkers in the second sample, and/or the results of the comparison of the levels of the biomarkers in the first and second samples to ALS-progression-positive and/or ALS-regression-positive reference levels (e.g., Example 11 below describes biomarkers for distinguishing early stage ALS vs. later stage ALS indicating whether certain biomarkers increase or decrease as ALS progresses; such trends and/or levels of biomarkers at a later stage of ALS versus an earlier stage of ALS are one example of ALS-progression positive reference levels). If the comparisons indicate that the level(s) of the one or more biomarkers are increasing or decreasing over time (e.g., in the second sample as compared to the first sample) to become more similar to the ALS-progression-positive reference levels (or less similar to the ALS-regression-positive reference levels), then the results are indicative of ALS progression. If the comparisons indicate that the level(s) of the one or more biomarkers are increasing or decreasing over time to become more similar to the ALS-regression-positive reference levels (or less similar to the ALS-progression-positive reference levels), then the results are indicative of ALS regression.

As with the other methods described herein, the comparisons made in the methods of monitoring progression/regression of ALS in a subject may be carried out using various techniques, including simple comparisons, one or more statistical analyses, and combinations thereof.

The results of the method may be used along with other methods (or the results thereof) useful in the clinical monitoring of progression/regression of ALS in a subject.

As described above in connection with methods of diagnosing (or aiding in the diagnosis of) ALS, any suitable method may be used to analyze the biological samples in order to determine the level(s) of the one or more biomarkers in the samples. In addition, the level(s) one or more biomarkers, including a combination of all of the biomarkers selected from xenobiotics (e.g., caffeine), metabolites of xenobiotics (e.g., paraxanthine, theophylline, and theobromine), and/or Tables 3, 4, 5, 6, 7, 8, 16, 17, and/or 18 or any fraction thereof, may be determined and used in methods of monitoring progression/regression of ALS in a subject.

Such methods could be conducted to monitor the course of ALS in subjects having ALS or could be used in subjects not having ALS (e.g., subjects suspected of being predisposed to developing ALS) in order to monitor levels of predisposition to ALS.

VI. Methods of Assessing Efficacy of Compositions for Treating ALS

The identification of biomarkers for ALS also allows for assessment of the efficacy of a composition for treating ALS as well as the assessment of the relative efficacy of two or more compositions for treating ALS. Such assessments may be used, for example, in efficacy studies as well as in lead selection of compositions for treating ALS.

A method of assessing the efficacy of a composition for treating amyotrophic lateral sclerosis comprises (1) analyzing, from a subject (or group of subjects) having amyotrophic lateral sclerosis and currently or previously being treated with a composition, a biological sample (or group of samples) to determine the level(s) of one or more biomarkers selected from xenobiotics (e.g., caffeine), metabolites of xenobiotics (e.g., paraxanthine, theophylline, and theobromine), and/or Tables 3, 4, 5, 6, 7, 8, 16, 17, and/or 18, and (2) comparing the level(s) of the one or more biomarkers in the sample (or group of samples) to (a) level(s) of the one or more biomarkers in a previously-taken biological sample (or group of samples) from the subject (or group of subjects), wherein the previously-taken biological sample was obtained from the subject (or group of subjects) before being treated with the composition, (b) ALS-positive reference levels of the one or more biomarkers, (c) ALS-negative reference levels of the one or more biomarkers (d) ALS-progression-positive reference levels of the one or more biomarkers, and/or (e) ALS-regression-positive reference levels of the one or more biomarkers. The results of the comparison are indicative of the efficacy of the composition for treating ALS.

Thus, in order to characterize the efficacy of the composition for treating ALS, the level(s) of the one or more biomarkers in the biological sample are compared to (1) ALS-positive reference levels, (2) ALS-negative reference levels, (3) ALS-progression-positive reference levels, (4) ALS-regression-positive reference levels, and/or (5) previous levels of the one or more biomarkers in the subject (or group of subjects) before treatment with the composition.

When comparing the level(s) of the one or more biomarkers in the biological sample (from a subject or group of subjects having amyotrophic lateral sclerosis and currently or previously being treated with a composition) to ALS-positive reference levels, ALS-negative reference levels, ALS-progression-positive reference levels, and/or ALS-regression-positive reference levels, level(s) in the sample(s) corresponding to the ALS-negative reference levels or ALS-regression-positive reference levels (e.g., levels that are the same as the reference levels, substantially the same as the reference levels, above and/or below the minimum and/or maximum of the reference levels, and/or within the range of the reference levels) are indicative of the composition having efficacy for treating ALS. Levels of the one or more biomarkers in the sample(s) corresponding to the ALS-positive reference levels or ALS-progression-positive reference levels (e.g., levels that are the same as the reference levels, substantially the same as the reference levels, above and/or below the minimum and/or maximum of the reference levels, and/or within the range of the reference levels) are indicative of the composition not having efficacy for treating ALS. The comparisons may also indicate degrees of efficacy for treating ALS based on the level(s) of the one or more biomarkers.

When the level(s) of the one or more biomarkers in the biological sample (from a subject or group of subjects having ALS and currently or previously being treated with a composition) are compared to level(s) of the one or more biomarkers in a previously-taken biological sample(s) from the subject (or group of subjects) before treatment with the composition, any changes in the level(s) of the one or more biomarkers are indicative of the efficacy of the composition for treating ALS. That is, if the comparisons indicate that the level(s) of the one or more biomarkers have increased or decreased after treatment with the composition to become more similar to the ALS-negative or ALS-regression-positive reference levels (or less similar to the ALS-positive or ALS-progression positive reference levels), then the results are indicative of the composition having efficacy for treating ALS. If the comparisons indicate that the level(s) of the one or more biomarkers have not increased or decreased after treatment with the composition to become more similar to the ALS-negative or ALS-regression-positive reference levels (or less similar to the ALS-positive or ALS-progression-positive reference levels), then the results are indicative of the composition not having efficacy for treating ALS. The comparisons may also indicate degrees of efficacy for treating ALS based on the amount of changes observed in the level(s) of the one or more biomarkers after treatment. In order to help characterize such a comparison, the changes in the level(s) of the one or more biomarkers, the level(s) of the one or more biomarkers before treatment, and/or the level(s) of the one or more biomarkers in the subject currently or previously being treated with the composition may be compared to ALS-positive, ALS-negative, ALS-progression-positive, and/or ALS-regression-positive reference levels of the one or more biomarkers.

Another method for assessing the efficacy of a composition in treating amyotrophic lateral sclerosis (ALS) comprises (1) analyzing a first biological sample (or group of samples) from a subject (or group of subjects) to determine the level(s) of one or more biomarkers selected from xenobiotics (e.g., caffeine), metabolites of xenobiotics (e.g., paraxanthine, theophylline, and theobromine), and/or Tables 3, 4, 5, 6, 7, 8, 16, 17, and/or 18, the first sample obtained from the subject at a first time point, (2) administering the composition to the subject, (3) analyzing a second biological sample from a subject to determine the level(s) of the one or more biomarkers, the second sample obtained from the subject at a second time point after administration of the composition, and (4) comparing the level(s) of one or more biomarkers in the first sample to the level(s) of the one or more biomarkers in the second sample in order to assess the efficacy of the composition for treating amyotrophic lateral sclerosis. As indicated above, if the comparison of the samples indicates that the level(s) of the one or more biomarkers have increased or decreased after administration of the composition to become more similar to the ALS-negative or ALS-regression-positive reference levels (or less similar to the ALS-positive or ALS-progression-positive reference levels), then the results are indicative of the composition having efficacy for treating ALS. If the comparison indicates that the level(s) of the one or more biomarkers have not increased or decreased after administration of the composition to become more similar to the ALS-negative or ALS-regression-positive reference levels (or less similar to the ALS-positive or ALS-progression-positive reference levels), then the results are indicative of the composition not having efficacy for treating ALS. The comparison may also indicate a degree of efficacy for treating ALS based on the amount of changes observed in the level(s) of the one or more biomarkers after administration of the composition. In order to help characterize such a comparison, the changes in the level(s) of the one or more biomarkers, the level(s) of the one or more biomarkers before administration of the composition, and/or the level(s) of the one or more biomarkers after administration of the composition may be compared to ALS-positive, ALS-negative, ALS-progression-positive, and/or ALS-regression-positive reference levels of the one or more biomarkers of the two compositions.

A method of assessing the relative efficacy of two or more compositions for treating amyotrophic lateral sclerosis comprises (1) analyzing, from a first subject having ALS and currently or previously being treated with a first composition, a first biological sample to determine the level(s) of one or more biomarkers selected from xenobiotics (e.g., caffeine), metabolites of xenobiotics (e.g., paraxanthine, theophylline, and theobromine), and/or Tables 3, 4, 5, 6, 7, 8, 16, 17, and/or 18, (2) analyzing, from a second subject having ALS and currently or previously being treated with a second composition, a second biological sample to determine the level(s) of the one or more biomarkers, and (3) comparing the level(s) of one or more biomarkers in the first sample to the level(s) of the one or more biomarkers in the second sample in order to assess the relative efficacy of the first and second compositions for treating amyotrophic lateral sclerosis. The results are indicative of the relative efficacy of the two compositions, and the results (or the levels of the one or more biomarkers in the first sample and/or the level(s) of the one or more biomarkers in the second sample) may be compared to ALS-positive, ALS-negative, ALS-progression-positive, and/or ALS-regression-positive reference levels to aid in characterizing the relative efficacy.

Each of the methods of assessing efficacy may be conducted on one or more subjects or one or more groups of subjects (e.g., a first group being treated with a first composition and a second group being treated with a second composition).

As with the other methods described herein, the comparisons made in the methods of assessing efficacy (or relative efficacy) of compositions for treating ALS may be carried out using various techniques, including simple comparisons, one or more statistical analyses, and combinations thereof. Any suitable method may be used to analyze the biological samples in order to determine the level(s) of the one or more biomarkers in the samples. In addition, the level(s) of one or more biomarkers, including a combination of all of the biomarkers selected from xenobiotics (e.g., caffeine), metabolites of xenobiotics (e.g., paraxanthine, theophylline, and theobromine), and/or Tables 3, 4, 5, 6, 7, 8, 16, 17, and/or 18 or any fraction thereof, may be determined and used in methods of assessing efficacy (or relative efficacy) of compositions for treating ALS.

Finally, the methods of assessing efficacy (or relative efficacy) of one or more compositions for treating ALS may further comprise analyzing the biological sample to determine the level(s) of one or more non-biomarker compounds. The non-biomarker compounds may then be compared to reference levels of non-biomarker compounds for subjects having (or not having) ALS.

VII. Methods of Screening a Composition for Activity in Modulating Biomarkers Associated with ALS The identification of biomarkers for ALS also allows for the screening of compositions for activity in modulating biomarkers associated with ALS, which may be useful in treating ALS. Methods of screening compositions useful for treatment of ALS comprise assaying test compositions for activity in modulating the levels of one or more biomarkers selected from xenobiotics (e.g., caffeine), metabolites of xenobiotics (e.g., paraxanthine, theophylline, and theobromine), and/or Tables 3, 4, 5, 6, 7, and/or 8. Such screening assays may be conducted in vitro and/or in vivo, and may be in any form known in the art useful for assaying modulation of such biomarkers in the presence of a test composition such as, for example, cell culture assays, organ culture assays, and in vivo assays (e.g., assays involving animal models).

In one embodiment, a method for screening a composition for activity in modulating one or more biomarkers of amyotrophic lateral sclerosis comprises (1) contacting one or more cells with a composition, (2) analyzing at least a portion of the one or more cells or a biological sample associated with the cells to determine the level(s) of one or more biomarkers of amyotrophic lateral sclerosis selected from xenobiotics (e.g., caffeine), metabolites of xenobiotics (e.g., paraxanthine, theophylline, and theobromine), and/or Tables 3, 4, 5, 6, 7, and/or 8; and (3) comparing the level(s) of the one or more biomarkers with predetermined standard levels for the one or more biomarkers to determine whether the composition modulated the level(s) of the one or more biomarkers. As discussed above, the cells may be contacted with the composition in vitro and/or in vivo. The predetermined standard levels for the one or more biomarkers may be the levels of the one or more biomarkers in the one or more cells in the absence of the composition. The predetermined standard levels for the one or more biomarkers may also be the level(s) of the one or more biomarkers in control cells not contacted with the composition.

In addition, the methods may further comprise analyzing at least a portion of the one or more cells or a biological sample associated with the cells to determine the level(s) of one or more non-biomarker compounds of amyotrophic lateral sclerosis. The levels of the non-biomarker compounds may then be compared to predetermined standard levels of the one or more non-biomarker compounds.

Any suitable method may be used to analyze at least a portion of the one or more cells or a biological sample associated with the cells in order to determine the level(s) of the one or more biomarkers (or levels of non-biomarker compounds). Suitable methods include chromatography (e.g., HPLC, gas chromatograph, liquid chromatography), mass spectrometry (e.g., MS, MS-MS), ELISA, antibody linkage, other immunochemical techniques, and combinations thereof. Further, the level(s) of the one or more biomarkers (or levels of non-biomarker compounds) may be measured indirectly, for example, by using an assay that measures the level of a compound (or compounds) that correlates with the level of the biomarker(s) (or non-biomarker compounds) that are desired to be measured.

VIII. Method of Identifying Potential Drug Targets

The identification of biomarkers for ALS also allows for the identification of potential drug targets for ALS. A method for identifying a potential drug target for amyotrophic lateral sclerosis (ALS) comprises (1) identifying one or more biochemical pathways associated with one or more biomarkers for ALS selected from xenobiotics (e.g., caffeine), metabolites of xenobiotics (e.g., paraxanthine, theophylline, and theobromine), and/or Tables 3, 4, 5, 6, 7, and/or 8 and (2) identifying a protein (e.g., an enzyme) affecting at least one of the one or more identified biochemical pathways, the protein being a potential drug target for amyotrophic lateral sclerosis.

Another method for identifying a potential drug target for amyotrophic lateral sclerosis (ALS) comprises (1) identifying one or more biochemical pathways associated with one or more biomarkers for ALS selected from xenobiotics (e.g., caffeine), metabolites of xenobiotics (e.g., paraxanthine, theophylline, and theobromine), and/or Tables 3, 4, 5, 6, 7, and/or 8 and one or more non-biomarker compounds of ALS selected from Tables 3, 4, 5, 6, 7, and/or 8 and (2) identifying a protein affecting at least one of the one or more identified biochemical pathways, the protein being a potential drug target for amyotrophic lateral sclerosis.

One or more biochemical pathways (e.g., biosynthetic and/or metabolic (catabolic) pathway) are identified that are associated with one or more biomarkers (or non-biomarker compounds). After the biochemical pathways are identified, one or more proteins affecting at least one of the pathways are identified. Preferably, those proteins affecting more than one of the pathways are identified.

A build-up of one metabolite (e.g., a pathway intermediate) may indicate the presence of a 'block' downstream of the metabolite and the block may result in a low/absent level of a downstream metabolite (e.g. product of a biosynthetic pathway). In a similar manner, the absence of a metabolite could indicate the presence of a 'block' in the pathway upstream of the metabolite resulting from inactive or non-functional enzyme(s) or from unavailability of biochemical intermediates that are required substrates to produce the product. Alternatively, an increase in the level of a metabolite could indicate a genetic mutation that produces an aberrant protein which results in the over-production and/or accumulation of a metabolite which then leads to an alteration of other related biochemical pathways and result in dysregulation of the normal flux through the pathway; further, the build-up of the biochemical intermediate metabolite may be toxic or may compromise the production of a necessary intermediate for a related pathway. It is possible that the relationship between pathways is currently unknown and this data could reveal such a relationship.

For example, it has been proposed that high glutamate levels in ALS lead to hyper-excitability of the glutamate receptors, causing neurotoxicity. The drug Riluzole is thought to work by lowering glutamate levels by pre-synaptically inhibiting glutamate release in the central nervous system. This drug, however, does not lower the overall glutamate levels in the body. The identity of glutamate as a biomarker that is elevated in ALS as compared to a normal subject would suggest that potential drug targets may be in the pathways leading to glutamate production. A composition that would function by inhibiting the synthesis of glutamate may suppress the levels of glutamate. An example of such an enzyme is glutaminase 2, which converts glutamine to glutamate. Pathways leading to the production of any elevated biomarker would provide a number of potential targets for drug discovery.

The proteins identified as potential drug targets may then be used to identify compositions that may be potential candidates for treating ALS, including compositions for gene therapy.

IX. Methods of Treating ALS

The identification of biomarkers for ALS also allows for the treatment of ALS. For example, in order to treat a subject having ALS, an effective amount of one or more ALS biomarkers that are lowered in ALS as compared to a healthy subjects not having ALS may be administered to the subject. The biomarkers that may be administered may comprise one or more of the biomarkers in Tables 3, 4, 5, 6, 7, and/or 8 that are decreased in ALS as compared to subjects not having ALS. Such biomarkers could be isolated based on the identity of the biomarker compound (i.e. compound name). The biomarkers that are currently unnamed metabolites could be isolated based on the analytical characterizations for the biomarkers listed in the Examples below. In some embodiments, the biomarkers that are administered are one or more biomarkers listed in Tables 3, 4, 5, 6, 7, and/or 8 that are decreased in ALS and that have a p-value less than 0.05 and/or a q-value of less than 0.10. In other embodiments, the biomarkers that are administered are one or biomarkers listed in Tables 3, 4, 5, 6, 7, and/or 8 that are decreased in ALS by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent).

X. Methods of Using the ALS Biomarkers for Other Neurodegenerative Diseases

It is believed that some of the biomarkers for ALS described herein may also be biomarkers for neurodegenerative diseases in general. Therefore, it is believed that at least some of the ALS biomarkers may be used in the methods described herein for neurodegenerative diseases in general. That is, the methods described herein with respect to ALS may also be used for diagnosing (or aiding in the diagnosis of) a neurodegenerative disease, methods of monitoring progression/regression of a neurodegenerative disease, methods of assessing efficacy of compositions for treating a neurodegenerative disease, methods of screening a composition for activity in modulating biomarkers associated with a neurodegenerative disease, methods of identifying potential drug targets for neurodegenerative diseases, and methods of treating a neurodegenerative disease. Such methods could be conducted as described herein with respect to ALS.

XI. Methods for Distinguishing ALS from Other Neurodegenerative Diseases

The identification of biomarkers for ALS allows for distinguishing whether a subject has amyotrophic lateral sclerosis or has another neurodegenerative disease with symptoms similar to ALS (e.g., peripheral neuropathy or myopathy). A method of distinguishing whether a subject has ALS or has another neurodegenerative disease with symptoms similar to ALS (e.g., peripheral neuropathy or myopathy) comprises (1) analyzing a biological sample from a subject to determine the level(s) of one or more biomarkers of amyotrophic lateral sclerosis in the sample and (2) comparing the level(s) of the one or more biomarkers in the sample to ALS-positive and/or ALS-negative reference levels of the one or more biomarkers in order to determine whether the subject has amyotrophic lateral sclerosis or the other neurodegenerative disease (e.g., peripheral neuropathy or myopathy). The ALS-positive and/or ALS-negative reference levels may be levels that are specific for comparison with another particular neurodegenerative disease (e.g., reference levels of biomarkers for ALS that distinguish between peripheral neuropathy or myopathy).

The one or more biomarkers that are used are selected from xenobiotics (e.g., caffeine), metabolites of xenobiotics (e.g., paraxanthine, theophylline, and theobromine), and/or Tables 14 and/or 15. For example, in another aspect, a method of distinguishing whether a subject has amyotrophic lateral sclerosis (ALS) or has peripheral neuropathy or myopathy comprises (1) analyzing a biological sample from a subject to determine the level(s) of one or more biomarkers for amyotrophic lateral sclerosis in the sample, wherein the one or more biomarkers comprise one or more xenobiotics, metabolites of xenobiotics, and/or biomarkers listed in Tables 14 and 15; and (2) comparing the level(s) of the one or more biomarkers in the sample to ALS-positive and/or ALS-negative reference levels of the one or more biomarkers in order to determine whether a subject has ALS or has peripheral neuropathy or myopathy.

Any suitable method may be used to analyze the biological sample in order to determine the level(s) of the one or more biomarkers in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured.

After the level(s) of the one or more biomarkers in the sample are determined, the level(s) are compared to ALS-positive and/or ALS-negative reference levels to distinguish whether the subject has ALS or has another disease (e.g., PN or myopathy) with symptoms related to ALS. Levels of the one or more biomarkers in a sample corresponding to the ALS-positive reference levels (e.g., levels that are the same as the reference levels, substantially the same as the reference levels, above and/or below the minimum and/or maximum of the reference levels, and/or within the range of the reference levels) are indicative of a diagnosis of ALS in the subject. Levels of the one or more biomarkers in a sample corresponding to the ALS-negative reference levels (e.g., levels that are the same as the reference levels, substantially the same as the reference levels, above and/or below the minimum and/or maximum of the reference levels, and/or within the range of the reference levels) are indicative of a diagnosis of no ALS in the subject. In addition, levels of the one or more biomarkers that are differentially present (especially at a level that is statistically significant) in the sample as compared to ALS-negative reference levels are indicative of a diagnosis of ALS in the subject. Levels of the one or more biomarkers that are differentially present (especially at a level that is statistically significant) in the sample as compared to ALS-positive reference levels are indicative of a diagnosis of no ALS in the subject. As described herein, ratios of biomarkers (e.g., a ratio of paraxanthine to caffeine) may be used as ALS-positive and/or ALS-negative reference levels.

The level(s) of the one or more biomarkers may be compared to ALS-positive and/or ALS-negative reference levels using various techniques, including a simple comparison (e.g., a manual comparison) of the level(s) of the one or more biomarkers in the biological sample to ALS-positive and/or ALS-negative reference levels. The level(s) of the one or more biomarkers in the biological sample may also be compared to ALS-positive and/or ALS-negative reference levels using one or more statistical analyses (e.g., t-test, Welch's T-test, Wilcoxon's rank sum test, random forest).

XII. Other Methods

Other methods of using the biomarkers discussed herein are also contemplated. For example, the methods described in U.S. Pat. No. 7,005,255 and U.S. patent application Ser. No. 10/695,265 may be conducted using a small molecule profile comprising one or more of the biomarkers disclosed herein and/or one or more of the non-biomarker compounds disclosed herein.

In any of the methods listed herein, the biomarkers that are used may be selected from those biomarkers in Tables 3, 4, 5, 6, 7, 8, 14, 15, 16, 17, and/or 18 having p-values of less than 0.05 and/or those biomarkers in Tables 3, 4, 5, 6, 7, 8, 14, 15, 16, 17, and/or 18 having q-values of less than 0.10. The biomarkers that are used in any of the methods described herein may also be selected from those biomarkers in Tables 3, 4, 5, 6, 7, 8, 14, 15, 16, 17, and/or 18 that are decreased as compared to the control group (e.g., subjects not having ALS, subjects having an earlier stage of ALS, etc.) by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent); and/or those biomarkers in Tables 3, 4, 5, 6, 7, 8, 14, 15, 16, 17, and/or 18 that are increased as compared to the control group by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 810%, by at least 120%, by at least 130%, by at least 140%, by at least 150%, or more.

In addition, in any of the methods described herein, the biomarkers that are used may be selected from one or more xenobiotics and/or one or more metabolites of xenobiotics (including a xenobiotic and/or one or more Phase I metabolites of the xenobiotic) such as, for example, caffeine and/or one or more metabolites of caffeine (e.g., paraxanthine, theophylline, and/or theobromine).

EXAMPLES

The invention will be further explained by the following illustrative examples that are intended to be non-limiting.

I. General Methods

A. Identification of Metabolic Profiles for ALS

Each sample was analyzed to determine the concentration of several hundred metabolites. Analytical techniques such as GC-MS (gas chromatography-mass spectrometry) and LC-MS (liquid chromatography-mass spectrometry) were used to analyze the metabolites. Multiple aliquots were simultaneously, and in parallel, analyzed, and, after appropriate quality control (QC), the information derived from each analysis was recombined. Every sample was characterized according to several thousand characteristics, which ultimately amount to several hundred chemical species. The techniques used were able to identify novel and chemically unnamed compounds.

B. Statistical Analysis

The data was analyzed using several statistical methods to identify molecules (either known, named metabolites or unnamed metabolites) present at differential levels in a definable population or subpopulation (e.g., biomarkers for ALS biological samples compared to control biological samples; biomarkers for ALS compared to other diseases having symptoms similar to ALS) useful for distinguishing between the definable populations (e.g., ALS and control; ALS and myopathy or peripheral neuropathy). Other molecules (either known, named metabolites or unnamed metabolites) in the definable population or subpopulation were also identified.

C. Biomarker Identification

Various peaks identified in the analyses (e.g. GC-MS, LC-MS, MS-MS), including those identified as statistically significant, were subjected to a mass spectrometry based chemical identification process.

Example 1

In one example, biomarkers were discovered by (1) analyzing CSF samples from different groups of human subjects to determine the levels of metabolites in the samples and then (2) statistically analyzing the results to determine those metabolites that are differentially present in the two groups.

The CSF samples used for the analysis were from 99 ALS subjects (14 FALS subjects and 85 SALS subjects) and 36 control subjects not diagnosed with ALS. After the levels of metabolites were determined, the data was analyzed using univariate T-tests (i.e., Welch's T-test) (Table 3), Wilcoxon's rank-sum tests (Table 4), and random forest analyses.

T-tests were used to determine differences in the unknown means of two populations (e.g., ALS vs. Control). Wilcoxon's rank sum test is a non-parametric test that was used to compare the central values of the two populations. Q-values were used to account for multiple comparisons. Q-values give an estimate of the false discovery rate (for example, if everything with a q-value<0.10 is declared significant, then approximately 10% of those in the list are false discoveries). Random forest analyses were used to classify individuals. The "Out-of-Bag" (OOB) Error rate gives an estimate of how accurately new observations can be predicted using the random forest model (e.g., whether a sample is from an ALS subject or a control subject).

Random Forest Models

The GC-MS data from the CSF samples was collected and the data was partially unblinded. A random forest model was constructed based on the unblinded data. The OOB error from this random forest was approximately 31%, and the model estimated that the identity of control subjects could be predicted correctly 71% of the time and ALS subjects could be predicted 68% of the time. The model was then applied to the blind portion of the GC-MS data. After the predictions were provided, the data was unblinded. The results of the predictions on the blinded portion of the data are shown in Table 1. The OOB error from the initial random forest model was very similar to the actual error (approximately 29%) determined when using the model on the blinded portion of the data.

TABLE 1

Results of Metabolomic Predictions

| | Random Forest Analysis |
|---|---|
| Overall | 71% |
| Control | 70% |
| ALS | 71% |

Finally, the random forest model was used to classify the complete GC-MS and LC-MS data. The confusion matrix for the random forest is shown in Table 2. In order to see which compounds were more important, an importance plot was constructed (shown in FIG. 1) ranking the compounds based on their importance for the predictions.

TABLE 2

Results of Random Forest, CSF: Controls vs. ALS, Full Dataset

| | ALS | Control | Error |
|---|---|---|---|
| ALS | 66 | 29 | 32% |
| Control | 10 | 24 | 29% |
| OOB Error | | | 30% |

Biomarkers

As listed below in Tables 3-4, biomarkers were discovered that were differentially present between samples from ALS subjects and Control subjects not diagnosed with ALS.

Tables 3 and 4 include, for each listed biomarker and non-biomarker compound, the p-value and the q-value determined in the statistical analysis of the data concerning the biomarkers, an indication of whether the mean of a particular compound was higher in the ALS or Control samples (a "+" indicating a higher mean in ALS samples as compared to the control samples and a "−" indicating a lower mean in ALS samples as compared to the control samples), and an indication of the percentage difference in the ALS mean as compared to the control mean. Throughout the tables, names of metabolites ending with the notation "−35" indicate that the levels of those compounds were measured using LC-MS, and names ending with the notation "−9" indicate that the levels of those compounds were measured using GC-MS. The term "Isobar" as used in the tables indicates the compounds that could not be distinguished from each other on the analytical platform used in the analysis (i.e., the compounds in an isobar elute at nearly the same time and have similar (and sometimes exactly) quant ions, and thus cannot be distinguished).

Non-biomarker compounds identified in the analyses are also listed in the Tables 3 and 4 below as those compounds that having a percentage change in ALS of 0%.

TABLE 3

ALS Biomarkers from CSF samples - T-tests of ALS vs. Controls

| Compound | p-value | q-value | Increase (+) or Decrease (−) in ALS | % change in ALS |
|---|---|---|---|---|
| 2-amino-heptanedioic acid - 9 | 2.19E−06 | 0.000352124 | + | 37% |
| Metabolite - 1113 - 35 | 4.55E−06 | 0.00036514 | + | 63% |
| amino-malinate-mixture - 9 | 7.90E−06 | 0.000423163 | + | 38% |
| trans-4-hydroxyproline - 35 | 3.90E−05 | 0.001566631 | + | 19% |
| Metabolite - 2185 - 35 | 7.00E−05 | 0.002204109 | + | 43% |
| Metabolite - 760 - 9 | 8.23E−05 | 0.002204109 | + | 32% |
| Metabolite - 2389 - 35 | 0.000108996 | 0.0024996 | + | 16% |
| Metabolite - 3138 - 35 | 0.000124478 | 0.0024996 | + | 88% |
| alpha-Hydroxyisobutyric acid-tms - 9 | 0.000352389 | 0.005660962 | + | 27% |
| 5-oxoproline - 9 | 0.000428964 | 0.005745226 | + | 13% |
| Metabolite - 522 - 9 | 0.000429161 | 0.005745226 | + | 70% |
| Methionine - 35 | 0.000592838 | 0.007325901 | + | 21% |
| Metabolite - 421 - 9 | 0.000861731 | 0.009888077 | + | 47% |
| Lactate (previously: Metabolite - 2694) - 35 | 0.000959996 | 0.010281254 | + | 14% |
| Metabolite - 268 - 9 | 0.001093458 | 0.010369188 | + | 51% |
| alpha-aminoadipic acid - 9 | 0.001108694 | 0.010369188 | + | 33% |
| Metabolite - 1086 - 35 | 0.001183749 | 0.010369188 | + | 61% |
| Pyridoxamine - 35 | 0.001237227 | 0.010369188 | + | 10% |
| Metabolite - 1116 - 35 | 0.001290942 | 0.010369188 | + | 29% |
| alpha-2-diamino-gamma-oxobenzenebutanoic acid - 35 | 0.001417441 | 0.010843108 | + | 76% |
| Metabolite - 1830 - 35 | 0.001851119 | 0.013516981 | + | 18% |
| DL-pipecolic acid - 35 | 0.002313539 | 0.015578068 | + | 108% |
| Metabolite - 2074 - 35 | 0.002327324 | 0.015578068 | + | 52% |
| Glycerol-2-phosphate (previously Metabolite - 1573) - 35 | 0.0024425 | 0.015695045 | + | 16% |
| Metabolite - 502 - 9 | 0.00261149 | 0.016135525 | + | 25% |
| Tyrosine - 35 | 0.002901792 | 0.016557204 | + | 19% |
| Metabolite - 2567 - 35 | 0.002952461 | 0.016557204 | + | 56% |
| Carnitine (previously: Metabolite - 1336) - 35 | 0.002988938 | 0.016557204 | + | 55% |
| Urea - 9 | 0.00399498 | 0.020751305 | + | 18% |
| Metabolite - 763 - 9 | 0.004038332 | 0.020751305 | + | 17% |
| 3-amino-isobutyrate - 9 | 0.004133589 | 0.020751305 | + | 31% |
| Tetradecanoic acid - 9 | 0.004756724 | 0.022701843 | + | 14% |
| Metabolite - 591 - 9 | 0.004804763 | 0.022701843 | + | 51% |
| Lactate (previously: Metabolite - 2563) - 35 | 0.004989671 | 0.022901923 | + | 18% |
| Uric acid - 35 | 0.005188319 | 0.023152196 | + | 22% |
| Uric acid (previously: Metabolite - 1910) - 35 | 0.007014232 | 0.029060165 | + | 22% |
| Metabolite - 1068 - 35 | 0.007054961 | 0.029060165 | + | 8% |
| Metabolite - 2697 - 35 | 0.007506605 | 0.030147523 | + | 40% |
| Citric acid - 9 | 0.008869079 | 0.034433835 | + | 12% |
| gamma-L-glutamyl-L-glutamine - 35 | 0.009002573 | 0.034433835 | + | 16% |
| Metabolite - 547 - 9 | 0.009488008 | 0.035446605 | + | 18% |
| Alanine - 9 | 0.010187174 | 0.037193674 | + | 14% |
| Isobar 1: includes-mannose-fructose-glucose-galactose-alpha-L-sorbopyranose-Inositol- 35 | 0.010876915 | 0.038829452 | + | 15% |
| Metabolite - 511 - 9 | 0.011390396 | 0.039584956 | + | 12% |
| Metabolite - 782 - 9 | 0.011629324 | 0.039584956 | + | 11% |
| Metabolite - 1597 - 35 | 0.012066512 | 0.039584956 | + | 19% |
| Metabolite - 2526 - 35 | 0.012074195 | 0.039584956 | + | 9% |
| Tryptophan - 35 | 0.012645849 | 0.040199985 | + | 15% |
| Metabolite - 609 - 9 | 0.012762272 | 0.040199985 | + | 6% |
| Phenylalanine - 35 | 0.013109863 | 0.040500732 | + | 12% |
| Metabolite - 655 - 9 | 0.016439043 | 0.049827456 | + | 32% |
| Metabolite - 1335 - 35 | 0.017359303 | 0.051642419 | + | 45% |
| o-phosphoethanolamine - 9 | 0.018100761 | 0.052869133 | + | 11% |
| Metabolite - 508 - 9 | 0.018977127 | 0.054439044 | + | 9% |
| Isobar-2-includes-3-amino-isobutyrate-2-amino-butyrate-4-aminobutanoic acid-dimethylglycine - 35 | 0.020126019 | 0.056721941 | + | 36% |
| 1-7-dihydro-6h-purin-6-one - 35 | 0.022868191 | 0.063339098 | − | −13% |
| Metabolite - 458 - 9 | 0.023483667 | 0.063941373 | + | 75% |
| Metabolite - 2686 - 35 | 0.025340922 | 0.06673607 | + | 8% |
| Valine - 9 | 0.027857126 | 0.070809473 | + | 34% |
| oxalic acid (previously: Metabolite - 1829) - 35 | 0.028075344 | 0.070809473 | + | 8% |

TABLE 3-continued

ALS Biomarkers from CSF samples - T-tests of ALS vs. Controls

| Compound | p-value | q-value | Increase (+) or Decrease (−) in ALS | % change in ALS |
|---|---|---|---|---|
| Metabolite - 2141 - 35 | 0.028210013 | 0.070809473 | + | 32% |
| Citrulline (previously: Metabolite - 2527) - 35 | 0.028923477 | 0.0714834 | + | 267% |
| Metabolite - 1126 - 35 | 0.029862565 | 0.072686077 | + | 40% |
| Lactate (previously: Metaboiite-3316) - 35 | 0.031228639 | 0.073937034 | + | 17% |
| Metabolite - 2390 - 35 | 0.031960638 | 0.073937034 | + | 55% |
| Serine - 9 | 0.032040923 | 0.073937034 | − | −11% |
| Metabolite - 2100 - 35 | 0.032234942 | 0.073937034 | + | 11% |
| Metabolite - 2139 - 35 | 0.032677763 | 0.073937034 | + | 47% |
| Arginine - 35 | 0.036081199 | 0.078737229 | + | 7% |
| Cytidine - 35 | 0.036269686 | 0.078737229 | − | −9% |
| Pantothenic acid - 35 | 0.037021263 | 0.079145001 | + | 27% |
| Metabolite - 393 - 9 | 0.03763587 | 0.079145001 | + | 16% |
| Lysine - 9 | 0.03793553 | 0.079145001 | + | 17% |
| Glycerate - 9 | 0.040187539 | 0.082768458 | − | −6% |
| Metabolite - 553 - 9 | 0.040934161 | 0.083239001 | − | −32% |
| Carnosine - 35 | 0.04337419 | 0.084597791 | − | −8% |
| Metabolite - 1346 - 35 | 0.043661053 | 0.084597791 | + | 7% |
| Metabolite - 2548-possible-Cl-adduct-of-uric acid - 35 | 0.043753093 | 0.084597791 | + | 14% |
| Metabolite - 992 - 9 | 0.044194475 | 0.084597791 | + | 28% |
| Metabolite - 2105 - 35 | 0.04423543 | 0.084597791 | + | 32% |
| Histamine - 35 | 0.048233785 | 0.091159192 | + | 19% |
| 4-Guanidinobutanoic acid (previously: Metabolite - 3179) - 35 | 0.049204594 | 0.091912644 | − | −24% |
| Metabolite - 3441 - 35 | 0.053750438 | 0.096784494 | − | −44% |
| Metabolite - 753 - 9 | 0.053940201 | 0.096784494 | + | 35% |
| 5-hydroxy-1H-indole-3-acetic acid - 9 | 0.053980979 | 0.096784494 | − | −15% |
| Metabolite - 988 - 9 | 0.054222587 | 0.096784494 | + | 16% |
| Metabolite - 1108 - 35 | 0.055886609 | 0.09787302 | + | 63% |
| Metabolite - 273 - 9 | 0.056050922 | 0.09787302 | + | 20% |
| Metabolite - 1131 - 35 | 0.062102093 | 0.107273226 | + | 13% |
| Metabolite - 383 - 9 | 0.064191049 | 0.109466474 | − | −5% |
| Metabolite - 289 - 9 | 0.064734631 | 0.109466474 | + | 9% |
| Isobar 4: includes-Gluconic acid-arabinose-D-ribose- 35 | 0.065577941 | 0.109737383 | + | 12% |
| Metabolite - 442 - 9 | 0.069402331 | 0.114939785 | − | −14% |
| Metabolite - 3182 - 35 | 0.071942834 | 0.117931419 | + | 20% |
| 5-S-methyl-5-thioadenosine - 35 | 0.073942622 | 0.11917087 | − | −7% |
| Metabolite - 783 - 9 | 0.074182601 | 0.11917087 | + | 5% |
| Metabolite - 568 - 9 | 0.07603354 | 0.120397213 | + | 7% |
| Metabolite - 2687 - 35 | 0.076683814 | 0.120397213 | + | 9% |
| Metabolite - 3127 - 35 | 0.077194366 | 0.120397213 | + | 21% |
| Metabolite - 276 - 9 | 0.0808386 | 0.124144964 | + | 4% |
| Metabolite - 780 - 9 | 0.081485757 | 0.124144964 | − | −7% |
| Metabolite - 3218 - 35 | 0.081915657 | 0.124144964 | + | 21% |
| Isoleucine - 9 | 0.084275078 | 0.126527067 | + | 18% |
| N,N-dimethylarginine (previously: Metabolite - 3162) - 35 | 0.08716966 | 0.129661085 | + | 24% |
| Metabolite - 121 - 9 | 0.088610953 | 0.130595726 | + | 42% |
| Metabolite - 577 - 9 | 0.09063077 | 0.132358258 | + | 40% |
| Metabolite - 961 - 9 | 0.093002954 | 0.133894384 | + | 12% |
| Metabolite - 226 - 9 | 0.093349572 | 0.133894384 | − | −19% |
| Metabolite - 645 - 9 | 0.095313283 | 0.135501168 | + | 40% |
| Metabolite - 1656 - 35 | 0.097604903 | 0.1366745 | + | 13% |
| Metabolite - 991 - 9 | 0.098141802 | 0.1366745 | + | 136% |
| Metabolite - 504 - 9 | 0.098690972 | 0.1366745 | + | 10% |
| Metabolite - 141 - 9 | 0.103478892 | 0.142080332 | + | 3% |
| Glutamic acid - 9 | 0.107899489 | 0.145713342 | + | 8% |
| Metabolite - 863 - 9 | 0.107938959 | 0.145713342 | + | 18% |
| Praline - 35 | 0.110450812 | 0.147366108 | + | 156% |
| Metabolite - 1344 retired: Na adduct of citric acid - 35 | 0.110997942 | 0.147366108 | + | 15% |
| Metabolite - 283 - 9 | 0.113558357 | 0.149529653 | + | 12% |
| Metabolite - 549 - 9 | 0.11625191 | 0.151831905 | + | 12% |
| 2-ethylhexanoic acid - 9 | 0.117393015 | 0.152085786 | + | 82% |
| Metabolite - 554 - 9 | 0.125065256 | 0.160729176 | + | 8% |
| alpha-4-dihydroxybenzenepropanoic acid - 35 | 0.126476082 | 0.160754983 | − | −38% |
| Metabolite - 2254 - 35 | 0.127676381 | 0.160754983 | − | −7% |

TABLE 3-continued

ALS Biomarkers from CSF samples - T-tests of ALS vs. Controls

| Compound | p-value | q-value | Increase (+) or Decrease (−) in ALS | % change in ALS |
|---|---|---|---|---|
| Uridine - 35 | 0.128087385 | 0.160754983 | − | −7% |
| Metabolite - 1289 - 35 | 0.132482766 | 0.164982443 | + | 28% |
| Metabolite - 706 - 9 | 0.133748806 | 0.165277836 | + | 13% |
| Metabolite - 3130 - 35 | 0.14060403 | 0.17043414 | + | 36% |
| monoethanolamine- 9 | 0.142625769 | 0.17043414 | − | −7% |
| Metabolite - 995 - 9 | 0.142904885 | 0.17043414 | + | 17% |
| Metabolite - 3416 - 35 | 0.144828316 | 0.17043414 | + | 283% |
| Metabolite - 2056 - 35 | 0.145202134 | 0.17043414 | + | 14% |
| Metabolite - 998 - 9 | 0.145788549 | 0.17043414 | + | 7% |
| Creatinine - 35 | 0.146484035 | 0.17043414 | − | −6% |
| Metabolite - 3334 - 35 | 0.147223519 | 0.17043414 | + | 16% |
| Metabolite - 386 - 9 | 0.148030311 | 0.17043414 | + | 40% |
| Metabolite - 595 - 9 | 0.148530818 | 0.17043414 | − | −13% |
| N-Acetylglutamine - 9 | 0.154040302 | 0.175502498 | + | 37% |
| Metabolite - 2558 - 35 | 0.159039442 | 0.178894231 | + | 23% |
| Metabolite - 1979 retired: CL adduct of Isobar 19 - 35 | 0.159244455 | 0.178894231 | + | 12% |
| Metabolite - 597 - 9 | 0.160725809 | 0.179304498 | − | −6% |
| Metabolite - 3180 - 35 | 0.170201134 | 0.188565615 | + | 19% |
| Metabolite - 761 - 9 | 0.171805475 | 0.18884866 | + | 4% |
| Glutamine - 35 | 0.176496672 | 0.18884866 | + | 6% |
| Metabolite - 3056 - 35 | 0.17771707 | 0.18884866 | + | 12% |
| Gamma-L-glutamyl-L-tyrosine - 35 | 0.177895914 | 0.18884866 | + | 18% |
| Metabolite - 3166 - 35 | 0.177901993 | 0.18884866 | − | −18% |
| 2-amino-butyrate - 9 | 0.178360612 | 0.18884866 | − | −65% |
| Metabolite - 286 - 9 | 0.179541418 | 0.18884866 | + | 4% |
| Butanoic acid - 9 | 0.18099469 | 0.18884866 | + | 18% |
| Metabolite - 1127 - 35 | 0.18144705 | 0.18884866 | + | 14% |
| Metabolite - 704 - 9 | 0.182212241 | 0.18884866 | + | 9% |
| Metabolite - 2052 retired: potassium adduct of Isobar 1 - 35 | 0.183957921 | 0.189435753 | + | 4% |
| Metabolite - 441 - 9 | 0.188489385 | 0.192170414 | − | −10% |
| Metabolite - 996 - 9 | 0.189005986 | 0.192170414 | − | −17% |
| Metabolite - 593 - 9 | 0.203992915 | 0.203543512 | + | 5% |
| Metabolite - 413 - 9 | 0.206529207 | 0.204157583 | + | 9% |
| Glycerol - 9 | 0.207150061 | 0.204157583 | + | 7% |
| Metabolite - 2366 - 35 | 0.208468364 | 0.204204056 | + | 9% |
| Caffeine - 35 | 0.213735439 | 0.208094522 | − | −24% |
| glycerol-2-phosphate (Metabolite - 1820) - 35 | 0.217073979 | 0.208835572 | + | 19% |
| Metabolite - 1498 - 35 | 0.217096535 | 0.208835572 | + | 10% |
| Metabolite - 1351 retired: urea adduct of Isobar 6 - 35 | 0.230741626 | 0.22064024 | + | 153% |
| Palmitoleic acid - 9 | 0.233003801 | 0.221485019 | − | −15% |
| Metabolite - 1612 - 35 | 0.236677617 | 0.223096352 | − | −18% |
| Metabolite - 387 - 9 | 0.242941898 | 0.223096352 | + | 8% |
| Phosphate - 9 | 0.243730034 | 0.223096352 | − | −7% |
| Metabolite - 777 - 9 | 0.24427133 | 0.223096352 | − | −12% |
| Metabolite - 1343 retired: p-hydroxyphenyllactic acid - 35 | 0.246474525 | 0.223096352 | − | −21% |
| Metabolite - 2181 - 35 | 0.24703859 | 0.223096352 | + | 11% |
| 2-aminobutanoic acid - 9 | 0.247663209 | 0.223096352 | − | −4% |
| Metabolite - 2696 - 35 | 0.248640586 | 0.223096352 | − | −14% |
| 4-hydroxy-2-quinolinecarboxylic acid - 35 | 0.249347817 | 0.223096352 | + | 12% |
| Isobar 3: includes-inositol-1-phosphate-mannose-6-phosphate-glucose-6-phosphate- 35 | 0.249799997 | 0.223096352 | + | 9% |
| Metabolite - 3468 retired: Metabolite - 1498 - 35 | 0.252721962 | 0.223096352 | − | −20% |
| Metabolite - 490 - 9 | 0.252752699 | 0.223096352 | − | −8% |
| Metabolite - 150 - 9 | 0.255977359 | 0.224707992 | + | 8% |
| Metabolite - 3370 - 35 | 0.257904419 | 0.225169215 | − | −74% |
| Orotidine-5-phosphate - 35 | 0.265088273 | 0.230190206 | + | 8% |
| Histidine - 35 | 0.273824931 | 0.235233643 | − | −10% |
| Metabolite - 1328 - 35 | 0.275859752 | 0.235721147 | + | 7% |
| Metabolite - 702 - 9 | 0.277827448 | 0.236146439 | + | 5% |
| Fumaric acid - 9 | 0.283250129 | 0.239488448 | + | 7% |
| Dulcitol - 9 | 0.285323023 | 0.239978042 | + | 4% |
| Metabolite - 2806 - 35 | 0.29333473 | 0.244954506 | + | 8% |
| Metabolite - 381 - 9 | 0.294289446 | 0.244954506 | + | 4% |
| Metabolite - 1132 - 35 | 0.295892018 | 0.245018894 | − | −6% |

TABLE 3-continued

ALS Biomarkers from CSF samples - T-tests of ALS vs. Controls

| Compound | p-value | q-value | Increase (+) or Decrease (−) in ALS | % change in ALS |
|---|---|---|---|---|
| Metabolite - 984 - 9 | 0.297537473 | 0.245117949 | + | 14% |
| Metabolite - 571 - 9 | 0.299399569 | 0.245393556 | + | 2% |
| Malic acid - 35 | 0.308206993 | 0.251154317 | − | −12% |
| Metabolite - 223 - 9 | 0.309554971 | 0.251154317 | − | −8% |
| Metabolite - 1114 - 35 | 0.317831617 | 0.25541317 | + | 8% |
| Lipoate - 9 | 0.31798397 | 0.25541317 | − | −2% |
| Metabolite - 614 - 9 | 0.321713851 | 0.256295075 | + | 5% |
| Allantoin - 35 | 0.322272743 | 0.256295075 | + | 7% |
| Metabolite - 1843 - 35 | 0.324346505 | 0.256673622 | + | 12% |
| 2-deoxy-D-ribose- 35 | 0.328366854 | 0.25810406 | + | 12% |
| Metabolite - 982 - 9 | 0.329367423 | 0.25810406 | + | 4% |
| Metabolite - 2607 - 35 | 0.332485579 | 0.259282764 | − | −21% |
| Decanoic acid - 9 | 0.34128867 | 0.264861955 | − | −6% |
| Metabolite - 861 - 9 | 0.345063396 | 0.266503927 | − | −41% |
| 4-hydroxy-3-methoxymandelate - 35 | 0.348526799 | 0.26789089 | − | −6% |
| N-6-trimethyl-l-lysine - 35 | 0.353559546 | 0.270276098 | + | 10% |
| Metabolite - 601 - 9 | 0.35499484 | 0.270276098 | − | −8% |
| Metabolite - 285 - 9 | 0.358666851 | 0.271223252 | − | −5% |
| Metabolite - 990 - 9 | 0.360695644 | 0.271223252 | + | 9% |
| Metabolite - 1281 - 35 | 0.361303891 | 0.271223252 | + | 28% |
| Metabolite - 1500 - 35 | 0.364587526 | 0.27241524 | − | −8% |
| Palmitate - 9 | 0.367715793 | 0.273480639 | − | −8% |
| Metabolite - 987 - 9 | 0.373659632 | 0.27662059 | − | −5% |
| Metabolite - 485 - 9 | 0.379063623 | 0.279333916 | − | −5% |
| pyrophosphate - 35 | 0.382841589 | 0.280829709 | + | 13% |
| Metabolite - 406 - 9 | 0.390748491 | 0.285326877 | + | 3% |
| Adenosine - 35 | 0.394176681 | 0.286527763 | + | 16% |
| Metabolite - 653 - 9 | 0.399137074 | 0.288794022 | − | −1% |
| Metabolite - 562 - 9 | 0.400889802 | 0.288794022 | + | 5% |
| Metabolite - 2047 - 35 | 0.414297111 | 0.296771543 | + | 21% |
| Glutarate - 35 | 0.41565855 | 0.296771543 | + | 8% |
| Metabolite - 1216 - 35 | 0.418475365 | 0.297460643 | − | −7% |
| Metabolite - 721 - 9 | 0.421048164 | 0.297970985 | + | 8% |
| Metabolite - 1818 - 35 | 0.435521173 | 0.304819961 | + | 7% |
| Selenocystine - 35 | 0.436672016 | 0.304819961 | + | 7% |
| N-acetyl-L-alanine - 35 | 0.437736783 | 0.304819961 | − | −12% |
| 1-Hexadecanol- 9 | 0.438478638 | 0.304819961 | + | 3% |
| Metabolite - 1252 - 35 | 0.440213476 | 0.304819961 | − | −12% |
| Metabolit-1142-possible-5-hydroxypentanoate-or-beta-hydroxyisovaleric acid - 35 | 0.444882966 | 0.30673117 | + | 12% |
| Adenosine-3-5-cyclic-monophosphate - 35 | 0.450930645 | 0.309572196 | − | −8% |
| gamma-aminobutyryl-L-histidine - 35 | 0.455069979 | 0.309985014 | − | −7% |
| Metabolite - 2053 - 35 | 0.458944767 | 0.309985014 | + | 4% |
| Metabolite - 2174 - 35 | 0.460239624 | 0.309985014 | − | −7% |
| Metabolite - 1608 - 35 | 0.462609798 | 0.309985014 | + | 27% |
| Metabolite - 263 - 9 | 0.463904587 | 0.309985014 | + | 1% |
| Metabolite - 985 - 9 | 0.464853426 | 0.309985014 | − | −4% |
| Metabolite - 382 - 9 | 0.465039333 | 0.309985014 | − | −2% |
| Xylitol - 35 | 0.475817567 | 0.315858931 | + | 8% |
| Metabolite - 2272 - 35 | 0.492650265 | 0.322589067 | + | 7% |
| Metabolite - 3183 - 35 | 0.494461332 | 0.322589067 | + | 5% |
| DOPA - 9 | 0.495698565 | 0.322589067 | + | 3% |
| Metabolite - 688 - 9 | 0.496520786 | 0.322589067 | + | 7% |
| Metabolite - 642 - 9 | 0.499110444 | 0.322589067 | − | −4% |
| alpha-L-sorbopyranose - 9 | 0.499556985 | 0.322589067 | + | 7% |
| Metabolite - 1340 - 35 | 0.500012586 | 0.322589067 | + | 5% |
| Cholesterol - 9 | 0.50866208 | 0.324370836 | + | 5% |
| Metabolite - 1304 - 35 | 0.509491594 | 0.324370836 | + | 9% |
| Glucarate - 35 | 0.513196658 | 0.324370836 | + | 7% |
| Mercaptopyruvate - 35 | 0.513635372 | 0.324370836 | − | −7% |
| 4-acetamidobutyric acid - 35 | 0.514581781 | 0.324370836 | − | −4% |
| 3-nitro-L-tyrosine - 35 | 0.51488937 | 0.324370836 | + | 10% |
| 5-6-dihydrouracil - 35 | 0.519318205 | 0.325882949 | + | 7% |
| Vitamin-B6 - 9 | 0.544364603 | 0.337416774 | − | −2% |
| N-acetyl-L-valine - 35 | 0.54652652 | 0.337416774 | + | 4% |
| Metabolite - 2051 - 35 | 0.547784575 | 0.337416774 | − | −7% |
| Metabolite - 138 - 9 | 0.548528574 | 0.337416774 | − | −9% |
| Hydroorotate - 9 | 0.551613949 | 0.337416774 | + | 2% |
| Metabolite - 1064 - 35 | 0.553423907 | 0.337416774 | + | 11% |
| Metabolite - 2753 - 35 | 0.554758141 | 0.337416774 | + | 8% |

TABLE 3-continued

ALS Biomarkers from CSF samples - T-tests of ALS vs. Controls

| Compound | p-value | q-value | Increase (+) or Decrease (−) in ALS | % change in ALS |
|---|---|---|---|---|
| Metabolite - 147 - 9 | 0.556601648 | 0.337416774 | + | 4% |
| Metabolite - 2821 - 35 | 0.563867234 | 0.3405361 93 | − | −7% |
| Metabolite - 505 - 9 | 0.567268276 | 0.341307074 | − | −9% |
| Metabolite - 1342-possible-phenylacetylglutamine-or-formyl-N-acetyl-5-methoxykynurenamine - 35 | 0.573882257 | 0.342584549 | + | 10% |
| N-carbamoyl-L-aspartate - 35 | 0.574286475 | 0.342584549 | + | 13% |
| Metabolite - 465 - 9 | 0.575789155 | 0.342584549 | + | 4% |
| Metabolite - 2752 - 35 | 0.58377483 | 0.346054204 | − | −5% |
| Metabolite - 771 - 9 | 0.588185627 | 0.346944856 | + | 2% |
| Metabolite - 128 - 9 | 0.589596701 | 0.346944856 | + | 7% |
| Metabolite - 443 - 9 | 0.59297 | 0.347656388 | + | 3% |
| Metabolite - 3249 - 35 | 0.596009946 | 0.348168012 | + | 5% |
| Metabolite - 394 - 9 | 0.605261043 | 0.352291119 | + | 1% |
| Metabolite - 2231 - 35 | 0.612649849 | 0.355251722 | − | −6% |
| Metabolite - 3143 - 35 | 0.61501394 | 0.355251722 | + | 5% |
| Octadecanoic acid - 9 | 0.616981782 | 0.355251722 | − | −5% |
| Metabolite - 606 - 9 | 0.620607359 | 0.35606308 | − | −28% |
| Inosine - 35 | 0.623260175 | 0.356312544 | + | 2% |
| Metabolite - 146 - 9 | 0.628441155 | 0.357149158 | + | 4% |
| Tetronic acid - 9 | 0.631331258 | 0.357149158 | − | −3% |
| alpha-keto-glutarate - 35 | 0.635939737 | 0.357149158 | + | 13% |
| Metabolite - 2313 - 35 | 0.636271358 | 0.357149158 | + | 6% |
| Sarcosine - 9 | 0.636477808 | 0.357149158 | − | −4% |
| 2-deoxyadenosine - 35 | 0.638062869 | 0.357149158 | + | 10% |
| Metabolite - 1842 retired: 4-Guanidinobutanoic acid - 35 | 0.650087912 | 0.361421083 | + | 11% |
| Metabolite - 2822 - 35 | 0.650640633 | 0.361421083 | − | −8% |
| alpha-D-ribose-5-phosphate - 35 | 0.652444278 | 0.361421083 | − | −2% |
| Threonine - 9 | 0.659478025 | 0.362815249 | − | −3% |
| Metabolite - 651 - 9 | 0.662379408 | 0.363167735 |  | 0% |
| n-dodecanoate - 9 | 0.666143596 | 0.363170201 | − | −2% |
| Ascorbate - 9 | 0.666905297 | 0.363170201 | + | 2% |
| Metabolite - 1104 - 35 | 0.673890691 | 0.36374061 | + | 5% |
| Metabolite - 221 - 9 | 0.676174243 | 0.36374061 | + | 2% |
| Metabolite - 274 - 9 | 0.676382961 | 0.36374061 | − | −7% |
| Glyoxylate - 9 | 0.677009752 | 0.36374061 | − | −4% |
| 3-phospho-d-glycerate - 9 | 0.683074 | 0.365775452 | − | −3% |
| Metabolite - 2593 - 35 | 0.692516059 | 0.369599528 | − | −8% |
| Metabolite - 501 - 9 | 0.695725874 | 0.370083112 | + | 1% |
| Metabolite - 2698 - 35 | 0.700319922 | 0.371297399 | − | −14% |
| 2-deoxyguanosine - 35 | 0.704753331 | 0.37241881 | + | 8% |
| Metabolite - 1713 retired: n-acetyl-L-aspartic acid - 35 | 0.709012601 | 0.373441148 | − | −9% |
| Metabolite - 3230 - 35 | 0.720758523 | 0.378387181 | + | 2% |
| Metabolite - 1286 - 35 | 0.736607481 | 0.385448007 | + | 2% |
| Guanosine - 35 | 0.74893034 | 0.390623856 | − | −3% |
| Metabolite - 2005 - 35 | 0.751999999 | 0.390955579 | − | −12% |
| Metabolite - 222 - 9 | 0.760063882 | 0.393873223 | + | 3% |
| Metabolite - 3313 - 35 | 0.768820999 | 0.3971301 89 | + | 6% |
| Metaboiite-2038 - 35 | 0.787393315 | 0.405420014 | − | −6% |
| Pentanedicic acid - 9 | 0.790930325 | 0.405940091 | + | 1% |
| Metabolite - 2726 - 35 | 0.796908559 | 0.407705808 | + | 2% |
| Xanthine - 35 | 0.804651542 | 0.41036031 | − | −1% |
| Metabolite - 691 - 9 | 0.814502755 | 0.413496839 | + | 1% |
| Saccharopine - 35 | 0.815949726 | 0.413496839 | − | −1% |
| Metabolite - 2266 retired 4-acetominophen sulfate - 35 | 0.829194515 | 0.418887456 | + | 5% |
| Metabolite - 2703 - 35 | 0.833868475 | 0.419351988 | − | −2% |
| Metabolite - 2026 - 35 | 0.835334906 | 0.419351988 | − | −3% |
| Metabolite - 594 - 9 | 0.840345843 | 0.420553332 | − | −1% |
| Isocitrate - 35 | 0.866017208 | 0.432054671 | + | 2% |
| Metabolite - 3401 - 35 | 0.868797857 | 0.432100007 | − | −2% |
| Phosphoenolpyruvate - 35 | 0.876478439 | 0.434228888 | − | −2% |
| Metabolite - 580 - 9 | 0.878484328 | 0.434228888 |  | 0% |
| 3-hydroxy-3-methylglutarate - 35 | 0.885311404 | 0.436261123 | + | 1% |
| Metabolite - 1192 - 35 | 0.898340337 | 0.439274785 | − | −2% |
| Metabolite - 278 - 9 | 0.899363797 | 0.439274785 | − | −1% |
| Metabolite - 136 - 9 | 0.89963039 | 0.439274785 | − | −1% |
| Metabolite - 472 - 9 | 0.904069476 | 0.440104614 | − | −1% |
| Metabolite - 3231 - 35 | 0.916045274 | 0.444587246 | − | −2% |

TABLE 3-continued

ALS Biomarkers from CSF samples - T-tests of ALS vs. Controls

| Compound | p-value | q-value | Increase (+) or Decrease (−) in ALS | % change in ALS |
|---|---|---|---|---|
| Gulono-1-4-lactone - 9 | 0.920525317 | 0.445415892 |  | 0% |
| Metabolite - 398 - 9 | 0.926806237 | 0.445658163 | − | −1% |
| Inositol - 9 | 0.92730147 | 0.445658163 |  | 0% |
| Tartarate - 9 | 0.929348533 | 0.445658163 |  | 0% |
| Metabolite - 2109 - 35 | 0.945063226 | 0.451845168 | + | 1% |
| Metabolite - 482 - 9 | 0.953927021 | 0.454297898 |  | 0% |
| 12-hydroxydodecanoic acid - 9 | 0.956865594 | 0.454297898 |  | 0% |
| Metabolite - 2867 - 35 | 0.959322876 | 0.454297898 | + | 2% |
| Metabolite - 388 - 9 | 0.963949535 | 0.454297898 |  | 0% |
| Metabolite - 145 - 9 | 0.964333051 | 0.454297898 |  | 0% |
| Metabolite - 1133 - 35 | 0.974467054 | 0.457729718 |  | 0% |
| 3-phospho-d-glycerate - 35 | 0.981402528 | 0.459142063 |  | 0% |
| 3-phospho-l-serine - 9 | 0.983190036 | 0.459142063 |  | 0% |
| Metabolite - 770 - 9 | 0.995319404 | 0.462252418 |  | 0% |
| Gluconic acid - 9 | 0.995605381 | 0.462252418 |  | 0% |
| Metabolite - 2854 - 35 | 0.999251787 | 0.462608399 |  | 0% |

TABLE 4

ALS Biomarkers from CSF: Wilcoxon's Rank Sum Test ALS v. Controls

| Compound | p-value | q-value | Increase (+) or Decrease (−) in ALS | % change in ALS |
|---|---|---|---|---|
| Metabolite - 1113 - 35 | 4.81E−05 | 0.00589796 | + | 63% |
| Metabolite - 2185 - 35 | 6.59E−05 | 0.00589796 | + | 43% |
| Metabolite - 1713 retired: n-acetyl-L-aspartic acid - 35 | 0.000140851 | 0.008410318 | − | −9% |
| alpha-Hydroxyisobutyric acid-tms - 9 | 0.000278249 | 0.012019186 | + | 27% |
| Metabolite - 1336 retired: carnitine - 35 | 0.00037254 | 0.012019186 | + | 55% |
| alpha-aminoadipic acid - 9 | 0.000491208 | 0.012019186 | + | 33% |
| amino-malinate-mixture - 9 | 0.000519388 | 0.012019186 | + | 38% |
| 2-amino-heptanedioic acid - 9 | 0.000624382 | 0.012427436 | + | 37% |
| Metabolite - 2389 - 35 | 0.000780424 | 0.01298768 | + | 16% |
| Metabolite - 763 - 9 | 0.000797537 | 0.01298768 | + | 17% |
| 3-amino-isobutyrate - 9 | 0.000928321 | 0.013537644 | + | 31% |
| Metabolite - 3138 - 35 | 0.000982455 | 0.013537644 | + | 88% |
| Metabolite - 2139 - 35 | 0.001196211 | 0.014291844 | + | 47% |
| Metabolite - 1086 - 35 | 0.001196757 | 0.014291844 | + | 61% |
| 5-oxoproline - 9 | 0.001342087 | 0.014421736 | + | 13% |
| Metabolite - 1116 - 35 | 0.001368651 | 0.014421736 | + | 29% |
| trans-4-hydroxyproline - 35 | 0.001455763 | 0.014487443 | + | 19% |
| alpha-2-diamino-gamma-oxobenzenebutanoic acid - 35 | 0.001605672 | 0.015138292 | + | 76% |
| Metabolite - 760 - 9 | 0.002070127 | 0.018541315 | + | 32% |
| DL-pipecolic acid - 35 | 0.002460098 | 0.020870333 | + | 108% |
| Metabolite - 421 - 9 | 0.002563176 | 0.020870333 | + | 47% |
| Metabolite - 2567 - 35 | 0.003042785 | 0.023653577 | + | 56% |
| Metabolite - 753 - 9 | 0.003171436 | 0.023653577 | + | 35% |
| Urea - 9 | 0.003301135 | 0.023653577 | + | 18% |
| Metabolite - 1830 - 35 | 0.003555749 | 0.024498043 | + | 18% |
| Metabolite - 2074 - 35 | 0.004045965 | 0.025905285 | + | 52% |
| Uric acid - 35 | 0.004049233 | 0.025905285 | + | 22% |
| Metabolite - 2686 - 35 | 0.004320203 | 0.026202897 | + | 8% |
| Pyridoxamine - 35 | 0.004461991 | 0.026202897 | + | 10% |
| Metabolite - 1346 - 35 | 0.004534583 | 0.026202897 | + | 7% |
| Methionine - 35 | 0.004754661 | 0.026401645 | + | 21% |
| Metabolite - 2526 - 35 | 0.004986999 | 0.026401645 | + | 9% |
| Citric acid - 9 | 0.005011137 | 0.026401645 | + | 12% |
| Valine - 9 | 0.006160305 | 0.031397644 | + | 34% |
| Glutamine - 35 | 0.006309951 | 0.031397644 | + | 6% |
| Metabolite - 2694 retired: lactate - 35 | 0.007031923 | 0.033150012 | + | 14% |
| Metabolite - 268 - 9 | 0.00703224 | 0.033150012 | + | 51% |
| gamma-L-glutamyl-L-glutamine - 35 | 0.007475374 | 0.034335385 | + | 16% |
| Metabolite - 1910 retired: uric acid - 35 | 0.008126877 | 0.036394628 | + | 22% |
| Metabolite - 961 - 9 | 0.009191951 | 0.040160347 | + | 12% |

TABLE 4-continued

ALS Biomarkers from CSF: Wilcoxon's Rank Sum Test ALS v. Controls

| Compound | p-value | q-value | Increase (+) or Decrease (−) in ALS | % change in ALS |
|---|---|---|---|---|
| Metabolite - 2527 retired: citrulline - 35 | 0.010313603 | 0.043988051 | + | 267% |
| Metabolite - 609 - 9 | 0.010770241 | 0.044867365 | + | 6% |
| Tetradecanoic acid - 9 | 0.011564259 | 0.047080248 | + | 14% |
| Metabolite - 547 - 9 | 0.011895473 | 0.047352487 | + | 18% |
| Metabolite - 1573 retired: glycerol-2-phosphate - 35 | 0.013301907 | 0.051799991 | + | 16% |
| Serine - 9 | 0.014264462 | 0.053295855 | − | −11% |
| Metabolite - 1829 retired: oxalic acid - 35 | 0.01428108 | 0.053295855 | + | 8% |
| Metabolite - 121 - 9 | 0.018224891 | 0.066182714 | + | 42% |
| Metabolite - 782 - 9 | 0.018473151 | 0.066182714 | + | 11% |
| Metabolite - 2563 retired: lactate - 35 | 0.019274499 | 0.067137694 | + | 18% |
| Metabolite - 1349 retired: Isobar 7 - 35 | 0.020162937 | 0.067137694 | + | 55% |
| Metabolite - 591 - 9 | 0.020199367 | 0.067137694 | + | 51% |
| 1-7-dihydro-6h-purin-6-one - 35 | 0.020491957 | 0.067137694 | − | −13% |
| Isobar 2: includes-3-amino-isobutyrate-2-amino-butyrate-4-aminobutanoic acid-dimethylglycine - 35 | 0.020613679 | 0.067137694 | + | 36% |
| Metabolite - 522 - 9 | 0.02193703 | 0.069347268 | + | 70% |
| Metabolite - 2687 - 35 | 0.022066355 | 0.069347268 | + | 9% |
| Metabolite - 3316 retired: lactate - 35 | 0.023746931 | 0.07334206 | + | 17% |
| gamma-L-glutamyl-L-tyrosine - 35 | 0.026183625 | 0.079497114 | + | 18% |
| Metabolite - 704 - 9 | 0.026986286 | 0.080568537 | + | 9% |
| Tyrosine - 35 | 0.027825502 | 0.080810989 | + | 19% |
| Metabolite - 2697 - 35 | 0.02800104 | 0.080810989 | + | 40% |
| Metabolite - 508 - 9 | 0.028936572 | 0.080810989 | + | 9% |
| Metabolite - 1335 - 35 | 0.02932312 | 0.080810989 | + | 45% |
| Metabolite - 1068 - 35 | 0.03124896 | 0.083591292 | + | 8% |
| Isobar 1: includes-mannose-fructose-glucose-galactose-alpha-L-sorbopyranose-Inositol - 35 | 0.031265274 | 0.083591292 | + | 15% |
| Alanine - 9 | 0.034246794 | 0.08935306 | + | 14% |
| Histamine - 35 | 0.034417943 | 0.08935306 | + | 19% |
| Metabolite - 995 - 9 | 0.036853002 | 0.094307979 | + | 17% |
| Pantothenic acid - 35 | 0.037556802 | 0.094347666 | + | 27% |
| Metabolite - 393 - 9 | 0.03869605 | 0.0949549 | + | 16% |
| Caffeine - 35 | 0.039651027 | 0.095983442 | − | −24% |
| Metabolite - 2100 - 35 | 0.040207393 | 0.096032506 | + | 11% |
| Metabolite - 283 - 9 | 0.040852014 | 0.096288292 | + | 12% |
| Metabolite - 2005 - 35 | 0.043644554 | 0.101534337 | − | −12% |
| Cytidine - 35 | 0.044363373 | 0.10188343 | − | −9% |
| Metabolite - 1343 retired: p-hydroxyphenyllactic acid - 35 | 0.048835069 | 0.109317592 | − | −21% |
| Metabolite - 655 - 9 | 0.049078982 | 0.109317592 | + | 32% |
| Carnosine - 35 | 0.050049316 | 0.109317592 | − | −8% |
| Metabolite - 1126 - 35 | 0.050906945 | 0.109317592 | + | 40% |
| Metabolite - 863 - 9 | 0.05109681 | 0.109317592 | + | 18% |
| Metabolite - 996 - 9 | 0.052123383 | 0.109317592 | − | −17% |
| Histidine - 35 | 0.052173845 | 0.109317592 | − | −10% |
| Metabolite - 1597 - 35 | 0.053116952 | 0.109367303 | + | 19% |
| Metabolite - 3179 retired: 4-Guanidinobutanoic acid - 35 | 0.055443465 | 0.111950626 | − | −24% |
| Arginine - 35 | 0.056338742 | 0.111950626 | + | 7% |
| Metabolite - 2390 - 35 | 0.056389919 | 0.111950626 | + | 55% |
| Metabolite - 458 - 9 | 0.056871452 | 0.111950626 | + | 75% |
| Metabolite - 3441 - 35 | 0.057664917 | 0.112278719 | − | −44% |
| Creatinine - 35 | 0.059347516 | 0.113196789 | − | −6% |
| Metabolite - 273 - 9 | 0.059995122 | 0.113196789 | + | 20% |
| Metabolite - 553 - 9 | 0.060032179 | 0.113196789 | − | −32% |
| Metabolite - 549 - 9 | 0.062403991 | 0.115890315 | + | 12% |
| Glycerate - 9 | 0.062754558 | 0.115890315 | − | −6% |
| Metabolite - 1108 - 35 | 0.06463188 | 0.11813928 | + | 63% |
| Metabolite - 502 - 9 | 0.068588529 | 0.124105178 | + | 25% |
| Metabolite - 289 - 9 | 0.070888141 | 0.126983471 | + | 9% |
| Metabolite - 3056 - 35 | 0.071674664 | 0.127121174 | + | 12% |
| Lysine - 9 | 0.074452222 | 0.130360941 | + | 17% |
| Metabolite - 2141 - 35 | 0.074956812 | 0.130360941 | + | 32% |
| Isobar 4: includes-Gluconic acid-arabinose-D-ribose - 35 | 0.075803406 | 0.130565665 | + | 12% |
| Allantoin - 35 | 0.076640443 | 0.130688955 | + | 7% |
| o-phosphoethanolamine - 9 | 0.07733412 | 0.130688955 | + | 11% |
| Praline - 35 | 0.081907325 | 0.137123714 | + | 156% |
| Metabolite - 1351 retired: urea adduct | 0.084293113 | 0.139811193 | + | 153% |

TABLE 4-continued

ALS Biomarkers from CSF: Wilcoxon's Rank Sum Test ALS v. Controls

| Compound | p-value | q-value | Increase (+) or Decrease (−) in ALS | % change in ALS |
|---|---|---|---|---|
| of Isobar 6 - 35 | | | | |
| Metabolite - 998 - 9 | 0.089274784 | 0.144477301 | + | 7% |
| Metabolite - 780 - 9 | 0.089278687 | 0.144477301 | − | −7% |
| Metabolite - 861 - 9 | 0.089525962 | 0.144477301 | − | −41% |
| Glutamic acid - 9 | 0.092128452 | 0.146354769 | + | 8% |
| Metabolite - 2105 - 35 | 0.092323385 | 0.146354769 | + | 32% |
| Tryptophan - 35 | 0.094745188 | 0.147861757 | + | 15% |
| 5-S-methyl-5-thioadenosine - 35 | 0.095257482 | 0.147861757 | − | −7% |
| Metabolite - 2548-possible-Cl-adduct-of-uric acid - 35 | 0.095750323 | 0.147861757 | + | 14% |
| Metabolite-1498 - 35 | 0.098329731 | 0.149079215 | + | 10% |
| Orotidine-5-phosphate - 35 | 0.098337631 | 0.149079215 | + | 8% |
| Metabolite - 988 - 9 | 0.099035399 | 0.149079215 | + | 16% |
| 5-hydroxy-1H-indole-3-acetic acid - 9 | 0.103596668 | 0.153796594 | − | −15% |
| Uridine - 35 | 0.104730874 | 0.153796594 | − | −7% |
| Metabolite - 1656 - 35 | 0.104744914 | 0.153796594 | + | 13% |
| Metabolite - 2056 - 35 | 0.108063805 | 0.155226181 | + | 14% |
| Metabolite - 413 - 9 | 0.108565144 | 0.155226181 | + | 9% |
| Metabolite - 441 - 9 | 0.109069778 | 0.155226181 | − | −10% |
| Metabolite - 1131 - 35 | 0.109184732 | 0.155226181 | + | 13% |
| Metabolite - 3182 - 35 | 0.111442107 | 0.157187931 | + | 20% |
| Metabolite - 761 - 9 | 0.113020563 | 0.157474372 | + | 4% |
| Metabolite - 1820 retired: glycerol-2-phosphate - 35 | 0.113403378 | 0.157474372 | + | 19% |
| Phosphate - 9 | 0.116453675 | 0.160466156 | − | −7% |
| Phenylalanine - 35 | 0.119736234 | 0.163729865 | + | 12% |
| Metabolite - 141 - 9 | 0.121159331 | 0.164420718 | + | 3% |
| adenosine - 35 | 0.123111413 | 0.16518472 | + | 16% |
| Metabolite - 562 - 9 | 0.123566591 | 0.16518472 | + | 5% |
| Metabolite - 777 - 9 | 0.126086251 | 0.166074299 | − | −12% |
| Metabolite - 286 - 9 | 0.129743888 | 0.169644563 | + | 4% |
| Metabolite - 595 - 9 | 0.135916731 | 0.176381625 | − | −13% |
| Metabolite - 702 - 9 | 0.137475446 | 0.176381625 | + | 5% |
| Metabolite - 597 - 9 | 0.139467115 | 0.176381625 | − | −6% |
| Metabolite - 577 - 9 | 0.140075305 | 0.176381625 | + | 40% |
| Isoleucine - 9 | 0.140133007 | 0.176381625 | + | 18% |
| Metabolite - 150 - 9 | 0.140804253 | 0.176381625 | + | 8% |
| Metabolite - 3370 - 35 | 0.142935013 | 0.177807361 | − | −74% |
| Metabolite - 465 - 9 | 0.148325944 | 0.182850399 | + | 4% |
| Metabolite - 383 - 9 | 0.149030502 | 0.182850399 | − | −5% |
| Metabolite - 2696 - 35 | 0.153809766 | 0.186396096 | − | −14% |
| Monoethanolamine - 9 | 0.15400149 | 0.186396096 | − | −7% |
| Metabolite - 226 - 9 | 0.158801006 | 0.190380284 | − | −19% |
| Metabolite - 2558 - 35 | 0.159598455 | 0.190380284 | + | 23% |
| Metabolite - 3180 - 35 | 0.160481625 | 0.190380284 | + | 19% |
| Isobar 3: includes-inositol-1-phosphate-mannose-6-phosphate-glucose-6-phosphate - 35 | 0.174900751 | 0.205975696 | + | 9% |
| Metabolite - 593 - 9 | 0.17592753 | 0.205975696 | + | 5% |
| Metabolite - 3166 - 35 | 0.180240282 | 0.209654767 | − | −18% |
| Metabolite - 2052 retired: potassium adduct of Isobar 1 - 35 | 0.182322211 | 0.210708223 | + | 4% |
| Metabolite - 992 - 9 | 0.186484988 | 0.214137576 | + | 28% |
| Metabolite - 406 - 9 | 0.188146172 | 0.214669002 | + | 3% |
| Metabolite - 3127 - 35 | 0.190857147 | 0.2163839 | + | 21% |
| 2-deoxyguanosine - 35 | 0.193567238 | 0.218076231 | + | 8% |
| Metabolite - 554 - 9 | 0.194913449 | 0.21822044 | + | 8% |
| Selenocystine - 35 | 0.201335108 | 0.220028347 | + | 7% |
| Metabolite - 386 - 9 | 0.201414005 | 0.220028347 | + | 40% |
| Metabolite - 3218 - 35 | 0.203272805 | 0.220028347 | + | 21% |
| Metabolite - 783 - 9 | 0.203621448 | 0.220028347 | + | 5% |
| alpha-4-dihydroxybenzenepropanoic acid - 35 | 0.203878302 | 0.220028347 | − | −38% |
| Metabolite - 442 - 9 | 0.203898073 | 0.220028347 | − | −14% |
| Metabolite - 501 - 9 | 0.20718613 | 0.22223774 | + | 1% |
| Metabolite - 511 - 9 | 0.212612601 | 0.226700941 | + | 12% |
| Metabolite - 984 - 9 | 0.218140976 | 0.231219337 | + | 14% |
| Palmitoleic acid - 9 | 0.224262761 | 0.236309862 | − | −15% |
| Metabolite - 276 - 9 | 0.227574093 | 0.238396741 | + | 4% |
| Metabolite - 263 - 9 | 0.229502634 | 0.239019224 | + | 1% |
| Metabolite - 651 - 9 | 0.231440451 | 0.239644115 | | 0% |
| Metabolite - 504 - 9 | 0.233382993 | 0.240266688 | + | 10% |

TABLE 4-continued

ALS Biomarkers from CSF: Wilcoxon's Rank Sum Test ALS v. Controls

| Compound | p-value | q-value | Increase (+) or Decrease (−) in ALS | % change in ALS |
|---|---|---|---|---|
| 4-hydroxy-2-quinolinecarboxylic acid - 35 | 0.239304945 | 0.244955519 | + | 12% |
| Octadecanoic acid - 9 | 0.251419685 | 0.255235134 | − | −5% |
| Metabolite - 3162 retired: N,N-dimethylarginine - 35 | 0.252197117 | 0.255235134 | + | 24% |
| Butanoic acid - 9 | 0.257647776 | 0.25864946 | + | 18% |
| Metabolite - 2822 - 35 | 0.258641334 | 0.25864946 | − | −8% |
| alpha-keto-glutarate - 35 | 0.261385634 | 0.25864946 | + | 13% |
| Metabolite - 982 - 9 | 0.26185002 | 0.25864946 | + | 4% |
| 2-aminobutanoic acid - 9 | 0.263974958 | 0.25864946 | − | −4% |
| Metabolite - 2254 - 35 | 0.26423422 | 0.25864946 | − | −7% |
| Dulcitol - 9 | 0.27257911 | 0.26439873 | + | 4% |
| Metabolite - 3334 - 35 | 0.273059625 | 0.26439873 | + | 16% |
| Metabolite - 771 - 9 | 0.276942999 | 0.266717217 | + | 2% |
| Metabolite - 1281 - 35 | 0.279811594 | 0.268038824 | + | 28% |
| Metabolite - 706 - 9 | 0.285832283 | 0.272349783 | + | 13% |
| Metabolite - 1328 - 35 | 0.289031265 | 0.27394074 | + | 7% |
| Metabolite - 1344 retired: Na adduct of citric acid - 35 | 0.296037148 | 0.279104099 | + | 15% |
| Metabolite - 485 - 9 | 0.312459322 | 0.29302628 | − | −5% |
| Metabolite - 2181 - 35 | 0.314075599 | 0.29302628 | + | 11% |
| Metabolite - 1289 - 35 | 0.318828456 | 0.295919355 | + | 28% |
| 2-deoxy-D-ribose - 35 | 0.327640183 | 0.302530409 | + | 12% |
| N-Acetylglutamine - 9 | 0.338148583 | 0.310632266 | + | 37% |
| N-acetyl-L-alanine - 35 | 0.340262913 | 0.310979777 | − | −12% |
| Metabolite - 642 - 9 | 0.343191395 | 0.31206407 | − | −4% |
| Metabolite - 2047 - 35 | 0.350060981 | 0.316702958 | + | 21% |
| N-carbamoyl-L-aspartate - 35 | 0.354620559 | 0.318474197 | + | 13% |
| Gulono-1-4-lactone - 9 | 0.35860987 | 0.318474197 |  | 0% |
| Metabolite - 1612 - 35 | 0.359291449 | 0.318474197 | − | −18% |
| 2-deoxyadenosine - 35 | 0.359841917 | 0.318474197 | + | 10% |
| Metabolite - 2698 - 35 | 0.360908147 | 0.318474197 | − | −14% |
| Cholesterol - 9 | 0.366349483 | 0.31925206 | + | 5% |
| Metabolite - 443 - 9 | 0.366468741 | 0.31925206 | + | 3% |
| Metabolite - 2867 - 35 | 0.367136298 | 0.31925206 | + | 2% |
| Metabolite - 1818 - 35 | 0.369855345 | 0.319462539 | + | 7% |
| Metabolite - 2752 - 35 | 0.370945127 | 0.319462539 | − | −5% |
| Glycerol - 9 | 0.379830663 | 0.32554973 | + | 7% |
| Vitamin-B6 - 9 | 0.387981091 | 0.326048061 | − | −2% |
| Metabolite - 3231 - 35 | 0.390040532 | 0.326048061 | − | −2% |
| Metabolite - 2607 - 35 | 0.391749243 | 0.326048061 | − | −21% |
| Metabolite - 1216 - 35 | 0.392050899 | 0.326048061 | − | −7% |
| N-acetyl-L-valine - 35 | 0.392051517 | 0.326048061 | + | 4% |
| Metabolite - 990 - 9 | 0.393153158 | 0.326048061 | + | 9% |
| Metabolite - 645 - 9 | 0.404507569 | 0.333918532 | + | 40% |
| Decanoic acid - 9 | 0.407413135 | 0.334099533 | − | −6% |
| 1-Hexadecanol - 9 | 0.410232328 | 0.334099533 | + | 3% |
| Metabolite - 991 - 9 | 0.411063002 | 0.334099533 | + | 136% |
| Metabolite - 381 - 9 | 0.413060843 | 0.334099533 | + | 4% |
| fumaric acid - 9 | 0.415906634 | 0.334099533 | + | 7% |
| Metabolite - 147 - 9 | 0.415917436 | 0.334099533 | + | 4% |
| Metabolite - 614 - 9 | 0.421638482 | 0.336484898 | + | 5% |
| 4-hydroxy-3-methoxymandelate - 35 | 0.423915743 | 0.336484898 | − | −6% |
| Metabolite - 571 - 9 | 0.424522206 | 0.336484898 | + | 2% |
| Metabolite - 1286 - 35 | 0.429813623 | 0.339178194 | + | 2% |
| Metabolite - 387 - 9 | 0.433222915 | 0.34036914 | + | 8% |
| Metabolite - 1252 - 35 | 0.442432665 | 0.345077745 | − | −12% |
| 4-acetamidobutyric acid - 35 | 0.444933181 | 0.345077745 | − | −4% |
| Metabolite - 688 - 9 | 0.444995201 | 0.345077745 | + | 7% |
| Metabolite - 568 - 9 | 0.450960129 | 0.34819599 | + | 7% |
| Metabolite - 1979 retired: CL adduct of Isobar 19 - 35 | 0.454122164 | 0.348802529 | + | 12% |
| Metabolite - 382 - 9 | 0.458459943 | 0.348802529 | − | −2% |
| Metabolite - 2313 - 35 | 0.45883368 | 0.348802529 | + | 6% |
| Pyrophosphate - 35 | 0.459568502 | 0.348802529 | + | 13% |
| Metabolite - 222 - 9 | 0.461481577 | 0.348802529 | + | 3% |
| Metabolite - 1114 - 35 | 0.46653021 | 0.351136858 | + | 8% |
| Metabolite - 490 - 9 | 0.46908899 | 0.35158549 | − | −8% |
| Metabolite - 1340 - 35 | 0.477566736 | 0.354969166 | + | 5% |
| Metabolite - 3183 - 35 | 0.482289383 | 0.356998129 | + | 5% |
| Metabolite - 1127 - 35 | 0.493684258 | 0.363928954 | + | 14% |
| Metabolite - 2266 retired 4-acetominophen sulfate - 35 | 0.499552922 | 0.36673206 | + | 5% |

TABLE 4-continued

ALS Biomarkers from CSF: Wilcoxon's Rank Sum Test ALS v. Controls

| Compound | p-value | q-value | Increase (+) or Decrease (−) in ALS | % change in ALS |
|---|---|---|---|---|
| Metabolite - 1843 - 35 | 0.501581325 | 0.36673206 | + | 12% |
| Metabolite - 2174 - 35 | 0.505912728 | 0.367626729 | − | −7% |
| Metabolite - 606 - 9 | 0.506909499 | 0.367626729 | − | −28% |
| Adenosine-3-5-cyclic-monophosphate - 35 | 0.510849566 | 0.368104568 | − | −8% |
| Metabolite - 2593 - 35 | 0.511678242 | 0.368104568 | − | −8% |
| Gluconic acid - 9 | 0.519338065 | 0.372120632 | | 0% |
| Metabolite - 146 - 9 | 0.525817923 | 0.375262587 | + | 4% |
| Metabolite - 1104 - 35 | 0.531281422 | 0.376220557 | + | 5% |
| Xylitol - 35 | 0.53136071 | 0.376220557 | + | 8% |
| gamma-aminobutyryl-L-histidine - 35 | 0.538066749 | 0.379468772 | − | −7% |
| Metabolite - 2051 - 35 | 0.545176701 | 0.382975252 | − | −7% |
| Metabolite - 3468 retired: Metabolite - 1498 - 35 | 0.551648935 | 0.386008104 | − | −20% |
| Metabolite - 388 - 9 | 0.560462208 | 0.388789259 | | 0% |
| 5-6-dihydrouracil - 35 | 0.562006502 | 0.388789259 | + | 7% |
| Lipoate - 9 | 0.562134731 | 0.388789259 | − | −2% |
| Metabolite - 128 - 9 | 0.565490896 | 0.389606212 | + | 7% |
| 12-hydroxydodecanoic acid - 9 | 0.568868993 | 0.390431958 | | 0% |
| Metabolite - 138 - 9 | 0.578770894 | 0.394383561 | − | −9% |
| Metabolite - 601 - 9 | 0.579029844 | 0.394383561 | − | −8% |
| Metabolite - 1342-possible-phenylacetylglutamine-or-formyl-N-acetyl-5-methoxykynurenamine - 35 | 0.588057538 | 0.399015254 | + | 10% |
| Metabolite - 987 - 9 | 0.594450189 | 0.401339274 | − | −5% |
| Metabolite - 2726 - 35 | 0.596919611 | 0.401339274 | + | 2% |
| Metabolite - 285 - 9 | 0.599627227 | 0.401339274 | − | −5% |
| alpha-D-ribose-5-phosphate - 35 | 0.600444471 | 0.401339274 | − | −2% |
| Metabolite - 3143 - 35 | 0.604016003 | 0.401870746 | + | 5% |
| Tartarate - 9 | 0.606556307 | 0.401870746 | | 0% |
| 3-nitro-L-tyrosine - 35 | 0.607969903 | 0.401870746 | + | 10% |
| Metabolite - 1132 - 35 | 0.611167267 | 0.402171481 | − | −6% |
| Metabolite - 2053 - 35 | 0.612959279 | 0.402171481 | + | 4% |
| Metabolite - 721 - 9 | 0.6151602 | 0.402171481 | + | 8% |
| 2-amino-butyrate - 9 | 0.620541504 | 0.404214366 | − | −65% |
| Metabolite - 1500 - 35 | 0.624875169 | 0.404544292 | − | −8% |
| Glutarate - 35 | 0.625564713 | 0.404544292 | + | 8% |
| Ascorbate - 9 | 0.631114451 | 0.406665128 | + | 2% |
| N-6-trimethyl-l-lysine - 35 | 0.643783109 | 0.411865249 | + | 10% |
| Metabolite - 1064 - 35 | 0.663978387 | 0.423273644 | + | 11% |
| DOPA - 9 | 0.670522586 | 0.424427025 | + | 3% |
| Metabolite - 770 - 9 | 0.670526368 | 0.424427025 | | 0% |
| 3-phospho-d-glycerate - 9 | 0.677948475 | 0.427614036 | − | −3% |
| n-dodecanoate - 9 | 0.692424536 | 0.433744571 | − | −2% |
| Mercaptopyruvate - 35 | 0.695879606 | 0.433744571 | − | −7% |
| 3-phospho-l-serine - 9 | 0.699317446 | 0.433744571 | | 0% |
| Phosphoenolpyruvate - 35 | 0.699652586 | 0.433744571 | − | −2% |
| Metabolite - 223 - 9 | 0.699774788 | 0.433744571 | − | −8% |
| Metabolite - 472 - 9 | 0.710092334 | 0.43862202 | − | −1% |
| Metabolite - 3230 - 35 | 0.714846376 | 0.440041194 | + | 2% |
| Metabolite - 2231 - 35 | 0.720405761 | 0.441881344 | − | −6% |
| Metabolite - 1192 - 35 | 0.723960835 | 0.441881344 | − | −2% |
| Glucarate - 35 | 0.728249412 | 0.441881344 | + | 7% |
| Metabolite - 2806 - 35 | 0.730169643 | 0.441881344 | + | 8% |
| 3-phospho-d-glycerate - 35 | 0.734016495 | 0.442713713 | | 0% |
| Metabolite - 985 - 9 | 0.737163153 | 0.443119599 | − | −4% |
| Metabolite - 653 - 9 | 0.740731925 | 0.44377566 | − | −1% |
| Metabolite - 594 - 9 | 0.755810126 | 0.449140955 | − | −1% |
| Metabolite - 136 - 9 | 0.755814739 | 0.449140955 | − | −1% |
| Malic acid - 35 | 0.757209401 | 0.449140955 | − | −12% |
| Isocitrate - 35 | 0.768315843 | 0.454224718 | + | 2% |
| Metabolite - 3416 - 35 | 0.781343103 | 0.460406878 | + | 283% |
| Metabolite - 3401 - 35 | 0.785742098 | 0.461480959 | − | −2% |
| Xanthine - 35 | 0.788498648 | 0.461586534 | − | −1% |

TABLE 4-continued

ALS Biomarkers from CSF: Wilcoxon's Rank Sum Test ALS v. Controls

| Compound | p-value | q-value | Increase (+) or Decrease (−) in ALS | % change in ALS |
|---|---|---|---|---|
| Metabolite - 394 - 9 | 0.793917988 | 0.461769189 | + | 1% |
| Saccharopine - 35 | 0.796380525 | 0.461769189 | − | −1% |
| Guanosine - 35 | 0.800324952 | 0.461769189 | − | −3% |
| Inositol - 9 | 0.801599262 | 0.461769189 | | 0% |
| Metabolite - 505 - 9 | 0.803385192 | 0.461769189 | − | −9% |
| Metabolite - 2366 - 35 | 0.804277542 | 0.461769189 | + | 9% |
| 2-ethylhexanoic acid - 9 | 0.811185482 | 0.463898116 | + | 82% |
| Glyoxylate - 9 | 0.813164953 | 0.463898116 | − | −4% |
| Metabolite - 3130 - 35 | 0.821844119 | 0.467361035 | + | 36% |
| Metabolite - 2272 - 35 | 0.829571496 | 0.470262494 | + | 7% |
| Metabolite - 274 - 9 | 0.835872048 | 0.470958082 | − | −7% |
| 3-hydroxy-3-methylglutarate - 35 | 0.836056775 | 0.470958082 | + | 1% |
| Metabolite - 145 - 9 | 0.840293993 | 0.471861104 | | 0% |
| Hydroorotate - 9 | 0.844187321 | 0.472565977 | + | 2% |
| Metabolite - 580 - 9 | 0.867614526 | 0.48210755 | − | −8% |
| Palmitate - 9 | 0.867614526 | 0.48210755 | − | 0% |
| Metabolite - 398 - 9 | 0.869575595 | 0.48210755 | − | −1% |
| Metabolite - 2753 - 35 | 0.871997698 | 0.48210755 | + | 8% |
| Metabolite - 1142-possible-5-hydroxypentanoate-or-beta-hydroxyisovaleric acid - 35 | 0.87816814 | 0.483474682 | + | 12% |
| Metabolite - 2854 - 35 | 0.881164116 | 0.483474682 | | 0% |
| Pentanedioic acid - 9 | 0.883303118 | 0.483474682 | + | 1% |
| Threonine - 9 | 0.88526639 | 0.483474682 | − | −3% |
| Metabolite - 1842 retired: 4-Guanidinobutanoic acid - 35 | 0.898184283 | 0.48903862 | + | 11% |
| Metabolite - 1608 - 35 | 0.901189233 | 0.489187846 | + | 27% |
| Metabolite - 482 - 9 | 0.91480612 | 0.49507919 | | 0% |
| Metabolite - 221 - 9 | 0.918754567 | 0.495718391 | + | 2% |
| Metabolite - 2026 - 35 | 0.931706512 | 0.500287059 | − | −3% |
| Inosine - 35 | 0.932807721 | 0.500287059 | + | 2% |
| Metabolite - 3313 - 35 | 0.94471359 | 0.50264336 | + | 6% |
| Metabolite - 278 - 9 | 0.9460492 | 0.50264336 | − | −1% |
| Tetronic acid - 9 | 0.946444393 | 0.50264336 | − | −3% |
| Metabolite - 691 - 9 | 0.948425116 | 0.50264336 | + | 1% |
| Metabolite - 3249 - 35 | 0.953102102 | 0.503632019 | + | 5% |
| Metabolite - 2109 - 35 | 0.963700048 | 0.507734375 | + | 1% |
| Sarcosine - 9 | 0.970231636 | 0.509676555 | − | −4% |
| Metabolite - 1304 - 35 | 0.977448006 | 0.511966051 | + | 9% |
| alpha-L-sorbopyranose - 9 | 0.982136198 | 0.512921852 | + | 7% |
| Metabolite - 1133 - 35 | 0.989808044 | 0.51350178 | | 0% |
| Metabolite - 2703 - 35 | 0.989808044 | 0.51350178 | − | −2% |
| Metabolite - 2821 - 35 | 0.991846462 | 0.51350178 | − | −7% |
| Metabolite - 2038 - 35 | 0.997806098 | 0.515098498 | − | −6% |

Example 2

In another example, biomarkers were discovered by (1) analyzing plasma samples from different groups of human subjects to determine the levels of metabolites in the samples and then (2) statistically analyzing the results to determine those metabolites that are differentially present in the two groups. As listed below in Tables 5-6, biomarkers were discovered that were differentially present between samples from ALS subjects and Control subjects not diagnosed with ALS.

The plasma samples used for the analysis were from 199 ALS subjects and 94 control subjects not diagnosed with ALS. After the levels of metabolites were determined, the data was analyzed using T-tests (Table 5) and Wilcoxon's rank-sum tests (Table 6).

Tables 5 and 6 include, for each listed biomarker and non-biomarker compound, the p-value and the q-value determined in the statistical analysis of the data concerning the biomarkers, an indication of whether the mean of a particular compound was higher in the ALS or Control samples (a "+" indicating a higher mean in ALS samples as compared to the control samples and a "−" indicating a lower mean in ALS samples as compared to the control samples), and an indication of the percentage difference in the ALS mean as compared to the control mean. Throughout the tables, names of metabolites ending with the notation "−35" indicate that the levels of those compounds were measured using LC-MS, and names ending with the notation "−9" indicate that the levels of those compounds were measured using GC-MS. The term "Isobar" as used in the tables indicates the compounds that could not be distinguished from each other on the analytical platform used in the analysis (i.e., the compounds in an isobar elute at nearly the same time and have similar (and sometimes exactly) quant ions, and thus cannot be distinguished).

Non-biomarker compounds identified in the analyses are also listed in the tables below as those compounds that having a percentage change in ALS of 0%.

TABLE 5

ALS Biomarkers from blood plasma samples - T-Test Analysis of Plasma from Control vs. ALS

| Compound | p-value | q-value | Increase (+) or Decrease (−) in ALS | % change in ALS |
|---|---|---|---|---|
| Metabolite - 2045 - 35 | 7.39E−28 | 1.09E−25 | + | 412% |
| Isobar: glutamine/lysine - 35 | 1.95E−27 | 1.44E−25 | − | −39% |
| Metabolite - 2567 - 35 | 6.35E−24 | 3.13E−22 | + | 744% |
| Glycerate - 9 | 2.23E−21 | 8.24E−20 | + | 125% |
| Glyceric acid - 9 | 4.90E−21 | 1.45E−19 | + | 124% |
| Metabolite - 1111-possible-methylnitronitrosoguanidine-or-ethyl-thiocarbamoylacetate - 35 | 7.52E−21 | 1.85E−19 | − | −38% |
| pyridoxamine - 35 | 1.59E−20 | 3.36E−19 | − | −36% |
| Methionine - 35 | 1.85E−20 | 3.42E−19 | − | −40% |
| Metabolite - 2033 retired: 2-isopropylmalic acid - 35 | 4.47E−20 | 7.35E−19 | − | −46% |
| Metabolite - 1192 - 35 | 4.30E−18 | 6.36E−17 | − | −45% |
| Metabolite - 2648 - 9 | 6.57E−18 | 8.83E−17 | + | 1548% |
| Glutamic acid - 9 | 7.23E−18 | 8.91E−17 | + | 580% |
| gamma-L-glutamyl-L-tyrosine - 35 | 3.14E−15 | 3.57E−14 | + | 70% |
| Metabolite - 2568 - 35 | 4.53E−14 | 4.78E−13 | + | 1569% |
| Metabolite - 1850 - 9 | 5.24E−14 | 5.17E−13 | + | 377% |
| 4-hydroxyphenylacetate - 35 | 1.37E−12 | 1.27E−11 | − | −40% |
| 3-hydroxy-3-methylglutarate - 35 | 1.85E−12 | 1.61E−11 | − | −52% |
| Metabolite - 1071 - 35 | 2.82E−12 | 2.20E−11 | + | 757% |
| Metabolite - 1302 - 35 | 2.82E−12 | 2.20E−11 | + | 757% |
| Metabolite - 128 - 9 | 5.44E−12 | 3.60E−11 | − | 91% |
| Metabolite - 264 - 9 | 5.44E−12 | 3.60E−11 | + | −45% |
| Metabolite - 1815 - 9 | 5.46E−12 | 3.60E−11 | − | −44% |
| Metabolite - 1575 - 35 | 5.60E−12 | 3.60E−11 | + | 141% |
| Metabolite - 499 - 9 | 4.59E−11 | 2.83E−10 | − | −44% |
| Metabolite - 1775 - 9 | 4.80E−11 | 2.84E−10 | + | 109% |
| Metabolite - 1261 - 35 | 9.67E−11 | 5.50E−10 | + | 496% |
| Metabolite - 1576 - 35 | 1.40E−10 | 7.66E−10 | − | −29% |
| Metabolite - 270 - 9 | 2.44E−10 | 1.29E−09 | + | 913% |
| Epinephrine - 9 | 2.61E−10 | 1.33E−09 | + | 41% |
| Metabolite - 763 - 9 | 4.94E−10 | 2.43E−09 | + | 60% |
| Metabolite - 2608 - 35 | 6.15E−10 | 2.94E−09 | + | 80% |
| Arginine - 35 | 1.38E−09 | 6.36E−09 | + | 53% |
| Metabolite - 736 - 9 | 1.58E−09 | 7.10E−09 | + | 196% |
| N-acetyl-L-glutamine - 9 | 1.89E−09 | 8.20E−09 | − | −46% |
| Metabolite - 1286 - 35 | 2.19E−09 | 9.27E−09 | − | −23% |
| trans-4-hydroxyproline - 35 | 5.29E−09 | 2.17E−08 | + | 241% |
| 3-phospho-l-serine - 35 | 6.03E−09 | 2.40E−08 | + | 236% |
| Metabolite - 1457 - 35 | 6.17E−09 | 2.40E−08 | + | 136% |
| Metabolite - 841 - 9 | 7.65E−09 | 2.90E−08 | − | −60% |
| Metabolite - 1129 - 35 | 7.85E−09 | 2.90E−08 | + | 355% |
| Ornithine - 35 | 1.64E−08 | 5.91E−08 | − | −30% |
| Isobar: 5-oxoproline/glutamine - 9 | 2.18E−08 | 7.68E−08 | + | 64% |
| Metabolite - 655 - 9 | 2.44E−08 | 8.41E−08 | − | −51% |
| Isobar: lysine/tyramine/putrescine - 9 | 6.22E−08 | 2.04E−07 | + | 114% |
| Metabolite - 1538 - 9 | 6.77E−08 | 2.18E−07 | − | −39% |
| Metabolite - 1220 - 35 | 9.40E−08 | 2.94E−07 | + | 1107% |
| Metabolite - 2237 - 35 | 9.55E−08 | 2.94E−07 | + | 398% |
| Metabolite - 1497 - 35 | 1.64E−07 | 4.94E−07 | − | −39% |
| Metabolite - 1092 - 35 | 2.10E−07 | 6.20E−07 | + | 5519% |
| Thyroxine - 35 | 2.69E−07 | 7.80E−07 | − | −25% |
| Metabolite - 1208 - 35 | 2.74E−07 | 7.80E−07 | + | 3120% |
| Metabolite - 1073 - 35 | 6.51E−07 | 1.82E−06 | + | 536% |
| Metabolite - 1265 - 35 | 1.06E−06 | 2.90E−06 | + | 662% |
| Metabolite - 2591 - 35 | 1.14E−06 | 3.07E−06 | + | 265% |
| Metabolite - 2220 - 9 | 1.49E−06 | 3.94E−06 | + | 65% |
| Metabolite - 2051 - 35 | 1.59E−06 | 4.13E−06 | − | −38% |
| Metabolite - 451 - 9 | 1.72E−06 | 4.38E−06 | + | 31% |
| o-phosphoethanolamine - 9 | 3.19E−06 | 8.00E−06 | + | 37% |
| Metabolite - 2041 - 35 | 4.84E−06 | 1.19E−05 | − | −37% |
| Metabolite - 1114 - 35 | 5.82E−06 | 1.41E−05 | + | 47% |
| Metabolite - 2192 - 9 | 6.61E−06 | 1.58E−05 | − | −37% |
| Carnosine - 35 | 8.07E−06 | 1.89E−05 | − | −18% |
| Glycerol - 9 | 8.36E−06 | 1.93E−05 | + | 34% |
| Metabolite - 1342 - possible-phenylacetylglutamine-or-formyl-N-acetyl-5-methoxykynurenamine - 35 | 9.09E−06 | 2.04E−05 | + | 49% |
| Metabolite - 1616 - 35 | 9.37E−06 | 2.07E−05 | − | −36% |
| Metabolite - 1738 - 35 | 1.42E−05 | 3.09E−05 | − | −22% |
| 4-acetamidobutyric acid - 35 | 1.50E−05 | 3.20E−05 | + | 122% |

TABLE 5-continued

ALS Biomarkers from blood plasma samples - T-Test Analysis of Plasma from Control vs. ALS

| Compound | p-value | q-value | Increase (+) or Decrease (−) in ALS | % change in ALS |
|---|---|---|---|---|
| Xanthine - 35 | 1.68E−05 | 3.54E−05 | + | 56% |
| 12-hydroxydodecanoic acid - 9 | 1.75E−05 | 3.64E−05 | − | −42% |
| N-formyl-L-glycine - 35 | 2.34E−05 | 4.81E−05 | + | 130% |
| Guanosine - 35 | 2.43E−05 | 4.93E−05 | − | −35% |
| Metabolite - 734 - 9 | 2.47E−05 | 4.94E−05 | + | 534% |
| Metabolite - 1322 retired: citric acid - 35 | 2.50E−05 | 4.94E−05 | − | −40% |
| Metabolite - 2559 - 35 | 2.66E−05 | 5.18E−05 | + | 192% |
| Phosphate - 9 | 2.91E−05 | 5.59E−05 | + | 12% |
| Metabolite - 1824 - 9 | 2.97E−05 | 5.64E−05 | − | −42% |
| Metabolite - 1910 retired: uric acid - 35 | 3.20E−05 | 5.98E−05 | − | −9% |
| Metabolite - 1064 - 35 | 3.82E−05 | 7.07E−05 | + | 20% |
| Creatinine - 35 | 4.00E−05 | 7.24E−05 | − | −12% |
| Tartarate - 9 | 4.01E−05 | 7.24E−05 | + | 20% |
| 5-oxoproline - 35 | 4.13E−05 | 7.36E−05 | + | 25% |
| Metabolite - 2564 - 35 | 5.74E−05 | 0.000101019 | + | 3145% |
| Serine - 9 | 6.60E−05 | 0.000114885 | + | 51% |
| N-formyl-L-methionine - 35 | 6.76E−05 | 0.000116223 | − | −29% |
| alpha-keto-glutarate - 35 | 0.000108372 | 0.000184178 | − | −33% |
| N-6-trimethyl-l-lysine - 35 | 0.000122658 | 0.000206088 | − | −16% |
| Metabolite - 1264 - 35 | 0.000125014 | 0.000207686 | + | 1018% |
| Pantothenic acid - 35 | 0.000139261 | 0.000228783 | + | 57% |
| Metabolite - 557 - 9 | 0.000232183 | 0.000377248 | − | −33% |
| Isobar 8: anthranilic/salicylamide - 35 | 0.000253385 | 0.000407222 | + | 25% |
| Caffeine - 35 | 0.0002863 | 0.000455173 | − | −44% |
| Metabolite - 1713 retired: n-acetyl-L-aspartic acid - 35 | 0.000304153 | 0.000478413 | − | −44% |
| Metabolite - 1203 - 35 | 0.000322714 | 0.000502265 | + | 1236% |
| alpha-4-dihydroxybenzenepropanoic acid - 35 | 0.000600004 | 0.000924105 | − | −20% |
| Metabolite - 1734 - 35 | 0.000776078 | 0.001182966 | + | 100% |
| Metabolite - 1839 - 35 | 0.000793991 | 0.001197921 | − | −39% |
| Metabolite - 1327 - 35 | 0.00081987 | 0.001224469 | − | −43% |
| Metabolite - 1465 - 35 | 0.000834511 | 0.001233873 | − | −17% |
| Metabolite - 2592 - 35 | 0.000876733 | 0.001283467 | + | 605% |
| Metabolite - 1065 - 35 | 0.001106654 | 0.001604169 | + | 386% |
| Arabinose-3 - 9 | 0.001384596 | 0.001987579 | + | 24% |
| Metabolite - 2546 - 35 | 0.001620675 | 0.002304098 | − | −25% |
| Metabolite - 404 - 9 | 0.001839823 | 0.002590748 | − | −45% |
| Metabolite - 1975 - 35 | 0.001955935 | 0.002728267 | + | 39% |
| Metabolite - 2005 - 35 | 0.002306833 | 0.00318765 | − | −18% |
| Metabolite - 1560 - 9 | 0.002726186 | 0.003732244 | − | −14% |
| Isobar 3: hydroxybutanoic acid/butanoic acid - 9 | 0.003239947 | 0.004394908 | + | 76% |
| Metabolite - 2589 - 35 | 0.003371248 | 0.004531442 | + | 3636% |
| Metabolite - 2105 - 35 | 0.003533514 | 0.004706762 | − | −30% |
| Metabolite - 1329 - 35 | 0.003757185 | 0.004960014 | − | −39% |
| gamma-L-glutamyl-L-glutamine - 35 | 0.003932359 | 0.005145328 | − | −12% |
| Metabolite - 2185 - 35 | 0.004001113 | 0.005189366 | − | −16% |
| Metabolite - 671 - 9 | 0.004085981 | 0.005253356 | − | −25% |
| Metabolite - 1289 - 35 | 0.004154452 | 0.005295343 | + | 40% |
| Metabolite - 1281 - 35 | 0.004805178 | 0.006072422 | + | 55% |
| Metabolite - 1564 - 9 | 0.004964043 | 0.006220022 | + | 263% |
| Metabolite - 470 - 9 | 0.005094596 | 0.006329963 | + | 11% |
| Metabolite - 621 - 9 | 0.005467513 | 0.006736695 | + | 30% |
| Metabolite - 2560 - 35 | 0.008082368 | 0.009876239 | − | −13% |
| Isoleucine - 9 | 0.008236378 | 0.009936974 | + | 30% |
| Selenocystine - 35 | 0.008316591 | 0.009936974 | + | 24% |
| Metabolite - 526 - 9 | 0.008333693 | 0.009936974 | + | 52% |
| Praline - 9 | 0.008931979 | 0.01056516 | + | 30% |
| Metabolite - 1346 - 35 | 0.009818614 | 0.011521738 | + | 7% |
| Metabolite - 613 - 9 | 0.009951622 | 0.011585867 | + | 18% |
| Metabolite - 423 - 9 | 0.010758074 | 0.012426904 | + | 25% |
| Metabolite - 1254 - 35 | 0.011347359 | 0.013005992 | + | 776% |
| Metabolite - 2565 - 35 | 0.012408919 | 0.014077917 | + | 7127% |
| Metabolite - 578 - 9 | 0.012473012 | 0.014077917 | − | −15% |
| 1-7-dihydro-6h-purin-6-one - 35 | 0.012726758 | 0.014173847 | + | 39% |
| Metabolite - 273 - 9 | 0.012749731 | 0.014173847 | + | 54% |
| Metabolite - 485 - 9 | 0.012910336 | 0.014245284 | − | −28% |
| Metabolite - 1347 - 35 | 0.013382345 | 0.014656721 | − | −35% |
| Metabolite - 1968 - 9 | 0.013609685 | 0.014796109 | + | 17% |
| Metabolite - 543 - 9 | 0.013966834 | 0.015073558 | + | 22% |
| Alanine - 9 | 0.014090334 | 0.01509665 | + | 20% |

TABLE 5-continued

ALS Biomarkers from blood plasma samples - T-Test Analysis of Plasma from Control vs. ALS

| Compound | p-value | q-value | Increase (+) or Decrease (−) in ALS | % change in ALS |
|---|---|---|---|---|
| Metabolite - 1368 - 35 | 0.014437459 | 0.015357281 | + | 241% |
| Biliverdin - 35 | 0.015296324 | 0.016154644 | − | −24% |
| Metabolite - 681 - 9 | 0.015414689 | 0.016164193 | − | −21% |
| Metabolite - 1829 retired: oxalic acid - 35 | 0.016038611 | 0.016700012 | − | −18% |
| Metabolite - 2588 - 35 | 0.017415823 | 0.017868851 | + | 19307% |
| Dulcitol - 35 | 0.017455524 | 0.017868851 | − | −35% |
| Metabolite - 1802 - 35 | 0.017523718 | 0.017868851 | + | 69% |
| Metabolite - 2058 - 35 | 0.019073993 | 0.019316442 | + | 31% |
| Metabolite - 1914 - 35 | 0.020437798 | 0.020556783 | + | 37% |
| Metabolite - 1127 - 35 | 0.022548236 | 0.022526267 | + | 14% |
| Metabolite - 2646 - 9 | 0.022793205 | 0.022618172 | + | 8% |
| N-acetylserotonin - 9 | 0.023088525 | 0.022758483 | + | 100% |
| Metabolite - 1086 - 35 | 0.023309365 | 0.022824006 | + | 24% |
| Metabolite - 941 - 9 | 0.023957892 | 0.023304693 | + | 30% |
| Uric acid - 9 | 0.024385783 | 0.023565879 | − | −19% |
| Metabolite - 279 - 9 | 0.026708443 | 0.025642846 | + | 15% |
| Oxitryptan - 9 | 0.027343916 | 0.026083591 | + | 86% |
| N-acetyl-D-galactosamine - 35 | 0.028901673 | 0.027392821 | − | −22% |
| Valine - 9 | 0.02939762 | 0.027685406 | + | 20% |
| Succinate - 35 | 0.031159619 | 0.029159054 | + | 46% |
| Metabolite - 1958 - 35 | 0.031422203 | 0.029219843 | − | −5% |
| 1-Hexadecanol - 9 | 0.031960447 | 0.029534609 | + | 14% |
| Oleic acid - 9 | 0.033392544 | 0.030666344 | + | 19% |
| Sugar6 - 9 | 0.033781761 | 0.03083228 | + | 22% |
| Metabolite - 1328 - 35 | 0.036574371 | 0.033176276 | − | −21% |
| Leucine - 9 | 0.039003514 | 0.035163999 | + | 24% |
| Metabolite - 1753 - 9 | 0.04001943 | 0.035861242 | − | −26% |
| Metabolite - 709 - 9 | 0.042700894 | 0.038033583 | + | 15% |
| Metabolite - 2053 - 35 | 0.04341973 | 0.038442269 | − | −19% |
| Metabolite - 706 - 9 | 0.047136936 | 0.041484937 | − | −24% |
| Metabolite - 664 - 9 | 0.048056012 | 0.042043551 | + | 18% |
| Metabolite - 2238 - 35 | 0.048543239 | 0.042219997 | − | −46% |
| Metabolite - 1831-possible-Cl-adduct-of-citrulline - 35 | 0.050953792 | 0.04405739 | − | −10% |
| Metabolite - 523 - 9 | 0.053721717 | 0.046180625 | + | 66% |
| Metaboilte-1834 - 35 | 0.055103249 | 0.047094422 | − | −28% |
| Arachidonic acid - 9 | 0.055892636 | 0.047494543 | + | 21% |
| Metabolite - 1288 - 35 | 0.057856072 | 0.048882034 | + | 22% |
| Metabolite - 1113 - 35 | 0.058628766 | 0.049253427 | − | −11% |
| Metabolite - 1974 - 35 | 0.059873167 | 0.050014661 | − | −17% |
| Metabolite - 407 - 9 | 0.06299404 | 0.052326035 | − | −11% |
| Uridine - 35 | 0.063957923 | 0.052829888 | − | −7% |
| Metabolite - 1340 - 35 | 0.064727436 | 0.053168483 | + | 27% |
| Metabolite - 293 - 9 | 0.066207989 | 0.054084173 | − | −12% |
| Metabolite - 1242 - 35 | 0.066834562 | 0.054296031 | + | 160% |
| Metabolite - 1979 retired: CL adduct of Isobar 19 - 35 | 0.067928295 | 0.054883019 | − | −7% |
| beta-D-Iactose - 35 | 0.068994416 | 0.055441438 | − | −13% |
| Metabolite - 1335 - 35 | 0.069502055 | 0.05554557 | − | −15% |
| Metabolite - 1826 - 9 | 0.069875352 | 0.05554557 | + | 20% |
| Metabolite - 1735 - 35 | 0.070976511 | 0.056119192 | + | 64% |
| Metabolite - 614 - 9 | 0.072710932 | 0.05718475 | + | 34% |
| 3-hydroxypropanoate - 9 | 0.074914507 | 0.058606055 | − | −19% |
| N-acetyl-L-leucine - 35 | 0.075970756 | 0.059093074 | + | 45% |
| Isobar 2: 2-amino-3amino-GABA-etc - 35 | 0.076336383 | 0.059093074 | − | −11% |
| Metabolite - 1849 - 9 | 0.078469044 | 0.060427622 | − | −14% |
| Metabolite - 2055 - 35 | 0.083028152 | 0.063607223 | + | 10% |
| Glutarate - 9 | 0.093628855 | 0.071358605 | − | −7% |
| Metabolite - 2009 - 9 | 0.097058153 | 0.073544335 | + | 15% |
| Metabolite - 1737 retired: 2,3-dihydroxybenzoic acid - 35 | 0.097491539 | 0.073544335 | − | −37% |
| N-acetyl-L-alanine - 9 | 0.09919831 | 0.074188172 | + | 11% |
| Metabolite - 268 - 9 | 0.09934854 | 0.074188172 | − | −10% |
| Glucarate - 35 | 0.100292799 | 0.074516946 | − | −7% |
| Metabolite - 2561 - 35 | 0.110075599 | 0.081376579 | − | −10% |
| Metabolite - 687 - 9 | 0.111814818 | 0.081878989 | + | 11% |
| Metabolite - 278 - 9 | 0.112277103 | 0.081878989 | − | −15% |
| Metabolite - 683 - 9 | 0.112416521 | 0.081878989 | − | −8% |
| 9,12-octadecadienoic acid-z-z- - 9 | 0.114309944 | 0.082849943 | + | 13% |
| Metabolite - 1835 - 35 | 0.115192818 | 0.083082568 | − | −12% |

TABLE 5-continued

ALS Biomarkers from blood plasma samples - T-Test Analysis of Plasma from Control vs. ALS

| Compound | p-value | q-value | Increase (+) or Decrease (−) in ALS | % change in ALS |
|---|---|---|---|---|
| Metabolite - 1842 retired: 4-Guanidinobutanoic acid - 35 | 0.116398556 | 0.083235488 | + | 18% |
| alpha-Hydroxyisobutyric acid-tms - 9 | 0.11653074 | 0.083235488 | + | 12% |
| Octadecanoic acid - 9 | 0.117406712 | 0.083457997 | + | 8% |
| DL-beta-hydroxyphenylethylamine - 9 | 0.11843302 | 0.083784732 | − | −15% |
| Metabolite - 1262 - 35 | 0.121255228 | 0.085372804 | + | 78% |
| Metabolite - 1332 - 35 | 0.123327654 | 0.086420423 | + | 15% |
| Metabolite - 1597 - 35 | 0.12915119 | 0.090074305 | + | 5% |
| Metabolite - 1911 - 35 | 0.130213426 | 0.090388781 | − | −18% |
| Metabolite - 2074 - 35 | 0.137538587 | 0.095027467 | + | 14% |
| D-fructose-3 - 9 | 0.142117307 | 0.097734271 | + | 11% |
| 3-phospho-d-glycerate - 35 | 0.14497791 | 0.098900438 | − | −22% |
| Metabolite - 285 - 9 | 0.145150849 | 0.098900438 | − | −10% |
| Metabolite - 1414 - 9 | 0.146044582 | 0.09905293 | − | −9% |
| Metabolite - 1285 - 35 | 0.147990693 | 0.099914532 | + | 14% |
| Palmitoleic acid - 9 | 0.150623557 | 0.101229848 | + | 17% |
| Threonine - 9 | 0.153628874 | 0.102636481 | + | 10% |
| Metabolite - 562 - 9 | 0.154104868 | 0.102636481 | − | −15% |
| Serotonin - 35 | 0.160251945 | 0.106251927 | − | −24% |
| Metabolite - 341 - 9 | 0.163056494 | 0.107628789 | − | −7% |
| Menadione-Vitamin-K3 - 9 | 0.166606947 | 0.109483572 | + | 17% |
| Metabolite - 596 - 9 | 0.168685081 | 0.110358707 | − | −2% |
| Metabolite - 2047 - 35 | 0.171447883 | 0.111672088 | − | −28% |
| Metabolite - 1133 - 35 | 0.174183086 | 0.112956051 | − | −12% |
| Isobar: noradrenaline/normetanephrine - 9 | 0.174963187 | 0.112966473 | − | −12% |
| Melatonin - 9 | 0.178155192 | 0.114527299 | + | 21% |
| Catechol - 35 | 0.179075129 | 0.114620332 | − | −28% |
| Palmitate - 9 | 0.183643648 | 0.117037839 | + | 9% |
| Methylmalonic acid - 35 | 0.185145649 | 0.117488662 | + | 37% |
| alpha-2-diamino-gamma-oxobenzenebutanoic acid - 35 | 0.187323719 | 0.118362814 | + | 6% |
| Metabolite - 393 - 9 | 0.195091625 | 0.12196942 | − | −15% |
| Metabolite - 506 - 9 | 0.195869414 | 0.12196942 | + | 62% |
| Raffinose - 35 | 0.196403743 | 0.12196942 | − | −19% |
| Metabolite - 594 - 9 | 0.197156223 | 0.12196942 | − | −2% |
| Metabolite - 1193-confirmed-3-indoxyl-sulfate - 35 | 0.198202595 | 0.122105848 | − | −10% |
| alpha-tocopherol - 9 | 0.203832871 | 0.125053413 | − | −18% |
| Metabolite - 2548-possible-Cl-adduct-of-uric acid - 35 | 0.20678472 | 0.126340167 | − | −10% |
| Metabolite - 406 - 9 | 0.216576459 | 0.131778131 | + | 5% |
| Arabinose - 35 | 0.219322041 | 0.132901787 | + | 8% |
| D-galactose-1 - 9 | 0.224626486 | 0.135560527 | + | 17% |
| Isobar 4: includes-Gluconic acid-arabinose-D-ribose - 35 | 0.226566037 | 0.136175215 | + | 8% |
| Ascorbic acid - 35 | 0.234397891 | 0.140312097 | − | −28% |
| Metabolite - 2052 retired: potassium adduct of Isobar 1 - 35 | 0.237227476 | 0.141433301 | + | 3% |
| GABA - 9 | 0.239348875 | 0.142124979 | + | 10% |
| Metabolite - 2056 - 35 | 0.240340459 | 0.142142924 | + | 7% |
| Cholesterol - 9 | 0.242543999 | 0.14287465 | + | 3% |
| Metabolite - 1336 retired: carnitine - 35 | 0.248315394 | 0.145693935 | + | 8% |
| gamma-aminobutyryl-L-histidine - 35 | 0.25030641 | 0.146281639 | − | −7% |
| Histidine - 35 | 0.252947678 | 0.147202235 | + | 4% |
| Saccaropine - 35 | 0.253872825 | 0.147202235 | − | −7% |
| Metabolite - 344 - 9 | 0.255171482 | 0.147377281 | + | 2% |
| Metabolite - 1818 - 35 | 0.259081498 | 0.149053317 | − | −7% |
| 2-ethylhexanoic acid - 9 | 0.261053451 | 0.149605687 | + | 7% |
| Metabolite - 1087 - 35 | 0.269521105 | 0.153862004 | − | −49% |
| Isobar 9: includes-sucrose-beta-D-lactose - 35 | 0.271113017 | 0.154175509 | + | 7% |
| Metabolite - 1830 - 35 | 0.291817041 | 0.165313572 | + | 10% |
| Metabolite - 669 - 9 | 0.293997308 | 0.165913006 | + | 7% |
| Metabolite - 1961 retired: glycocholic acid - 35 | 0.30118226 | 0.169321461 | + | 31% |
| D-galactose - 9 | 0.309019203 | 0.173069249 | + | 22% |
| Metabolite - 1108 - 35 | 0.322091853 | 0.179709996 | + | 24% |
| Metabolite - 618 - 9 | 0.326687264 | 0.181588748 | − | −7% |
| Metabolite - 2175 - 35 | 0.329732268 | 0.182594864 | + | 23% |
| Metabolite - 2067 retired: carnitine - 35 | 0.333357393 | 0.183913524 | + | 5% |
| Metabolite - 1554 - 9 | 0.339523452 | 0.186619004 | − | −8% |
| Metabolite - 1388 - 35 | 0.341786646 | 0.187167179 | − | −37% |

TABLE 5-continued

ALS Biomarkers from blood plasma samples - T-Test Analysis of Plasma from Control vs. ALS

| Compound | p-value | q-value | Increase (+) or Decrease (−) in ALS | % change in ALS |
|---|---|---|---|---|
| N-tigloylglycine - 9 | 0.348797066 | 0.190301364 | − | −7% |
| N-acetyl-L-valine - 35 | 0.365795072 | 0.198204653 | − | −7% |
| Metabolite - 1537 - 9 | 0.365963796 | 0.198204653 | + | 2% |
| Metabolite - 1373 - 9 | 0.370489091 | 0.199923217 | + | 11% |
| Metabolite - 2587 retired: p-acetaminophen-beta-d-glucuronide - 35 | 0.391165589 | 0.209179781 | + | 96% |
| Metabolite - 2173 - 35 | 0.395316592 | 0.209179781 | − | −12% |
| Metabolite - 2100 - 35 | 0.395962201 | 0.209179781 | − | −5% |
| glyoxylate - 9 | 0.396052353 | 0.209179781 | + | 4% |
| Metabolite - 1847 - 9 | 0.396131489 | 0.209179781 | + | 15% |
| Hydroorotate - 9 | 0.400862911 | 0.210924935 | + | 5% |
| Metabolite - 2627 - 9 | 0.404199735 | 0.211926509 | + | 6% |
| Aspartate - 9 | 0.407978149 | 0.212792325 | − | −4% |
| Metabolite - 443 - 9 | 0.408729451 | 0.212792325 | − | −5% |
| Inosine - 35 | 0.412349643 | 0.213923814 | + | 12% |
| Metabolite - 1609 - 35 | 0.418144646 | 0.215709956 | − | −8% |
| Mannose-6-phosphate - 9 | 0.418710371 | 0.215709956 | − | −7% |
| Metabolite - 1915 - 35 | 0.421984962 | 0.216642099 | − | −15% |
| DL-pipecolic acid - 35 | 0.424698921 | 0.217280966 | + | 5% |
| Metabolite - 1358 - 9 | 0.432673424 | 0.22002834 | + | 8% |
| Metabolite - 1926 retired: trans-2,3,4-trimethoxycinnamic acid - 35 | 0.433917571 | 0.22002834 | + | 12% |
| Metabolite - 1088 - 35 | 0.434533341 | 0.22002834 | − | −11% |
| Metabolite - 1909 - 35 | 0.440430936 | 0.222253477 | + | 4% |
| Metabolite - 1379 retired: hippuric acid - 35 | 0.443748867 | 0.223166137 | − | −8% |
| Metabolite - 1656 - 35 | 0.449762567 | 0.225293772 | − | −4% |
| alpha-aminoadipic acid - 9 | 0.451026986 | 0.225293772 | − | −4% |
| Metabolite - 760 - 9 | 0.456530231 | 0.227274892 | − | −7% |
| Metabolite - 1827 - 9 | 0.459166692 | 0.227450012 | − | −19% |
| Metabolite - 1323-possible-p-cresol-sulfate - 35 | 0.459958643 | 0.227450012 | + | 7% |
| Inositol - 9 | 0.465306265 | 0.229327435 | + | 4% |
| n-dodecanoate - 9 | 0.472829606 | 0.231037316 | + | 4% |
| Metabolite - 642 - 9 | 0.473217914 | 0.231037316 | + | 5% |
| Metabolite - 222 - 9 | 0.475603781 | 0.231037316 | − | −25% |
| Metabolite - 2628 - 9 | 0.476223155 | 0.231037316 | − | −7% |
| Xylitol - 35 | 0.476588546 | 0.231037316 | − | −8% |
| Malic acid - 9 | 0.49107708 | 0.237282991 | − | −5% |
| 3-amino-isobutyrate - 9 | 0.498710623 | 0.240186511 | − | −4% |
| Metabolite - 1337 - 35 | 0.504305575 | 0.242092548 | − | −21% |
| Metabolite - 1888 - 9 | 0.520203859 | 0.248113414 | − | −10% |
| Tryptophan - 9 | 0.537450724 | 0.255515136 | − | −3% |
| Metabolite - 702 - 9 | 0.540311079 | 0.256051691 | − | −7% |
| Riboflavine - 35 | 0.554100659 | 0.261747594 | + | 5% |
| Metabolite - 704 - 9 | 0.564163338 | 0.265652301 | + | 3% |
| N-5--aminocarbonyl-L-ornithine - 35 | 0.57285708 | 0.268889659 | − | −7% |
| Isobar: adenosine-5-diphosphoribose/glucosamine-6-phosphate - 9 | 0.581997865 | 0.272315698 | − | −4% |
| Metabolite - 386 - 9 | 0.589206334 | 0.273366105 | − | −5% |
| tetradecanoic acid - 9 | 0.59005299 | 0.273366105 | − | −3% |
| Pyrophosphate - 35 | 0.591202821 | 0.273366105 | + | 7% |
| 2-amino-heptanedioic acid - 9 | 0.593249594 | 0.273366105 | − | −4% |
| Metabolite - 2221 - 9 | 0.593487161 | 0.273366105 | + | 2% |
| Isobar 3: includes-inositol-1-phosphate-mannose-6-phosphate-glucose-6-phosphate - 35 | 0.596940535 | 0.274102861 | − | −4% |
| Metabolite - 1353 - 9 | 0.615158877 | 0.281526493 | − | −1% |
| Metabolite - 1324 - 35 | 0.616915825 | 0.281526493 | − | −3% |
| Urea - 9 | 0.628289902 | 0.285647975 | + | 3% |
| Metabolite - 1372 retired: 2-hydroxyhippuric acid- 35 | 0.629811201 | 0.285647975 | + | 35% |
| Isobar-1-includes-mannose-fructose-galactose-alpha-L-sorbopyranose-Inositol - 35 | 0.634082142 | 0.286130487 | − | −3% |
| Hypotaurine - 9 | 0.634745468 | 0.286130487 | − | −5% |
| Phenylalanine - 35 | 0.647093547 | 0.290810136 | − | −1% |
| Cystine - 9 | 0.650602972 | 0.291403283 | − | −4% |
| Metabolite - 2606 - 35 | 0.652586845 | 0.291403283 | + | 3% |
| Metabolite - 670 - 9 | 0.654325967 | 0.291403283 | + | 3% |
| Metabolite - 1956 - 9 | 0.657136073 | 0.291775918 | − | −3% |

TABLE 5-continued

ALS Biomarkers from blood plasma samples - T-Test Analysis of Plasma from Control vs. ALS

| Compound | p-value | q-value | Increase (+) or Decrease (−) in ALS | % change in ALS |
| --- | --- | --- | --- | --- |
| 4-hydroxy-3-methoxymandelate - 35 | 0.660435881 | 0.292363103 | + | 17% |
| Niacinamide - 35 | 0.664682393 | 0.29336462 | + | 7% |
| Metabolite - 1534 - 9 | 0.682062879 | 0.300139742 | − | −2% |
| Gulono-1-4-lactone - 35 | 0.687540997 | 0.301608282 | − | −6% |
| Gluconic acid- 9 | 0.689479876 | 0.301608282 | + | 2% |
| Metabolite - 1104 - 35 | 0.69402083 | 0.302699132 | − | −2% |
| Isobar: 2'deoxyguanosine/adenosine | 0.700152632 | 0.304475377 | − | −14% |
| Decanoic acid - 9 | 0.708493079 | 0.305642167 | + | 2% |
| Metabolite - 1351 retired: urea adduct of Isobar 6 - 35 | 0.708962978 | 0.305642167 | + | 2% |
| Metabolite - 1814 - 9 | 0.709037199 | 0.305642167 | + | 3% |
| Metabolite - 638 - 9 | 0.714388343 | 0.306809695 | + | 2% |
| Metabolite - 1110 - 35 | 0.715895785 | 0.306809695 | + | 5% |
| Metabolite - 1066 - 35 | 0.719566441 | 0.307491539 | − | −1% |
| N-carbamoyl-L-aspartate - 35 | 0.722887146 | 0.30802034 | − | −4% |
| Metabolite - 1929 - 35 | 0.725669118 | 0.308317209 | − | −1% |
| Metabolite - 1757 - 9 | 0.729181159 | 0.308643713 | + | 4% |
| Metabolite - 1836 - 35 | 0.730612521 | 0.308643713 | + | 2% |
| methyl-indole-3-acetate - 35 | 0.751524835 | 0.316560675 | − | −2% |
| Metabolite - 1349 retired: Isobar 7 - 35 | 0.753635343 | 0.316560675 | + | 5% |
| Metabolite - 2558 - 35 | 0.756093832 | 0.316693652 | − | −4% |
| Metabolite - 1551 - 9 | 0.760209374 | 0.317517983 | − | −3% |
| Metabolite - 1247 - 35 | 0.76870665 | 0.320051482 | − | −5% |
| alpha-D-ribose-5-phosphate - 35 | 0.772433908 | 0.320051482 | + | 1% |
| Metabolite - 1331 - 35 | 0.772768996 | 0.320051482 | + | 5% |
| Metabolite - 645 - 9 | 0.784052343 | 0.323201768 | + | 2% |
| Metabolite - 1397 - 35 | 0.786425931 | 0.323201768 | + | 2% |
| Metabolite - 1754 - 9 | 0.786933185 | 0.323201768 | − | −2% |
| Histamine - 35 | 0.789366783 | 0.323303208 | − | −1% |
| Metabolite - 1514 - 9 | 0.794016761 | 0.324309349 | + | 1% |
| Metabolite - 1131 - 35 | 0.797130463 | 0.324684196 | + | 1% |
| Isobar: dulcitol/gluano-1,4-lactone - 9 | 0.80313861 | 0.3262327 | + | 1% |
| Glycine - 9 | 0.80574515 | 0.32639478 | + | 3% |
| Isobar: 3-chloro-L-tyrosine/DOPA - 9 | 0.817232873 | 0.330143774 | + | 2% |
| Metabolite - 2550 - 35 | 0.861492712 | 0.347075464 | + | 13% |
| Metabolite - 1142-possible-5-hydroxypentanoate-or-beta-hydroxyisovaleric acid - 35 | 0.886566846 | 0.356206661 | − | −2% |
| Metabolite - 1068 - 35 | 0.893493324 | 0.357049193 |  | 0% |
| Metabolite - 1181 - 35 | 0.893493527 | 0.357049193 |  | 0% |
| Metabolite - 1981 - 35 | 0.896639415 | 0.357340537 | − | −1% |
| 5-hydroxyindoleacetate - 35 | 0.900414132 | 0.35788025 | − | −1% |
| Guanidine acetic acid - 9 | 0.908351312 | 0.359336309 | + | 1% |
| Lactate - 9 | 0.908938159 | 0.359336309 |  | 0% |
| Metabolite - 1736 retired: p-hydroxybenzaldehyde - 35 | 0.916609401 | 0.361402713 | + | 1% |
| Metabolite - 1519 - 9 | 0.932420387 | 0.366658945 |  | 0% |
| Metabolite - 1161 - 35 | 0.93882901 | 0.367225704 | − | −1% |
| Metabolite - 1334 - 35 | 0.938829015 | 0.367225704 | − | −1% |
| Metabolite - 580 - 9 | 0.941646587 | 0.367355965 |  | 0% |
| Metabolite - 749 - 9 | 0.949144807 | 0.368863678 | + | 1% |
| Metabolite - 1972 - 35 | 0.950500827 | 0.368863678 | − | −1% |
| Metabolite - 1673 - 9 | 0.963796766 | 0.372339766 | − | −1% |
| Tyrosine - 35 | 0.964494657 | 0.372339766 |  | 0% |
| Metabolite - 1385 - 35 | 0.969660397 | 0.373359153 | − | −1% |
| Metabolite - 995 - 9 | 0.974705328 | 0.37432685 |  | 0% |
| Metabolite - 1383 - 35 | 0.990215844 | 0.378318235 | + | 1% |
| Metabolite - 1201 - 35 | 0.996666982 | 0.379801534 |  | 0% |

TABLE 6

ALS Biomarkers from blood plasma samples - Wilcoxon's Rank Sum-Tests
ALS vs. Control

| Compound | p-value | q-value | Increase (+) or Decrease (−) in ALS | % change in ALS |
|---|---|---|---|---|
| trans-4-hydroxyproline - 35 | 7.95E−19 | 1.13E−16 | + | 241% |
| Glycerate - 9 | 2.13E−17 | 1.51E−15 | + | 125% |
| Glyceric acid - 9 | 1.31E−16 | 6.17E−15 | + | 124% |
| Metabolite - 841 - 9 | 4.44E−16 | 1.52E−14 | − | −60% |
| Metabolite - 2045 - 35 | 5.37E−16 | 1.52E−14 | + | 412% |
| Metabolite - 2550 - 35 | 8.80E−16 | 2.08E−14 | + | 13% |
| Isobar: glutamine/lysine - 35 | 2.00E−15 | 4.04E−14 | − | −39% |
| Metabolite - 128 - 9 | 2.89E−15 | 5.11E−14 | − | −45% |
| Methionine - 35 | 7.55E−15 | 1.19E−13 | − | −40% |
| Metabolite - 2033 retired: 2-isopropylmalic acid - 35 | 4.35E−14 | 6.16E−13 | − | −46% |
| Metabolite - 2568 - 35 | 1.24E−13 | 1.60E−12 | + | 1569% |
| Metabolite - 1192 - 35 | 5.70E−13 | 6.73E−12 | − | −45% |
| 3-hydroxy-3-methylglutarate - 35 | 1.31E−12 | 1.43E−11 | − | −52% |
| Metabolite - 1111-possible-methylnitronitrosoguanidine-or-ethyl thiocarbamoylacetate - 35 | 2.54E−12 | 2.57E−11 | − | −38% |
| Glutamic acid - 9 | 6.18E−12 | 5.47E−11 | + | 1548% |
| Metabolite - 2648 - 9 | 6.18E−12 | 5.47E−11 | + | 580% |
| Metabolite - 655 - 9 | 7.63E−12 | 6.36E−11 | − | −51% |
| Metabolite - 499 - 9 | 1.37E−11 | 1.07E−10 | − | −44% |
| Metabolite - 2588 - 35 | 1.77E−11 | 1.32E−10 | + | 19307% |
| N-acetyl-L-glutamine - 9 | 3.65E−11 | 2.59E−10 | − | −46% |
| Pyridoxamine - 35 | 4.12E−11 | 2.78E−10 | − | −36% |
| Metabolite - 1850 - 9 | 9.06E−11 | 5.83E−10 | + | 377% |
| Metabolite - 1815 - 9 | 1.29E−10 | 7.96E−10 | − | −44% |
| Metabolite - 1071 - 35 | 2.01E−10 | 1.10E−09 | + | 757% |
| Metabolite - 1302 - 35 | 2.01E−10 | 1.10E−09 | + | 757% |
| Metabolite - 270 - 9 | 2.02E−10 | 1.10E−09 | + | 913% |
| Metabolite - 2567 - 35 | 2.74E−10 | 1.43E−09 | + | 744% |
| Metabolite - 1286 - 35 | 2.83E−10 | 1.43E−09 | − | −23% |
| 4-hydroxyphenylacetate - 35 | 8.59E−10 | 4.20E−09 | − | −40% |
| Metabolite - 1220 - 35 | 2.16E−09 | 1.01E−08 | + | 1107% |
| Metabolite - 1208 - 35 | 2.22E−09 | 1.01E−08 | + | 3120% |
| Metabolite - 1327 - 35 | 2.41E−09 | 1.07E−08 | − | −43% |
| Guanosine - 35 | 2.80E−09 | 1.20E−08 | − | −35% |
| Metabolite - 1497 - 35 | 8.04E−09 | 3.35E−08 | − | −39% |
| Metabolite - 1261 - 35 | 8.51E−09 | 3.44E−08 | + | 496% |
| Metabolite - 264 - 9 | 1.85E−08 | 7.26E−08 | + | 91% |
| alpha-keto-glutarate - 35 | 4.28E−08 | 1.61E−07 | − | −33% |
| Metabolite - 1073 - 35 | 4.31E−08 | 1.61E−07 | + | 536% |
| Metabolite - 2105 - 35 | 4.76E−08 | 1.68E−07 | − | −30% |
| Metabolite - 1538 - 9 | 5.80E−08 | 2.00E−07 | − | −39% |
| Metabolite - 2589 - 35 | 7.19E−08 | 2.43E−07 | + | 3636% |
| Metabolite - 763 - 9 | 7.38E−08 | 2.43E−07 | + | 60% |
| Metabolite - 1265 - 35 | 7.77E−08 | 2.50E−07 | + | 662% |
| Metabolite - 1824 - 9 | 1.41E−07 | 4.45E−07 | − | −42% |
| Ornithine - 35 | 2.57E−07 | 7.93E−07 | − | −30% |
| Metabolite - 2051 - 35 | 2.70E−07 | 8.13E−07 | − | −38% |
| Thyroxine - 35 | 3.68E−07 | 1.07E−06 | − | −25% |
| Metabolite - 451 - 9 | 3.77E−07 | 1.07E−06 | + | 31% |
| Metabolite - 1576 - 35 | 3.79E−07 | 1.07E−06 | − | −29% |
| gamma-L-glutamyl-L-tyrosine - 35 | 4.24E−07 | 1.18E−06 | + | 70% |
| 3-phospho-I-serine - 35 | 4.36E−07 | 1.19E−06 | + | 236% |
| Metabolite - 1129 - 35 | 4.59E−07 | 1.20E−06 | + | 196% |
| Metabolite - 736 - 9 | 4.59E−07 | 1.20E−06 | + | 355% |
| Metabolite - 1738 - 35 | 4.75E−07 | 1.22E−06 | − | −22% |
| Metabolite - 1329 - 35 | 6.52E−07 | 1.65E−06 | − | −39% |
| Caffeine - 35 | 6.87E−07 | 1.71E−06 | − | −44% |
| Isobar: 5-oxoproline/glutamine - 9 | 7.91E−07 | 1.93E−06 | + | 64% |
| Metabolite - 1203 - 35 | 9.88E−07 | 2.31E−06 | + | 1236% |
| Metabolite - 1616 - 35 | 9.91E−07 | 2.31E−06 | − | −36% |
| Metabolite - 2041 - 35 | 9.95E−07 | 2.31E−06 | − | −37% |
| Metabolite - 734 - 9 | 1.02E−06 | 2.32E−06 | + | 534% |
| Metabolite - 1465 - 35 | 1.53E−06 | 3.44E−06 | − | −17% |
| Metabolite - 1775 - 9 | 1.60E−06 | 3.54E−06 | + | 109% |
| Dulcitol - 35 | 1.71E−06 | 3.73E−06 | − | −35% |
| Metabolite - 1575 - 35 | 2.89E−06 | 6.21E−06 | + | 141% |
| Metabolite - 404 - 9 | 3.27E−06 | 6.90E−06 | − | −45% |
| Metabolite - 1457 - 35 | 3.38E−06 | 7.04E−06 | + | 136% |
| Phosphate - 9 | 4.21E−06 | 8.65E−06 | + | 12% |
| Epinephrine - 9 | 4.53E−06 | 9.05E−06 | + | 41% |

TABLE 6-continued

ALS Biomarkers from blood plasma samples - Wilcoxon's Rank Sum-Tests
ALS vs. Control

| Compound | p-value | q-value | Increase (+) or Decrease (−) in ALS | % change in ALS |
|---|---|---|---|---|
| Metabolite - 2608 - 35 | 4.53E−06 | 9.05E−06 | + | 80% |
| Isobar: 2'deoxyguanosine/adenosine | 5.34E−06 | 1.05E−05 | − | −14% |
| Metabolite - 1713 retired: n-acetyl-L-aspartic acid - 35 | 5.59E−06 | 1.07E−05 | − | −44% |
| Metabolite - 2564 - 35 | 5.83E−06 | 1.10E−05 | + | 3145% |
| Metabolite - 1322 retired: citric acid- 35 | 9.50E−06 | 1.77E−05 | − | −40% |
| Metabolite - 2565 - 35 | 1.04E−05 | 1.91E−05 | + | 7127% |
| Metabolite - 2192 - 9 | 1.24E−05 | 2.25E−05 | − | −37% |
| o-phosphoethanolamine - 9 | 1.27E−05 | 2.28E−05 | + | 37% |
| Carnosine - 35 | 1.48E−05 | 2.62E−05 | − | −18% |
| Metabolite - 470 - 9 | 2.01E−05 | 3.51E−05 | + | 11% |
| N-6-trimethyl-I-lysine - 35 | 2.03E−05 | 3.51E−05 | − | −16% |
| 12-hydroxydodecanoic acid - 9 | 2.48E−05 | 4.23E−05 | − | −42% |
| Metabolite - 1092 - 35 | 2.59E−05 | 4.37E−05 | + | 5519% |
| N-formyl-L-methionine - 35 | 2.66E−05 | 4.39E−05 | − | −29% |
| Xanthine - 35 | 2.67E−05 | 4.39E−05 | + | 56% |
| Metabolite - 2546 - 35 | 3.73E−05 | 6.07E−05 | − | −25% |
| Metabolite - 2220 - 9 | 4.25E−05 | 6.85E−05 | + | 65% |
| Metabolite - 1839 - 35 | 6.64E−05 | 0.00010564 | − | −39% |
| Metabolite - 485 - 9 | 7.28E−05 | 0.000114563 | − | −28% |
| Metabolite - 2560 - 35 | 8.81E−05 | 0.0001372 | − | −13% |
| Metabolite - 1254 - 35 | 9.07E−05 | 0.000139626 | + | 776% |
| Metabolite - 1829 retired: oxalic acid - 35 | 0.00010345 | 0.000157572 | − | −18% |
| Serotonin - 35 | 0.000113 | 0.000170287 | − | −24% |
| Metabolite - 2047 - 35 | 0.000132691 | 0.000197857 | − | −28% |
| Metabolite - 2559 - 35 | 0.00014073 | 0.000207659 | + | 192% |
| alpha-4-dihydroxybenzenepropanoic acid - 35 | 0.00016961 | 0.000247693 | − | −20% |
| Metabolite - 2646 - 9 | 0.000176617 | 0.000255293 | + | 8% |
| Metabolite - 1968 - 9 | 0.000185937 | 0.000266049 | + | 17% |
| Creatinine - 35 | 0.000188809 | 0.000267458 | − | −12% |
| Metabolite - 557 - 9 | 0.000217403 | 0.000304913 | − | −33% |
| Metabolite - 1342-possible-phenylacetylglutamine-or-formyl-N-acetyl-5-methoxykynurenamine - 35 | 0.000254676 | 0.000353309 | + | 49% |
| gamma-L-glutamyl-L-glutamine - 35 | 0.000256897 | 0.000353309 | − | −12% |
| Ascorbic acid - 35 | 0.000330688 | 0.000449733 | − | −28% |
| Metabolite - 1560 - 9 | 0.000333359 | 0.000449733 | − | −14% |
| Tartarate - 9 | 0.000371962 | 0.000497079 | + | 20% |
| Metabolite - 1264 - 35 | 0.000458966 | 0.000604582 | + | 1018% |
| Metabolite - 1735 - 35 | 0.000460942 | 0.000604582 | + | 64% |
| Biliverdin - 35 | 0.000499595 | 0.000649269 | − | −24% |
| Metabolite - 1910 retired: uric acid - 35 | 0.000566772 | 0.000727419 | − | −9% |
| Metabolite - 344 - 9 | 0.00057 | 0.000727419 | + | 2% |
| Arginine - 35 | 0.000589024 | 0.000744985 | + | 53% |
| Pantothenic acid - 35 | 0.000603624 | 0.000756696 | + | 57% |
| Serine - 9 | 0.000649558 | 0.000807134 | + | 51% |
| Metabolite - 2592 - 35 | 0.000685228 | 0.000844053 | + | 605% |
| Isobar: lysine/tyramine/putrescine- 9 | 0.000808049 | 0.000986762 | + | 114% |
| Metabolite - 1114 - 35 | 0.000836548 | 0.001012833 | + | 47% |
| Metabolite - 2005 - 35 | 0.000854054 | 0.001025266 | − | −18% |
| Metabolite - 2237 - 35 | 0.000864524 | 0.001029113 | + | 398% |
| Glycerol - 9 | 0.001035023 | 0.001221804 | + | 34% |
| Metabolite - 273 - 9 | 0.00114569 | 0.001341265 | + | 54% |
| Arabinose-3 - 9 | 0.001173106 | 0.001362103 | + | 24% |
| Metabolite - 671 - 9 | 0.001216735 | 0.001401276 | − | −25% |
| 5-oxoproline - 35 | 0.001437638 | 0.001642331 | + | 25% |
| 4-acetamidobutyric acid - 35 | 0.001459636 | 0.001654121 | + | 122% |
| Metabolite - 1734 - 35 | 0.001498197 | 0.001684345 | + | 100% |
| Metabolite - 2173 - 35 | 0.001525064 | 0.001701051 | − | −12% |
| Metabolite - 1335 - 35 | 0.002025014 | 0.002241046 | − | −15% |
| Metabolite - 706 - 9 | 0.002158019 | 0.002369727 | − | −24% |
| Metabolite - 1064 - 35 | 0.002197332 | 0.002394336 | + | 20% |
| Metabolite - 1242 - 35 | 0.002388033 | 0.002582271 | + | 160% |
| Metabolite - 1281 - 35 | 0.003022562 | 0.003243651 | + | 55% |
| Metabolite - 1834 - 35 | 0.003372683 | 0.003592168 | − | −28% |
| 3-hydroxypropanoate - 9 | 0.003501016 | 0.003680208 | − | −19% |
| Raffinose - 35 | 0.003507303 | 0.003680208 | − | −19% |
| Catechol - 35 | 0.004257739 | 0.004434789 | − | −28% |
| Metabolite - 1346 - 35 | 0.004482293 | 0.004634603 | + | 7% |
| Isobar 8: anthranilic/salicylamide - 35 | 0.004608619 | 0.00470831 | + | 25% |

TABLE 6-continued

ALS Biomarkers from blood plasma samples - Wilcoxon's Rank Sum-Tests
ALS vs. Control

| Compound | p-value | q-value | Increase (+) or Decrease (−) in ALS | % change in ALS |
|---|---|---|---|---|
| Metabolite - 1087 - 35 | 0.004620054 | 0.00470831 | − | −49% |
| Metabolite - 1347 - 35 | 0.004696061 | 0.004751585 | − | −35% |
| Uridine - 35 | 0.005661959 | 0.005688273 | − | −7% |
| Metabolite - 1911 - 35 | 0.006615412 | 0.006578227 | − | −18% |
| Uric acid - 9 | 0.006640673 | 0.006578227 | − | −19% |
| Metabolite - 1065 - 35 | 0.007251176 | 0.007133107 | + | 386% |
| Metabolite - 526 - 9 | 0.007729522 | 0.007551225 | + | 52% |
| Xylitol - 35 | 0.008558145 | 0.00830347 | − | −8% |
| Metabolite - 2185 - 35 | 0.009068095 | 0.008738392 | − | −16% |
| Metabolite - 1849 - 9 | 0.009824748 | 0.009403564 | − | −14% |
| Metabolite - 681 - 9 | 0.010216325 | 0.009712728 | − | −21% |
| Metabolite - 279 - 9 | 0.010974852 | 0.010364306 | + | 15% |
| Oxitryptan - 9 | 0.012769081 | 0.01197886 | + | 86% |
| Metabolite - 1127 - 35 | 0.013601982 | 0.012676268 | + | 14% |
| Metabolite - 278 - 9 | 0.013824904 | 0.012799809 | − | −15% |
| alpha-tocopherol - 9 | 0.01408719 | 0.012957954 | − | −18% |
| N-acetylserotonin - 9 | 0.014928383 | 0.013643126 | + | 100% |
| Metabolite - 1974 - 35 | 0.015032093 | 0.013649843 | − | −17% |
| Metabolite - 1554 - 9 | 0.015441641 | 0.013932421 | − | −8% |
| Metabolite - 1088 - 35 | 0.015755837 | 0.014125935 | − | −11% |
| Metabolite - 543 - 9 | 0.0180751 | 0.016038689 | + | 22% |
| Metabolite - 613 - 9 | 0.018115739 | 0.016038689 | + | 18% |
| Metabolite - 2591 - 35 | 0.018617915 | 0.016380908 | + | 265% |
| Isobar: 3-hydroxybutanoic acid/butanoic acid - 9 | 0.019560566 | 0.017104059 | + | 76% |
| Metabolite - 578 - 9 | 0.01968929 | 0.017110995 | − | −15% |
| Inosine - 35 | 0.023673433 | 0.02044797 | + | 12% |
| Metabolite - 1958 - 35 | 0.02610764 | 0.02241385 | − | −5% |
| Metabolite - 407 - 9 | 0.026532892 | 0.022641714 | − | −11% |
| Metabolite - 1328 - 35 | 0.026815296 | 0.02274568 | − | −21% |
| Metabolite - 1379 retired: hippuric acid - 35 | 0.028105709 | 0.023698348 | − | −8% |
| Praline - 9 | 0.028692147 | 0.024049671 | + | 30% |
| Metabolite - 1113 - 35 | 0.028962419 | 0.024133411 | − | −11% |
| 1-Hexadecanol - 9 | 0.029546959 | 0.024476509 | + | 14% |
| N-acetyl-D-galactosamine- 35 | 0.037024349 | 0.030460228 | − | −22% |
| Glutarate - 9 | 0.037200301 | 0.030460228 | − | −7% |
| Metabolite - 2009 - 9 | 0.039234333 | 0.031941097 | + | 15% |
| Isoleucine - 9 | 0.043920994 | 0.035552235 | + | 30% |
| 4-hydroxy-3-methoxymandelate - 35 | 0.046820624 | 0.037580744 | + | 17% |
| N-formyl-L-glycine - 35 | 0.046957594 | 0.037580744 | + | 130% |
| Metabolite - 1753 - 9 | 0.047736553 | 0.037989365 | − | −26% |
| Cholesterol - 9 | 0.051016232 | 0.040372733 | + | 3% |
| Isobar 2: 2-amino-3amino-GABA-etc - 35 | 0.052977943 | 0.041692255 | − | −11% |
| Metabolite - 1336 retired: carnitine - 35 | 0.053534798 | 0.04189772 | + | 8% |
| Metabolite - 1826 - 9 | 0.056530983 | 0.043999521 | + | 20% |
| Metabolite - 621 - 9 | 0.058160055 | 0.044884379 | + | 30% |
| N-acetyl-L-alanine - 9 | 0.05830157 | 0.044884379 | + | 11% |
| Metabolite - 2053 - 35 | 0.061188067 | 0.046851965 | − | −19% |
| Metabolite - 1915 - 35 | 0.061720642 | 0.047005675 | − | −15% |
| Metabolite - 2627 - 9 | 0.064605585 | 0.048939695 | + | 6% |
| Arachidonic acid - 9 | 0.066466939 | 0.050081881 | + | 21% |
| Metabolite - 1736 retired: p-hydroxybenzaldehyde - 35 | 0.067663771 | 0.050713921 | + | 1% |
| Metabolite - 341 - 9 | 0.068268247 | 0.050897676 | − | −7% |
| DL-beta-hydroxyphenylethylamine - 9 | 0.070205187 | 0.052067729 | − | −15% |
| Metabolite - 687 - 9 | 0.071440216 | 0.052707732 | + | 11% |
| Isobar 9: includes-sucrose-beta-D-lactose - 35 | 0.072457954 | 0.053181619 | + | 7% |
| Glucarate - 35 | 0.073165256 | 0.053423946 | − | −7% |
| Metabolite - 423 - 9 | 0.074943355 | 0.054441655 | + | 25% |
| Metabolite - 1975 - 35 | 0.078489196 | 0.056726581 | + | 39% |
| Metabolite - 285 - 9 | 0.083915392 | 0.060340402 | − | −10% |
| Leucine - 9 | 0.091494377 | 0.065457892 | + | 24% |
| 2-ethylhexanoic acid - 9 | 0.092707835 | 0.06599274 | + | 7% |
| Metabolite - 1835 - 35 | 0.093301471 | 0.066083235 | − | −12% |
| Metabolite - 1133 - 35 | 0.094018603 | 0.066259864 | − | −12% |
| Metabolite - 393 - 9 | 0.095389256 | 0.066653314 | − | −15% |
| Metabolite - 2561 - 35 | 0.095517949 | 0.066653314 | − | −10% |
| Metabolite - 1597 - 35 | 0.096845978 | 0.067248751 | + | 5% |
| Metabolite - 1414 - 9 | 0.097590754 | 0.067435349 | − | −9% |
| Metabolite - 760 - 9 | 0.102318258 | 0.070331993 | − | −7% |

TABLE 6-continued

ALS Biomarkers from blood plasma samples - Wilcoxon's Rank Sum-Tests
ALS vs. Control

| Compound | p-value | q-value | Increase (+) or Decrease (−) in ALS | % change in ALS |
|---|---|---|---|---|
| Metabolite - 1979 retired: CL adduct of Isobar 19 - 35 | 0.102775706 | 0.070331993 | − | −7% |
| Niacinamide - 35 | 0.112955903 | 0.076926929 | + | 7% |
| Valine - 9 | 0.123934053 | 0.08399959 | + | 20% |
| Metabolite - 709 - 9 | 0.125381408 | 0.084575904 | + | 15% |
| Metabolite - 1142 - possible-5-hydroxypentanoate-or-beta-hydroxyisovaleric acid - 35 | 0.128826455 | 0.08648791 | − | −2% |
| N-acetyl-L-valine - 35 | 0.131541799 | 0.08758105 | − | −7% |
| N-acetyl-L-leucine - 35 | 0.13169126 | 0.08758105 | + | 45% |
| Metabolite - 1262 - 35 | 0.132521917 | 0.087721639 | + | 78% |
| gamma-aminobutyryl-L-histidine - 35 | 0.13706282 | 0.090305458 | − | −7% |
| Metabolite - 1551 - 9 | 0.140029039 | 0.091832659 | − | −3% |
| Metabolite - 664 - 9 | 0.14880096 | 0.097135683 | + | 18% |
| Metabolite - 1737 retired: 2,3-dihydroxybenzoic acid - 35 | 0.150196526 | 0.097596938 | − | −37% |
| Alanine - 9 | 0.154234783 | 0.099763347 | + | 20% |
| D-galactose - 9 | 0.155488128 | 0.10011689 | + | 22% |
| Metabolite - 1831-possible-Cl-adduct-of-citrulline - 35 | 0.158637911 | 0.101682803 | − | −10% |
| Metabolite - 2058 - 35 | 0.159657851 | 0.101875582 | + | 31% |
| Metabolite - 596 - 9 | 0.161628617 | 0.102670622 | − | −2% |
| Metabolite - 2055 - 35 | 0.165607853 | 0.104728699 | + | 10% |
| Metabolite - 2606 - 35 | 0.169515822 | 0.106723614 | + | 3% |
| Metabolite - 2100 - 35 | 0.172035129 | 0.10783047 | − | −5% |
| Isobar: noradrenaline/normetanephrine - 9 | 0.174990745 | 0.109045616 | − | −12% |
| Metabolite - 614 - 9 | 0.175513392 | 0.109045616 | + | 34% |
| Isobar 3: includes-inositol-1-phosphate-mannose-6-phosphate-glucose-6-phosphate - 35 | 0.180431829 | 0.111611892 | − | −4% |
| Oleic acid - 9 | 0.186145422 | 0.114645582 | + | 19% |
| Metabolite - 1961 retired: glycocholic acid - 35 | 0.19133582 | 0.11733217 | + | 31% |
| beta-D-lactose - 35 | 0.195019064 | 0.119075354 | − | −13% |
| Metabolite - 1324 - 35 | 0.198740723 | 0.120826931 | − | −3% |
| Arabinose - 35 | 0.204819003 | 0.123990151 | + | 8% |
| Isobar 4: includes-Gluconic acid-arabinose-D-ribose - 35 | 0.206407713 | 0.12442019 | + | 8% |
| Methyl-indole-3-acetate - 35 | 0.214527642 | 0.128766845 | − | −2% |
| Metabolite - 1383 - 35 | 0.216364677 | 0.12926928 | + | 1% |
| Metabolite - 1288 - 35 | 0.217536402 | 0.12926928 | + | 22% |
| Metabolite - 2238 - 35 | 0.218102394 | 0.12926928 | − | −46% |
| Tryptophan - 9 | 0.221846663 | 0.13094064 | − | −3% |
| Metabolite - 268 - 9 | 0.225783468 | 0.132711298 | − | −10% |
| Hydroorotate - 9 | 0.230150861 | 0.134719368 | + | 5% |
| Metabolite - 1368 - 35 | 0.233591591 | 0.136170719 | + | 241% |
| Metabolite - 1289 - 35 | 0.236763471 | 0.137454092 | + | 40% |
| alpha-Hydroxyisobutyric acid-tms - 9 | 0.244720651 | 0.141493775 | + | 12% |
| Metabolite - 594 - 9 | 0.250759914 | 0.144396214 | − | −2% |
| Metabolite - 1193 - confirmed-3-indoxyl-sulfate - 35 | 0.252904153 | 0.145041341 | − | −10% |
| Metabolite - 1914 - 35 | 0.259413238 | 0.147579348 | + | 37% |
| Metabolite - 2221 - 9 | 0.262843415 | 0.148932641 | + | 2% |
| Metabolite - 1981 - 35 | 0.266853676 | 0.15060253 | − | −1% |
| Melatonin - 9 | 0.269895636 | 0.15137824 | + | 21% |
| D-fructose-3 - 9 | 0.270365439 | 0.15137824 | + | 11% |
| 3-phospho-d-glycerate - 35 | 0.271439573 | 0.151381305 | − | −22% |
| Metabolite - 293 - 9 | 0.272708164 | 0.15149237 | − | −12% |
| Metabolite - 704 - 9 | 0.277602508 | 0.153608844 | + | 3% |
| 1-7-dihydro-6h-purin-6-one - 35 | 0.282866742 | 0.155912726 | + | 39% |
| Metabolite - 2587 retired: p-acetaminophen-beta-d-glucuronide - 35 | 0.286465619 | 0.157284382 | + | 96% |
| Metabolite - 1066 - 35 | 0.29122259 | 0.158593867 | − | −1% |
| Metabolite - 2067 retired: carnitine - 35 | 0.291897238 | 0.158593867 | + | 5% |
| Metabolite - 683 - 9 | 0.292209342 | 0.158593867 | − | −8% |
| 9,12-octadecadienoic acid - 9 | 0.293621439 | 0.158752024 | + | 13% |
| Metabolite - 1929 - 35 | 0.296658476 | 0.159784193 | − | −1% |
| Metabolite - 1537 - 9 | 0.305289189 | 0.163809957 | + | 2% |
| alpha-D-ribose-5-phosphate - 35 | 0.313376853 | 0.167515053 | + | 1% |
| Metabolite - 941 - 9 | 0.323784479 | 0.172427761 | + | 30% |
| Palmitoleic acid - 9 | 0.327398741 | 0.17369949 | + | 17% |
| Metabolite - 1110 - 35 | 0.333616326 | 0.176337753 | + | 5% |

TABLE 6-continued

ALS Biomarkers from blood plasma samples - Wilcoxon's Rank Sum-Tests
ALS vs. Control

| Compound | p-value | q-value | Increase (+) or Decrease (−) in ALS | % change in ALS |
|---|---|---|---|---|
| Sugar 6 - 9 | 0.33653011 | 0.17709421 | + | 22% |
| Mannose-6-phosphate - 9 | 0.337547834 | 0.17709421 | − | −7% |
| Metabolite - 1814 - 9 | 0.339582604 | 0.177235683 | + | 3% |
| Metabolite - 702 - 9 | 0.340319839 | 0.177235683 | − | −7% |
| Metabolite - 1201 - 35 | 0.347867888 | 0.180236718 | | 0% |
| Tyrosine - 35 | 0.348627012 | 0.180236718 | | 0% |
| Pyrophosphate - 35 | 0.351583476 | 0.181104217 | + | 7% |
| Metabolite - 2056 - 35 | 0.355678177 | 0.182549622 | + | 7% |
| Metabolite - 1337 - 35 | 0.357011191 | 0.182572289 | − | −21% |
| Lactate - 9 | 0.360039201 | 0.183115973 | | 0% |
| Isobar: adenosine-5-diphosphoribose/glucosamine-6-phosphate - 9 | 0.362902611 | 0.183115973 | − | −4% |
| Metabolite - 1909 - 35 | 0.363241082 | 0.183115973 | + | 4% |
| Metabolite - 1086 - 35 | 0.363245088 | 0.183115973 | + | 24% |
| palmitate - 9 | 0.367154133 | 0.183808241 | + | 9% |
| Metabolite - 1888 - 9 | 0.367213479 | 0.183808241 | − | −10% |
| Cystine - 9 | 0.38705669 | 0.19238115 | − | −4% |
| Metabolite - 1372 retired: 2-hydroxyhippuric acid - 35 | 0.393185108 | 0.194743884 | + | 35% |
| Inositol - 9 | 0.398559375 | 0.195469757 | + | 4% |
| Octadecanoic acid - 9 | 0.399174013 | 0.195469757 | + | 8% |
| Metabolite - 1754 - 9 | 0.400147965 | 0.195469757 | − | −2% |
| Glyoxylate - 9 | 0.400170225 | 0.195469757 | + | 4% |
| Urea - 9 | 0.410210662 | 0.199391682 | + | 3% |
| Metabolite - 1656 - 35 | 0.411014449 | 0.199391682 | − | −4% |
| alpha-2-diamino-gamma-oxobenzenebutanoic acid - 35 | 0.413581035 | 0.199952019 | + | 6% |
| Metabolite - 1340 - 35 | 0.415523104 | 0.200180266 | + | 27% |
| Metabolite - 2558 - 35 | 0.416879441 | 0.200180266 | − | −4% |
| Tetradecanoic acid - 9 | 0.421956382 | 0.201933628 | − | −3% |
| Metabolite - 642 - 9 | 0.424576017 | 0.202416604 | + | 5% |
| Metabolite - 1802 - 35 | 0.425823475 | 0.202416604 | + | 69% |
| Metabolite - 506 - 9 | 0.436096446 | 0.206350302 | + | 62% |
| Metabolite - 1842 retired: 4-Guanidinobutanoic acid - 35 | 0.437891207 | 0.206350302 | + | 18% |
| Metabolite - 1534 - 9 | 0.438920776 | 0.206350302 | − | −2% |
| N-5-aminocarbonyl-L-ornithine - 35 | 0.439925617 | 0.206350302 | − | −7% |
| Saccaropine - 35 | 0.443725996 | 0.20744599 | − | −7% |
| Metabolite - 1247 - 35 | 0.44819327 | 0.208845224 | − | −5% |
| Metabolite - 1358 - 9 | 0.455211922 | 0.211420253 | + | 8% |
| Metabolite - 2548-possible-Cl-adduct-of-uric acid - 35 | 0.461217293 | 0.213509378 | − | −10% |
| Metabolite - 2052 retired: potassium adduct of Isobar 1 - 35 | 0.475091649 | 0.218745839 | + | 3% |
| Metabolite - 222 - 9 | 0.475617382 | 0.218745839 | − | −25% |
| Histamine - 35 | 0.481435239 | 0.21999306 | − | −1% |
| Metabolite - 406 - 9 | 0.484208862 | 0.220549026 | + | 5% |
| Metabolite - 1131 - 35 | 0.487971612 | 0.22102226 | + | 1% |
| gulono-1-4-lactone - 35 | 0.488368398 | 0.22102226 | − | −6% |
| Histidine - 35 | 0.502924778 | 0.225879949 | + | 4% |
| Metabolite - 1609 - 35 | 0.503194155 | 0.225879949 | − | −8% |
| Metabolite - 1373 - 9 | 0.50388562 | 0.225879949 | + | 11% |
| Isobar 1: includes-mannose-fructose-galactose-alpha-L-sorbopyranose-Inositol - 35 | 0.520966974 | 0.232800404 | − | −3% |
| Metabolite - 1108 - 35 | 0.536390627 | 0.238867648 | + | 24% |
| n-dodecanoate - 9 | 0.537916934 | 0.238867648 | + | 4% |
| Metabolite - 995 - 9 | 0.543076999 | 0.240405407 | | 0% |
| Metabolite - 1332 - 35 | 0.555102236 | 0.244963142 | + | 15% |
| Succinate - 35 | 0.560617086 | 0.246628498 | + | 46% |
| Metabolite - 1331 - 35 | 0.569051953 | 0.249564148 | + | 5% |
| N-tigloylglycine - 9 | 0.571240346 | 0.24975067 | − | −7% |
| Phenylalanine - 35 | 0.576089348 | 0.251095705 | − | −1% |
| Hypotaurine - 9 | 0.579240029 | 0.251694524 | − | −5% |
| Metabolite - 1285 - 35 | 0.592320498 | 0.25659123 | + | 14% |
| Metabolite - 1673 - 9 | 0.612947221 | 0.264717124 | − | −1% |
| Metabolite - 1323-possible-p-cresol-sulfate - 35 | 0.61860681 | 0.265186844 | + | 7% |
| Metabolite - 2563 retired: lactate - 35 | 0.61912429 | 0.265186844 | + | 11% |
| Metabolite - 2074 - 35 | 0.622269085 | 0.265186844 | + | 14% |
| Metabolite - 523 - 9 | 0.624114598 | 0.265186844 | + | 66% |

TABLE 6-continued

ALS Biomarkers from blood plasma samples - Wilcoxon's Rank Sum-Tests
ALS vs. Control

| Compound | p-value | q-value | Increase (+) or Decrease (−) in ALS | % change in ALS |
|---|---|---|---|---|
| 5-hydroxyindoleacetate - 35 | 0.625925876 | 0.265186844 | − | −1% |
| Metabolite - 2175 - 35 | 0.626397572 | 0.265186844 | + | 23% |
| Metabolite - 1827 - 9 | 0.627139249 | 0.265186844 | − | −19% |
| Metabolite - 1161 - 35 | 0.640126082 | 0.268828198 | − | −1% |
| Metabolite - 1334 - 35 | 0.640126082 | 0.268828198 | − | −1% |
| Metabolite - 1847 - 9 | 0.641443963 | 0.268828198 | + | 15% |
| Metabolite - 562 - 9 | 0.659500458 | 0.27438888 | − | −15% |
| Metabolite - 1514 - 9 | 0.66032802 | 0.27438888 | + | 1% |
| N-carbamoyl-L-aspartate - 35 | 0.660523215 | 0.27438888 | − | −4% |
| Metabolite - 1353 - 9 | 0.664614073 | 0.275280993 | − | −1% |
| Aspartate - 9 | 0.679701031 | 0.280327428 | − | −4% |
| Metabolite - 1104 - 35 | 0.680755621 | 0.280327428 | − | −2% |
| Metabolite - 638 - 9 | 0.689784761 | 0.283222205 | + | 2% |
| DL-pipecolic acid - 35 | 0.713563633 | 0.292138913 | + | 5% |
| Isobar: dulcitol/gluano-1,4-lactone - 9 | 0.726823595 | 0.296710109 | + | 1% |
| alpha-aminoadipic acid - 9 | 0.737943315 | 0.299825714 | − | −4% |
| Metabolite - 1818 - 35 | 0.740158119 | 0.299825714 | − | −7% |
| Isobar: 3-chloro-L-tyrosine/DOPA - 9 | 0.740805369 | 0.299825714 | + | 2% |
| Selenocystine - 35 | 0.744615875 | 0.30050934 | + | 24% |
| Metabolite - 1388 - 35 | 0.750101919 | 0.301863367 | − | −37% |
| Metabolite - 1972 - 35 | 0.759306974 | 0.304702125 | − | −1% |
| Metabolite - 1836 - 35 | 0.769196748 | 0.30706915 | + | 2% |
| Glycine - 9 | 0.770801436 | 0.30706915 | + | 3% |
| Metabolite - 1349 retired: Isobar 7 - 35 | 0.773026197 | 0.30706915 | + | 5% |
| Metabolite - 386 - 9 | 0.7738764 | 0.30706915 | − | −5% |
| Methylmalonic acid - 35 | 0.777999626 | 0.307842914 | + | 37% |
| Metabolite - 1564 - 9 | 0.782695577 | 0.308838355 | + | 263% |
| Metabolite - 645 - 9 | 0.789345703 | 0.310597209 | + | 2% |
| D-galactose-1 - 9 | 0.805459667 | 0.316059898 | + | 17% |
| Metabolite - 618 - 9 | 0.816440265 | 0.319483655 | − | −7% |
| Threonine - 9 | 0.820620665 | 0.320234873 | + | 10% |
| Metabolite - 670 - 9 | 0.842922157 | 0.32739804 | + | 3% |
| Metabolite - 1926 retired: trans-2,3,4-trimethoxycinnamic acid - 35 | 0.846964798 | 0.32739804 | + | 12% |
| Gluconic acid - 9 | 0.848156442 | 0.32739804 | + | 2% |
| Decanoic acid - 9 | 0.849254587 | 0.32739804 | + | 2% |
| Metabolite - 669 - 9 | 0.850532853 | 0.32739804 | + | 7% |
| Metabolite - 580 - 9 | 0.861036973 | 0.330543205 | | 0% |
| Metabolite - 1397 - 35 | 0.867406129 | 0.33208829 | + | 2% |
| Metabolite - 1956 - 9 | 0.884897064 | 0.337871566 | − | −3% |
| Metabolite - 1385 - 35 | 0.89021962 | 0.338990105 | − | −1% |
| Metabolite - 749 - 9 | 0.901760902 | 0.34246435 | + | 1% |
| Menadione-Vitamin-K3 - 9 | 0.907156807 | 0.34359241 | + | 17% |
| Riboflavine - 35 | 0.910014277 | 0.343755565 | + | 5% |
| Malic acid - 9 | 0.92863219 | 0.349427329 | − | −5% |
| Metabolite - 1519 - 9 | 0.929962462 | 0.349427329 | | 0% |
| GABA - 9 | 0.949912268 | 0.355979097 | + | 10% |
| 3-amino-isobutyrate - 9 | 0.952883348 | 0.35615031 | − | −4% |
| Metabolite - 1351 retired: urea adduct of Isobar 6 - 35 | 0.955825028 | 0.356309664 | + | 2% |
| Metabolite - 443 - 9 | 0.961671599 | 0.357548215 | − | −5% |
| Metabolite - 1830 - 35 | 0.970420648 | 0.359856594 | + | 10% |
| Metabolite - 2628 - 9 | 0.980511879 | 0.362590137 | − | −7% |
| 2-amino-heptanedioic acid - 9 | 0.982911488 | 0.362590137 | − | −4% |
| Metabolite - 1068 - 35 | 0.991160619 | 0.363738719 | | 0% |
| Metabolite - 1181 - 35 | 0.991160619 | 0.363738719 | | 0% |
| Guanidine acetic acid - 9 | 0.997630416 | 0.364656039 | + | 1% |
| Metabolite - 1757 - 9 | 0.998808745 | 0.364656039 | + | 4% |

Example 3

Biomarkers were discovered by (1) analyzing plasma samples from different groups of human subjects to determine the levels of metabolites in the samples and then (2) statistically analyzing the results to determine those metabolites that were differentially present in the two groups. As listed below in Tables 7-8, biomarkers were discovered that were differentially present between samples from ALS subjects and Control subjects not diagnosed with ALS. Non-biomarker compounds identified in the analyses are also listed in the tables below as those compounds that having a percentage change in ALS of 0%.

The plasma samples used for the analysis were from 62 ALS subjects and 62 control subjects not diagnosed with ALS. After the levels of metabolites were determined, the data was analyzed using T-tests (Table 7) and Wilcoxon's rank-sum tests (Table 8).

Tables 7 and 8 include, for each listed biomarker and non-biomarker compound, the analytical method used to detect the compound, the p-value and the q-value determined in the statistical analysis of the data concerning the biomarkers, and an indication of the percentage difference in the ALS mean level as compared to the control mean level. A percentage change that is positive indicates an increase in ALS compared to control and a negative percentage change indicates a decrease in ALS compared to control. The term "Isobar" as used in the tables indicates the compounds that could not be distinguished from each other on the analytical platform used in the analysis (i.e., the compounds in an isobar elute at nearly the same time and have similar (and sometimes exactly) quant ions, and thus cannot be distinguished).

TABLE 7

ALS Biomarkers from blood plasma samples - T-Test Analysis of Plasma from Control vs. ALS

| Name | Analytical Platform | p-value | q-value | % change in ALS |
|---|---|---|---|---|
| Metabolite - 2550 | LC-MS | <0.0001 | 0.0031 | 289% |
| alpha-4-dihydroxybenzenepropanoic acid | GC-MS | 0.0012 | 0.0925 | −29% |
| N-6-trimethyl-l-lysine | LC-MS | 0.0014 | 0.0925 | −34% |
| Carnosine | LC-MS | 0.0018 | 0.1048 | −35% |
| Metabolite - 3033 | GC-MS | 0.0031 | 0.1342 | −20% |
| glutamic acid | GC-MS | 0.0038 | 0.1342 | 47% |
| Xanthine | LC-MS | 0.0038 | 0.1342 | 42% |
| Metabolite - 1114 | LC-MS | 0.0039 | 0.1342 | 30% |
| alpha-tocopherol | GC-MS | 0.0052 | 0.1509 | 48% |
| Metabolite - 2256 | LC-MS | 0.0053 | 0.1509 | −45% |
| Metabolite - 2139 | LC-MS | 0.0059 | 0.1542 | 30% |
| arachidonic acid | GC-MS | 0.0073 | 0.1781 | 47% |
| D-lyxose | GC-MS | 0.008 | 0.1815 | −16% |
| Metabolite - 3498 | LC-MS | 0.0099 | 0.2081 | −15% |
| Metabolite - 4019 | GC-MS | 0.0104 | 0.2081 | 26% |
| Metabolite - 1497 | LC-MS | 0.0115 | 0.2081 | 34% |
| 6-phosphogluconic acid | LC-MS | 0.0122 | 0.2081 | −22% |
| Ornithine | GC-MS | 0.0122 | 0.2081 | 36% |
| Metabolite - 3030 | GC-MS | 0.0134 | 0.2162 | −15% |
| Creatinine | LC-MS | 0.0139 | 0.2162 | −17% |
| Isobar-28-includes-L-threonine-L-allothreonine | LC-MS | 0.016 | 0.2318 | −16% |
| Metabolite - 3977 | LC-MS | 0.0164 | 0.2318 | −27% |
| Methionine | LC-MS | 0.0171 | 0.2318 | −14% |
| Metabolite - 3058 | GC-MS | 0.0176 | 0.2318 | −24% |
| Metabolite - 3881 retired: azelaic acid | LC-MS | 0.0188 | 0.2374 | −29% |
| Metabolite - 2041 | LC-MS | 0.0196 | 0.2384 | 29% |
| Metabolite - 3088 | GC-MS | 0.0208 | 0.2384 | −31% |
| D-arabitol | GC-MS | 0.0216 | 0.2384 | −14% |
| Metabolite - 3181 | LC-MS | 0.0216 | 0.2384 | 36% |
| Metabolite - 2407 | LC-MS | 0.0244 | 0.2558 | 53% |
| Metabolite - 2313 | LC-MS | 0.0248 | 0.2558 | −52% |
| Metabolite - 3994 | LC-MS | 0.0258 | 0.2558 | 35% |
| L-allo-threonine | GC-MS | 0.0262 | 0.2558 | −17% |
| Isobar-27-includes-L-kynurenine-alpha-2-diamino-gamma-oxobenzenebutanoic acid | LC-MS | 0.0324 | 0.2888 | 15% |
| Metabolite - 3218 | LC-MS | 0.033 | 0.2888 | 24% |
| Normetanephrine | GC-MS | 0.0366 | 0.3049 | 23% |
| Metabolite - 3073 | GC-MS | 0.0381 | 0.3084 | 26% |
| Metabolite - 1089 | LC-MS | 0.0388 | 0.3084 | −30% |
| Metabolite - 2886 retired: CL adduct of p-acetiminophen-beta-d-glucuronide | LC-MS | 0.0441 | 0.337 | 151% |
| Threonine | GC-MS | 0.0444 | 0.337 | −16% |
| 1-methyladenine | GC-MS | 0.0484 | 0.3578 | −16% |
| Metabolite - 3056 | LC-MS | 0.0492 | 0.3578 | 17% |
| Metabolite - 3108 | GC-MS | 0.0536 | 0.3809 | −15% |
| Metabolite - 3180 | LC-MS | 0.0555 | 0.3809 | 25% |
| anthranilic acid | GC-MS | 0.0557 | 0.3809 | −15% |
| Selenocystine | LC-MS | 0.057 | 0.3822 | 19% |
| 5-6-dihydroorotic acid | GC-MS | 0.0599 | 0.3936 | −7% |
| Metabolite - 3951 | LC-MS | 0.061 | 0.3936 | 9% |
| Metabolite - 2266 retired 4-acetominophen sulfate | LC-MS | 0.0637 | 0.4034 | 571% |
| 5-hydroxylysine | LC-MS | 0.0659 | 0.4095 | −24% |
| 4-methyl-2-oxopentanoate | GC-MS | 0.0675 | 0.4118 | −12% |
| Isobar-19-includes-D-saccharic acid-2-deoxy-D-galactose-2-deoxy-D-glucose-L-fucose-L-rhamnose | LC-MS | 0.0692 | 0.4149 | −25% |
| alpha-methyl-L-beta-3-4-dihydroxyphenylalanine | GC-MS | 0.0742 | 0.415 | 24% |
| Metabolite - 3320 | LC-MS | 0.0755 | 0.415 | −47% |
| 2-deoxy-D-glucose | GC-MS | 0.0763 | 0.415 | 22% |
| Metabolite - 1127 | LC-MS | 0.0764 | 0.415 | −18% |
| Metabolite - 2546 | LC-MS | 0.0786 | 0.415 | −25% |
| Metabolite - 2130 | LC-MS | 0.0789 | 0.415 | 57% |

TABLE 7-continued

ALS Biomarkers from blood plasma samples - T-Test Analysis of Plasma from Control vs. ALS

| Name | Analytical Platform | p-value | q-value | % change in ALS |
|---|---|---|---|---|
| Metabolite - 4134 | GC-MS | 0.0789 | 0.415 | 19% |
| Metabolite - 2973 | GC-MS | 0.0804 | 0.4165 | −9% |
| Saccharopine | LC-MS | 0.0823 | 0.4199 | −20% |
| Metabolite - 2687 | LC-MS | 0.0887 | 0.4458 | −8% |
| Metabolite - 4196 | GC-MS | 0.0905 | 0.4482 | 39% |
| Metabolite - 3534 | LC-MS | 0.0948 | 0.4629 | 65% |
| Metabolite - 3134 | LC-MS | 0.097 | 0.4668 | 66% |
| Metabolite - 3183 | LC-MS | 0.0991 | 0.4704 | −14% |
| Metabolite - 2316 | LC-MS | 0.1022 | 0.4761 | 58% |
| p-acetamidophenyl-beta-D-gluguronide | LC-MS | 0.1031 | 0.4761 | 137% |
| Metabolite - 1656 | LC-MS | 0.1055 | 0.4772 | −18% |
| Metabolite - 3040 | GC-MS | 0.1074 | 0.4772 | 26% |
| Metabolite - 3813 | LC-MS | 0.1076 | 0.4772 | 23% |
| Metabolite - 3331 | LC-MS | 0.1089 | 0.4772 | −69% |
| Metabolite - 1831-possible-Cl-adduct-of-citrulline | LC-MS | 0.1147 | 0.4936 | −17% |
| Metabolite - 1979 retired: CL adduct of Isobar 19 | LC-MS | 0.1177 | 0.4936 | −13% |
| Metabolite - 2894 | LC-MS | 0.1208 | 0.4936 | −63% |
| Metabolite - 3098 | GC-MS | 0.1252 | 0.4936 | −13% |
| Metabolite - 1839 | LC-MS | 0.1253 | 0.4936 | −39% |
| Metabolite - 3843 | LC-MS | 0.1262 | 0.4936 | −21% |
| Metabolite - 1975 | LC-MS | 0.1284 | 0.4936 | 25% |
| Metabolite - 3078 | GC-MS | 0.1294 | 0.4936 | −9% |
| 4-hydroxyphenylacetate | LC-MS | 0.1305 | 0.4936 | −21% |
| Metabolite - 3313 | LC-MS | 0.1326 | 0.4936 | 18% |
| Metabolite - 4275 | GC-MS | 0.1366 | 0.4936 | −11% |
| Metabolite - 3090 | GC-MS | 0.1379 | 0.4936 | −51% |
| Metabolite - 2924 retired: 2-hydroxybutanoic acid (also called (s)-2-hydroxybutyric acid) | GC-MS | 0.1385 | 0.4936 | 21% |
| Metabolite - 4274 | GC-MS | 0.1389 | 0.4936 | 14% |
| beta-hydroxypyruvic acid | LC-MS | 0.1403 | 0.4936 | 30% |
| Metabolite - 1220 | LC-MS | 0.1422 | 0.4936 | 35% |
| Cholesterol | GC-MS | 0.1449 | 0.4936 | 10% |
| Metabolite - 1817 | LC-MS | 0.1466 | 0.4936 | 14% |
| 3alpha-7alpha-12alpha-trihydroxy-5beta-cholanate | GC-MS | 0.1488 | 0.4936 | 11% |
| Metabolite - 3022 | GC-MS | 0.1502 | 0.4936 | −11% |
| octadecanoic acid | GC-MS | 0.1504 | 0.4936 | 11% |
| Metabolite - 3002 | GC-MS | 0.1519 | 0.4936 | 13% |
| Metabolite - 4077 | GC-MS | 0.1526 | 0.4936 | −23% |
| Urea | GC-MS | 0.1527 | 0.4936 | 15% |
| Isobar-5-includes-asparagine-ornithine | LC-MS | 0.1528 | 0.4936 | −19% |
| Metabolite - 2051 | LC-MS | 0.1531 | 0.4936 | 63% |
| Metabolite - 3113 | GC-MS | 0.1584 | 0.503 | −33% |
| Metabolite - 2270 | LC-MS | 0.1592 | 0.503 | −31% |
| 1-Hexadecanol | GC-MS | 0.1609 | 0.503 | −16% |
| Metabolite - 3012 | GC-MS | 0.1619 | 0.503 | −11% |
| Metabolite - 2915 | GC-MS | 0.1702 | 0.5122 | −7% |
| Metabolite - 3099 | GC-MS | 0.1708 | 0.5122 | −15% |
| N-carbamoyl-L-aspartate | LC-MS | 0.1709 | 0.5122 | 54% |
| Metabolite - 3125 | LC-MS | 0.1736 | 0.5122 | 11% |
| Mercaptopyruvate | LC-MS | 0.174 | 0.5122 | −23% |
| Metabolite - 1085-possible-isolobinine-or-4-aminoestra-1,3-5-10-triene-3-17beta-diol | LC-MS | 0.1746 | 0.5122 | 14% |
| Metabolite - 2366 | LC-MS | 0.1753 | 0.5122 | 35% |
| pantothenic acid | LC-MS | 0.184 | 0.5326 | 30% |
| Metabolite - 1335 | LC-MS | 0.1901 | 0.5326 | 19% |
| Metabolite - 3077 | GC-MS | 0.1903 | 0.5326 | −7% |
| Metabolite - 3103 | GC-MS | 0.1907 | 0.5326 | −17% |
| Metabolite - 2698 | LC-MS | 0.1925 | 0.5326 | 39% |
| Metabolite - 1655 | LC-MS | 0.1931 | 0.5326 | 13% |
| Metabolite - 2866 | LC-MS | 0.1932 | 0.5326 | −33% |
| Metabolite - 3160 | LC-MS | 0.1961 | 0.5361 | −8% |
| n-dodecanoate | GC-MS | 0.2068 | 0.5567 | −13% |
| Metabolite - 1104 | LC-MS | 0.2079 | 0.5567 | 12% |
| Metabolite - 4365 | GC-MS | 0.2085 | 0.5567 | 17% |
| Metabolite - 4272 | GC-MS | 0.2164 | 0.5695 | −12% |
| Metabolite - 1251 | LC-MS | 0.2178 | 0.5695 | 49% |
| Metabolite - 3365 | LC-MS | 0.2183 | 0.5695 | 47% |
| Metabolite - 2392 | LC-MS | 0.2224 | 0.5746 | −30% |
| Metabolite - 2329 | LC-MS | 0.2236 | 0.5746 | 23% |
| citric acid | GC-MS | 0.2268 | 0.5752 | −9% |

TABLE 7-continued

ALS Biomarkers from blood plasma samples - T-Test Analysis of Plasma from Control vs. ALS

| Name | Analytical Platform | p-value | q-value | % change in ALS |
|---|---|---|---|---|
| Metabolite - 2697 | LC-MS | 0.2272 | 0.5752 | 17% |
| Metabolite - 4043 retired: lysine | GC-MS | 0.2315 | 0.5795 | 15% |
| Metabolite - 1346 | LC-MS | 0.2351 | 0.5795 | 20% |
| Metabolite - 1351 retired: urea adduct of Isobar 6 | LC-MS | 0.2372 | 0.5795 | 19% |
| Metabolite - 3624 | LC-MS | 0.2378 | 0.5795 | −18% |
| alpha-D-ribose-5-phosphate | LC-MS | 0.2383 | 0.5795 | 22% |
| Glyceraldehydes | GC-MS | 0.2391 | 0.5795 | 38% |
| Metabolite - 1988 | LC-MS | 0.246 | 0.5892 | −37% |
| ethyl-3-indoleacetate | GC-MS | 0.2502 | 0.5892 | 16% |
| Tyramine | GC-MS | 0.2517 | 0.5892 | 15% |
| Metabolite - 2249 | LC-MS | 0.2525 | 0.5892 | −14% |
| alpha-keto-glutarate | LC-MS | 0.2544 | 0.5892 | 12% |
| Metabolite - 3457 | LC-MS | 0.2551 | 0.5892 | 13% |
| Metabolite - 2074 | LC-MS | 0.2609 | 0.5892 | 18% |
| Metabolite - 2986 | GC-MS | 0.2612 | 0.5892 | 28% |
| Metabolite - 2005 | LC-MS | 0.2619 | 0.5892 | 13% |
| Metabolite - 2194 | LC-MS | 0.2619 | 0.5892 | 26% |
| Metabolite - 1368 | LC-MS | 0.262 | 0.5892 | 58% |
| Metabolite - 4357 | GC-MS | 0.2648 | 0.5915 | −14% |
| Metabolite - 3027 retired: arginine | GC-MS | 0.2674 | 0.5935 | −8% |
| Metabolite - 3896 | LC-MS | 0.2717 | 0.5992 | −19% |
| Metabolite - 2255 | LC-MS | 0.2815 | 0.606 | −35% |
| Isobar-9-includes-sucrose-beta-D-lactose-D-trehalose-D-cellobiose-D-Maltose-palatinose-melibiose-alpha-D-lactose | LC-MS | 0.2845 | 0.606 | 25% |
| methyl-indole-3-acetate | LC-MS | 0.2858 | 0.606 | 14% |
| trans-4-hydroxyproline | GC-MS | 0.2863 | 0.606 | 10% |
| Metabolite - 2387 retired: gamma glu leu | LC-MS | 0.2868 | 0.606 | 63% |
| diaminopimelic acid | LC-MS | 0.2884 | 0.606 | 7% |
| Metabolite - 3517 | LC-MS | 0.2901 | 0.606 | 52% |
| Metabolite - 3131 retired: N4 adduct of indole-3-acetic acid | LC-MS | 0.2902 | 0.606 | 19% |
| Metabolite - 4276 | GC-MS | 0.2908 | 0.606 | −18% |
| Metabolite - 1961 retired: glycocholic acid | LC-MS | 0.2949 | 0.6109 | 39% |
| Metabolite - 3100 | GC-MS | 0.3048 | 0.622 | 22% |
| Metabolite - 2212 | LC-MS | 0.3058 | 0.622 | −16% |
| Metabolite - 4364 | GC-MS | 0.308 | 0.622 | −9% |
| Metabolite - 2052 retired: potassium adduct of Isobar 1 | LC-MS | 0.3085 | 0.622 | 5% |
| adenosine-inosine-uridine-xanthosine-5-monophosphate | GC-MS | 0.3112 | 0.622 | −17% |
| Metabolite - 3067 | GC-MS | 0.3112 | 0.622 | −10% |
| 4-Guanidinobutanoic acid | LC-MS | 0.317 | 0.6293 | −7% |
| Metabolite - 2347 | LC-MS | 0.3185 | 0.6293 | 26% |
| Metabolite - 3143 | LC-MS | 0.3205 | 0.6295 | −12% |
| Metabolite - 2306 retired: gamma glu leu | LC-MS | 0.3266 | 0.6313 | 6% |
| benzoic acid | GC-MS | 0.3278 | 0.6313 | −4% |
| Histidine | GC-MS | 0.3364 | 0.6313 | −7% |
| Metabolite - 3317 | LC-MS | 0.3393 | 0.6313 | 222% |
| 2-deoxyinosine | LC-MS | 0.3398 | 0.6313 | 293% |
| Metabolite - 2386 | LC-MS | 0.3398 | 0.6313 | 8% |
| Metabolite - 1834 | LC-MS | 0.3431 | 0.6313 | −27% |
| Metabolite - 2806 | LC-MS | 0.3432 | 0.6313 | 5% |
| 1-7-dihydro-6h-purin-6-one | LC-MS | 0.3453 | 0.6313 | −15% |
| Metabolite - 3075 | GC-MS | 0.3466 | 0.6313 | −5% |
| Metabolite - 2111 | LC-MS | 0.3472 | 0.6313 | 24% |
| Metabolite - 3334 | LC-MS | 0.3484 | 0.6313 | 15% |
| Metabolite - 4084 | GC-MS | 0.3495 | 0.6313 | −9% |
| Metabolite - 3830 | LC-MS | 0.3508 | 0.6313 | −15% |
| Metabolite - 1389 | LC-MS | 0.3523 | 0.6313 | 227% |
| pyridoxamine-phosphate | LC-MS | 0.3525 | 0.6313 | 12% |
| Metabolite - 2287 | LC-MS | 0.3528 | 0.6313 | 89% |
| 3-amino-isobutyrate | GC-MS | 0.359 | 0.6351 | −7% |
| Metabolite - 1086 | LC-MS | 0.3617 | 0.6351 | 17% |
| Metabolite - 2506 | LC-MS | 0.3623 | 0.6351 | 29% |
| Metabolite - 3074 | GC-MS | 0.3743 | 0.6473 | −27% |
| N-acetylserotonin | GC-MS | 0.3749 | 0.6473 | −8% |
| Metabolite - 2389 | LC-MS | 0.381 | 0.6544 | −12% |
| Metabolite - 3093 | GC-MS | 0.3866 | 0.6585 | −23% |
| Valine | GC-MS | 0.3872 | 0.6585 | 7% |
| Glutamine | GC-MS | 0.3941 | 0.6615 | −8% |
| Metabolite - 3097 | GC-MS | 0.3951 | 0.6615 | −12% |

TABLE 7-continued

ALS Biomarkers from blood plasma samples - T-Test Analysis of Plasma from Control vs. ALS

| Name | Analytical Platform | p-value | q-value | % change in ALS |
|---|---|---|---|---|
| 4-hydroxy-2-quinolinecarboxylic acid | LC-MS | 0.3956 | 0.6615 | 5% |
| shikimic acid | GC-MS | 0.3972 | 0.6615 | 32% |
| Metabolite - 4031 | LC-MS | 0.4 | 0.6615 | 11% |
| Metabolite - 1350 | LC-MS | 0.4036 | 0.6615 | −17% |
| Pyridoxamine | LC-MS | 0.4038 | 0.6615 | −3% |
| Phosphate | GC-MS | 0.4045 | 0.6615 | 4% |
| 3-methoxy-L-tyrosine | GC-MS | 0.4084 | 0.6621 | 15% |
| Metabolite - 2285 | LC-MS | 0.4087 | 0.6621 | 8% |
| tartaric acid | LC-MS | 0.4119 | 0.6641 | −15% |
| Metabolite - 3023 | GC-MS | 0.4186 | 0.666 | −6% |
| Metabolite - 3653 | LC-MS | 0.4188 | 0.666 | −22% |
| Metabolite - 1960 retired: adduct of EDTA | LC-MS | 0.4199 | 0.666 | −10% |
| palmitoleic acid | GC-MS | 0.4225 | 0.666 | −17% |
| Oxitryptan | LC-MS | 0.4228 | 0.666 | −7% |
| Metabolite - 4361 | GC-MS | 0.4326 | 0.6709 | −22% |
| Metabolite - 3017 | GC-MS | 0.4393 | 0.6709 | −8% |
| Possible-Isobar-DL-aspartic acid--aspartate- | GC-MS | 0.4397 | 0.6709 | −10% |
| tetradecanoic acid | GC-MS | 0.4436 | 0.6709 | −11% |
| decanoic acid | GC-MS | 0.4446 | 0.6709 | 10% |
| Metabolite - 4080 | GC-MS | 0.4472 | 0.6709 | −11% |
| Metabolite - 3003 | GC-MS | 0.4476 | 0.6709 | −6% |
| Asparagines | GC-MS | 0.4483 | 0.6709 | −9% |
| Nonanate | GC-MS | 0.4487 | 0.6709 | −4% |
| Metabolite - 4032 retired: lysine | GC-MS | 0.4494 | 0.6709 | −16% |
| Metabolite - 3019 | GC-MS | 0.4495 | 0.6709 | −4% |
| Metabolite - 2151 | LC-MS | 0.4519 | 0.6709 | 25% |
| Metabolite - 4198 | GC-MS | 0.4535 | 0.6709 | −4% |
| Metabolite - 1216 | LC-MS | 0.4556 | 0.6709 | 16% |
| Metabolite - 1349 retired: Isobar 7 | LC-MS | 0.4557 | 0.6709 | −6% |
| Glycine | GC-MS | 0.4629 | 0.6709 | 9% |
| Mannitol | GC-MS | 0.4633 | 0.6709 | 38% |
| D-alanyl-D-alanine | LC-MS | 0.4638 | 0.6709 | 7% |
| Metabolite - 3102 | GC-MS | 0.4647 | 0.6709 | −7% |
| 3-methyl-2-oxovaleric acid | GC-MS | 0.4652 | 0.6709 | −9% |
| Metabolite - 4133 | GC-MS | 0.4724 | 0.678 | −7% |
| Metabolite - 1736 retired: p-hydroxybenzaldehyde | LC-MS | 0.4742 | 0.678 | 12% |
| Metabolite - 2989 | GC-MS | 0.4761 | 0.678 | −12% |
| Niacinamide | LC-MS | 0.48 | 0.6808 | 14% |
| Metabolite - 4003 | LC-MS | 0.4873 | 0.6878 | −15% |
| Metabolite - 2100 | LC-MS | 0.489 | 0.6878 | −3% |
| Isobar-6-includes-valine-betaine | LC-MS | 0.4918 | 0.6881 | 5% |
| 25-hydroxycholesterol | GC-MS | 0.4932 | 0.6881 | 3% |
| Metabolite - 4096 | LC-MS | 0.4999 | 0.6896 | 7% |
| Metabolite - 1342-possible-phenylacetylglutamine-or-formyl-N-acetyl-5-methoxykynurenamine | LC-MS | 0.5015 | 0.6896 | 14% |
| Isobar-21-includes-gamma-aminobutyryl-L-histidine-L-anserine | LC-MS | 0.5043 | 0.6896 | −12% |
| Metabolite - 1116 | LC-MS | 0.5043 | 0.6896 | 15% |
| 3-methyl-L-histidine | LC-MS | 0.5073 | 0.6896 | 12% |
| Metabolite - 4020 | GC-MS | 0.5084 | 0.6896 | 6% |
| Metabolite - 4362 | GC-MS | 0.5097 | 0.6896 | 10% |
| Phenylalanine | LC-MS | 0.5105 | 0.6896 | −2% |
| Metabolite - 1323-possible-4-sulfobenzyl-alcohol-possible-p-cresol-sulfate | LC-MS | 0.5135 | 0.691 | 16% |
| Metabolite - 4360 | GC-MS | 0.5198 | 0.6927 | −14% |
| Metabolite - 2046 | LC-MS | 0.5202 | 0.6927 | 13% |
| Metabolite - 4055 | GC-MS | 0.5229 | 0.6927 | 11% |
| Metabolite - 3165 | LC-MS | 0.5343 | 0.7026 | −4% |
| Metabolite - 1283 | LC-MS | 0.5354 | 0.7026 | −14% |
| Melatonin | GC-MS | 0.5385 | 0.7026 | −4% |
| Metabolite - 1911 | LC-MS | 0.5386 | 0.7026 | 16% |
| N-acetylneuraminate | GC-MS | 0.5441 | 0.706 | −8% |
| creatine-creatinine | GC-MS | 0.5481 | 0.706 | 45% |
| Serine | GC-MS | 0.5494 | 0.706 | −4% |
| Metabolite - 3025 | GC-MS | 0.5515 | 0.706 | −5% |
| Glycerol | GC-MS | 0.5527 | 0.706 | −7% |
| uric acid | GC-MS | 0.5553 | 0.706 | −5% |
| Metabolite - 3085 retired: inositol | GC-MS | 0.5556 | 0.706 | 4% |
| Metabolite - 3668 | LC-MS | 0.5585 | 0.706 | 32% |
| Metabolite - 3707 | LC-MS | 0.5598 | 0.706 | 20% |
| Metabolite - 1301 | LC-MS | 0.5684 | 0.7116 | 3% |

TABLE 7-continued

ALS Biomarkers from blood plasma samples - T-Test Analysis of Plasma from Control vs. ALS

| Name | Analytical Platform | p-value | q-value | % change in ALS |
|---|---|---|---|---|
| Metabolite - 2388 | LC-MS | 0.5723 | 0.7137 | 16% |
| Metabolite - 3065 retired: 1,5-anhydro-d-glucitol | GC-MS | 0.5758 | 0.7137 | 10% |
| malic acid | LC-MS | 0.5763 | 0.7137 | −8% |
| Galactose | GC-MS | 0.5801 | 0.7158 | −2% |
| Carnitine | LC-MS | 0.5862 | 0.7203 | 9% |
| glucono-gamma-lactone | GC-MS | 0.5909 | 0.7203 | 7% |
| elaidic acid | GC-MS | 0.5921 | 0.7203 | 9% |
| Isobar-1-includes-mannose-fructose-glucose-galactose-alpha-L-sorbopyranose-Inositol-D-allose | LC-MS | 0.5922 | 0.7203 | 5% |
| Metabolite - 3044 | LC-MS | 0.5952 | 0.7214 | 8% |
| Metabolite - 3370 | LC-MS | 0.5983 | 0.7227 | −3% |
| Metabolite - 2047 | LC-MS | 0.6005 | 0.7227 | 8% |
| Metabolite - 1843 | LC-MS | 0.6086 | 0.7294 | 8% |
| Metabolite - 3781 retired: Na adduct of Isobar 21 | LC-MS | 0.6103 | 0.7294 | 5% |
| Metabolite - 1498 | LC-MS | 0.6157 | 0.7314 | 6% |
| Metabolite - 4271 | GC-MS | 0.6208 | 0.7314 | −6% |
| Metabolite - 2055 | LC-MS | 0.6211 | 0.7314 | −10% |
| Metabolite - 4147 | GC-MS | 0.623 | 0.7314 | 7% |
| Metabolite - 3138 | LC-MS | 0.6279 | 0.7314 | 11% |
| 3-nitro-L-tyrosine | GC-MS | 0.6294 | 0.7314 | −5% |
| Metabolite - 1113 | LC-MS | 0.6307 | 0.7314 | 6% |
| Metabolite - 3807 | LC-MS | 0.6312 | 0.7314 | −4% |
| Metabolite - 3698 | LC-MS | 0.6385 | 0.7373 | −10% |
| DL-homocysteine | LC-MS | 0.6416 | 0.7384 | 8% |
| Metabolite - 3166 | LC-MS | 0.6508 | 0.7434 | −14% |
| Tryptamine | GC-MS | 0.655 | 0.7434 | 5% |
| ascorbic acid | LC-MS | 0.6562 | 0.7434 | −12% |
| n-hexadecanoic acid | GC-MS | 0.6574 | 0.7434 | 5% |
| Metabolite - 3832 | LC-MS | 0.6586 | 0.7434 | −14% |
| Metabolite - 2026 | LC-MS | 0.659 | 0.7434 | −5% |
| Metabolite - 1915 | LC-MS | 0.6637 | 0.7462 | 15% |
| lactate | LC-MS | 0.6689 | 0.7479 | −4% |
| Acetylphosphate | LC-MS | 0.6755 | 0.7479 | −10% |
| Serotonin | LC-MS | 0.6788 | 0.7479 | 11% |
| Isobar-2-includes-3-amino-isobutyrate-2-amino-butyrate-4-aminobutanoic acid-dimethylglycine-choline | LC-MS | 0.6796 | 0.7479 | 5% |
| 5-hydroxyindoleacetate | GC-MS | 0.6811 | 0.7479 | 11% |
| Metabolite - 4012 | GC-MS | 0.6817 | 0.7479 | 5% |
| Metabolite - 3489 | LC-MS | 0.6836 | 0.7479 | −10% |
| Metabolite - 3402 | LC-MS | 0.6856 | 0.7479 | 21% |
| N-N-dimethylarginine | LC-MS | 0.6873 | 0.7479 | −8% |
| Metabolite - 3708 | LC-MS | 0.6923 | 0.7479 | 4% |
| Thyroxine | LC-MS | 0.6983 | 0.7479 | −4% |
| Metabolite - 1829 retired: oxalic acid | LC-MS | 0.6994 | 0.7479 | 8% |
| Metabolite - 3615 | LC-MS | 0.6998 | 0.7479 | −6% |
| vitamin-B6 | GC-MS | 0.7025 | 0.7479 | 5% |
| Metabolite - 3055 | LC-MS | 0.7027 | 0.7479 | −9% |
| Metabolite - 3081 | GC-MS | 0.7034 | 0.7479 | 4% |
| Isobar-8-includes-anthranilic acid-salicylamide | LC-MS | 0.7041 | 0.7479 | 5% |
| Metabolite - 2774 | LC-MS | 0.7045 | 0.7479 | −6% |
| Epinephrine | GC-MS | 0.7089 | 0.7501 | 3% |
| Metabolite - 4044 | GC-MS | 0.7126 | 0.7502 | 3% |
| Fructose | GC-MS | 0.7148 | 0.7502 | 14% |
| Octopamine | GC-MS | 0.7159 | 0.7502 | −2% |
| guanidineacetic acid | LC-MS | 0.7177 | 0.7502 | −5% |
| Histamine | LC-MS | 0.7321 | 0.7615 | 2% |
| hydroxyacetic acid | GC-MS | 0.7402 | 0.7615 | −2% |
| Metabolite - 1329 | LC-MS | 0.7432 | 0.7615 | 5% |
| Lactate | GC-MS | 0.7451 | 0.7615 | 3% |
| Biliverdin | LC-MS | 0.7473 | 0.7615 | 4% |
| 4-hydroxyphenylpyruvate | GC-MS | 0.7474 | 0.7615 | −5% |
| Metabolite - 1914 | LC-MS | 0.7474 | 0.7615 | 11% |
| gulono-1-4-lactone | GC-MS | 0.7493 | 0.7615 | −3% |
| Metabolite - 3952 | LC-MS | 0.7508 | 0.7615 | 3% |
| Alanine | GC-MS | 0.753 | 0.7615 | −3% |
| Metabolite - 2898 | LC-MS | 0.7531 | 0.7615 | 21% |
| L-beta-imidazolelactic acid | GC-MS | 0.7634 | 0.7619 | 4% |
| Metabolite - 2242 | LC-MS | 0.7661 | 0.7619 | 28% |

TABLE 7-continued

ALS Biomarkers from blood plasma samples - T-Test Analysis of Plasma from Control vs. ALS

| Name | Analytical Platform | p-value | q-value | % change in ALS |
|---|---|---|---|---|
| N-5-aminocarbonyl-L-ornithine | LC-MS | 0.7669 | 0.7619 | −3% |
| Glucarate | GC-MS | 0.7678 | 0.7619 | 4% |
| Leucine | GC-MS | 0.7696 | 0.7619 | 3% |
| N-acetyl-L-alanine | GC-MS | 0.7696 | 0.7619 | 3% |
| Inositol | GC-MS | 0.7723 | 0.7619 | 2% |
| Metabolite - 3314 | LC-MS | 0.7794 | 0.7619 | 3% |
| Xylitol | LC-MS | 0.78 | 0.7619 | 7% |
| Metabolite - 3014 retired: meso-erythritol | GC-MS | 0.7801 | 0.7619 | −2% |
| Aspartate | LC-MS | 0.7833 | 0.7619 | 3% |
| Metabolite - 2567 | LC-MS | 0.7879 | 0.7619 | 2% |
| 2-keto-L-gulonic acid | GC-MS | 0.7887 | 0.7619 | 6% |
| Metabolite - 3129 | LC-MS | 0.7897 | 0.7619 | −1% |
| Metabolite - 2486 | LC-MS | 0.7904 | 0.7619 | 5% |
| Metabolite - 3235 retired: DL-indole-3-lactic acid | LC-MS | 0.7925 | 0.7619 | 3% |
| Dopamine | GC-MS | 0.7963 | 0.7619 | −3% |
| Metabolite - 3139 | LC-MS | 0.7974 | 0.7619 | 4% |
| Metabolite - 2694 retired: lactate | LC-MS | 0.8024 | 0.7619 | −3% |
| Metabolite - 3430 | LC-MS | 0.8043 | 0.7619 | −3% |
| 5-oxoproline | GC-MS | 0.8069 | 0.7619 | −2% |
| Metabolite - 3894 retired: pyroglutamic acid (5-oxoproline)-pyroglutamic acid | LC-MS | 0.8084 | 0.7619 | 4% |
| Metabolite - 1974 | LC-MS | 0.8086 | 0.7619 | −3% |
| Metabolite - 2370 | LC-MS | 0.8127 | 0.7619 | 4% |
| Praline | GC-MS | 0.8131 | 0.7619 | 3% |
| Metabolite - 3696 | LC-MS | 0.8137 | 0.7619 | 8% |
| Metabolite - 3758 | LC-MS | 0.8184 | 0.7638 | −10% |
| Metabolite - 3020 retired: threonic acid | GC-MS | 0.8297 | 0.7706 | 2% |
| Metabolite - 3327 | LC-MS | 0.8354 | 0.7713 | 6% |
| 9-12-octadecadienoic acid-z-z | GC-MS | 0.8372 | 0.7713 | 3% |
| glyceric acid | GC-MS | 0.8377 | 0.7713 | −2% |
| Succinate | GC-MS | 0.8404 | 0.7713 | 1% |
| Metabolite - 1458 retired: hypoxanthine | LC-MS | 0.8429 | 0.7713 | 3% |
| Glycerate | LC-MS | 0.844 | 0.7713 | 3% |
| hippuric acid | LC-MS | 0.8515 | 0.7761 | 6% |
| Metabolite - 2056 | LC-MS | 0.858 | 0.7782 | 3% |
| Allantoin | LC-MS | 0.859 | 0.7782 | −3% |
| Isoleucine | GC-MS | 0.8606 | 0.7782 | 2% |
| Metabolite - 1926 retired: trans-2,3,4-trimethoxycinnamic acid | LC-MS | 0.8699 | 0.7845 | −5% |
| Isocitrate | LC-MS | 0.8751 | 0.7857 | 1% |
| Metabolite - 1597 | LC-MS | 0.8785 | 0.7857 | 1% |
| Metabolite - 1209 | LC-MS | 0.8801 | 0.7857 | 4% |
| Metabolite - 2269 | LC-MS | 0.8804 | 0.7857 | 4% |
| Metabolite - 3992 | LC-MS | 0.8836 | 0.7865 | −1% |
| Mannose | GC-MS | 0.8922 | 0.7891 | 0% |
| 2-amino-butyrate | GC-MS | 0.893 | 0.7891 | 1% |
| Metabolite - 3900 | LC-MS | 0.8977 | 0.7891 | 0% |
| Metabolite - 4354 | GC-MS | 0.9006 | 0.7891 | 1% |
| sn-Glycerol-3-phosphate | LC-MS | 0.9013 | 0.7891 | 1% |
| Metabolite - 3450 retired: 1-methylnicotinamide | LC-MS | 0.9019 | 0.7891 | 2% |
| Tryptophan | LC-MS | 0.9027 | 0.7891 | 0% |
| Metabolite - 2279 | LC-MS | 0.9066 | 0.7902 | 4% |
| 5-6-Dimethylbenzimidazole- | GC-MS | 0.9106 | 0.7902 | 2% |
| 3-hydroxybutanoic acid | GC-MS | 0.9109 | 0.7902 | −4% |
| Metabolite - 1465 | LC-MS | 0.9146 | 0.7907 | 3% |
| Metabolite - 2469 | LC-MS | 0.9161 | 0.7907 | −1% |
| Metabolite - 3101 | GC-MS | 0.9222 | 0.7914 | −1% |
| alpha-L-sorbopyranose | GC-MS | 0.9264 | 0.7914 | 2% |
| Tyrosine | GC-MS | 0.9269 | 0.7914 | −1% |
| Metabolite - 2563 retired: lactate | LC-MS | 0.9276 | 0.7914 | −1% |
| 3-chloro-L-tyrosine | GC-MS | 0.9341 | 0.7914 | 1% |
| DOPA | GC-MS | 0.9341 | 0.7914 | 1% |
| Metabolite - 4251 | GC-MS | 0.9344 | 0.7914 | 1% |
| Metabolite - 1063 | LC-MS | 0.9354 | 0.7914 | 1% |
| Metabolite - 1286 | LC-MS | 0.9525 | 0.7967 | 0% |
| Metabolite - 2250 | LC-MS | 0.9539 | 0.7967 | 2% |
| 3-phospho-d-glycerate | LC-MS | 0.954 | 0.7967 | −1% |
| Metabolite - 1110 | LC-MS | 0.9588 | 0.7967 | 1% |
| Dethiobiotin | GC-MS | 0.9595 | 0.7967 | 0% |
| glucose-6-phosphate | GC-MS | 0.9642 | 0.7967 | 0% |
| Metabolite - 3783 | LC-MS | 0.9647 | 0.7967 | 0% |

TABLE 7-continued

ALS Biomarkers from blood plasma samples - T-Test Analysis of Plasma from Control vs. ALS

| Name | Analytical Platform | p-value | q-value | % change in ALS |
|---|---|---|---|---|
| Metabolite - 3837 retired: 3-indoxylsulfate | LC-MS | 0.9647 | 0.7967 | 0% |
| Metabolite - 1111-possible-methylnitronitrosoguanidine-or-ethyl-thiocarbamoylacetate | LC-MS | 0.9649 | 0.7967 | 0% |
| Metabolite - 1573 retired: glycerol-2-phosphate | LC-MS | 0.9649 | 0.7967 | −1% |
| Metabolite - 3178 retired: NH3 adduct of citric acid | LC-MS | 0.9735 | 0.8002 | −1% |
| Metabolite - 2027 | LC-MS | 0.9749 | 0.8002 | 0% |
| Metabolite - 3094 | GC-MS | 0.9791 | 0.8002 | 0% |
| Metabolite - 3604 retired: CL adduct of hippuric acid | LC-MS | 0.9799 | 0.8002 | 1% |
| L-alpha-glycerophosphorylcholine | LC-MS | 0.9829 | 0.8002 | 0% |
| Metabolite - 4148 | GC-MS | 0.9833 | 0.8002 | 0% |
| Arabinose | GC-MS | 0.9938 | 0.8068 | 0% |
| Metabolite - 2292 | LC-MS | 0.9985 | 0.8073 | 0% |
| Metabolite - 3132 | LC-MS | 0.999 | 0.8073 | 0% |

TABLE 8

ALS Biomarkers from blood plasma samples - Wilcoxon's Rank Sum-Tests ALS vs. Control

| Name | Analytical Platform | p-value | q-value | % change in ALS |
|---|---|---|---|---|
| Metabolite - 2550 | LC-MS | <0.0001 | 1.00E−04 | 289% |
| creatine-creatinine | GC-MS | 1.00E−04 | 0.0053 | 45% |
| alpha-4-dihydroxybenzenepropanoic acid | GC-MS | 0.001 | 0.0494 | −29% |
| Metabolite - 2256 | LC-MS | 0.0011 | 0.0494 | −45% |
| Metabolite - 3033 | GC-MS | 0.0012 | 0.0502 | −20% |
| Carnosine | LC-MS | 0.0017 | 0.0627 | −35% |
| N-6-trimethyl-l-lysine | LC-MS | 0.002 | 0.0699 | −34% |
| Metabolite - 1114 | LC-MS | 0.0024 | 0.0738 | 30% |
| alpha-tocopherol | GC-MS | 0.0028 | 0.0757 | 48% |
| glutamic acid | GC-MS | 0.0029 | 0.0757 | 47% |
| Metabolite - 3881 retired: azelaic acid | LC-MS | 0.0031 | 0.0757 | −29% |
| Xanthine | LC-MS | 0.0032 | 0.0757 | 42% |
| Metabolite - 3218 | LC-MS | 0.0048 | 0.101 | 24% |
| Metabolite - 3977 | LC-MS | 0.0048 | 0.101 | −27% |
| Metabolite - 1368 | LC-MS | 0.0052 | 0.102 | 58% |
| Metabolite - 2139 | LC-MS | 0.0054 | 0.102 | 30% |
| Metabolite - 3088 | GC-MS | 0.006 | 0.107 | −31% |
| arachidonic acid | GC-MS | 0.0063 | 0.107 | 47% |
| 6-phosphogluconic acid | LC-MS | 0.0096 | 0.1564 | −22% |
| Metabolite - 3058 | GC-MS | 0.0106 | 0.1661 | −24% |
| Ornithine | GC-MS | 0.012 | 0.1801 | 36% |
| D-lyxose | GC-MS | 0.013 | 0.1873 | −16% |
| Metabolite - 3498 | LC-MS | 0.0136 | 0.1888 | −15% |
| Isobar-28-includes-L-threonine-L-allothreonine | LC-MS | 0.0149 | 0.1995 | −16% |
| Metabolite - 2313 | LC-MS | 0.0164 | 0.2122 | −52% |
| 5-6-dihydroorotic acid | GC-MS | 0.0173 | 0.2172 | −7% |
| Metabolite - 2041 | LC-MS | 0.0187 | 0.2189 | 29% |
| Creatinine | LC-MS | 0.0198 | 0.2189 | −17% |
| D-arabitol | GC-MS | 0.0198 | 0.2189 | −14% |
| Metabolite - 3073 | GC-MS | 0.0206 | 0.2207 | 26% |
| Metabolite - 2407 | LC-MS | 0.022 | 0.2298 | 53% |
| Metabolite - 3331 | LC-MS | 0.0234 | 0.2328 | −69% |
| Metabolite - 4019 | GC-MS | 0.0235 | 0.2328 | 26% |
| Metabolite - 3090 | GC-MS | 0.0252 | 0.2385 | −51% |
| Metabolite - 3653 | LC-MS | 0.0254 | 0.2385 | −22% |
| Metabolite - 2266 retired 4-acetominophen sulfate | LC-MS | 0.0262 | 0.2403 | 571% |
| Metabolite - 1497 | LC-MS | 0.0276 | 0.2415 | 34% |
| Metabolite - 3030 | GC-MS | 0.0276 | 0.2415 | −15% |
| L-allo-threonine | GC-MS | 0.0291 | 0.2485 | −17% |
| Metabolite - 3758 | LC-MS | 0.0321 | 0.2683 | −10% |
| Isobar-19-includes-D-saccharic acid-2-deoxy-D-galactose-2-deoxy-D-glucose-L-fucose-L-rhamnose | LC-MS | 0.0329 | 0.269 | −25% |

TABLE 8-continued

ALS Biomarkers from blood plasma samples- Wilcoxon's Rank Sum-Tests ALS vs. Control

| Name | Analytical Platform | p-value | q-value | % change in ALS |
|---|---|---|---|---|
| Metabolite - 3994 | LC-MS | 0.0353 | 0.2813 | 35% |
| Isobar-27-includes-L-kynurenine-alpha-2-diamino-gamma-oxobenzenebutanoic acid | LC-MS | 0.0359 | 0.2813 | 15% |
| Metabolite - 3183 | LC-MS | 0.0392 | 0.3003 | −14% |
| octadecanoic acid | GC-MS | 0.0405 | 0.3045 | 11% |
| Metabolite - 3951 | LC-MS | 0.0434 | 0.3171 | 9% |
| Metabolite - 1089 | LC-MS | 0.0454 | 0.3171 | −30% |
| Metabolite - 2387 retired: gamma glu leu | LC-MS | 0.0454 | 0.3171 | 63% |
| Threonine | GC-MS | 0.0456 | 0.3171 | −16% |
| Metabolite - 3181 | LC-MS | 0.0465 | 0.3171 | 36% |
| 2-deoxy-D-glucose | GC-MS | 0.0479 | 0.3171 | 22% |
| Metabolite - 2130 | LC-MS | 0.0481 | 0.3171 | 57% |
| Metabolite - 3108 | GC-MS | 0.0499 | 0.3202 | −15% |
| Metabolite - 2316 | LC-MS | 0.0503 | 0.3202 | 58% |
| Methionine | LC-MS | 0.0546 | 0.3422 | −14% |
| anthranilic acid | GC-MS | 0.057 | 0.3509 | −15% |
| pantothenic acid | LC-MS | 0.0588 | 0.3566 | 30% |
| Metabolite - 3012 | GC-MS | 0.0602 | 0.3589 | −11% |
| alpha-methyl-L-beta-3-4-dihydroxyphenylalanine | GC-MS | 0.0621 | 0.3591 | 24% |
| Metabolite - 2973 | GC-MS | 0.0621 | 0.3591 | −9% |
| Metabolite - 3813 | LC-MS | 0.0632 | 0.3596 | 23% |
| Metabolite - 2886 retired: CL adduct of p-acetiminophen-beta-d-glucuronide | LC-MS | 0.066 | 0.3699 | 151% |
| Isobar-21-includes-gamma-aminobutyryl-L-histidine-L-anserine | LC-MS | 0.0693 | 0.3829 | −12% |
| 5-hydroxylysine | LC-MS | 0.0703 | 0.3829 | −24% |
| Metabolite - 3002 | GC-MS | 0.0715 | 0.384 | 13% |
| Metabolite - 1656 | LC-MS | 0.0738 | 0.385 | −18% |
| Metabolite - 3098 | GC-MS | 0.0738 | 0.385 | −13% |
| Metabolite - 3180 | LC-MS | 0.0749 | 0.3856 | 25% |
| Metabolite - 2392 | LC-MS | 0.078 | 0.3897 | −30% |
| Metabolite - 3313 | LC-MS | 0.0818 | 0.3897 | 18% |
| Saccharopine | LC-MS | 0.0821 | 0.3897 | −20% |
| Metabolite - 1127 | LC-MS | 0.0846 | 0.3897 | −18% |
| Metabolite - 4043 retired: lysine | GC-MS | 0.0846 | 0.3897 | 15% |
| Normetanephrine | GC-MS | 0.0859 | 0.3897 | 23% |
| Metabolite - 3134 | LC-MS | 0.0871 | 0.3897 | 66% |
| Metabolite - 2924 retired: 2-hydroxybutanoic acid (also called (s)-2-hydroxybutyric acid) | GC-MS | 0.0872 | 0.3897 | 21% |
| Selenocystine | LC-MS | 0.0882 | 0.3897 | 19% |
| Metabolite - 2866 | LC-MS | 0.0883 | 0.3897 | −33% |
| Metabolite - 1351 retired: urea adduct of Isobar 6 | LC-MS | 0.0898 | 0.3897 | 19% |
| 3alpha-7alpha-12alpha-trihydroxy-5beta-cholanate | GC-MS | 0.0911 | 0.3897 | 11% |
| Metabolite - 2687 | LC-MS | 0.0911 | 0.3897 | −8% |
| Metabolite - 3056 | LC-MS | 0.0913 | 0.3897 | 17% |
| 3-amino-isobutyrate | GC-MS | 0.0925 | 0.3905 | −7% |
| Metabolite - 3843 | LC-MS | 0.094 | 0.3923 | −21% |
| Metabolite - 2074 | LC-MS | 0.0995 | 0.4109 | 18% |
| Metabolite - 4196 | GC-MS | 0.1049 | 0.4286 | 39% |
| 4-methyl-2-oxopentanoate | GC-MS | 0.1085 | 0.4337 | −12% |
| Metabolite - 1086 | LC-MS | 0.1085 | 0.4337 | 17% |
| Metabolite - 1817 | LC-MS | 0.1116 | 0.4415 | 14% |
| Mercaptopyruvate | LC-MS | 0.1156 | 0.448 | −23% |
| Metabolite - 2546 | LC-MS | 0.1165 | 0.448 | −25% |
| Metabolite - 2255 | LC-MS | 0.1175 | 0.448 | −35% |
| beta-hydroxypyruvic acid | LC-MS | 0.118 | 0.448 | 30% |
| Metabolite - 4134 | GC-MS | 0.1215 | 0.4537 | 19% |
| Metabolite - 1975 | LC-MS | 0.122 | 0.4537 | 25% |
| Metabolite - 3160 | LC-MS | 0.1232 | 0.4537 | −8% |
| 1-methyladenine | GC-MS | 0.1319 | 0.4813 | −16% |
| Metabolite - 3067 | GC-MS | 0.1392 | 0.5031 | −10% |
| Isobar-9-includes-sucrose-beta-D-lactose-D-trehalose-D-cellobiose-D-Maltose-palatinose-melibiose-alpha-D-lactose | LC-MS | 0.1444 | 0.5068 | 25% |
| Tyramine | GC-MS | 0.1451 | 0.5068 | 15% |
| Metabolite - 3365 | LC-MS | 0.1456 | 0.5068 | 47% |
| Metabolite - 1220 | LC-MS | 0.1467 | 0.5068 | 35% |
| Metabolite - 3143 | LC-MS | 0.147 | 0.5068 | −12% |
| N-carbamoyl-L-aspartate | LC-MS | 0.1496 | 0.5111 | 54% |
| Metabolite - 1979 retired: CL adduct of Isobar 19 | LC-MS | 0.155 | 0.521 | −13% |
| Metabolite - 3077 | GC-MS | 0.1571 | 0.521 | −7% |

TABLE 8-continued

ALS Biomarkers from blood plasma samples- Wilcoxon's Rank Sum-Tests ALS vs. Control

| Name | Analytical Platform | p-value | q-value | % change in ALS |
|---|---|---|---|---|
| Metabolite - 4275 | GC-MS | 0.1571 | 0.521 | −11% |
| Metabolite - 3113 | GC-MS | 0.1581 | 0.521 | −33% |
| Metabolite - 1839 | LC-MS | 0.1627 | 0.5318 | −39% |
| Metabolite - 1085-possible-isolobinine-or-4-aminoestra-1,3-5-10-triene-3-17beta-diol | LC-MS | 0.1655 | 0.5361 | 14% |
| Metabolite - 3022 | GC-MS | 0.1699 | 0.5363 | −11% |
| Metabolite - 3078 | GC-MS | 0.1699 | 0.5363 | −9% |
| Metabolite - 4361 | GC-MS | 0.1699 | 0.5363 | −22% |
| pyridoxamine-phosphate | LC-MS | 0.1743 | 0.5413 | 12% |
| Metabolite - 4077 | GC-MS | 0.1743 | 0.5413 | −23% |
| 3-methyl-2-oxovaleric acid | GC-MS | 0.1786 | 0.5442 | −9% |
| Metabolite - 1335 | LC-MS | 0.1788 | 0.5442 | 19% |
| Metabolite - 3320 | LC-MS | 0.1796 | 0.5442 | −47% |
| Metabolite - 1831-possible-Cl-adduct-of-citrulline | LC-MS | 0.188 | 0.5608 | −17% |
| Carnitine | LC-MS | 0.1881 | 0.5608 | 9% |
| Metabolite - 2249 | LC-MS | 0.1928 | 0.5668 | −14% |
| Metabolite - 1961 retired: glycocholic acid | LC-MS | 0.1942 | 0.5668 | 39% |
| p-acetamidophenyl-beta-D-gluguronide | LC-MS | 0.1946 | 0.5668 | 137% |
| Metabolite - 1283 | LC-MS | 0.1989 | 0.5682 | −14% |
| Cholesterol | GC-MS | 0.2001 | 0.5682 | 10% |
| Metabolite - 4272 | GC-MS | 0.2001 | 0.5682 | −12% |
| Metabolite - 2915 | GC-MS | 0.2026 | 0.5682 | −7% |
| Metabolite - 4357 | GC-MS | 0.2026 | 0.5682 | −14% |
| Metabolite - 4276 | GC-MS | 0.2055 | 0.5719 | −18% |
| Metabolite - 3832 | LC-MS | 0.2077 | 0.572 | −14% |
| Metabolite - 3103 | GC-MS | 0.2086 | 0.572 | −17% |
| Metabolite - 3027 retired: arginine | GC-MS | 0.2102 | 0.5723 | −8% |
| Metabolite - 2697 | LC-MS | 0.2128 | 0.5752 | 17% |
| Metabolite - 3402 | LC-MS | 0.2154 | 0.578 | 21% |
| Metabolite - 2806 | LC-MS | 0.218 | 0.5809 | 5% |
| Metabolite - 3166 | LC-MS | 0.2201 | 0.5825 | −14% |
| Metabolite - 1113 | LC-MS | 0.2233 | 0.5827 | 6% |
| Metabolite - 3040 | GC-MS | 0.2233 | 0.5827 | 26% |
| 4-hydroxyphenylacetate | LC-MS | 0.2277 | 0.5884 | −21% |
| Metabolite - 3624 | LC-MS | 0.2286 | 0.5884 | −18% |
| Metabolite - 3457 | LC-MS | 0.2369 | 0.6057 | 13% |
| Metaboiite-1655 | LC-MS | 0.2426 | 0.6114 | 13% |
| Metabolite - 2051 | LC-MS | 0.2436 | 0.6114 | 63% |
| adenosine-inosine-uridine-xanthosine-5-monophosphate | GC-MS | 0.2456 | 0.6114 | −17% |
| Metabolite - 3003 | GC-MS | 0.2503 | 0.6114 | −6% |
| citric acid | GC-MS | 0.2512 | 0.6114 | −9% |
| alpha-D-ribose-5-phosphate | LC-MS | 0.2527 | 0.6114 | 22% |
| Metabolite - 2366 | LC-MS | 0.2541 | 0.6114 | 35% |
| Metabolite - 2388 | LC-MS | 0.2559 | 0.6114 | 16% |
| Metabolite - 3099 | GC-MS | 0.2571 | 0.6114 | −15% |
| Metabolite - 3830 | LC-MS | 0.2571 | 0.6114 | −15% |
| Metabolite - 4274 | GC-MS | 0.2571 | 0.6114 | 14% |
| methyl-indole-3-acetate | LC-MS | 0.2587 | 0.6114 | 14% |
| Metabolite - 2329 | LC-MS | 0.2621 | 0.6155 | 23% |
| L-beta-imidazolelactic acid | GC-MS | 0.266 | 0.6201 | 4% |
| Metabolite - 1251 | LC-MS | 0.2673 | 0.6201 | 49% |
| Metabolite - 1104 | LC-MS | 0.2743 | 0.6323 | 12% |
| Metabolite - 1960 retired: adduct of EDTA | LC-MS | 0.2782 | 0.6328 | −10% |
| trans-4-hydroxyproline | GC-MS | 0.2783 | 0.6328 | 10% |
| benzoic acid | GC-MS | 0.2815 | 0.6328 | −4% |
| vitamin-B6 | GC-MS | 0.2815 | 0.6328 | 5% |
| elaidic acid | GC-MS | 0.2846 | 0.6328 | 9% |
| Mannose | GC-MS | 0.2846 | 0.6328 | 0% |
| Metabolite - 1988 | LC-MS | 0.2868 | 0.634 | −37% |
| 4-hydroxy-2-quinolinecarboxylic acid | LC-MS | 0.291 | 0.6357 | 5% |
| Metabolite - 1911 | LC-MS | 0.291 | 0.6357 | 16% |
| Metabolite - 2212 | LC-MS | 0.2942 | 0.6391 | −16% |
| Urea | GC-MS | 0.3041 | 0.6566 | 15% |
| Metabolite - 4096 | LC-MS | 0.3073 | 0.6599 | 7% |
| 25-hydroxycholesterol | GC-MS | 0.3175 | 0.6779 | 3% |
| Metabolite - 1389 | LC-MS | 0.3206 | 0.6805 | 227% |
| Phosphate | GC-MS | 0.3244 | 0.6847 | 4% |
| 1-Hexadecanol | GC-MS | 0.3291 | 0.6909 | −16% |
| n-hexadecanoic acid | GC-MS | 0.3348 | 0.6986 | 5% |
| Biliverdin | LC-MS | 0.3384 | 0.6986 | 4% |
| diaminopimelic acid | LC-MS | 0.3384 | 0.6986 | 7% |
| Metabolite - 4365 | GC-MS | 0.3421 | 0.6986 | 17% |
| Isobar-5-includes-asparagine-ornithine | LC-MS | 0.3454 | 0.6986 | −19% |

TABLE 8-continued

ALS Biomarkers from blood plasma samples- Wilcoxon's Rank Sum-Tests ALS vs. Control

| Name | Analytical Platform | p-value | q-value | % change in ALS |
|---|---|---|---|---|
| Metabolite - 1116 | LC-MS | 0.3455 | 0.6986 | 15% |
| Metabolite - 1350 | LC-MS | 0.3474 | 0.6986 | −17% |
| Metabolite - 4364 | GC-MS | 0.3492 | 0.6986 | −9% |
| Metabolite - 3125 | LC-MS | 0.3523 | 0.6986 | 11% |
| Metabolite - 3334 | LC-MS | 0.3523 | 0.6986 | 15% |
| Metabolite - 3696 | LC-MS | 0.3532 | 0.6986 | 8% |
| Metabolite - 3075 | GC-MS | 0.3601 | 0.7011 | −5% |
| Metabolite - 1346 | LC-MS | 0.3621 | 0.7011 | 20% |
| Metabolite - 3896 | LC-MS | 0.3635 | 0.7011 | −19% |
| Metabolite - 3131 retired: N4 adduct of indole-3-acetic acid | LC-MS | 0.3638 | 0.7011 | 19% |
| Metabolite - 3837 retired: 3-indoxylsulfate | LC-MS | 0.3638 | 0.7011 | 0% |
| tartaric acid | LC-MS | 0.3662 | 0.7011 | −15% |
| Inositol | GC-MS | 0.3676 | 0.7011 | 2% |
| Metabolite - 3017 | GC-MS | 0.3713 | 0.7047 | −8% |
| Serotonin | LC-MS | 0.3748 | 0.7077 | 11% |
| alpha-keto-glutarate | LC-MS | 0.3827 | 0.717 | 12% |
| Metabolite - 4031 | LC-MS | 0.3835 | 0.717 | 11% |
| Metabolite - 3430 | LC-MS | 0.3904 | 0.7227 | −3% |
| Metabolite - 3370 | LC-MS | 0.3931 | 0.7228 | −3% |
| Metabolite - 2100 | LC-MS | 0.3943 | 0.7228 | −3% |
| Metabolite - 3097 | GC-MS | 0.3973 | 0.7229 | −12% |
| Phenylalanine | LC-MS | 0.3983 | 0.7229 | −2% |
| Metabolite - 1843 | LC-MS | 0.4009 | 0.7243 | 8% |
| Metabolite - 2270 | LC-MS | 0.408 | 0.7336 | −31% |
| 9-12-octadecadienoic acid-z-z- | GC-MS | 0.4142 | 0.7343 | 3% |
| 4-hydroxyphenylpyruvate | GC-MS | 0.4155 | 0.7343 | −5% |
| Galactose | GC-MS | 0.4182 | 0.7343 | −2% |
| Tyrosine | GC-MS | 0.4182 | 0.7343 | −1% |
| Metabolite - 3894 retired: pyroglutamic acid (5-oxoproline)-pyroglutamic acid | LC-MS | 0.4182 | 0.7343 | 4% |
| Thyroxine | LC-MS | 0.4223 | 0.738 | −4% |
| Metabolite - 2005 | LC-MS | 0.425 | 0.7393 | 13% |
| gulono-1-4-lactone | GC-MS | 0.4305 | 0.7454 | −3% |
| Metabolite - 3534 | LC-MS | 0.4325 | 0.7455 | 65% |
| Metabolite - 3489 | LC-MS | 0.4425 | 0.7525 | −10% |
| Metabolite - 2986 | GC-MS | 0.4429 | 0.7525 | 28% |
| 5-6-Dimethylbenzimidazole- | GC-MS | 0.4447 | 0.7525 | 2% |
| Metabolite - 3327 | LC-MS | 0.4447 | 0.7525 | 6% |
| 4-Guanidinobutanoic acid | LC-MS | 0.4471 | 0.7525 | −7% |
| Metabolite - 3074 | GC-MS | 0.4486 | 0.7525 | −27% |
| glucose-6-phosphate | GC-MS | 0.4556 | 0.7541 | 0% |
| Nonanate | GC-MS | 0.4556 | 0.7541 | −4% |
| Metabolite - 3783 | LC-MS | 0.4556 | 0.7541 | 0% |
| Metabolite - 2285 | LC-MS | 0.4598 | 0.7578 | 8% |
| Metabolite - 1498 | LC-MS | 0.4721 | 0.7657 | 6% |
| 3-hydroxybutanoic acid | GC-MS | 0.4727 | 0.7657 | −4% |
| Metabolite - 3139 | LC-MS | 0.4727 | 0.7657 | 4% |
| Metabolite - 2306 retired: gamma glu leu | LC-MS | 0.4771 | 0.7661 | 6% |
| Metabolite - 3044 | LC-MS | 0.4771 | 0.7661 | 8% |
| Metabolite - 3023 | GC | 0.4859 | 0.7746 | −6% |
| Metabolite - 1829 retired: oxalic acid | LC-MS | 0.4937 | 0.7827 | 8% |
| Oxitryptan | LC-MS | 0.4992 | 0.7853 | −7% |
| Metabolite - 2506 | LC-MS | 0.5035 | 0.7853 | 29% |
| Lactate | GC-MS | 0.5037 | 0.7853 | 3% |
| Metabolite - 4044 | GC-MS | 0.5037 | 0.7853 | 3% |
| Metabolite - 4080 | GC-MS | 0.507 | 0.7853 | −11% |
| Metabolite - 2194 | LC-MS | 0.5079 | 0.7853 | 26% |
| Metabolite - 1974 | LC-MS | 0.5126 | 0.7894 | −3% |
| Metabolite - 2386 | LC-MS | 0.5172 | 0.7933 | 8% |
| Epinephrine | GC-MS | 0.5218 | 0.797 | 3% |
| Metabolite - 2347 | LC-MS | 0.5286 | 0.8033 | 26% |
| Metabolite - 4133 | GC-MS | 0.531 | 0.8033 | −7% |
| 3-methyl-L-histidine | LC-MS | 0.5333 | 0.8033 | 12% |
| Metabolite - 3093 | GC-MS | 0.5345 | 0.8033 | −23% |
| Metabolite - 3019 | GC-MS | 0.5449 | 0.8098 | −4% |
| Asparagines | GC-MS | 0.5496 | 0.8098 | −9% |
| glucono-gamma-lactone | GC-MS | 0.5496 | 0.8098 | 7% |
| Metabolite - 2052 retired: potassium adduct of Isobar 1 | LC-MS | 0.5543 | 0.8098 | 5% |
| Alanine | GC-MS | 0.559 | 0.8098 | −3% |
| Metabolite - 4147 | GC-MS | 0.5627 | 0.8098 | 7% |
| 3-nitro-L-tyrosine | GC-MS | 0.5685 | 0.8098 | −5% |
| sn-Glycerol-3-phosphate | LC-MS | 0.5685 | 0.8098 | 1% |
| Metabolite - 3615 | LC-MS | 0.5685 | 0.8098 | −6% |

TABLE 8-continued

ALS Biomarkers from blood plasma samples- Wilcoxon's Rank Sum-Tests ALS vs. Control

| Name | Analytical Platform | p-value | q-value | % change in ALS |
|---|---|---|---|---|
| Metabolite - 2698 | LC-MS | 0.5773 | 0.8098 | 39% |
| Metabolite - 3698 | LC-MS | 0.5776 | 0.8098 | −10% |
| Tryptamine | GC-MS | 0.5781 | 0.8098 | 5% |
| uric acid | GC-MS | 0.5781 | 0.8098 | −5% |
| N-acetylneuraminate | GC-MS | 0.5803 | 0.8098 | −8% |
| Metabolite - 1915 | LC-MS | 0.5944 | 0.8098 | 15% |
| Metabolite - 2055 | LC-MS | 0.5967 | 0.8098 | −10% |
| Metabolite - 1301 | LC-MS | 0.5975 | 0.8098 | 3% |
| Metabolite - 4354 | GC-MS | 0.5975 | 0.8098 | 1% |
| 2-deoxyinosine | LC-MS | 0.5986 | 0.8098 | 293% |
| Xylitol | LC-MS | 0.6023 | 0.8098 | 7% |
| N-5-aminocarbonyl-L-ornithine | LC-MS | 0.6024 | 0.8098 | −3% |
| Metabolite - 3604 retired: CL adduct of hippuric acid | LC-MS | 0.607 | 0.8098 | 1% |
| Praline | GC-MS | 0.6073 | 0.8098 | 3% |
| Metabolite - 2279 | LC-MS | 0.6087 | 0.8098 | 4% |
| Isobar-8-includes-anthranilic acid-salicylamide | LC-MS | 0.6106 | 0.8098 | 5% |
| Melatonin | GC-MS | 0.6123 | 0.8098 | −4% |
| Metabolite - 1216 | LC-MS | 0.6123 | 0.8098 | 16% |
| Metabolite - 3316 retired: lactate | LC-MS | 0.6123 | 0.8098 | −2% |
| shikimic acid | GC-MS | 0.6172 | 0.8098 | 32% |
| Metabolite - 3025 | GC-MS | 0.6172 | 0.8098 | −5% |
| Niacinamide | LC-MS | 0.6186 | 0.8098 | 14% |
| Acetylphosphate | LC-MS | 0.6194 | 0.8098 | −10% |
| Metabolite - 1573 retired: glycerol-2-phosphate | LC-MS | 0.6232 | 0.8098 | −1% |
| Metabolite - 4148 | GC-MS | 0.6245 | 0.8098 | 0% |
| Metabolite - 1323-possible-4-sulfobenzyl-alcohol-possible-p-cresol-sulfate | LC-MS | 0.6254 | 0.8098 | 16% |
| Metabolite - 4020 | GC-MS | 0.6272 | 0.8098 | 6% |
| Metabolite - 3517 | LC-MS | 0.6301 | 0.8098 | 52% |
| 2-keto-L-gulonic acid | GC-MS | 0.6321 | 0.8098 | 6% |
| 1-7-dihydro-6h-purin-6-one | LC-MS | 0.6322 | 0.8098 | −15% |
| D-alanyl-D-alanine | LC-MS | 0.6345 | 0.8098 | 7% |
| Metabolite - 4271 | GC-MS | 0.6345 | 0.8098 | −6% |
| Metabolite - 2151 | LC-MS | 0.6356 | 0.8098 | 25% |
| Glyceraldehydes | GC-MS | 0.6399 | 0.8098 | 38% |
| Metabolite - 1063 | LC-MS | 0.6407 | 0.8098 | 1% |
| Glycine | GC-MS | 0.6473 | 0.8098 | 9% |
| Serine | GC-MS | 0.6473 | 0.8098 | −4% |
| Metabolite - 2287 | LC-MS | 0.6516 | 0.8098 | 89% |
| n-dodecanoate | GC-MS | 0.6523 | 0.8098 | −13% |
| Metabolite - 1349 retired: Isobar 7 | LC-MS | 0.6523 | 0.8098 | −6% |
| Metabolite - 3165 | LC-MS | 0.6523 | 0.8098 | −4% |
| Metabolite - 2242 | LC-MS | 0.6538 | 0.8098 | 28% |
| Fructose | GC-MS | 0.6562 | 0.8098 | 14% |
| Mannitol | GC-MS | 0.6571 | 0.8098 | 38% |
| Metabolite - 2292 | LC-MS | 0.6574 | 0.8098 | 0% |
| Metabolite - 3100 | GC-MS | 0.6598 | 0.8098 | 22% |
| Metabolite - 3055 | LC-MS | 0.6611 | 0.8098 | −9% |
| N-acetylserotonin | GC-MS | 0.6625 | 0.8098 | −8% |
| Metabolite - 3101 | GC-MS | 0.6647 | 0.8098 | −1% |
| malic acid | LC-MS | 0.6728 | 0.8098 | −8% |
| Pyridoxamine | LC-MS | 0.6779 | 0.8098 | −3% |
| Lactate | LC-MS | 0.6779 | 0.8098 | −4% |
| Metabolite - 3317 | LC-MS | 0.6813 | 0.8098 | 222% |
| ethyl-3-indoleacetate | GC-MS | 0.683 | 0.8098 | 16% |
| 2-amino-butyrate | GC-MS | 0.6831 | 0.8098 | 1% |
| Isobar-1-includes-mannose-fructose-glucose-galactose-alpha-L-sorbopyranose-Inositol-D-allose | LC-MS | 0.6831 | 0.8098 | 5% |
| Glutamine | GC-MS | 0.6882 | 0.8098 | −8% |
| Metabolite - 2469 | LC-MS | 0.6882 | 0.8098 | −1% |
| 3-chloro-L-tyrosine | GC-MS | 0.6933 | 0.8098 | 1% |
| DOPA | GC-MS | 0.6933 | 0.8098 | 1% |
| Metabolite - 3132 | LC-MS | 0.6955 | 0.8098 | 0% |
| Metabolite - 2486 | LC-MS | 0.6986 | 0.8098 | 5% |
| Metabolite - 3707 | LC-MS | 0.6986 | 0.8098 | 20% |
| DL-homocysteine | LC-MS | 0.7031 | 0.8098 | 8% |
| Metabolite - 2567 | LC-MS | 0.7058 | 0.8098 | 2% |
| Metabolite - 2894 | LC-MS | 0.7086 | 0.8098 | −63% |
| Glycerol | GC-MS | 0.7091 | 0.8098 | −7% |
| Isobar-6-includes-valine-betaine | LC-MS | 0.7091 | 0.8098 | 5% |
| Metabolite - 4198 | GC-MS | 0.7091 | 0.8098 | −4% |

TABLE 8-continued

ALS Biomarkers from blood plasma samples- Wilcoxon's Rank Sum-Tests ALS vs. Control

| Name | Analytical Platform | p-value | q-value | % change in ALS |
|---|---|---|---|---|
| Metabolite - 2046 | LC-MS | 0.7143 | 0.8133 | 13% |
| Isobar-2-includes-3-amino-isobutyrate-2-amino-butyrate-4-aminobutanoic acid-dimethyiglycine-choline | LC-MS | 0.7267 | 0.8227 | 5% |
| 3-methoxy-L-tyrosine | GC-MS | 0.7269 | 0.8227 | 15% |
| hydroxyacetic acid | GC-MS | 0.7301 | 0.8238 | −2% |
| Dethiobiotin | GC-MS | 0.7354 | 0.827 | 0% |
| Metabolite - 2269 | LC-MS | 0.7407 | 0.827 | 4% |
| Metabolite - 2111 | LC-MS | 0.7425 | 0.827 | 24% |
| Metabolite - 3235 retired: DL-indole-3-lactic acid | LC-MS | 0.7459 | 0.827 | 3% |
| Possible-Isobar-DL-aspartic acid--aspartate | GC-MS | 0.7461 | 0.827 | −10% |
| Metabolite - 2250 | LC-MS | 0.7547 | 0.8306 | 2% |
| 5-oxoproline | GC-MS | 0.7568 | 0.8306 | −2% |
| Metabolite - 3952 | LC-MS | 0.7568 | 0.8306 | 3% |
| Metabolite - 3138 | LC-MS | 0.7582 | 0.8306 | 11% |
| Metabolite - 4012 | GC-MS | 0.7674 | 0.8377 | 5% |
| Metabolite - 3085 retired: inositol | GC-MS | 0.7691 | 0.8377 | 4% |
| Allantoin | LC-MS | 0.7726 | 0.8391 | −3% |
| Histidine | GC-MS | 0.7783 | 0.8428 | −7% |
| Octopamine | GC-MS | 0.7837 | 0.8439 | −2% |
| N-N-dimethylarginine | LC-MS | 0.7869 | 0.8439 | −8% |
| Metabolite - 3102 | GC-MS | 0.789 | 0.8439 | −7% |
| Metabolite - 2047 | LC-MS | 0.7891 | 0.8439 | 8% |
| alpha-L-sorbopyranose | GC-MS | 0.7906 | 0.8439 | 2% |
| Arabinose | GC-MS | 0.7966 | 0.8479 | 0% |
| decanoic acid | GC-MS | 0.7999 | 0.8482 | 10% |
| Metabolite - 2989 | GC-MS | 0.8014 | 0.8482 | −12% |
| Metabolite - 3992 | LC-MS | 0.8163 | 0.8616 | −1% |
| Valine | GC-MS | 0.8218 | 0.8649 | 7% |
| Metabolite - 1926 retired: trans-2,3,4-trimethoxycinnamic acid | LC-MS | 0.8246 | 0.8655 | −5% |
| Metabolite - 2563 retired: lactate | LC-MS | 0.8327 | 0.8698 | −1% |
| Metabolite - 3781 retired: Na adduct of Isobar 21 | LC-MS | 0.8382 | 0.8698 | 5% |
| Glucarate | GC-MS | 0.8435 | 0.8698 | 4% |
| Leucine | GC-MS | 0.8437 | 0.8698 | 3% |
| N-acetyl-L-alanine | GC-MS | 0.8437 | 0.8698 | 3% |
| Metabolite - 1834 | LC-MS | 0.8449 | 0.8698 | −27% |
| Metabolite - 3081 | GC-MS | 0.8533 | 0.8738 | 4% |
| Isocitrate | LC-MS | 0.8558 | 0.8738 | 1% |
| Metabolite - 1342-possible-phenylacetylglutamine-or-formyl-N-acetyl-5-methoxykynurenamine | LC-MS | 0.8558 | 0.8738 | 14% |
| Glycerate | LC-MS | 0.8603 | 0.8746 | 3% |
| guanidineacetic acid | LC-MS | 0.8645 | 0.8746 | −5% |
| Metabolite - 1110 | LC-MS | 0.8657 | 0.8746 | 1% |
| Metabolite - 3020 retired: threonic acid | GC-MS | 0.8658 | 0.8746 | 2% |
| Tryptophan | LC-MS | 0.8714 | 0.8778 | 0% |
| Metabolite - 4360 | GC-MS | 0.8767 | 0.8796 | −14% |
| Metabolite - 1465 | LC-MS | 0.8778 | 0.8796 | 3% |
| Succinate | GC-MS | 0.8821 | 0.8796 | 1% |
| Metabolite - 2774 | LC-MS | 0.8825 | 0.8796 | −6% |
| hippuric acid | LC-MS | 0.888 | 0.8828 | 6% |
| Metabolite - 1329 | LC-MS | 0.8965 | 0.8845 | 5% |
| Metabolite - 4032 retired: lysine | GC-MS | 0.8981 | 0.8845 | −16% |
| Metabolite - 3129 | LC-MS | 0.8992 | 0.8845 | −1% |
| palmitoleic acid | GC-MS | 0.9047 | 0.8861 | −17% |
| Dopamine | GC-MS | 0.9102 | 0.8861 | −3% |
| Metabolite - 4251 | GC-MS | 0.9159 | 0.8861 | 1% |
| Metabolite - 4003 | LC-MS | 0.9167 | 0.8861 | −15% |
| 5-hydroxyindoleacetate | GC-MS | 0.9172 | 0.8861 | 11% |
| Metabolite - 1736 retired: p-hydroxybenzaldehyde | LC-MS | 0.9207 | 0.8861 | 12% |
| Isoleucine | GC-MS | 0.9215 | 0.8861 | 2% |
| Metabolite - 1286 | LC-MS | 0.9215 | 0.8861 | 0% |
| Metabolite - 3178 retired: NH3 adduct of citric acid | LC-MS | 0.9221 | 0.8861 | −1% |
| Metabolite - 4084 | GC-MS | 0.9271 | 0.8867 | −9% |
| Metabolite - 3450 retired: 1-methylnicotinamide | LC-MS | 0.929 | 0.8867 | 2% |
| Metabolite - 1914 | LC-MS | 0.9359 | 0.8867 | 11% |
| Metabolite - 3708 | LC-MS | 0.9383 | 0.8867 | 4% |
| Metabolite - 4055 | GC-MS | 0.9383 | 0.8867 | 11% |
| Metabolite - 3014 retired: meso-erythritol | GC-MS | 0.9439 | 0.8867 | −2% |

TABLE 8-continued

ALS Biomarkers from blood plasma samples- Wilcoxon's Rank Sum-Tests ALS vs. Control

| Name | Analytical Platform | p-value | q-value | % change in ALS |
|---|---|---|---|---|
| glyceric acid | GC-MS | 0.9495 | 0.8867 | −2% |
| Metabolite - 4362 | GC-MS | 0.9495 | 0.8867 | 10% |
| 3-phospho-d-glycerate | LC-MS | 0.9549 | 0.8867 | −1% |
| Metabolite - 3807 | LC-MS | 0.9551 | 0.8867 | −4% |
| Metabolite - 2026 | LC-MS | 0.9554 | 0.8867 | −5% |
| Aspartate | LC-MS | 0.9663 | 0.8867 | 3% |
| Metabolite - 3065 retired: 1,5-anhydro-d-glucitol | GC-MS | 0.9663 | 0.8867 | 10% |
| Histamine | LC-MS | 0.9719 | 0.8867 | 2% |
| Metabolite - 3900 | LC-MS | 0.9719 | 0.8867 | 0% |
| Metabolite - 3668 | LC-MS | 0.9761 | 0.8867 | 32% |
| tetradecanoic acid | GC-MS | 0.9775 | 0.8867 | −11% |
| Metabolite - 2056 | LC-MS | 0.9775 | 0.8867 | 3% |
| Metabolite - 2370 | LC-MS | 0.9775 | 0.8867 | 4% |
| Metabolite - 2694 retired: lactate | LC-MS | 0.9775 | 0.8867 | −3% |
| Metabolite - 1209 | LC-MS | 0.9823 | 0.8867 | 4% |
| ascorbic acid | LC-MS | 0.9831 | 0.8867 | −12% |
| L-alpha-glycerophosphorylcholine | LC-MS | 0.9832 | 0.8867 | 0% |
| Metabolite - 3094 | GC-MS | 0.9832 | 0.8867 | 0% |
| Metabolite - 1458 retired: hypoxanthine | LC-MS | 0.988 | 0.8867 | 3% |
| Metabolite - 1111-possible-methylnitronitrosoguanidine-or-ethyl-thiocarbamoylacetate | LC-MS | 0.9888 | 0.8867 | 0% |
| Metabolite - 2389 | LC-MS | 0.9888 | 0.8867 | −12% |
| Metabolite - 1597 | LC-MS | 0.9944 | 0.8883 | 1% |
| Metabolite - 2027 | LC-MS | 1 | 0.8883 | 0% |
| Metabolite - 2898 | LC-MS | 1 | 0.8883 | 21% |
| Metabolite - 3314 | LC-MS | 1 | 0.8883 | 3% |

Example 4

Caffeine and Caffeine Metabolites in ALS Patients and in Healthy Control Individuals Metabolomic analysis of two independent ALS studies was carried out to assess the changes of metabolite levels in plasma from ALS patients relative to healthy control subjects. Thirty-one healthy control volunteers and 31 participants with ALS enrolled in Study 1. Study 2 was comprised of ninety-nine participants with ALS and 94 healthy volunteers. All research participants provided informed consent. A board-certified neurologist reviewed and confirmed diagnosis for all participants. Data on gender, age, weight, and medications was collected. For participants with ALS, date and site of symptom onset, date of diagnosis, and family history of ALS was recorded. Healthy control subjects were defined by the absence of a known neurological disorder.

Table 9 lists the results of T-test analysis between levels of caffeine and caffeine metabolites (i.e., 1,7-dimethylxanthine, theobromine, and theophylline) in plasma samples from ALS patients as compared to plasma samples from healthy control subjects. The mean levels of caffeine and caffeine metabolites were lower in the ALS patients compared to the healthy control volunteers (Table 9).

The difference in levels is highly statistically significant with the p-value of 0.001 or lower, with the exception of theobromine where the p-value is 0.0591. In addition, the q-value, a measure of the false discovery rate, is also significant, with all values lower than 0.1 with the exception of theobromine where the q-value is 0.3478.

TABLE 9

Levels of Caffeine and Caffeine Metabolites in ALS Patients Compared to Control Subjects.

| COMPOUND | Library | p-value | q-value | Higher Mean | % Change in ALS |
|---|---|---|---|---|---|
| Caffeine | LC-MS | 0.001 | 0.0349 | Control | −73% |
| 1-7-dimethylxanthine | LC-MS | 0.001 | 0.0349 | Control | −50% |
| Theobromine | LC-MS | 0.0591 | 0.3478 | Control | −42% |
| Theophylline | LC-MS | 4.00E−04 | 0.0245 | Control | −58% |

Example 5

Xenobiotic Metabolism in ALS Patients

As shown in Table 9, ALS patients have lower levels of caffeine than control subjects. This may be due to lower caffeine intake in ALS patients. Alternatively it may indicate increased activity of enzymes that metabolize xenobiotics (e.g. CYP1A2).

A measure of caffeine clearance rate is reflected in the ratio of caffeine metabolites to caffeine. A higher ratio is observed in both the ratios of P/C and T/C for ALS patients than for control individuals (Table 10). This indicates that ALS patients may metabolize caffeine more rapidly than healthy control subjects (rather than indicating lower caffeine intake in ALS patients). Further, subjects with ALS may generally metabolize xenobiotics differently than healthy individuals or individuals suffering from illnesses that have symptoms similar to ALS symptoms.

For example, the rate of caffeine clearance is used to measure the activity of CYP1A2, an inducible Cytochrome P450 enzyme in the liver that metabolizes xenobiotics, including caffeine. Rapid metabolism of caffeine is associated with "pathological detoxifiers" because the products of the P450s include toxins and free radicals. The Phase II conjugation reactions further metabolize these products turning them into less toxic, water soluble compounds that can be excreted. Possibly an overactive xenobiotic metabolizing process (e.g. hepatic P450 enzyme system) and/or an under active Phase II detoxification process may contribute to the etiology of ALS and provide a target for drug discovery and therapeutic intervention.

TABLE 10

Ratios of Caffeine Metabolites to Caffeine in plasma from Control subjects and ALS subjects

| Subject Group | Paraxanthine/Caffeine (P/C) Ratio | Theophylline/Caffeine (T/C) Ratio |
|---|---|---|
| Control | 0.8214 | 0.8857 |
| ALS | 1.5000 | 1.3684 |

In a metabolomics demographic study of plasma from 270 healthy volunteers the levels of both caffeine and the metabolite paraxanthine increase with age (Table 11). However, the P/C ratio is essentially the same in the younger 2 age groups and is lower in the oldest age group (Table 11). This older age group is the group that is similar in age to the ALS patients and control subjects for the ALS studies.

TABLE 11

Ratios of Caffeine Metabolites to Caffeine in Plasma from Normal Adults of Various Ages.

|  | 25-35 | 36-50 | 51-65 |
|---|---|---|---|
| Paraxanthine | 0.32 | 0.69 | 0.81 |
| Caffeine | 0.28 | 0.67 | 1.15 |
| Paraxanthine/Caffeine (P/C) Ratio | 1.1467 | 1.0358 | 0.7105 |

Example 6

Caffeine and Caffeine Metabolites in ALS Patients and in Patients with Symptoms Similar to ALS Metabolomic analysis was carried out to assess the changes of metabolite levels in plasma from ALS patients relative to patients with peripheral neuropathy or myopathy, two neurodegenerative diseases that have symptoms similar to those of ALS. The study was comprised of 99 participants with ALS, 36 participants with myopathy, and 52 participants with peripheral neuropathy. All research participants provided informed consent. A board-certified neurologist reviewed and confirmed diagnosis for all participants. Data on gender, age, weight, and medications was collected. For participants with ALS, date and site of symptom onset, date of diagnosis, and family history of ALS was recorded.

Table 12 lists the results of T-test analysis between levels of caffeine and paraxanthine in plasma samples from (1) ALS patients as compared to plasma samples from peripheral neuropathy patients as well as (2) ALS patients as compared to plasma samples from myopathy patients. The mean levels of caffeine and caffeine metabolites (Table 12) were shown to be lower in the ALS patients compared to the patients with peripheral neuropathy (PN) or myopathy. The difference in levels is statistically significant with the p-value of 0.05. In addition, the q-value, a measure of the false discovery rate, is also significant, especially for the individuals with PN.

TABLE 12

Lower Caffeine and Paraxanthine Levels in Plasma from ALS Patients Compared to Plasma from Patients with Myopathy or Peripheral Neuropathy.

| | ALS vs. Peripheral Neuropathy | | | ALS vs. Myopathy | | |
|---|---|---|---|---|---|---|
| Compound | p-value | q-value | ALS/PN | p-value | q-value | ALS/myopathy |
| Caffeine | 0.0193 | 0.0816 | 0.60 | 0.0066 | 0.1489 | 0.38 |
| Paraxanthine | 0.0348 | 0.1017 | 0.68 | 0.0427 | 0.4519 | 0.57 |

Example 7

Xenobiotic Metabolism in Neurodegenerative Diseases with Symptoms Similar to Symptoms of ALS Lower caffeine and caffeine metabolite levels in ALS than in myopathy or PN are possibly due to lower caffeine intake, but may also be the result of a higher rate of caffeine metabolism. One well-characterized system for caffeine metabolism is the Phase I detoxification system carried out in the liver by cytochrome P450 enzymes.

Table 13 lists the mean levels of paraxanthine and caffeine as well as the paraxanthine/caffeine ratio in plasma samples from subjects having ALS, subjects having peripheral neuropathy, and subjects having myopathy. Ratios of caffeine metabolites to caffeine are higher in ALS patients compared to the subjects with diseases with similar symptoms (i.e., PN and myopathy) (Table 13). The difference in ratios is more pronounced when ALS is compared to PN. Thus, the data indicates higher levels and/or higher activity of CYP1A2 and/or similar xenobiotic metabolizing enzymes in ALS patients (rather than suggesting lower caffeine intake) as compared to normal levels and/or activity of CYP1A2 and/or similar xenobiotic metabolizing enzymes in patients having diseases with related symptoms. This result supports the idea that caffeine and/or xenobiotic metabolism (e.g. enzyme levels and/or activity of CYP1A2 and/or other similar enzyme systems) is altered in ALS. Thus, the metabolism of caffeine provides a useful way to distinguish ALS patients from patients with similar symptoms to ALS.

TABLE 13

Ratios of the Caffeine Metabolite Paraxanthine to Caffeine in Plasma from Patients with ALS, Myopathy or Peripheral Neuropathy.

| | ALS | PN | Myopathy |
|---|---|---|---|
| Paraxanthine | 0.68 | 0.02 | 1.20 |
| Caffeine | 0.92 | 0.72 | 2.44 |
| Paraxanthine/Caffeine Ratio | 0.7389 | 0.0294 | 0.4900 |

Example 8e

Biomarkers for Differentiating ALS from Other Neurodegenerative Diseases

Metabolomic analysis was carried out to assess the changes of metabolite levels in ALS patients relative to patients with peripheral neuropathy or myopathy, two neurodegenerative diseases that have symptoms similar to those of ALS.

Table 14 below lists the biomarkers that were discovered that distinguish ALS subjects from subjects with peripheral neuropathy.

Table 15 below lists the biomarkers that were discovered that distinguish ALS subjects from myopathy subjects.

Tables 14 and 15 include, for each listed biomarker, the p-value and the q-value determined in the statistical analysis of the data concerning the biomarkers and an indication of the median level of each biomarker in the control, ALS, peripheral neuropathy (Table 14), and myopathy (Table 15) samples. The term "Isobar" as used in the tables indicates the compounds that could not be distinguished from each other on the analytical platform used in the analysis (i.e., the compounds in an isobar elute at nearly the same time and have similar (and sometimes exactly) quant ions, and thus cannot be distinguished).

TABLE 14

Biomarkers that distinguish ALS subjects from subjects with Peripheral Neuropathy (PN).

| Metabolite | p-value | q-value | Control | ALS | PN |
|---|---|---|---|---|---|
| Aspartate | 2.36E−05 | 0.0009 | 0.97 | 0.97 | 1.18 |
| Isobar citric acid-isocitrate | 0.0001 | 0.0025 | 0.98 | 0.85 | 1.08 |
| p-hydroxyphenyllactate | 0.0001 | 0.0025 | 1.02 | 0.80 | 1.12 |
| Alanine | 0.0001 | 0.0025 | 0.98 | 0.84 | 1.09 |
| Isobar lysine-tyramine-putrescine | 0.0001 | 0.0027 | 0.83 | 0.70 | 1.00 |
| Histamine | 0.0003 | 0.0058 | 1.00 | 0.89 | 1.06 |
| Creatinine | 0.0008 | 0.0114 | 1.03 | 0.91 | 1.03 |
| 3-hydroxybutanoic acid | 0.001 | 0.0123 | 0.93 | 1.53 | 0.83 |
| N-6-trimethyl-1-lysine | 0.0010 | 0.0123 | 1.05 | 0.87 | 1.05 |
| Inosine | 0.0015 | 0.0150 | 1.09 | 1.08 | 0.83 |
| Proline | 0.0015 | 0.0150 | 0.95 | 0.81 | 1.15 |
| Adenosine | 0.0021 | 0.0169 | 0.92 | 0.93 | 0.63 |
| Arachidonic acid | 0.0022 | 0.0169 | 0.20 | 0.68 | 0.20 |
| Paraxanthine | 0.0032 | 0.0227 | 1.14 | 0.27 | 0.98 |
| Guanosine | 0.0051 | 0.0285 | 1.00 | 1.00 | 0.73 |
| Malic acid | 0.0051 | 0.0285 | 0.90 | 0.91 | 1.11 |
| Threonine | 0.0053 | 0.0285 | 0.99 | 0.82 | 1.04 |
| Oleic acid | 0.0062 | 0.0315 | 1.00 | 1.23 | 0.91 |
| Tetradecanoic acid | 0.0083 | 0.0351 | 0.99 | 1.09 | 0.82 |
| Caffeine | 0.0084 | 0.0351 | 1.34 | 0.43 | 0.93 |
| 3-phospho-d-glycerate | 0.0102 | 0.0392 | 0.80 | 0.36 | 0.98 |
| Citrulline | 0.0114 | 0.0413 | 0.38 | 0.01 | 0.81 |
| Palmitoleic acid | 0.0120 | 0.0428 | 1.02 | 1.23 | 0.90 |
| Palmitate | 0.0128 | 0.0445 | 0.99 | 1.10 | 0.96 |
| alpha-Hydroxyisobutyric acid | 0.0134 | 0.0451 | 0.99 | 1.09 | 0.93 |
| Arginine | 0.0176 | 0.0557 | 1.02 | 0.78 | 0.92 |
| 3-hydroxypropanoate | 0.0180 | 0.0550 | 0.84 | 0.98 | 0.86 |
| Valine | 0.0194 | 0.0568 | 0.97 | 0.83 | 1.00 |
| Uric acid | 0.0197 | 0.0568 | 1.10 | 0.99 | 1.29 |
| N-formyl-L-glycine | 0.0218 | 0.0594 | 0.12 | 0.12 | 0.56 |
| Glutarate | 0.0315 | 0.0783 | 1.04 | 0.87 | 1.01 |
| Kynurenine | 0.0372 | 0.0860 | 0.97 | 0.98 | 1.05 |

TABLE 15

Biomarkers that distinguish ALS from Myopathy

| Metabolite | p-value | q-value | Median Control | Median ALS | Median Myopathy |
|---|---|---|---|---|---|
| Isobar citric acid-isocitrate | 0.0005 | 0.0354 | 0.98 | 0.85 | 1.16 |
| Caffeine | 0.0055 | 0.2132 | 1.34 | 0.43 | 1.04 |
| Aspartate | 0.0090 | 0.2425 | 0.97 | 0.97 | 1.06 |
| Kynurenine | 0.0132 | 0.3076 | 0.97 | 0.98 | 1.12 |
| 3-hydroxybutanoic acid | 0.0173 | 0.3377 | 0.93 | 1.53 | 0.92 |
| Glutarate | 0.0249 | 0.3377 | 1.04 | 0.87 | 1.07 |
| uric acid | 0.0290 | 0.3605 | 1.10 | 0.99 | 1.26 |
| Dulcitol | 0.0318 | 0.3729 | 0.94 | 0.40 | 1.00 |
| Palmitate | 0.0337 | 0.3729 | 0.99 | 1.10 | 0.89 |
| selenocystine | 0.0375 | 0.3729 | 0.99 | 0.92 | 1.06 |
| N-acetyl-L-glutamine | 0.0389 | 0.3764 | 1.03 | 1.05 | 1.35 |
| Threonine | 0.0496 | 0.4298 | 0.99 | 0.82 | 0.99 |

Example 9

Biomarkers for Disease Progression

As listed below in Tables 16, 17 and 18, biomarkers were discovered that were differentially present among samples from ALS subjects over the course of the disease that indicate the progression of the disease. Tables 16, 17, and 18 include, for each listed biomarker and non-biomarker compound, the p-value and the q-value determined in the statistical analysis of the data concerning the biomarkers. Throughout the tables, the column heading "LIB_ID" indicates the analytical platform used to measure the level of the compound. The number "61" indicates that the levels of those compounds were measured using LC-MS, and the number "50" indicates that the levels of those compounds were measured using GC-MS. The term "Isobar" as used in the tables indicates the compounds that could not be distinguished from each other on the analytical platform used in the analysis (i.e., the compounds in an isobar elute at nearly the same time and have similar (and sometimes exactly the same) quant ions, and thus cannot be distinguished).

Non-biomarker compounds identified in the analyses are also listed in the Tables 16, 17 and 18 below as those compounds having a slope of 0 and/or a percentage change over time of 0%.

Biomarkers were discovered by (1) analyzing plasma samples from human subjects with ALS at various times to determine the levels of metabolites in the samples and then (2) statistically analyzing the results to determine those metabolites that are differentially present at various time points. As listed below in Tables 16-18, biomarkers were discovered that were differentially present in samples from ALS subjects early in the disease compared to samples collected at later times when the disease severity had progressed. The metabolite changes were also evaluated relative to changes in the Forced Vital Capacity (FVC), a clinical measurement that indicates disease severity. As the disease progresses the FVC measurement decreases. The most severely affected ALS patients have the lowest FVC scores.

The plasma samples used for the analysis were collected from 40 ALS subjects at several times during the course of the disease. Samples were collected early (screening/month 0 and/or month 1), at 6 months after screening, and at 12 months after screening. After the levels of metabolites were determined, the data from the subjects was analyzed using random coefficient regression analysis and T-tests.

For the initial random coefficient regression analysis, a random coefficient regression (Little, R., Milliken G., Stroup, W., Wolfinger, R. (1996) SAS System for Mixed Models, Chapter 7, SAS® Institute, Cary, N.C.) was first performed for each compound. This model allows for different intercepts and different slopes for each subject with a common intercept and slope across all subjects. The analysis tests whether or not the common slope is zero. The x-variable was the month, which had possible values of 0, 1, 6, and 12. The results of this analysis are shown in Table 16. If the slope is positive, it means the level of the compound increased over time; likewise, if the slope is negative, it means the level of the compound decreased over time.

Another random coefficient regression was performed for each compound on the FVC (forced vital capacity). The x-values were the average FVC values since the original FVC values were measured in triplicate per time point. The 40 patients used in the initial analysis were also used for this random coefficient regression analysis. The results are shown in Table 17. A positive slope means that the compound was positively correlated with FVC (i.e., as FVC increased, the compound increased or as FVC decreased, the compound decreased). A negative slope indicates that as the FVC increased, the compound decreased (or vice-versa).

A T-test was performed by comparing the levels of the compounds in the samples collected at month 1 to the levels of the compounds in the samples at month 12. All patients with both the 1 month and 12 month time points were included in the analysis (37 patients total). The standard matched-pairs T-test was used to perform this analysis. The results are shown in Table 18. The table includes, for each listed biomarker and non-biomarker compound, an indication of the percentage difference in the mean level at 1 month after screening as compared to the mean level at 12 months after screening, where a positive percentage change indicates that there was an increase in the metabolite level as the disease progressed and a negative percentage change indicates that there was a decrease in the metabolite level as the disease progressed.

TABLE 16

Random Coefficient Regression Analysis Over Time

| COMPOUND | LIB_ID | p-value | q-value | SLOPE |
|---|---|---|---|---|
| Metabolite - 3073 | 50 | 5.93E−08 | 1.09E−05 | −0.020 |
| gamma-L-glutamyl-L-tyrosine | 61 | 1.15E−05 | 0.0011 | −0.019 |
| Metabolite - 3183-possible-gamma-L-glutamyl-L-phenylalanine | 61 | 3.21E−05 | 0.0020 | −0.017 |
| Metabolite - 6246 | 50 | 5.36E−05 | 0.0025 | −0.011 |
| inositol-1-phosphate | 50 | 9.40E−05 | 0.0035 | −0.026 |
| Metabolite - 1208 | 61 | 0.0005 | 0.0139 | −0.049 |
| methionine-sulfoxide | 61 | 0.0007 | 0.0139 | −0.023 |
| Metabolite - 4275 | 50 | 0.0007 | 0.0139 | 0.029 |
| Metabolite - 3078 | 50 | 0.0008 | 0.0139 | 0.028 |
| Metabolite - 3088 | 50 | 0.0008 | 0.0139 | −0.027 |
| Metabolite - 3026 | 50 | 0.0008 | 0.0139 | −0.015 |
| O-acetyl-L-carnitine-hydrochloride | 61 | 0.0009 | 0.0139 | 0.027 |
| Isobar-22-includes-glutamic acid-O-acetyl-L-serine | 61 | 0.0011 | 0.0151 | −0.012 |
| Metabolite - 5233 | 61 | 0.0012 | 0.0151 | −0.043 |
| gamma-glu-leu | 61 | 0.0014 | 0.0173 | −0.015 |
| Metabolite - 3098 | 50 | 0.0015 | 0.0174 | −0.014 |
| Metabolite - 3022 | 50 | 0.0018 | 0.0194 | −0.010 |
| Metabolite - 2567 | 61 | 0.0021 | 0.0214 | −0.014 |
| Arginine | 61 | 0.0024 | 0.0231 | −0.019 |
| Metabolite - 3143 | 61 | 0.0026 | 0.0238 | −0.049 |
| hippuric acid | 61 | 0.0029 | 0.0251 | −0.040 |
| Metabolite - 3114 | 50 | 0.0032 | 0.0267 | −0.035 |
| Metabolite - 5976 | 61 | 0.0036 | 0.0278 | −0.043 |
| Metabolite - 3019 | 50 | 0.0037 | 0.0278 | −0.008 |
| Metabolite - 3025 | 50 | 0.0038 | 0.0278 | −0.012 |
| Metabolite - 7050 | 61 | 0.0047 | 0.0331 | −0.024 |
| N-6-trimethyl-l-lysine | 61 | 0.0053 | 0.0362 | −0.022 |
| Metabolite - 4769 | 50 | 0.0058 | 0.0384 | 0.021 |
| Glutamine | 50 | 0.0062 | 0.0396 | 0.049 |
| Metabolite - 4627 | 61 | 0.0065 | 0.0400 | −0.041 |
| 4-Guanidinobutanoic acid | 61 | 0.0073 | 0.0431 | −0.016 |
| Metabolite - 5346 | 50 | 0.0075 | 0.0431 | −0.015 |
| Metabolite - 2688 | 61 | 0.0085 | 0.0473 | −0.017 |
| Metabolite - 5907 | 50 | 0.0089 | 0.0481 | −0.013 |
| Metabolite - 7009 | 61 | 0.0096 | 0.0503 | −0.017 |
| Metabolite - 3830 | 61 | 0.0104 | 0.0503 | −0.037 |
| Thyroxine | 61 | 0.0105 | 0.0503 | 0.025 |
| Isobar-8-includes-anthranilic acid-salicylamide | 61 | 0.0105 | 0.0503 | −0.021 |
| Metabolite - 3077 | 50 | 0.0109 | 0.0503 | −0.012 |
| Metabolite - 2546 | 61 | 0.0109 | 0.0503 | −0.061 |
| Metabolite - 3109 | 50 | 0.0121 | 0.0531 | −0.027 |
| Metabolite - 6326 | 50 | 0.0121 | 0.0531 | −0.007 |
| glyceric acid | 50 | 0.0137 | 0.0581 | −0.014 |
| Metabolite - 2005 | 61 | 0.0140 | 0.0581 | 0.028 |
| Metabolite - 2319 | 61 | 0.0142 | 0.0581 | −0.022 |
| Methionine | 61 | 0.0149 | 0.0594 | 0.046 |
| 1-7-dimethylxanthine | 61 | 0.0152 | 0.0594 | −0.025 |
| Isobar-19-includes-D-saccharic acid-1,5-anhydro-D-glucitol-2'-deoxy-D-galactose-2'-deoxy-D-glucose-L-fucose-L-rhamnose | 61 | 0.0175 | 0.0671 | 0.014 |
| Creatinine | 61 | 0.0194 | 0.0730 | −0.016 |
| Metabolite - 1988 | 61 | 0.0202 | 0.0743 | −0.020 |
| 3-methyl-L-histidine | 61 | 0.0217 | 0.0765 | −0.013 |
| Tyrosine | 61 | 0.0219 | 0.0765 | −0.008 |

TABLE 16-continued

Random Coefficient Regression Analysis Over Time

| COMPOUND | LIB_ID | p-value | q-value | SLOPE |
|---|---|---|---|---|
| Metabolite - 6907 | 50 | 0.0221 | 0.0765 | −0.012 |
| Biotin | 61 | 0.0234 | 0.0797 | −0.028 |
| Metabolite - 4511 | 50 | 0.0255 | 0.0854 | −0.011 |
| Metabolite - 5887 | 61 | 0.0265 | 0.0871 | −0.094 |
| Arabinose | 50 | 0.0273 | 0.0881 | −0.016 |
| Metabolite - 3012 | 50 | 0.0280 | 0.0887 | −0.005 |
| Metabolite - 1206-possible-methyltestosterone-and-others | 61 | 0.0294 | 0.0917 | −0.029 |
| Metabolite - 7089 | 61 | 0.0323 | 0.0990 | −0.012 |
| Metabolite - 4252 | 50 | 0.0339 | 0.1002 | −0.024 |
| D-quinic acid | 50 | 0.0343 | 0.1002 | −0.045 |
| Metabolite - 5349 | 50 | 0.0343 | 0.1002 | −0.005 |
| Metabolite - 3138 | 61 | 0.0360 | 0.1033 | −0.017 |
| Metabolite - 3094 | 50 | 0.0375 | 0.1060 | −0.012 |
| DL-pipecolic acid | 61 | 0.0385 | 0.1071 | −0.015 |
| Metabolite - 5086 | 61 | 0.0456 | 0.1250 | 0.022 |
| Metabolite - 1111-possible-methylnitronitrosoguanidine-or-ethyl-thiocarbamoylacetate | 61 | 0.0489 | 0.1323 | 0.019 |
| Metabolite - 3783 | 61 | 0.0521 | 0.1387 | 0.013 |
| Metabolite - 5728 | 61 | 0.0530 | 0.1391 | −0.027 |
| Metabolite - 1092 | 61 | 0.0557 | 0.1442 | −0.047 |
| Metabolite - 6955 | 50 | 0.0593 | 0.1480 | −0.011 |
| Metabolite - 3653-Possible-stachydrine | 61 | 0.0594 | 0.1480 | −0.072 |
| Mannose | 50 | 0.0603 | 0.1480 | 0.009 |
| Metabolite - 4611 | 50 | 0.0607 | 0.1480 | −0.008 |
| Metabolite - 1911 | 61 | 0.0612 | 0.1480 | −0.022 |
| Oleic-Acid | 50 | 0.0683 | 0.1629 | 0.019 |
| beta-hydroxypyruvic acid | 50 | 0.0743 | 0.1734 | 0.010 |
| Metabolite - 7846 | 50 | 0.0745 | 0.1734 | −0.014 |
| Metabolite - 3951 | 61 | 0.0772 | 0.1773 | 0.009 |
| 1-methyl-guanidine | 50 | 0.0896 | 0.1969 | −0.006 |
| Histamine | 61 | 0.0903 | 0.1969 | 0.017 |
| Metabolite - 6272 | 50 | 0.0905 | 0.1969 | −0.014 |
| Metabolite - 1656 | 61 | 0.0907 | 0.1969 | 0.018 |
| Metabolite - 1127 | 61 | 0.0929 | 0.1969 | 0.012 |
| 1,5-anhydro-D-glucitol | 50 | 0.0931 | 0.1969 | −0.005 |
| Lactate | 50 | 0.0932 | 0.1969 | 0.018 |
| Metabolite - 6346 | 50 | 0.0960 | 0.2004 | −0.006 |
| (p-Hydroxyphenyl)lactic acid | 50 | 0.1024 | 0.2115 | −0.012 |
| Metabolite - 1286 | 61 | 0.1038 | 0.2119 | 0.009 |
| Metabolite - 4586 | 61 | 0.1144 | 0.2283 | 0.009 |
| Metabolite - Metabolite - 5982 retired: 1-oleoyl-rac glycerol | 50 | 0.1153 | 0.2283 | −0.018 |
| Metabolite - 2139 | 61 | 0.1155 | 0.2283 | 0.011 |
| Hypoxanthine | 61 | 0.1196 | 0.2339 | 0.141 |
| Metabolite - 4351 | 61 | 0.1261 | 0.2439 | 0.011 |
| L-alpha-glycerophosphorylcholine | 61 | 0.1290 | 0.2469 | −0.028 |
| Metabolite - 1345 | 61 | 0.1312 | 0.2487 | −0.016 |
| alpha-tocopherol | 50 | 0.1332 | 0.2499 | −0.046 |
| Metabolite - 4767 | 50 | 0.1382 | 0.2552 | −0.005 |
| Metabolite - 1086 | 61 | 0.1398 | 0.2552 | −0.036 |
| Metabolite - 3707 | 61 | 0.1402 | 0.2552 | 0.047 |
| Metabolite - 1819 | 61 | 0.1416 | 0.2553 | −0.011 |
| Metabolite - 3030 | 50 | 0.1466 | 0.2603 | −0.005 |
| Metabolite - 6711 | 61 | 0.1473 | 0.2603 | 0.011 |
| Inosine | 61 | 0.1581 | 0.2768 | 0.060 |
| Caffeine | 61 | 0.1615 | 0.2778 | −0.030 |
| Metabolite - 2168 | 61 | 0.1617 | 0.2778 | 0.005 |
| N-5-aminocarbonyl-L-ornithine | 50 | 0.1702 | 0.2873 | −0.010 |
| Isobar-21-includes-gamma-aminobutyryl-L-histidine-L-anserine | 61 | 0.1717 | 0.2873 | 0.005 |
| Glycine | 50 | 0.1720 | 0.2873 | 0.070 |
| Metabolite - 2568 | 61 | 0.1737 | 0.2876 | −0.019 |
| Metabolite - 3033-possible-threonine-deriv | 50 | 0.1820 | 0.2987 | −0.004 |
| Metabolite - 3044 | 61 | 0.1856 | 0.2993 | 0.018 |
| Metabolite - 5247 | 61 | 0.1881 | 0.2993 | 0.010 |
| Metabolite - 4020 | 50 | 0.1887 | 0.2993 | −0.007 |
| Metabolite - 2390 | 61 | 0.1911 | 0.2993 | −0.011 |
| Tryptophan | 61 | 0.1916 | 0.2993 | −0.004 |
| Eythrose | 50 | 0.1921 | 0.2993 | −0.010 |
| pantothenic acid | 61 | 0.1947 | 0.3000 | 0.057 |
| Serine | 50 | 0.1959 | 0.3000 | 0.026 |
| Metabolite - 1975 | 61 | 0.1995 | 0.3031 | −0.038 |
| Metabolite - 2074 | 61 | 0.2165 | 0.3236 | −0.025 |
| Riboflavine | 61 | 0.2225 | 0.3249 | −0.024 |

TABLE 16-continued

Random Coefficient Regression Analysis Over Time

| COMPOUND | LIB_ID | p-value | q-value | SLOPE |
| --- | --- | --- | --- | --- |
| Metabolite - 3131 retired: N4 adduct of indole-3-acetic acid | 61 | 0.2230 | 0.3249 | −0.007 |
| Metabolite - 3052 | 61 | 0.2241 | 0.3249 | −0.010 |
| n-dodecanoate | 50 | 0.2245 | 0.3249 | −0.018 |
| Cholesterol | 50 | 0.2322 | 0.3334 | −0.004 |
| arachidonic acid | 50 | 0.2357 | 0.3358 | −0.006 |
| Praline | 61 | 0.2396 | 0.3376 | −0.004 |
| Metabolite - 2109 | 61 | 0.2406 | 0.3376 | −0.007 |
| Metabolite - 5791 | 61 | 0.2543 | 0.3541 | 0.033 |
| Metabolite - 6347 | 50 | 0.2580 | 0.3546 | −0.009 |
| Metabolite - 5788 | 61 | 0.2615 | 0.3546 | −0.038 |
| Inositol | 50 | 0.2632 | 0.3546 | −0.005 |
| Metabolite - 6126 | 61 | 0.2648 | 0.3546 | −0.016 |
| Metabolite - 1193-confirmed-3-indoxyl-sulfate | 61 | 0.2658 | 0.3546 | −0.009 |
| Metabolite - 4732 | 61 | 0.2715 | 0.3546 | 0.013 |
| Metabolite - 3708 | 61 | 0.2716 | 0.3546 | −0.023 |
| Metabolite - 7888 | 50 | 0.2719 | 0.3546 | −0.005 |
| Metabolite - 2027 | 61 | 0.2758 | 0.3546 | 0.007 |
| Threonine | 50 | 0.2787 | 0.3546 | 0.017 |
| Metabolite - 1835 | 61 | 0.2788 | 0.3546 | −0.006 |
| palmitoleic acid | 50 | 0.2798 | 0.3546 | 0.015 |
| Metabolite - 1831-possible-Cl-adduct-of-citrulline | 61 | 0.2807 | 0.3546 | −0.005 |
| Alanine | 50 | 0.2817 | 0.3546 | 0.017 |
| Biliverdin | 61 | 0.2851 | 0.3551 | −0.015 |
| Metabolite - 6226 | 50 | 0.2872 | 0.3551 | −0.010 |
| Metabolite - 3093 | 50 | 0.2891 | 0.3551 | −0.007 |
| Metabolite - 7765 | 61 | 0.2909 | 0.3551 | −0.042 |
| Metabolite - 3017 | 50 | 0.2920 | 0.3551 | −0.005 |
| Metabolite - 7008 | 61 | 0.2967 | 0.3551 | −0.006 |
| Metabolite - 4274 | 50 | 0.3021 | 0.3551 | 0.026 |
| Metabolite - 1597 | 61 | 0.3041 | 0.3551 | −0.003 |
| Metabolite - 1142-possible-5-hydroxypentanoate-or-beta-hydroxyisovaleric acid | 61 | 0.3052 | 0.3551 | −0.010 |
| Metabolite - 6488 | 50 | 0.3065 | 0.3551 | −0.014 |
| Glycerol | 50 | 0.3067 | 0.3551 | 0.007 |
| Metabolite - 4612 | 61 | 0.3100 | 0.3551 | −0.010 |
| Metabolite - 5847 | 50 | 0.3117 | 0.3551 | −0.019 |
| Metabolite - 6467 | 50 | 0.3135 | 0.3551 | −0.010 |
| Carnitine | 61 | 0.3139 | 0.3551 | −0.007 |
| Metabolite - 5231 | 61 | 0.3140 | 0.3551 | −0.007 |
| Metabolite - 3603 | 61 | 0.3149 | 0.3551 | −0.012 |
| L-kynurenine | 61 | 0.3208 | 0.3574 | −0.004 |
| Metabolite - 2053 | 61 | 0.3208 | 0.3574 | 0.011 |
| Metabolite - 1114 | 61 | 0.3243 | 0.3575 | 0.017 |
| Metabolite - 3040 | 50 | 0.3249 | 0.3575 | 0.004 |
| Metabolite - 2321 | 61 | 0.3267 | 0.3575 | −0.011 |
| Metabolite - 3099 | 50 | 0.3308 | 0.3598 | −0.008 |
| citric acid | 50 | 0.3396 | 0.3672 | −0.005 |
| Metabolite - 4055 | 50 | 0.3492 | 0.3753 | −0.013 |
| Bicine | 61 | 0.3532 | 0.3775 | 0.008 |
| phosphoenolpyruvate | 61 | 0.3613 | 0.3797 | 0.007 |
| Uridine | 61 | 0.3626 | 0.3797 | 0.009 |
| Metabolite - 4523 | 50 | 0.3643 | 0.3797 | −0.006 |
| benzoic acid | 61 | 0.3660 | 0.3797 | 0.013 |
| glycochenodeoxycholic acid | 61 | 0.3661 | 0.3797 | −0.017 |
| Metabolite - 3377 | 61 | 0.3677 | 0.3797 | 0.026 |
| Metabolite - 2506 | 61 | 0.3698 | 0.3797 | −0.008 |
| 3-phospho-d-glycerate | 61 | 0.3802 | 0.3883 | −0.009 |
| malic acid | 50 | 0.3827 | 0.3887 | 0.019 |
| Metabolite - 4522 | 50 | 0.3861 | 0.3899 | 0.003 |
| Metabolite - 4547 | 61 | 0.3897 | 0.3915 | −0.011 |
| Metabolite - 5730 | 61 | 0.3926 | 0.3922 | 0.006 |
| hydroxyacetic acid | 50 | 0.3974 | 0.3947 | −0.004 |
| Metabolite - 5366 | 50 | 0.4016 | 0.3947 | −0.013 |
| methyl-indole-3-acetate | 61 | 0.4021 | 0.3947 | −0.009 |
| Metabolite - 3002 | 50 | 0.4039 | 0.3947 | −0.014 |
| Metabolite - 2249 | 61 | 0.4075 | 0.3947 | −0.006 |
| Metabolite - 4806 | 50 | 0.4080 | 0.3947 | −0.006 |
| Metabolite - 4658 | 61 | 0.4129 | 0.3973 | −0.006 |
| Theobromine | 61 | 0.4246 | 0.4010 | 0.011 |
| Isobar-28-includes-L-threonine-L-allothreonine-L-homoserine-S-4-amino-2-hydroxybutyric acid | 61 | 0.4265 | 0.4010 | −0.005 |
| Metabolite - 6269 | 50 | 0.4271 | 0.4010 | −0.003 |
| Metabolite - 6227 | 50 | 0.4291 | 0.4010 | −0.009 |
| Lysine | 50 | 0.4301 | 0.4010 | 0.011 |
| Metabolite - 2594 | 61 | 0.4303 | 0.4010 | 0.161 |

TABLE 16-continued

Random Coefficient Regression Analysis Over Time

| COMPOUND | LIB_ID | p-value | q-value | SLOPE |
|---|---|---|---|---|
| Metabolite - 2370 | 61 | 0.4320 | 0.4010 | −0.008 |
| Metabolite - 3100 | 50 | 0.4361 | 0.4028 | −0.012 |
| Ornithine | 50 | 0.4419 | 0.4043 | 0.023 |
| Metabolite - 2559 | 61 | 0.4439 | 0.4043 | −0.015 |
| Metabolite - 3772 | 61 | 0.4485 | 0.4043 | 0.015 |
| Metabolite - 7706 | 61 | 0.4488 | 0.4043 | 0.005 |
| Metabolite - 2469 | 61 | 0.4490 | 0.4043 | 0.009 |
| Metabolite - 6869 | 50 | 0.4508 | 0.4043 | −0.008 |
| Metabolite - 4624 | 50 | 0.4552 | 0.4048 | −0.007 |
| Valine | 50 | 0.4580 | 0.4048 | 0.011 |
| Metabolite - 6963 | 50 | 0.4581 | 0.4048 | −0.008 |
| Metabolite - 4362 | 50 | 0.4623 | 0.4066 | −0.007 |
| 2-hydroxybutyric acid | 50 | 0.4676 | 0.4093 | 0.005 |
| Metabolite - 1335 | 61 | 0.4706 | 0.4097 | −0.013 |
| heptadecanoic acid | 50 | 0.4725 | 0.4097 | −0.005 |
| Isobar-1-includes-mannose-fructose-glucose-galactose-alpha-L-sorbopyranose-Inositol-D-allose-D-altrose-D-psicone | 61 | 0.4749 | 0.4098 | −0.003 |
| 2-keto-L-gulonic acid | 50 | 0.4857 | 0.4172 | −0.006 |
| n-hexadecanoic acid | 50 | 0.4916 | 0.4203 | 0.004 |
| Metabolite - 2269 | 61 | 0.4959 | 0.4220 | 0.021 |
| Metabolite - 3832-possible-phenol-sulfate | 61 | 0.5044 | 0.4231 | −0.018 |
| Metabolite - 7807 | 61 | 0.5083 | 0.4231 | −0.003 |
| Metabolite - 3056 | 61 | 0.5095 | 0.4231 | 0.003 |
| Metabolite - 7815 | 61 | 0.5098 | 0.4231 | −0.002 |
| Metabolite - 5848 | 61 | 0.5109 | 0.4231 | −0.005 |
| Metabolite - 7707 | 61 | 0.5110 | 0.4231 | 0.003 |
| Metabolite - 2973 | 50 | 0.5282 | 0.4342 | 0.001 |
| Metabolite - 4931 | 61 | 0.5323 | 0.4342 | 0.010 |
| Metabolite - 4986 | 50 | 0.5352 | 0.4342 | −0.004 |
| Urea | 50 | 0.5355 | 0.4342 | −0.002 |
| Metabolite - 3087 | 50 | 0.5362 | 0.4342 | 0.020 |
| Isobar-6-includes-valine-betaine | 61 | 0.5422 | 0.4352 | −0.002 |
| Metabolite - 1914 | 61 | 0.5422 | 0.4352 | 0.016 |
| p-hydroxybenzaldehyde | 61 | 0.5474 | 0.4375 | −0.002 |
| Metabolite - 1254 | 61 | 0.5520 | 0.4392 | −0.033 |
| Metabolite - 1834 | 61 | 0.5590 | 0.4429 | 0.008 |
| Metabolite - 2825-possible-Riluzole | 61 | 0.5632 | 0.4440 | 0.006 |
| Metabolite - 1085-possible-isolobinine-or-4-aminoestra-1,3-5-10-triene-3-17beta-diol | 61 | 0.5676 | 0.4440 | −0.003 |
| glycocholic acid | 61 | 0.5677 | 0.4440 | 0.015 |
| Metabolite - 2548-possible-Cl-adduct-of-uric acid | 61 | 0.5741 | 0.4471 | 0.005 |
| Metabolite - 2395 | 61 | 0.5766 | 0.4472 | −0.006 |
| Metabolite - 5983 | 50 | 0.5817 | 0.4492 | −0.004 |
| Isobar-2-includes-2-aminoisobutyric acid-3-amino-isobutyrate-2-amino-butyrate-4-aminobutanoic acid-dimethylglycine-choline | 61 | 0.5861 | 0.4508 | 0.008 |
| Metabolite - 4510 | 50 | 0.5888 | 0.4510 | −0.012 |
| Leucine | 50 | 0.5961 | 0.4547 | 0.010 |
| Saccharopine | 61 | 0.6059 | 0.4602 | −0.004 |
| dehydroisoandrosterone-3-sulfate-sodium-salt-hydrate | 61 | 0.6108 | 0.4621 | −0.005 |
| DL-homocysteine | 61 | 0.6165 | 0.4645 | −0.005 |
| Metabolite - 2100 | 61 | 0.6341 | 0.4750 | 0.003 |
| meso-erythritol | 50 | 0.6357 | 0.4750 | −0.002 |
| oxalic acid | 61 | 0.6440 | 0.4765 | −0.004 |
| Metabolite - 7336 | 61 | 0.6444 | 0.4765 | −0.008 |
| Metabolite - 3097 | 50 | 0.6482 | 0.4765 | −0.005 |
| Metabolite - 1323-possible-p-cresol-sulfate | 61 | 0.6505 | 0.4765 | 0.004 |
| octadecanoic acid | 50 | 0.6524 | 0.4765 | −0.002 |
| Metabolite - 2386 | 61 | 0.6581 | 0.4765 | 0.003 |
| Metabolite - 1110 | 61 | 0.6601 | 0.4765 | 0.016 |
| Histidine | 50 | 0.6617 | 0.4765 | 0.006 |
| DL-indole-3-lactic acid | 61 | 0.6650 | 0.4765 | −0.002 |
| glutamic acid | 50 | 0.6663 | 0.4765 | 0.006 |
| Phosphate | 50 | 0.6663 | 0.4765 | 0.002 |
| Creatine | 61 | 0.6689 | 0.4765 | −0.011 |
| 4-O-beta-galactopyranosyl-D-mannopyranose | 61 | 0.6759 | 0.4797 | 0.004 |
| Acetylpyrazine | 61 | 0.6805 | 0.4800 | −0.002 |
| Metabolite - 2952 | 50 | 0.6852 | 0.4800 | 0.030 |
| Metabolite - 3441 | 61 | 0.6861 | 0.4800 | −0.003 |
| Metabolite - 5769 | 61 | 0.6868 | 0.4800 | 0.002 |
| Metabolite - 6551 | 61 | 0.6905 | 0.4808 | 0.006 |
| Metabolite - 4470 | 61 | 0.6960 | 0.4811 | −0.003 |
| Phenylalanine | 61 | 0.6963 | 0.4811 | −0.001 |
| Metabolite - 5403 | 50 | 0.7196 | 0.4954 | −0.001 |

TABLE 16-continued

Random Coefficient Regression Analysis Over Time

| COMPOUND | LIB_ID | p-value | q-value | SLOPE |
|---|---|---|---|---|
| Metabolite - 3003 | 50 | 0.7408 | 0.5081 | 0.002 |
| Metabolite - 3972 | 61 | 0.7453 | 0.5092 | 0.002 |
| Metabolite - 2056 | 61 | 0.7614 | 0.5155 | 0.001 |
| Metabolite - 7146 | 61 | 0.7626 | 0.5155 | −0.002 |
| 3-hydroxybutanoic acid | 50 | 0.7628 | 0.5155 | 0.010 |
| decanoic acid | 50 | 0.7687 | 0.5174 | −0.001 |
| Metabolite - 1836 | 61 | 0.7750 | 0.5174 | 0.002 |
| Nonanate | 50 | 0.7757 | 0.5174 | −0.001 |
| Metabolite - 4428 | 61 | 0.7768 | 0.5174 | −0.002 |
| Metabolite - 6270 | 50 | 0.7812 | 0.5182 | −0.004 |
| D-glucose | 50 | 0.7873 | 0.5182 | 0.001 |
| Metabolite - 4167 | 61 | 0.7883 | 0.5182 | −0.002 |
| Fructose | 50 | 0.7929 | 0.5182 | 0.007 |
| Metabolite - 1342-possible-phenylacetylglutamine-or-formyl-N-acetyl-5-methoxykynurenamine | 61 | 0.7945 | 0.5182 | 0.002 |
| tetradecanoic acid | 50 | 0.7949 | 0.5182 | 0.003 |
| 5-oxoproline | 50 | 0.7993 | 0.5192 | −0.003 |
| Metabolite - 4873 | 61 | 0.8047 | 0.5193 | 0.004 |
| Metabolite - 2753 | 61 | 0.8069 | 0.5193 | −0.003 |
| Metabolite - 4363 | 61 | 0.8080 | 0.5193 | 0.007 |
| Isobar-13-includes-5-keto-D-gluconic acid-2-keto-L-gulonic acid-D-glucuronic acid-D-galacturonic acid | 61 | 0.8171 | 0.5220 | 0.004 |
| Metabolite - 3808 | 61 | 0.8179 | 0.5220 | 0.002 |
| Metabolite - 1264 | 61 | 0.8402 | 0.5344 | 0.014 |
| Metabolite - 3218 | 61 | 0.8456 | 0.5354 | 0.003 |
| Isoleucine | 50 | 0.8476 | 0.5354 | 0.003 |
| Allantoin | 50 | 0.8566 | 0.5392 | 0.005 |
| 5-6-dihydrouracil | 50 | 0.8606 | 0.5399 | 0.002 |
| Metabolite - 2986 | 50 | 0.8656 | 0.5412 | −0.001 |
| Aspartate | 50 | 0.8696 | 0.5419 | −0.002 |
| Metabolite - 1498 | 61 | 0.8783 | 0.5454 | −0.001 |
| Metabolite - 2561 | 61 | 0.8850 | 0.5477 | 0.001 |
| Metabolite - 2981 | 50 | 0.8934 | 0.5478 | 0.001 |
| Metabolite - 1215 | 61 | 0.8952 | 0.5478 | −0.001 |
| Metabolite - 4364 | 50 | 0.8964 | 0.5478 | −0.001 |
| Metabolite - 1261 | 61 | 0.8971 | 0.5478 | 0.002 |
| Metabolite - 2915 | 50 | 0.9275 | 0.5646 | 0.001 |
| Metabolite - 7147 | 61 | 0.9338 | 0.5646 | 0.000 |
| Metabolite - 4795 | 50 | 0.9371 | 0.5646 | 0.001 |
| Metabolite - 7890 | 50 | 0.9470 | 0.5646 | −0.001 |
| Metabolite - 3125 | 61 | 0.9497 | 0.5646 | −0.001 |
| sn-Glycerol-3-phosphate | 50 | 0.9524 | 0.5646 | 0.001 |
| Metabolite - 2185 | 61 | 0.9544 | 0.5646 | 0.000 |
| Aldosterone | 61 | 0.9564 | 0.5646 | 0.000 |
| Metabolite - 4906 | 61 | 0.9612 | 0.5646 | −0.001 |
| Metabolite - 6931 | 50 | 0.9619 | 0.5646 | 0.000 |
| Metabolite - 3129 | 61 | 0.9631 | 0.5646 | 0.000 |
| Metabolite - 5234 | 61 | 0.9638 | 0.5646 | 0.001 |
| Linoleic acid | 50 | 0.9671 | 0.5646 | 0.000 |
| Metabolite - 7762 | 61 | 0.9675 | 0.5646 | −0.001 |
| Metabolite - 5673 | 61 | 0.9814 | 0.5709 | 0.000 |
| uric acid | 50 | 0.9890 | 0.5715 | 0.000 |
| Metabolite - 6827 | 61 | 0.9918 | 0.5715 | 0.000 |
| Metabolite - 7889 | 50 | 0.9919 | 0.5715 | 0.000 |
| Metabolite - 7177 | 61 | 0.9975 | 0.5730 | 0.000 |

TABLE 17

Random Coefficient Regression Analysis Over Forced Vital Capacity.

| COMPOUND | LIB_ID | p-value | q-value | slope |
|---|---|---|---|---|
| Creatinine | 61 | 0.0003 | 0.0782 | 0.109 |
| Metabolite - 7089 | 61 | 0.0032 | 0.2716 | 0.099 |
| Metabolite - 4769 | 50 | 0.0036 | 0.2716 | −0.148 |
| Metabolite - 3951 | 61 | 0.0048 | 0.2716 | −0.078 |
| Metabolite - 1988 | 61 | 0.0068 | 0.2716 | 0.138 |
| Aspartate | 50 | 0.0072 | 0.2716 | 0.155 |
| glutamic acid | 50 | 0.0080 | 0.2716 | 0.135 |
| 3-methyl-L-histidine | 61 | 0.0081 | 0.2716 | 0.064 |
| Metabolite - 3073 | 50 | 0.0106 | 0.3157 | 0.066 |
| Metabolite - 4275 | 50 | 0.0127 | 0.3293 | −0.121 |
| Metabolite - 2249 | 61 | 0.0135 | 0.3293 | 0.152 |

TABLE 17-continued

Random Coefficient Regression Analysis Over Forced Vital Capacity.

| COMPOUND | LIB_ID | p-value | q-value | slope |
|---|---|---|---|---|
| Metabolite - 2973 | 50 | 0.0156 | 0.3458 | −0.029 |
| Isobar-22-includes-glutamic acid-O-acetyl-L-serine | 61 | 0.0204 | 0.3458 | 0.051 |
| 4-Guanidinobutanoic acid | 61 | 0.0206 | 0.3458 | 0.088 |
| Metabolite - 3183-possible-gamma-L-glutamyl-L-phenylalanine | 61 | 0.0219 | 0.3458 | 0.073 |
| 1-7-dimethylxanthine | 61 | 0.0225 | 0.3458 | 0.220 |
| Metabolite - 2688 | 61 | 0.0240 | 0.3458 | 0.068 |
| gamma-glu-leu | 61 | 0.0253 | 0.3458 | 0.100 |
| Metabolite - 1142-possible-5-hydroxypentanoate-or-beta-hydroxyisovaleric acid | 61 | 0.0271 | 0.3458 | 0.163 |
| Metabolite - 1345 | 61 | 0.0286 | 0.3458 | 0.201 |
| Metabolite - 3078 | 50 | 0.0286 | 0.3458 | −0.123 |
| Metabolite - 7889 | 50 | 0.0295 | 0.3458 | −0.084 |
| Metabolite - 2567 | 61 | 0.0297 | 0.3458 | 0.074 |
| Metabolite - 4364 | 50 | 0.0326 | 0.3645 | −0.072 |
| Metabolite - 4547 | 61 | 0.0353 | 0.3787 | −0.114 |
| Metabolite - 5976 | 61 | 0.0417 | 0.4297 | 0.180 |
| Metabolite - 4511 | 50 | 0.0454 | 0.4412 | 0.078 |
| Metabolite - 7846 | 50 | 0.0463 | 0.4412 | 0.114 |
| Metabolite - 1208 | 61 | 0.0486 | 0.4412 | 0.128 |
| Leucine | 50 | 0.0517 | 0.4412 | 0.123 |
| Metabolite - 1254 | 61 | 0.0528 | 0.4412 | 0.308 |
| Metabolite - 2005 | 61 | 0.0561 | 0.4412 | −0.107 |
| Metabolite - 1834 | 61 | 0.0563 | 0.4412 | 0.246 |
| Arginine | 61 | 0.0564 | 0.4412 | 0.055 |
| Metabolite - 3143 | 61 | 0.0576 | 0.4412 | 0.236 |
| Metabolite - 7050 | 61 | 0.0612 | 0.4522 | 0.101 |
| DL-indole-3-lactic acid | 61 | 0.0639 | 0.4522 | 0.079 |
| Isoleucine | 50 | 0.0681 | 0.4522 | 0.108 |
| Metabolite - 1597 | 61 | 0.0713 | 0.4522 | 0.033 |
| Metabolite - 4767 | 50 | 0.0718 | 0.4522 | −0.041 |
| Metabolite - 6907 | 50 | 0.0729 | 0.4522 | −0.056 |
| Metabolite - 5788 | 61 | 0.0731 | 0.4522 | 0.272 |
| Tryptophan | 61 | 0.0742 | 0.4522 | 0.042 |
| Metabolite - 1911 | 61 | 0.0744 | 0.4522 | 0.211 |
| Metabolite - 1206-possible-methyltestosterone-and-others | 61 | 0.0759 | 0.4522 | 0.108 |
| Creatine | 61 | 0.0781 | 0.4550 | −0.181 |
| Metabolite - 3783 | 61 | 0.0868 | 0.4948 | −0.062 |
| Metabolite - 5848 | 61 | 0.0889 | 0.4966 | 0.089 |
| 1,5-anhydro-D-glucitol | 50 | 0.0965 | 0.5251 | 0.042 |
| Acetylpyrazine | 61 | 0.0979 | 0.5251 | −0.033 |
| Metabolite - 4732 | 61 | 0.1037 | 0.5450 | −0.123 |
| N-5-aminocarbonyl-L-ornithine | 50 | 0.1076 | 0.5493 | 0.059 |
| inositol-1-phosphate | 50 | 0.1086 | 0.5493 | 0.064 |
| Valine | 50 | 0.1159 | 0.5756 | 0.084 |
| Metabolite - 2395 | 61 | 0.1197 | 0.5835 | 0.108 |
| Metabolite - 1835 | 61 | 0.1291 | 0.5916 | 0.046 |
| 5-6-dihydrouracil | 50 | 0.1318 | 0.5916 | −0.071 |
| Metabolite - 7147 | 61 | 0.1319 | 0.5916 | −0.040 |
| O-acetyl-L-carnitine-hydrochloride | 61 | 0.1343 | 0.5916 | −0.067 |
| Biotin | 61 | 0.1364 | 0.5916 | 0.113 |
| Metabolite - 4522 | 50 | 0.1369 | 0.5916 | −0.032 |
| Metabolite - 4873 | 61 | 0.1415 | 0.5916 | −0.118 |
| Isobar-8-includes-anthranilic acid-salicylamide | 61 | 0.1432 | 0.5916 | 0.104 |
| Metabolite - 2981 | 50 | 0.1451 | 0.5916 | −0.035 |
| D-quinic acid | 50 | 0.1467 | 0.5916 | 0.166 |
| 4-O-beta-galactopyranosyl-D-mannopyranose | 61 | 0.1480 | 0.5916 | −0.051 |
| Glycerol | 50 | 0.1497 | 0.5916 | −0.074 |
| Histamine | 61 | 0.1501 | 0.5916 | −0.051 |
| citric acid | 50 | 0.1546 | 0.6009 | −0.048 |
| Metabolite - 7888 | 50 | 0.1571 | 0.6016 | −0.039 |
| Metabolite - 6270 | 50 | 0.1600 | 0.6043 | −0.108 |
| Metabolite - 5234 | 61 | 0.1624 | 0.6049 | −0.113 |
| Metabolite - 6467 | 50 | 0.1695 | 0.6069 | −0.082 |
| Metabolite - 1819 | 61 | 0.1705 | 0.6069 | 0.045 |
| Metabolite - 7765 | 61 | 0.1712 | 0.6069 | 0.200 |
| Metabolite - 1193-confirmed-3-indoxyl-sulfate | 61 | 0.1720 | 0.6069 | 0.076 |
| Metabolite - 2185 | 61 | 0.1774 | 0.6088 | 0.050 |
| Metabolite - 5086 | 61 | 0.1812 | 0.6088 | −0.231 |
| Metabolite - 3044 | 61 | 0.1862 | 0.6088 | −0.065 |
| Metabolite - 1127 | 61 | 0.1869 | 0.6088 | −0.044 |
| Caffeine | 61 | 0.1910 | 0.6088 | 0.232 |
| 1-oleoyl-rac glycerol | 50 | 0.1920 | 0.6088 | 0.073 |
| Metabolite - 3114 | 50 | 0.1977 | 0.6088 | 0.063 |
| Metabolite - 5728 | 61 | 0.2012 | 0.6088 | 0.082 |

TABLE 17-continued

Random Coefficient Regression Analysis Over Forced Vital Capacity.

| COMPOUND | LIB_ID | p-value | q-value | slope |
| --- | --- | --- | --- | --- |
| Lysine | 50 | 0.2036 | 0.6088 | 0.071 |
| malic acid | 50 | 0.2055 | 0.6088 | 0.096 |
| Glutamine | 50 | 0.2099 | 0.6088 | −0.088 |
| Metabolite - 5247 | 61 | 0.2145 | 0.6088 | −0.078 |
| Phosphate | 50 | 0.2183 | 0.6088 | −0.028 |
| Metabolite - 1831-possible-Cl-adduct-of-citrulline | 61 | 0.2233 | 0.6088 | −0.032 |
| Isobar-6-includes-valine-betaine | 61 | 0.2240 | 0.6088 | 0.022 |
| Metabolite - 3077 | 50 | 0.2250 | 0.6088 | 0.031 |
| Metabolite - 7815 | 61 | 0.2254 | 0.6088 | 0.014 |
| Metabolite - 1656 | 61 | 0.2265 | 0.6088 | −0.043 |
| Metabolite - 5730 | 61 | 0.2268 | 0.6088 | −0.035 |
| Metabolite - 3087 | 50 | 0.2277 | 0.6088 | 0.116 |
| Allantoin | 50 | 0.2292 | 0.6088 | −0.135 |
| Metabolite - 3040 | 50 | 0.2305 | 0.6088 | 0.005 |
| (p-Hydroxyphenyl)lactic acid | 50 | 0.2311 | 0.6088 | 0.049 |
| Metabolite - 2056 | 61 | 0.2316 | 0.6088 | −0.028 |
| Phenylalanine | 61 | 0.2348 | 0.6088 | 0.015 |
| Metabolite - 2825-possible-Riluzole | 61 | 0.2389 | 0.6088 | −0.079 |
| Metabolite - 3097 | 50 | 0.2394 | 0.6088 | 0.060 |
| Metabolite - 6488 | 50 | 0.2426 | 0.6088 | 0.059 |
| glyceric acid | 50 | 0.2438 | 0.6088 | 0.039 |
| gamma-L-glutamyl-L-tyrosine | 61 | 0.2464 | 0.6088 | 0.034 |
| Metabolite - 1092 | 61 | 0.2481 | 0.6088 | 0.140 |
| Metabolite - 3025 | 50 | 0.2493 | 0.6088 | 0.022 |
| Oleic-Acid | 50 | 0.2497 | 0.6088 | −0.070 |
| Metabolite - 3109 | 50 | 0.2498 | 0.6088 | 0.052 |
| Metabolite - 1086 | 61 | 0.2539 | 0.6133 | 0.118 |
| glycochenodeoxycholic acid | 61 | 0.2640 | 0.6230 | 0.111 |
| Alanine | 50 | 0.2648 | 0.6230 | 0.063 |
| Metabolite - 2561 | 61 | 0.2659 | 0.6230 | −0.053 |
| Metabolite - 2952 | 50 | 0.2672 | 0.6230 | −0.216 |
| Biliverdin | 61 | 0.2778 | 0.6387 | 0.068 |
| Metabolite - 3088 | 50 | 0.2787 | 0.6387 | 0.047 |
| methyl-indole-3-acetate | 61 | 0.2994 | 0.6803 | 0.072 |
| Metabolite - 5791 | 61 | 0.3028 | 0.6812 | −0.333 |
| Metabolite - 3138 | 61 | 0.3091 | 0.6812 | 0.038 |
| Metabolite - 1335 | 61 | 0.3102 | 0.6812 | 0.079 |
| phosphoenolpyruvate | 61 | 0.3110 | 0.6812 | −0.030 |
| alpha-tocopherol | 50 | 0.3127 | 0.6812 | 0.245 |
| Metabolite - 4906 | 61 | 0.3179 | 0.6812 | 0.074 |
| Metabolite - 4363 | 61 | 0.3244 | 0.6812 | −0.214 |
| 2-keto-L-gulonic acid | 50 | 0.3248 | 0.6812 | −0.051 |
| Mannose | 50 | 0.3267 | 0.6812 | −0.043 |
| Metabolite - 5403 | 50 | 0.3345 | 0.6812 | 0.023 |
| Histidine | 50 | 0.3346 | 0.6812 | 0.065 |
| DL-homocysteine | 61 | 0.3391 | 0.6812 | 0.056 |
| Metabolite - 3832-possible-phenol-sulfate | 61 | 0.3398 | 0.6812 | 0.116 |
| beta-hydroxypyruvic acid | 50 | 0.3419 | 0.6812 | −0.033 |
| Metabolite - 4627 | 61 | 0.3423 | 0.6812 | 0.080 |
| sn-Glycerol-3-phosphate | 50 | 0.3487 | 0.6812 | −0.053 |
| p-hydroxybenzaldehyde | 61 | 0.3548 | 0.6812 | −0.018 |
| Metabolite - 1286 | 61 | 0.3578 | 0.6812 | −0.025 |
| Metabolite - 2168 | 61 | 0.3598 | 0.6812 | −0.015 |
| Metabolite - 5233 | 61 | 0.3612 | 0.6812 | 0.100 |
| Metabolite - 2321 | 61 | 0.3624 | 0.6812 | −0.068 |
| hippuric acid | 61 | 0.3627 | 0.6812 | 0.067 |
| Metabolite - 4586 | 61 | 0.3636 | 0.6812 | −0.027 |
| Metabolite - 4510 | 50 | 0.3641 | 0.6812 | −0.091 |
| decanoic acid | 50 | 0.3663 | 0.6812 | −0.032 |
| Metabolite - 4986 | 50 | 0.3674 | 0.6812 | 0.060 |
| DL-pipecolic acid | 61 | 0.3714 | 0.6812 | −0.042 |
| Metabolite - 2594 | 61 | 0.3719 | 0.6812 | −1.133 |
| Metabolite - 2074 | 61 | 0.3748 | 0.6812 | 0.072 |
| Metabolite - 3653-Possible-stachydrine | 61 | 0.3760 | 0.6812 | −0.332 |
| Isobar-21-includes-gamma-aminobutyryl-L-histidine-L-anserine | 61 | 0.3801 | 0.6839 | −0.021 |
| Ornithine | 50 | 0.3874 | 0.6851 | 0.066 |
| Metabolite - 2506 | 61 | 0.3875 | 0.6851 | 0.078 |
| Uridine | 61 | 0.3884 | 0.6851 | −0.043 |
| Isobar-19-includes-D-saccharic acid-1,5-anhydro-D-glucitol-2'-deoxy-D-galactose-2'-deoxy-D-glucose-L-fucose-L-rhamnose | 61 | 0.3941 | 0.6897 | −0.018 |
| Metabolite - 2386 | 61 | 0.3983 | 0.6897 | −0.032 |
| Metabolite - 4362 | 50 | 0.3988 | 0.6897 | −0.050 |
| Metabolite - 3377 | 61 | 0.4022 | 0.6912 | −0.188 |
| benzoic acid | 61 | 0.4136 | 0.6976 | 0.013 |

TABLE 17-continued

Random Coefficient Regression Analysis Over Forced Vital Capacity.

| COMPOUND | LIB_ID | p-value | q-value | slope |
|---|---|---|---|---|
| Thyroxine | 61 | 0.4143 | 0.6976 | 0.036 |
| Metabolite - 3003 | 50 | 0.4162 | 0.6976 | −0.018 |
| Metabolite - 6347 | 50 | 0.4186 | 0.6976 | −0.031 |
| Metabolite - 5349 | 50 | 0.4193 | 0.6976 | −0.010 |
| Metabolite - 7008 | 61 | 0.4255 | 0.6976 | −0.035 |
| Metabolite - 7177 | 61 | 0.4266 | 0.6976 | 0.075 |
| Metabolite - 3830 | 61 | 0.4267 | 0.6976 | 0.083 |
| Metabolite - 2053 | 61 | 0.4344 | 0.7059 | −0.031 |
| Metabolite - 6827 | 61 | 0.4388 | 0.7084 | 0.027 |
| Metabolite - 5231 | 61 | 0.4413 | 0.7084 | 0.030 |
| Metabolite - 3002 | 50 | 0.4508 | 0.7165 | −0.111 |
| heptadecanoic acid | 50 | 0.4537 | 0.7165 | 0.023 |
| Metabolite - 4806 | 50 | 0.4544 | 0.7165 | 0.033 |
| Metabolite - 6272 | 50 | 0.4588 | 0.7193 | −0.035 |
| Metabolite - 2027 | 61 | 0.4715 | 0.7287 | −0.024 |
| Isobar-28-includes-L-threonine-L-allothreonine-L-homoserine-S-4-amino-2-hydroxybutyric acid | 61 | 0.4748 | 0.7287 | −0.021 |
| Metabolite - 2370 | 61 | 0.4757 | 0.7287 | 0.036 |
| uric acid | 50 | 0.4764 | 0.7287 | 0.038 |
| Metabolite - 6246 | 50 | 0.4829 | 0.7287 | −0.015 |
| Metabolite - 3026 | 50 | 0.4832 | 0.7287 | 0.023 |
| Metabolite - 3093 | 50 | 0.4838 | 0.7287 | 0.039 |
| Metabolite - 5487 retired: eythrose | 50 | 0.4913 | 0.7352 | −0.023 |
| Metabolite - 3019 | 50 | 0.4936 | 0.7352 | 0.012 |
| Metabolite - 1498 | 61 | 0.5012 | 0.7364 | 0.027 |
| arachidonic acid | 50 | 0.5045 | 0.7364 | −0.019 |
| Fructose | 50 | 0.5050 | 0.7364 | −0.068 |
| Metabolite - 4167 | 61 | 0.5054 | 0.7364 | −0.028 |
| Metabolite - 4428 | 61 | 0.5152 | 0.7447 | 0.025 |
| 2-hydroxybutyric acid | 50 | 0.5167 | 0.7447 | 0.024 |
| Metabolite - 3708 | 61 | 0.5199 | 0.7453 | −0.093 |
| Metabolite - 5983 | 50 | 0.5394 | 0.7508 | 0.020 |
| Metabolite - 5346 | 50 | 0.5423 | 0.7508 | −0.009 |
| Lactate | 50 | 0.5525 | 0.7508 | −0.040 |
| Metabolite - 2915 | 50 | 0.5540 | 0.7508 | −0.019 |
| Metabolite - 6551 | 61 | 0.5542 | 0.7508 | −0.019 |
| Isobar-1-includes-mannose-fructose-glucose-galactose-alpha-L-sorbopyranose-Inositol-D-allose-D-altrose-D-psicone | 61 | 0.5551 | 0.7508 | 0.013 |
| Urea | 50 | 0.5563 | 0.7508 | 0.015 |
| Metabolite - 3056 | 61 | 0.5570 | 0.7508 | 0.019 |
| Metabolite - 6227 | 50 | 0.5590 | 0.7508 | −0.041 |
| Metabolite - 2986 retired: CL adduct of p-acetiminophen-beta-d-glucuronide | 50 | 0.5611 | 0.7508 | −0.015 |
| methionine-sulfoxide | 61 | 0.5674 | 0.7508 | 0.020 |
| 1-methyl-guanidine | 50 | 0.5729 | 0.7508 | 0.012 |
| Metabolite - 4274 | 50 | 0.5752 | 0.7508 | 0.042 |
| Metabolite - 3218 | 61 | 0.5796 | 0.7508 | 0.027 |
| Isobar-13-includes-5-keto-D-gluconic acid-2-keto-L-gulonic acid-D-glucuronic acid-D-galacturonic acid | 61 | 0.5816 | 0.7508 | −0.035 |
| Hypoxanthine | 61 | 0.5818 | 0.7508 | −0.136 |
| Metabolite - 3033-possible-threonine-deriv | 50 | 0.5827 | 0.7508 | −0.011 |
| Metabolite - 1342-possible-phenylacetylglutamine-or-formyl-N-acetyl-5-methoxykynurenamine | 61 | 0.5835 | 0.7508 | 0.035 |
| Metabolite - 3100 | 50 | 0.5865 | 0.7508 | 0.021 |
| Glycine | 50 | 0.5887 | 0.7508 | 0.048 |
| 3-phospho-d-glycerate | 61 | 0.5903 | 0.7508 | −0.026 |
| Metabolite - 7009 | 61 | 0.5968 | 0.7508 | 0.015 |
| Saccharopine | 61 | 0.5975 | 0.7508 | −0.022 |
| L-alpha-glycerophosphorylcholine | 61 | 0.5988 | 0.7508 | −0.030 |
| Metabolite - 3603 | 61 | 0.6010 | 0.7508 | −0.033 |
| Isobar-2-includes-2-aminoisobutyric acid-3-amino-isobutyrate-2-amino-butyrate-4-aminobutanoic acid-dimethylglycine-choline | 61 | 0.6019 | 0.7508 | 0.027 |
| Metabolite - 3707 | 61 | 0.6149 | 0.7508 | −0.099 |
| glycocholic acid | 61 | 0.6167 | 0.7508 | 0.071 |
| Metabolite - 2753 | 61 | 0.6211 | 0.7508 | −0.031 |
| Metabolite - 1085-possible-isolobinine-or-4-aminoestra-1,3-5-10-triene-3-17beta-diol | 61 | 0.6276 | 0.7508 | −0.010 |
| n-hexadecanoic acid | 50 | 0.6314 | 0.7508 | −0.016 |
| Methionine | 61 | 0.6324 | 0.7508 | −0.046 |
| Metabolite - 6711 | 61 | 0.6374 | 0.7508 | 0.016 |
| Metabolite - 2568 | 61 | 0.6399 | 0.7508 | 0.053 |
| Metabolite - 1261 | 61 | 0.6407 | 0.7508 | 0.033 |
| Metabolite - 3030 | 50 | 0.6409 | 0.7508 | 0.010 |
| Metabolite - 7146 | 61 | 0.6459 | 0.7508 | 0.013 |

TABLE 17-continued

Random Coefficient Regression Analysis Over Forced Vital Capacity.

| COMPOUND | LIB_ID | p-value | q-value | slope |
|---|---|---|---|---|
| Metabolite - 4252 | 50 | 0.6468 | 0.7508 | −0.027 |
| Metabolite - 1836 | 61 | 0.6472 | 0.7508 | −0.024 |
| Cholesterol | 50 | 0.6482 | 0.7508 | −0.010 |
| Metabolite - 4611 | 50 | 0.6496 | 0.7508 | 0.013 |
| L-kynurenine | 61 | 0.6505 | 0.7508 | −0.019 |
| Metabolite - 6226 | 50 | 0.6528 | 0.7508 | −0.027 |
| Tyrosine | 61 | 0.6534 | 0.7508 | 0.013 |
| Metabolite - 5769 | 61 | 0.6540 | 0.7508 | 0.016 |
| Metabolite - 7890 | 50 | 0.6553 | 0.7508 | 0.025 |
| palmitoleic acid | 50 | 0.6635 | 0.7570 | −0.035 |
| Metabolite - 7706 | 61 | 0.6695 | 0.7588 | 0.024 |
| Metabolite - 1323-possible-p-cresol-sulfate | 61 | 0.6708 | 0.7588 | 0.026 |
| D-glucose | 50 | 0.6847 | 0.7698 | −0.007 |
| Metabolite - 1111-possible-methylnitronitrosoguanidine-or-ethyl-thiocarbamoylacetate | 61 | 0.6882 | 0.7698 | −0.022 |
| Metabolite - 6869 | 50 | 0.6891 | 0.7698 | −0.026 |
| hydroxyacetic acid | 50 | 0.6927 | 0.7705 | 0.009 |
| Metabolite - 3052 | 61 | 0.6990 | 0.7734 | −0.016 |
| Metabolite - 1975 | 61 | 0.7010 | 0.7734 | −0.045 |
| Metabolite - 2469 | 61 | 0.7106 | 0.7775 | −0.017 |
| Metabolite - 3772 pieces of lactate | 61 | 0.7116 | 0.7775 | 0.038 |
| Metabolite - 2319 | 61 | 0.7134 | 0.7775 | −0.027 |
| Bicine | 61 | 0.7201 | 0.7816 | 0.016 |
| Metabolite - 3972 | 61 | 0.7338 | 0.7891 | −0.014 |
| Aldosterone | 61 | 0.7368 | 0.7891 | 0.021 |
| Linoleic acid | 50 | 0.7382 | 0.7891 | −0.012 |
| Metabolite - 4470 | 61 | 0.7388 | 0.7891 | −0.009 |
| Metabolite - 5907 | 50 | 0.7417 | 0.7891 | −0.012 |
| Metabolite - 3808 | 61 | 0.7467 | 0.7913 | −0.018 |
| Metabolite - 6346 | 50 | 0.7514 | 0.7929 | −0.008 |
| Threonine | 50 | 0.7581 | 0.7929 | −0.013 |
| Metabolite - 4055 | 50 | 0.7602 | 0.7929 | 0.017 |
| Metabolite - 2139 | 61 | 0.7638 | 0.7929 | −0.013 |
| Riboflavine | 61 | 0.7643 | 0.7929 | 0.005 |
| Metabolite - 7707 | 61 | 0.7680 | 0.7929 | −0.009 |
| Metabolite - 3129 | 61 | 0.7774 | 0.7929 | 0.014 |
| Metabolite - 6126 | 61 | 0.7775 | 0.7929 | 0.028 |
| Metabolite - 6931 | 50 | 0.7792 | 0.7929 | 0.008 |
| Metabolite - 2269 | 61 | 0.7804 | 0.7929 | 0.112 |
| Metabolite - 3441 | 61 | 0.7808 | 0.7929 | −0.009 |
| 3-hydroxybutanoic acid | 50 | 0.7864 | 0.7956 | 0.065 |
| Metabolite - 3098 | 50 | 0.7970 | 0.8024 | −0.006 |
| Metabolite - 4931 | 61 | 0.8000 | 0.8024 | 0.015 |
| Metabolite - 4624 | 50 | 0.8041 | 0.8024 | −0.012 |
| Metabolite - 1114 | 61 | 0.8051 | 0.8024 | 0.008 |
| Metabolite - 2109 | 61 | 0.8094 | 0.8037 | −0.004 |
| Metabolite - 3017 | 50 | 0.8198 | 0.8077 | 0.007 |
| Metabolite - 7762 | 61 | 0.8223 | 0.8077 | 0.024 |
| Theobromine | 61 | 0.8271 | 0.8077 | 0.016 |
| Metabolite - 1914 | 61 | 0.8278 | 0.8077 | 0.055 |
| Metabolite - 2548-possible-CI-adduct-of-uric acid | 61 | 0.8285 | 0.8077 | −0.008 |
| Metabolite - 5887 | 61 | 0.8423 | 0.8181 | 0.026 |
| Metabolite - 2100 | 61 | 0.8454 | 0.8181 | −0.007 |
| Metabolite - 3012 | 50 | 0.8486 | 0.8181 | −0.004 |
| 5-oxoproline | 50 | 0.8520 | 0.8181 | 0.005 |
| Inosine | 61 | 0.8544 | 0.8181 | −0.028 |
| Arabinose | 50 | 0.8663 | 0.8230 | −0.006 |
| Carnitine | 61 | 0.8690 | 0.8230 | 0.005 |
| Metabolite - 7336 | 61 | 0.8716 | 0.8230 | 0.013 |
| Metabolite - 2390 | 61 | 0.8719 | 0.8230 | −0.006 |
| Nonanate | 50 | 0.8793 | 0.8230 | 0.002 |
| Metabolite - 4658 | 61 | 0.8866 | 0.8230 | −0.004 |
| tetradecanoic acid | 50 | 0.8897 | 0.8230 | −0.007 |
| Metabolite - 3125 | 61 | 0.8931 | 0.8230 | 0.008 |
| Metabolite - 1110 | 61 | 0.8945 | 0.8230 | 0.066 |
| Metabolite - 3131 retired: N4 adduct of indole-3-acetic acid | 61 | 0.8955 | 0.8230 | 0.005 |
| Metabolite - 4795 | 50 | 0.8961 | 0.8230 | −0.011 |
| Metabolite - 6963 | 50 | 0.8987 | 0.8230 | 0.007 |
| Metabolite - 3094 | 50 | 0.8995 | 0.8230 | 0.004 |
| octadecanoic acid | 50 | 0.9048 | 0.8230 | 0.003 |
| Metabolite - 6269 | 50 | 0.9056 | 0.8230 | 0.003 |
| Metabolite - 6326 | 50 | 0.9087 | 0.8230 | 0.002 |
| Metabolite - 4523 | 50 | 0.9126 | 0.8238 | 0.002 |
| Metabolite - 6955 | 50 | 0.9190 | 0.8268 | −0.003 |

TABLE 17-continued

Random Coefficient Regression Analysis Over Forced Vital Capacity.

| COMPOUND | LIB_ID | p-value | q-value | slope |
|---|---|---|---|---|
| Metabolite - 2546 | 61 | 0.9264 | 0.8278 | −0.024 |
| Metabolite - 1215 | 61 | 0.9296 | 0.8278 | 0.005 |
| Metabolite - 3099 | 50 | 0.9354 | 0.8278 | 0.004 |
| Metabolite - 2559 | 61 | 0.9423 | 0.8278 | 0.009 |
| Metabolite - 5847 | 50 | 0.9441 | 0.8278 | 0.003 |
| Metabolite - 4612 | 61 | 0.9484 | 0.8278 | 0.005 |
| pantothenic acid | 61 | 0.9493 | 0.8278 | −0.026 |
| Metabolite - 3022 | 50 | 0.9526 | 0.8278 | −0.001 |
| dehydroisoandrosterone-3-sulfate-sodium-salt-hydrate | 61 | 0.9536 | 0.8278 | 0.019 |
| Metabolite - 5673 | 61 | 0.9538 | 0.8278 | −0.004 |
| n-dodecanoate | 50 | 0.9541 | 0.8278 | 0.005 |
| Metabolite - 4351 | 61 | 0.9632 | 0.8291 | 0.005 |
| Metabolite - 1264 | 61 | 0.9643 | 0.8291 | 0.009 |
| Metabolite - 4020 | 50 | 0.9691 | 0.8291 | −0.001 |
| Metabolite - 7807 | 61 | 0.9695 | 0.8291 | 0.001 |
| N-6-trimethyl-l-lysine | 61 | 0.9737 | 0.8291 | 0.038 |
| Metabolite - 5366 | 50 | 0.9760 | 0.8291 | −0.002 |
| Inositol | 50 | 0.9787 | 0.8291 | 0.001 |
| meso-erythritol | 50 | 0.9803 | 0.8291 | −0.001 |
| oxalic acid | 61 | 0.9900 | 0.8346 | 0.000 |
| Praline | 61 | 0.9964 | 0.8374 | 0.000 |
| Serine | 50 | 1.0000 | 0.8378 | 0.104 |

TABLE 18

T-tests comparing month 1 with month 12.

| COMPOUND | LIB_ID | p-value | q-value | % Change with disease progression |
|---|---|---|---|---|
| Metabolite - 3073 | 50 | 0 | 1.00E−04 | −19% |
| Metabolite - 5233 | 61 | 0 | 0.0022 | −46% |
| Metabolite - 3183-possible-gamma-L-glutamyl-L-phenylalanine | 61 | 0 | 0.0022 | −22% |
| gamma-L-glutamyl-L-tyrosine | 61 | 1.00E−04 | 0.0056 | −22% |
| Metabolite - 6246 | 50 | 1.00E−04 | 0.0056 | −17% |
| Metabolite - 3022 | 50 | 4.00E−04 | 0.0172 | −14% |
| O-acetyl-L-carnitine-hydrochloride | 61 | 7.00E−04 | 0.0234 | 39% |
| Metabolite - 5887 | 61 | 8.00E−04 | 0.0234 | −49% |
| Metabolite - 4275 | 50 | 0.0014 | 0.0396 | 49% |
| Metabolite - 6907 | 50 | 0.0018 | 0.0435 | −19% |
| Metabolite - 1208 | 61 | 0.002 | 0.0435 | −45% |
| Metabolite - 3088 | 50 | 0.0022 | 0.0435 | −26% |
| Metabolite - 4611 | 50 | 0.0026 | 0.0435 | −15% |
| Isobar-19-includes-D-saccharic acid-1-5-anhydro-D-glucitol-2-deoxy-D-galactose-2-deoxy-D-glucose-L-fucose-L-rhamnose | 61 | 0.0027 | 0.0435 | 28% |
| Metabolite - 7009 | 61 | 0.0027 | 0.0435 | −23% |
| Metabolite - 2567 | 61 | 0.0028 | 0.0435 | −17% |
| gamma-glu-leu | 61 | 0.0035 | 0.0486 | −16% |
| Metabolite - 3012 | 50 | 0.0036 | 0.0486 | −9% |
| hippuric acid | 61 | 0.0037 | 0.0486 | −37% |
| L-alpha-glycerophosphorylcholine | 61 | 0.0055 | 0.0668 | −43% |
| Metabolite - 3026 | 50 | 0.0059 | 0.0668 | −14% |
| glyceric acid | 50 | 0.006 | 0.0668 | −16% |
| Metabolite - 4769 | 50 | 0.0064 | 0.0668 | 29% |
| Metabolite - 3830 | 61 | 0.0064 | 0.0668 | −37% |
| inositol-1-phosphate | 50 | 0.0076 | 0.076 | −25% |
| Metabolite - 3078 | 50 | 0.0081 | 0.0772 | 37% |
| Metabolite - 3109 | 50 | 0.0087 | 0.0772 | −33% |
| Isobar-22-includes-glutamic acid-O-acetyl-L-serine | 61 | 0.0094 | 0.0772 | −11% |
| Metabolite - 3098 | 50 | 0.0095 | 0.0772 | −14% |
| Metabolite - 3114 | 50 | 0.0096 | 0.0772 | −34% |
| Biotin | 61 | 0.0096 | 0.0772 | −32% |
| Metabolite - 7177 | 61 | 0.0109 | 0.0846 | 36% |
| Glutamine | 50 | 0.0133 | 0.0987 | 65% |
| Metabolite - 4020 | 50 | 0.0136 | 0.0987 | −14% |
| glycochenodeoxycholic acid | 61 | 0.0139 | 0.0987 | −33% |
| 4-Guanidinobutanoic acid | 61 | 0.0144 | 0.0999 | −16% |
| Metabolite - 2319 | 61 | 0.0156 | 0.1048 | −33% |
| Metabolite - 3019 | 50 | 0.0189 | 0.1235 | −8% |

TABLE 18-continued

T-tests comparing month 1 with month 12.

| COMPOUND | LIB_ID | p-value | q-value | % Change with disease progression |
|---|---|---|---|---|
| Metabolite - 3094 | 50 | 0.0202 | 0.1261 | −14% |
| Metabolite - 2688 | 61 | 0.0203 | 0.1261 | −16% |
| Metabolite - 3138 | 61 | 0.022 | 0.1335 | −20% |
| Arabinose | 50 | 0.0278 | 0.1619 | −22% |
| Metabolite - 1988 | 61 | 0.0286 | 0.1619 | −21% |
| 1-7-dimethylxanthine | 61 | 0.0295 | 0.1619 | −27% |
| Metabolite - 5346 | 50 | 0.0305 | 0.1619 | −12% |
| Metabolite - 3143 | 61 | 0.0305 | 0.1619 | −27% |
| Metabolite - 3025 | 50 | 0.0311 | 0.1619 | −9% |
| Metabolite - 3077 | 50 | 0.0312 | 0.1619 | −15% |
| methionine-sulfoxide | 61 | 0.0335 | 0.1702 | −19% |
| Metabolite - 4627 | 61 | 0.0357 | 0.1749 | −44% |
| 3-methyl-L-histidine | 61 | 0.0359 | 0.1749 | −15% |
| Metabolite - 7050 | 61 | 0.0375 | 0.1782 | −23% |
| D-quinic acid | 50 | 0.0385 | 0.1782 | −43% |
| Metabolite - 2546 | 61 | 0.0387 | 0.1782 | −37% |
| Metabolite - 5907 | 50 | 0.0394 | 0.1782 | −11% |
| Metabolite - 7846 | 50 | 0.0438 | 0.1945 | −13% |
| Metabolite - 2568 | 61 | 0.0459 | 0.1953 | −26% |
| N-6-trimethyl-l-lysine | 61 | 0.0459 | 0.1953 | −22% |
| 1-5-anhydro-D-glucitol | 50 | 0.0471 | 0.1953 | −8% |
| Metabolite - 6272 | 50 | 0.0477 | 0.1953 | −15% |
| Metabolite - 7089 | 61 | 0.0485 | 0.1953 | −13% |
| Methionine | 61 | 0.0487 | 0.1953 | 48% |
| Metabolite - 2005 | 61 | 0.051 | 0.1981 | 39% |
| Metabolite - 4986 | 50 | 0.0511 | 0.1981 | −14% |
| Metabolite - 4511 | 50 | 0.0517 | 0.1981 | −12% |
| Metabolite - 1286 | 61 | 0.0568 | 0.214 | 13% |
| Metabolite - 5231 | 61 | 0.0603 | 0.2241 | −18% |
| Oleic-Acid | 50 | 0.0615 | 0.2249 | 31% |
| Metabolite - 3783 | 61 | 0.068 | 0.2397 | 18% |
| Metabolite - 5349 | 50 | 0.0707 | 0.2397 | −6% |
| Tyrosine | 61 | 0.0709 | 0.2397 | −8% |
| Metabolite - 3707 | 61 | 0.0712 | 0.2397 | 43% |
| Metabolite - 5976 | 61 | 0.0712 | 0.2397 | −34% |
| palmitoleic acid | 50 | 0.0713 | 0.2397 | 29% |
| 3-phospho-d-glycerate | 61 | 0.0745 | 0.2473 | −19% |
| Arginine | 61 | 0.0763 | 0.2499 | −12% |
| Metabolite - 3653-Possible-stachydrine | 61 | 0.0809 | 0.2566 | −34% |
| Metabolite - 2386 | 61 | 0.0814 | 0.2566 | 13% |
| Metabolite - 3951 | 61 | 0.0815 | 0.2566 | 11% |
| Metabolite - 4767 | 50 | 0.0858 | 0.2631 | −7% |
| Metabolite - 3033-possible-threonine-deriv | 50 | 0.0866 | 0.2631 | −6% |
| Metabolite - 3603 | 61 | 0.0867 | 0.2631 | −21% |
| Metabolite - 4612 | 61 | 0.0881 | 0.2642 | −19% |
| Caffeine | 61 | 0.0912 | 0.2701 | −36% |
| Metabolite - 6126 | 61 | 0.0926 | 0.2711 | −21% |
| Metabolite - 1345 | 61 | 0.0948 | 0.2717 | −35% |
| Metabolite - 6711 | 61 | 0.095 | 0.2717 | 23% |
| Histamine | 61 | 0.0968 | 0.2737 | 24% |
| Inositol | 50 | 0.1018 | 0.2828 | −10% |
| Mannose | 50 | 0.1023 | 0.2828 | 12% |
| Metabolite - 7008 | 61 | 0.1061 | 0.2903 | −11% |
| Metabolite - 6326 | 50 | 0.1075 | 0.2907 | −7% |
| Metabolite - 1142-possible-5-hydroxypentanoate-or-beta-hydroxyisovaleric acid | 61 | 0.1096 | 0.2933 | −14% |
| DL-indole-3-lactic acid | 61 | 0.1113 | 0.2947 | −9% |
| meso-erythritol | 50 | 0.1215 | 0.3165 | −7% |
| Metabolite - 5728 | 61 | 0.1221 | 0.3165 | −32% |
| Fructose | 50 | 0.1265 | 0.3219 | −32% |
| alpha-tocopherol | 50 | 0.1268 | 0.3219 | −21% |
| Bicine | 61 | 0.1298 | 0.3237 | 17% |
| Isobar-8-includes-anthranilic acid-salicylamide | 61 | 0.1301 | 0.3237 | −15% |
| Metabolite - 1092 | 61 | 0.1361 | 0.3339 | −36% |
| Metabolite - 4252 | 50 | 0.1368 | 0.3339 | −23% |
| Metabolite - 1111-possible-methylnitronitrosoguanidine-or-ethyl-thiocarbamoylacetate | 61 | 0.1389 | 0.3339 | 19% |
| Metabolite - 3052 | 61 | 0.1396 | 0.3339 | −21% |
| Metabolite - 3044 | 61 | 0.142 | 0.3364 | 24% |
| Metabolite - 7707 | 61 | 0.1433 | 0.3364 | −8% |
| Metabolite - 7807 | 61 | 0.1483 | 0.342 | −13% |
| Metabolite - 6346 | 50 | 0.1484 | 0.342 | −6% |
| Metabolite - 3030 | 50 | 0.1541 | 0.3519 | −6% |

TABLE 18-continued

T-tests comparing month 1 with month 12.

| COMPOUND | LIB_ID | p-value | q-value | % Change with disease progression |
|---|---|---|---|---|
| Metabolite - 1127 | 61 | 0.1569 | 0.355 | 13% |
| Metabolite - 5487 retired: eythrose | 50 | 0.1652 | 0.3699 | −13% |
| Aldosterone | 61 | 0.1665 | 0.3699 | 10% |
| Metabolite - 3131 retired: N4 adduct of indole-3-acetic acid | 61 | 0.1733 | 0.3817 | −12% |
| Metabolite - 2168 | 61 | 0.1783 | 0.3885 | 9% |
| Metabolite - 2561 | 61 | 0.1795 | 0.3885 | 22% |
| (p-Hydroxyphenyl)lactic acid | 50 | 0.1874 | 0.402 | −15% |
| Metabolite - 6269 | 50 | 0.1919 | 0.4082 | −7% |
| Metabolite - 2027 | 61 | 0.1969 | 0.4153 | 18% |
| Metabolite - 2139 | 61 | 0.2034 | 0.4255 | 12% |
| L-kynurenine | 61 | 0.2054 | 0.426 | −6% |
| Metabolite - 1911 | 61 | 0.2116 | 0.4351 | −16% |
| Glycine | 50 | 0.2148 | 0.4383 | 69% |
| Hypoxanthine | 61 | 0.22 | 0.4429 | 73% |
| Metabolite - 6955 | 50 | 0.2213 | 0.4429 | −11% |
| Tryptophan | 61 | 0.2237 | 0.4429 | −5% |
| DL-pipecolic acid | 61 | 0.2258 | 0.4429 | −9% |
| Metabolite - 3002 | 50 | 0.226 | 0.4429 | −27% |
| Isobar-1-includes-mannose-fructose-glucose-galactose-alpha-L-sorbopyranose-Inositol-D-allose-D-altrose-D-psicone | 61 | 0.2326 | 0.4523 | −6% |
| 1-methyl-guanidine | 50 | 0.2407 | 0.4644 | −5% |
| Glycerol | 50 | 0.2485 | 0.4757 | 12% |
| Metabolite - 3097 | 50 | 0.2611 | 0.496 | −12% |
| 2-hydroxybutyric acid | 50 | 0.2663 | 0.5021 | 11% |
| Metabolite - 1193-confirmed-3-indoxyl-sulfate | 61 | 0.2685 | 0.5024 | −11% |
| n-hexadecanoic acid | 50 | 0.2754 | 0.5115 | 9% |
| pantothenic acid | 61 | 0.2801 | 0.5165 | 33% |
| Metabolite - 6226 | 50 | 0.2843 | 0.5167 | −9% |
| Riboflavine | 61 | 0.2844 | 0.5167 | −24% |
| Serine | 50 | 0.2881 | 0.5196 | 28% |
| Metabolite - 5847 | 50 | 0.2914 | 0.5218 | −21% |
| n-dodecanoate | 50 | 0.2959 | 0.526 | −22% |
| Creatinine | 61 | 0.3005 | 0.528 | −10% |
| Metabolite - 6347 | 50 | 0.303 | 0.528 | −8% |
| Praline | 61 | 0.3049 | 0.528 | −6% |
| Metabolite - 1835 | 61 | 0.3055 | 0.528 | −7% |
| Metabolite - 1831-possible-Cl-adduct-of-citrulline | 61 | 0.3104 | 0.5328 | −6% |
| Metabolite - 2506 | 61 | 0.3135 | 0.5331 | −12% |
| Metabolite - 6963 | 50 | 0.3198 | 0.5331 | −14% |
| Metabolite - 2469 | 61 | 0.3199 | 0.5331 | 12% |
| Metabolite - 1086 | 61 | 0.32 | 0.5331 | −18% |
| Metabolite - 5086 | 61 | 0.3213 | 0.5331 | 9% |
| Metabolite - 4364 | 50 | 0.3352 | 0.5511 | 8% |
| Metabolite - Metabolite - 5982 retired: 1-oleoyl-rac glycerol | 50 | 0.3366 | 0.5511 | −13% |
| Metabolite - 4931 | 61 | 0.3422 | 0.5567 | 22% |
| Metabolite - 7765 | 61 | 0.3468 | 0.5586 | −21% |
| Metabolite - 1261 | 61 | 0.3479 | 0.5586 | 13% |
| Metabolite - 2053 | 61 | 0.3527 | 0.5626 | 15% |
| Metabolite - 6931 | 50 | 0.3581 | 0.566 | −5% |
| Metabolite - 6227 | 50 | 0.3601 | 0.566 | −11% |
| Metabolite - 3708 | 61 | 0.3616 | 0.566 | −15% |
| Metabolite - 3093 | 50 | 0.3655 | 0.5686 | −9% |
| Metabolite - 4523 | 50 | 0.3698 | 0.5716 | −7% |
| Metabolite - 2269 | 61 | 0.375 | 0.5761 | 17% |
| 2-keto-L-gulonic acid | 50 | 0.3795 | 0.5795 | −8% |
| dehydroisoandrosterone-3-sulfate-sodium-salt-hydrate | 61 | 0.3853 | 0.5847 | −5% |
| Metabolite - 4624 | 50 | 0.3923 | 0.5885 | −9% |
| Linoleic acid | 50 | 0.3925 | 0.5885 | 6% |
| Metabolite - 1656 | 61 | 0.4005 | 0.5945 | 9% |
| Inosine | 61 | 0.4021 | 0.5945 | 41% |
| Metabolite - 5366 | 50 | 0.4037 | 0.5945 | −14% |
| Metabolite - 4510 | 50 | 0.4134 | 0.5952 | −17% |
| Cholesterol | 50 | 0.4137 | 0.5952 | −3% |
| Isobar-28-includes-L-threonine-L-allothreonine-L-homoserine-S-4-amino-2-hydroxybutyric acid | 61 | 0.4184 | 0.5952 | −6% |
| Metabolite - 4586 | 61 | 0.4212 | 0.5952 | 6% |
| Metabolite - 1206-possible-methyltestosterone-and-others | 61 | 0.426 | 0.5952 | −14% |
| Metabolite - 1975 | 61 | 0.4288 | 0.5952 | −11% |
| Metabolite - 6869 | 50 | 0.4294 | 0.5952 | −8% |

TABLE 18-continued

T-tests comparing month 1 with month 12.

| COMPOUND | LIB_ID | p-value | q-value | % Change with disease progression |
|---|---|---|---|---|
| Metabolite - 4362 | 50 | 0.4312 | 0.5952 | −8% |
| Metabolite - 2390 | 61 | 0.4321 | 0.5952 | −7% |
| Metabolite - 2074 | 61 | 0.4326 | 0.5952 | −14% |
| Metabolite - 3100 | 50 | 0.4338 | 0.5952 | −12% |
| arachidonic acid | 50 | 0.4369 | 0.5952 | −5% |
| Threonine | 50 | 0.4376 | 0.5952 | 16% |
| Metabolite - 4658 | 61 | 0.4377 | 0.5952 | −7% |
| Metabolite - 4522 | 50 | 0.4516 | 0.61 | 4% |
| Alanine | 50 | 0.4534 | 0.61 | 16% |
| Thyroxine | 61 | 0.4594 | 0.6135 | 10% |
| hydroxyacetic acid | 50 | 0.461 | 0.6135 | −5% |
| Metabolite - 7815 | 61 | 0.4664 | 0.6148 | −3% |
| N-5-aminocarbonyl-L-ornithine | 50 | 0.4669 | 0.6148 | −7% |
| Metabolite - 2594 | 61 | 0.4827 | 0.6323 | 146% |
| glycocholic acid | 61 | 0.4869 | 0.6342 | −16% |
| Metabolite - 2395 | 61 | 0.4893 | 0.6342 | −8% |
| Metabolite - 1215 | 61 | 0.4933 | 0.6359 | 9% |
| Metabolite - 2548-possible-Cl-adduct-of-uric acid | 61 | 0.5035 | 0.6359 | 8% |
| Valine | 50 | 0.5043 | 0.6359 | 12% |
| Metabolite - 7890 | 50 | 0.505 | 0.6359 | −8% |
| Metabolite - 5848 | 61 | 0.5063 | 0.6359 | 6% |
| Metabolite - 2559 | 61 | 0.5077 | 0.6359 | −11% |
| Lysine | 50 | 0.5103 | 0.6359 | 12% |
| Metabolite - 3377 | 61 | 0.512 | 0.6359 | 15% |
| Acetylpyrazine | 61 | 0.5136 | 0.6359 | −4% |
| Metabolite - 3832-possible-phenol-sulfate | 61 | 0.5245 | 0.6438 | −13% |
| Metabolite - 4363 | 61 | 0.5294 | 0.6438 | 13% |
| Ornithine | 50 | 0.5303 | 0.6438 | 23% |
| Metabolite - 7888 | 50 | 0.5303 | 0.6438 | −3% |
| Metabolite - 7336 | 61 | 0.5421 | 0.6479 | −15% |
| Metabolite - 3056 | 61 | 0.5457 | 0.6479 | 4% |
| Metabolite - 7706 | 61 | 0.5477 | 0.6479 | 7% |
| Metabolite - 4732 | 61 | 0.5482 | 0.6479 | 12% |
| Isobar-13-includes-5-keto-D-gluconic acid-2-keto-L-gulonic acid-D-glucuronic acid-D-galacturonic acid | 61 | 0.5509 | 0.6479 | −11% |
| Metabolite - 4274 | 50 | 0.5512 | 0.6479 | 18% |
| Metabolite - 1834 | 61 | 0.5526 | 0.6479 | 4% |
| decanoic acid | 50 | 0.5545 | 0.6479 | 3% |
| Metabolite - 3099 | 50 | 0.5574 | 0.6483 | −6% |
| Saccharopine | 61 | 0.5656 | 0.6547 | −7% |
| Metabolite - 5983 | 50 | 0.569 | 0.6556 | 8% |
| Phenylalanine | 61 | 0.5746 | 0.6581 | −3% |
| oxalic acid | 61 | 0.5765 | 0.6581 | −6% |
| Uridine | 61 | 0.592 | 0.6704 | 5% |
| 5-oxoproline | 50 | 0.5956 | 0.6704 | −7% |
| malic acid | 50 | 0.5961 | 0.6704 | 13% |
| Metabolite - 1264 | 61 | 0.598 | 0.6704 | 32% |
| Metabolite - 4806 | 50 | 0.6192 | 0.6911 | −5% |
| Metabolite - 3441 | 61 | 0.6232 | 0.6925 | 5% |
| Metabolite - 1914 | 61 | 0.637 | 0.6993 | 9% |
| Leucine | 50 | 0.6405 | 0.6993 | 10% |
| Metabolite - 1836 | 61 | 0.6407 | 0.6993 | −6% |
| Metabolite - 1085-possible-isolobinine-or-4-aminoestra-1-3-5-10-triene-3-17beta-diol | 61 | 0.6509 | 0.7035 | −4% |
| Metabolite - 2825-possible-Riluzole | 61 | 0.6519 | 0.7035 | −7% |
| Metabolite - 6551 | 61 | 0.6584 | 0.7035 | 13% |
| Metabolite - 1498 | 61 | 0.6621 | 0.7035 | −4% |
| Metabolite - 5791 | 61 | 0.6626 | 0.7035 | 4% |
| Metabolite - 1335 | 61 | 0.6691 | 0.7035 | −9% |
| citric acid | 50 | 0.6694 | 0.7035 | −3% |
| Metabolite - 3129 | 61 | 0.6711 | 0.7035 | −5% |
| beta-hydroxypyruvic acid | 50 | 0.679 | 0.7035 | 3% |
| Isobar-6-includes-valine-betaine | 61 | 0.679 | 0.7035 | −2% |
| methyl-indole-3-acetate | 61 | 0.6795 | 0.7035 | −6% |
| Metabolite - 6488 | 50 | 0.6842 | 0.7035 | −8% |
| D-glucose | 50 | 0.6866 | 0.7035 | −1% |
| Metabolite - 2249 | 61 | 0.6868 | 0.7035 | −3% |
| Metabolite - 4055 | 50 | 0.6869 | 0.7035 | −8% |
| Metabolite - 4470 | 61 | 0.6946 | 0.7038 | −2% |
| tetradecanoic acid | 50 | 0.6972 | 0.7038 | 5% |
| Metabolite - 2056 | 61 | 0.6983 | 0.7038 | 3% |
| Metabolite - 6270 | 50 | 0.7005 | 0.7038 | 6% |
| Metabolite - 4906 | 61 | 0.7013 | 0.7038 | 11% |

TABLE 18-continued

T-tests comparing month 1 with month 12.

| COMPOUND | LIB_ID | p-value | q-value | % Change with disease progression |
|---|---|---|---|---|
| Metabolite - 3003 | 50 | 0.7059 | 0.7055 | −3% |
| Metabolite - 7889 | 50 | 0.7108 | 0.7076 | −3% |
| Metabolite - 1254 | 61 | 0.7149 | 0.7088 | −15% |
| Metabolite - 3040 | 50 | 0.7211 | 0.7104 | 1% |
| DL-homocysteine | 61 | 0.7222 | 0.7104 | −5% |
| Metabolite - 5730 | 61 | 0.7295 | 0.7148 | 3% |
| Metabolite - 4167 | 61 | 0.7332 | 0.7156 | −3% |
| Metabolite - 1342-possible-phenylacetylglutamine-or-formyl-N-acetyl-5-methoxykynurenamine | 61 | 0.7373 | 0.7168 | 3% |
| glutamic acid | 50 | 0.7453 | 0.7182 | 5% |
| Metabolite - 1114 | 61 | 0.749 | 0.7182 | 7% |
| Metabolite - 2370 | 61 | 0.7509 | 0.7182 | −4% |
| Metabolite - 7762 | 61 | 0.755 | 0.7182 | 6% |
| Phosphate | 50 | 0.7557 | 0.7182 | 2% |
| Metabolite - 4795 | 50 | 0.7587 | 0.7182 | −4% |
| Isobar-21-includes-gamma-aminobutyryl-L-histidine-L-anserine | 61 | 0.759 | 0.7182 | 2% |
| Metabolite - 2986 | 50 | 0.7649 | 0.7211 | 2% |
| Metabolite - 5403 | 50 | 0.7693 | 0.7225 | 2% |
| Metabolite - 5788 | 61 | 0.7751 | 0.7229 | −10% |
| Nonanate | 50 | 0.7809 | 0.7229 | 0% |
| Metabolite - 1819 | 61 | 0.7832 | 0.7229 | −2% |
| benzoic acid | 61 | 0.7845 | 0.7229 | 2% |
| Metabolite - 6467 | 50 | 0.7846 | 0.7229 | −4% |
| Metabolite - 2981 | 50 | 0.7884 | 0.7229 | −1% |
| Metabolite - 3017 | 50 | 0.7901 | 0.7229 | −2% |
| Histidine | 50 | 0.7975 | 0.7246 | 4% |
| Allantoin | 50 | 0.7998 | 0.7246 | −8% |
| Metabolite - 2753 | 61 | 0.8025 | 0.7246 | −3% |
| Metabolite - 2973 | 50 | 0.8036 | 0.7246 | 1% |
| Metabolite - 5247 | 61 | 0.8088 | 0.7266 | 2% |
| Metabolite - 1323-possible-p-cresol-sulfate | 61 | 0.8124 | 0.7266 | 2% |
| Metabolite - 7146 | 61 | 0.8146 | 0.7266 | −2% |
| Metabolite - 3087 | 50 | 0.8213 | 0.7271 | 8% |
| Metabolite - 4235 | 61 | 0.8235 | 0.7271 | 2% |
| 4-O-beta-galactopyranosyl-D-mannopyranose | 61 | 0.8239 | 0.7271 | 3% |
| Isoleucine | 50 | 0.829 | 0.7277 | 4% |
| Metabolite - 3218 | 61 | 0.8304 | 0.7277 | 4% |
| Metabolite - 5673 | 61 | 0.8384 | 0.7321 | 3% |
| Metabolite - 4428 | 61 | 0.8469 | 0.737 | 2% |
| uric acid | 50 | 0.8635 | 0.7488 | −2% |
| Metabolite - 2100 | 61 | 0.8676 | 0.7492 | 1% |
| octadecanoic acid | 50 | 0.87 | 0.7492 | −1% |
| sn-Glycerol-3-phosphate | 50 | 0.8783 | 0.7538 | −2% |
| Metabolite - 3125 | 61 | 0.8898 | 0.761 | −2% |
| Metabolite - 2321 | 61 | 0.8933 | 0.7613 | 2% |
| phosphoenolpyruvate | 61 | 0.9033 | 0.7635 | 1% |
| Metabolite - 6827 | 61 | 0.906 | 0.7635 | −1% |
| Metabolite - 1597 | 61 | 0.9085 | 0.7635 | 0% |
| heptadecanoic acid | 50 | 0.9106 | 0.7635 | −1% |
| Metabolite - 2185 | 61 | 0.9112 | 0.7635 | 1% |
| Metabolite - 3808 | 61 | 0.9235 | 0.766 | −1% |
| Biliverdin | 61 | 0.9263 | 0.766 | 1% |
| p-hydroxybenzaldehyde | 61 | 0.9273 | 0.766 | 0% |
| 5-6-dihydrouracil | 50 | 0.9289 | 0.766 | 1% |
| Metabolite - 2109 | 61 | 0.9316 | 0.766 | −1% |
| Lactate | 50 | 0.9331 | 0.766 | 2% |
| Metabolite - 7147 | 61 | 0.9393 | 0.766 | −1% |
| Isobar-2-includes-2-aminoisobutyric acid-3-amino-isobutyrate-2-amino-butyrate-4-aminobutanoic acid-dimethylglycine-choline | 61 | 0.9407 | 0.766 | −2% |
| Metabolite - 2711 | 61 | 0.9442 | 0.766 | −2% |
| Theobromine | 61 | 0.9449 | 0.766 | 2% |
| Aspartate | 50 | 0.9491 | 0.7662 | 1% |
| Metabolite - 1110 | 61 | 0.9513 | 0.7662 | −1% |
| Metabolite - 2952 | 50 | 0.9725 | 0.7739 | 2% |
| Urea | 50 | 0.9731 | 0.7739 | 1% |
| Carnitine | 61 | 0.9734 | 0.7739 | 1% |
| Metabolite - 4873 | 61 | 0.9752 | 0.7739 | 1% |
| 3-hydroxybutanoic acid | 50 | 0.9785 | 0.7739 | 1% |
| Metabolite - 2915 | 50 | 0.9841 | 0.7739 | −1% |
| Creatine | 61 | 0.986 | 0.7739 | −1% |
| Metabolite - 5769 | 61 | 0.9874 | 0.7739 | 0% |

TABLE 18-continued

T-tests comparing month 1 with month 12.

| COMPOUND | LIB_ID | p-value | q-value | % Change with disease progression |
|---|---|---|---|---|
| Metabolite - 3972 | 61 | 0.9891 | 0.7739 | 0% |
| Metabolite - 5234 | 61 | 0.9932 | 0.7739 | 0% |
| Metabolite - 4351 | 61 | 0.9951 | 0.7739 | 0% |

Example 10

Analytical Characterization of Isobars, Unnamed Biomarkers, and Unnamed Non-Biomarker Compounds Table 19 below includes analytical characteristics of each of the Isobars and the unnamed metabolites listed in Tables 3, 4, 5, 6, 7, 8, 16, 17, and 18 above. The table includes, for each listed Isobar and Metabolite, the retention time (RT), retention index (RI), mass, quant mass, and polarity obtained using the analytical methods described above. "Mass" refers to the mass of the C12 isotope of the parent ion used in quantification of the compound. The values for "Quant Mass" give an indication of the analytical method used for quantification: "Y" indicates GC-MS and "1" indicates LC-MS. "Polarity" indicates the polarity of the quantitative ion as being either positive (+) or negative (−).

TABLE 19

Analytical Characteristics of Isobars and Unnamed Metabolites

| Name | Platform | RT | RI | MASS | QUANT_MASS | Polarity |
|---|---|---|---|---|---|---|
| Isobar-13-includes-5-keto-D-gluconic acid; 2-keto-L-gulonic acid-D-glucuronic acid; D-galacturonic acid | LC | 1.4 | 1530 | 193.1 | 1 | −i |
| Isobar-19-includes-D-saccharic acid; 2-deoxy-D-galactose; 2-deoxy-D-glucose; L-fucose; L-rhamnose | LC | 1.55 | 1700 | 209 | 1 | − |
| Isobar-1-includes-mannose-fructose-glucose-galactose-alpha-L-sorbopyranose-Inositol-D-allose | LC | 1.45 | 1481 | 224.9 | 1 | − |
| Isobar-21-includes-gamma-aminobutyryl-L-histidine-L-anserine | LC | 1.59 | 1620 | 241 | 1 | + |
| Isobar-22-includes-glutamic acid; O-acetyl-L-serine | LC | 1.55 | 1635 | 148.0 | 1 | +i |
| Isobar-27-includes-L-kynurenine-alpha-2-diamino-gamma-oxobenzenebutanoic acid | LC | 8.23 | 8470 | 209.1 | 1 | + |
| Isobar-28-includes-L-threonine-L-allothreonine | LC | 1.46 | 1525 | 120 | 1 | + |
| Isobar-2-includes-3-amino-isobutyrate-2-amino-butyrate-4-aminobutanoic acid-dimethylglycine-choline- | LC | 1.6 | 1671 | 104.1 | 1 | + |
| Isobar-5-includes-asparagine-ornithine | LC | 1.5 | 1395 | 133.1 | 1 | + |
| Isobar-6-includes-valine-betaine | LC | 2.13 | 2160 | 118.1 | 1 | + |
| Isobar-8-includes-anthranilic acid-salicylamide | LC | 10 | 10116 | 138.1 | 1 | + |
| Isobar-9-includes-sucrose-beta-D-lactose-D-trehalose-D-cellobiose-D-Maltose-palatinose-melibiose-alpha-D-lactose | LC | 1.6 | 1605 | 386.9 | 1 | − |
| Metabolite - 1063 | LC | 8.5 | 8845 | 391.4 | 1 | + |
| Metabolite - 1064 | LC | 1.9 | 1950 | 258.1 | 1 | + |
| Metabolite - 1065 | LC | 9.66 | 9870 | 769 | 1 | + |
| Metabolite - 1066 | LC | 1.57 | 1520 | 215.1 | 1 | − |
| Metabolite - 1068 | LC | 1.44 | 1490 | 203.1 | 1 | + |
| Metabolite - 1071 | LC | 15.2 | 15445 | 279.3 | 1 | + |
| Metabolite - 1073 | LC | 15.4 | 15630 | 338 | 1 | + |
| Metabolite - 1085 isolobinine or 4-aminoestra-1,3-5-10-triene-3-17beta-diol | LC | 15.8 | 15964 | 288.1 | 1 | + |
| Metabolite - 1086 | LC | 4.56 | 4811 | 294.1 | 1 | + |
| Metabolite - 1087 | LC | 9.2 | 9440 | 371.7 | 1 | + |
| Metabolite - 1088 | LC | 13.1 | 13298 | 369.1 | 1 | − |
| Metabolite - 1089 | LC | 2.01 | 2017 | 346.9 | 1 | + |
| Metabolite - 1092 | LC | 11.5 | 11684 | 1006 | 1 | + |
| Metabolite - 1104 | LC | 2.43 | 2410 | 201 | 1 | − |
| Metabolite - 1108 | LC | 4.15 | 4369 | 144.1 | 1 | + |
| Metabolite - 1110 | LC | 11.7 | 11841 | 269.1 | 1 | − |
| Metabolite - 1111-methylnitronitrosoguanidine or ethyl-thiocarbamoylacetate | LC | 2.69 | 2782 | 148.1 | 1 | + |
| Metabolite - 1113 | LC | 4.91 | 5190 | 204.2 | 1 | + |
| Metabolite - 1114 | LC | 2.19 | 2198 | 104.1 | 1 | + |
| Metabolite - 1116 | LC | 4.2 | 4480 | 103.4 | 1 | − |
| Metabolite - 1126 | LC | 3.04 | 3188 | 175.1 | 1 | + |
| Metabolite - 1127 | LC | 12.2 | 12369 | 363.1 | 1 | + |
| Metabolite - 1129 | LC | 5.16 | 5419 | 260.1 | 1 | + |

TABLE 19-continued

Analytical Characteristics of Isobars and Unnamed Metabolites

| Name | Platform | RT | RI | MASS | QUANT_MASS | Polarity |
|---|---|---|---|---|---|---|
| Metabolite - 1131 | LC | 1.62 | 1649 | 121 | 1 | + |
| Metabolite - 1132 | LC | 1.66 | 1689 | 291.1 | 1 | − |
| Metabolite - 1133 | LC | 1.63 | 1636 | 315 | 1 | + |
| Metabolite - 1142-5-hydroxypentanoat or beta-hydroxyisovaleric acid | LC | 8.54 | 8739 | 117 | 1 | − |
| Metabolite - 1161 | LC | 2.31 | 2350 | 135 | 1 | − |
| Metabolite - 1181 | LC | 1.44 | 1486 | 203.1 | 1 | + |
| Metabolite - 1192 | LC | 8.78 | 8983 | 129.1 | 1 | − |
| Metabolite - 1193 3-indoxyl-sulfate | LC | 8.85 | 9031 | 212.1 | 1 | − |
| Metabolite - 1201 | LC | 5.75 | 5999 | 182 | 1 | + |
| Metabolite - 1203 | LC | 9.11 | 9288 | 510.2 | 1 | + |
| Metabolite - 1206 methyltestosterone | LC | 15.3 | 15475 | 303.2 | 1 | +i |
| Metabolite - 1208 | LC | 15.3 | 15494 | 319.4 | 1 | − |
| Metabolite - 1209 | LC | 8.89 | 9077.8 | 426.9 | 1 | + |
| Metabolite - 121 | GC | 5.54 | 1161.4 | 102.079 | Y | + |
| Metabolite - 1215 | LC | 8.96 | 9390 | 550.1 | 1 | +i |
| Metabolite - 1216 | LC | 1.6 | 1631.4 | 343.9 | 1 | − |
| Metabolite - 1220 | LC | 15.2 | 15403 | 319.2 | 1 | + |
| Metabolite - 1242 | LC | 8.43 | 8627.6 | 355.9 | 1 | + |
| Metabolite - 1247 | LC | 14.8 | 14959 | 448.3 | 1 | − |
| Metabolite - 1251 | LC | 16.3 | 16406 | 718.2 | 1 | + |
| Metabolite - 1252 | LC | 8.12 | 8326 | 229.9 | 1 | + |
| Metabolite - 1254 | LC | 9.8 | 9987.5 | 733.4 | 1 | + |
| Metabolite - 1261 | LC | 10.7 | 10905 | 528.4 | 1 | + |
| Metabolite - 1262 | LC | 9.97 | 10163 | 808.9 | 1 | + |
| Metabolite - 1264 | LC | 10.7 | 10879 | 617.8 | 1 | − |
| Metabolite - 1265 | LC | 15.3 | 15440 | 361.9 | 1 | + |
| Metabolite - 128 | GC | 10.1 | 1697.1 | 227.171 | Y | + |
| Metabolite - 1281 | LC | 8.39 | 8591.3 | 328.1 | 1 | + |
| Metabolite - 1283 | LC | 9.04 | 9244.5 | 434.8 | 1 | + |
| Metabolite - 1285 | LC | 2.33 | 2342 | 280.1 | 1 | + |
| Metabolite - 1286 | LC | 14.4 | 14580 | 229 | 1 | + |
| Metabolite - 1288 | LC | 2.11 | 2120.5 | 302 | 1 | − |
| Metabolite - 1289 | LC | 8.96 | 9139.7 | 338.4 | 1 | + |
| Metabolite - 1301 | LC | 8.62 | 8819 | 243.3 | 1 | + |
| Metabolite - 1302 | LC | 15.2 | 15391 | 279.2 | 1 | + |
| Metabolite - 1304 | LC | 9.74 | 9930.5 | 729.5 | 1 | + |
| Metabolite - 1322 retired: citric acid | LC | 2.78 | 2892 | 190.9 | 1 | − |
| Metabolite - 1323 | LC | 9.31 | 9719.8 | 187 | 1 | − |
| Metabolite - 1323 p-cresol-sulfate | LC | 9.31 | 9719.8 | 187 | 1 | − |
| Metabolite - 1324 | LC | 3.19 | 3393.9 | 191 | 1 | − |
| Metabolite - 1327 | LC | 13.2 | 13706 | 585.4 | 1 | + |
| Metabolite - 1328 | LC | 3.21 | 3430.7 | 210.1 | 1 | + |
| Metabolite - 1329 | LC | 2.69 | 2791 | 210.1 | 1 | + |
| Metabolite - 1331 | LC | 12.9 | 13343 | 239.2 | 1 | − |
| Metabolite - 1332 | LC | 2.27 | 2400 | 280.1 | 1 | + |
| Metabolite - 1333 retired: citric acid | LC | 3.05 | 3194.6 | 321.9 | 1 | + |
| Metabolite - 1334 | LC | 2.06 | 2217.7 | 135 | 1 | − |
| Metabolite - 1335 | LC | 8.74 | 9162.2 | 367.2 | 1 | + |
| Metabolite - 1336 retired: carnitine | LC | 1.87 | 2039 | 162.2 | 1 | + |
| Metabolite - 1337 | LC | 8.28 | 8696 | 173 | 1 | − |
| Metabolite - 1340 | LC | 3.76 | 4214.5 | 173.1 | 1 | − |
| Metabolite - 1342 phenylacetylglutamine-or-formyl-N-acetyl-5-methoxykynurenamine | LC | 9.04 | 9459.4 | 265.2 | 1 | + |
| Metabolite - 1343 retired: p-hydroxyphenyllactic acid | LC | 8.91 | 9327 | 181.2 | 1 | + |
| Metabolite - 1344 retired: Na adduct of citric acid | LC | 3.29 | 3511.8 | 406.7 | 1 | + |
| Metabolite - 1345 | LC | 13.3 | 14600 | 369.3 | 1 | −i |
| Metabolite - 1346 | LC | 1.27 | 1449.5 | 113 | 1 | − |
| Metabolite - 1347 | LC | 9.37 | 9777.7 | 247.2 | 1 | + |
| Metabolite - 1349 retired: Isobar 7 | LC | 3.5 | 3876 | 323.9 | 1 | + |
| Metabolite - 1350 | LC | 13.8 | 14249 | 909.8 | 1 | + |
| Metabolite - 1351 retired: urea adduct of Isobar 6 | LC | 1.77 | 1936.5 | 177.9 | 1 | + |
| Metabolite - 1353 | GC | 13.2 | 2104.2 | 371.94 | Y | + |
| Metabolite - 1358 | GC | 12.7 | 2038.3 | 288.015 | Y | + |
| Metabolite - 136 | GC | 6.07 | 1221.7 | 211.034 | Y | + |
| Metabolite - 1368 | LC | 8.18 | 8607.4 | 184.1 | 1 | + |
| Metabolite - 1372 retired: 2-hydroxyhippuric acid | LC | 9.63 | 10038 | 194.1 | 1 | − |
| Metabolite - 1373 | GC | 10.3 | 1749.6 | 218.014 | Y | + |
| Metabolite - 1379 retired: hippuric acid | LC | 9.06 | 9454.8 | 180.1 | 1 | + |
| Metabolite - 138 | GC | 10.8 | 1770.3 | 156.123 | Y | + |
| Metabolite - 1383 | LC | 8.66 | 9077.9 | 370.1 | 1 | − |
| Metabolite - 1385 | LC | 11.9 | 12303 | 225.1 | 1 | − |
| Metabolite - 1388 | LC | 12.5 | 12940 | 456.9 | 1 | + |

TABLE 19-continued

Analytical Characteristics of Isobars and Unnamed Metabolites

| Name | Platform | RT | RI | MASS | QUANT_MASS | Polarity |
|---|---|---|---|---|---|---|
| Metabolite - 1389 | LC | 13.6 | 14111 | 425.3 | 1 | − |
| Metabolite - 1397 | LC | 15.7 | 16277 | 425.5 | 1 | + |
| Metabolite - 141 | GC | 6.13 | 1228.9 | 221.119 | Y | + |
| Metabolite - 1414 | GC | 10.6 | 1788.9 | 259.012 | Y | + |
| Metabolite - 145 | GC | 12.7 | 1991.9 | 204.129 | Y | + |
| Metabolite - 1457 | LC | 1.59 | 1675 | 188.2 | 1 | + |
| Metabolite - 1458 retired: hypoxanthine | LC | 6.5 | 6815.7 | 137.1 | 1 | + |
| Metabolite - 146 | GC | 6.58 | 1279.5 | 231.108 | Y | + |
| Metabolite - 1465 | LC | 3.45 | 3600 | 162.1 | 1 | + |
| Metabolite - 147 | GC | 8.58 | 1513.2 | 217.127 | Y | + |
| Metabolite - 1497 | LC | 13.9 | 14032 | 332.2 | 1 | + |
| Metabolite - 1498 | LC | 1.56 | 1650 | 143.1 | 1 | − |
| Metabolite - 150 | GC | 6.21 | 1237.9 | 174.076 | Y | + |
| Metabolite - 1500 | LC | 1.72 | 1760.4 | 391.1 | 1 | + |
| Metabolite - 1514 | GC | 6.24 | 1239.8 | 148.068 | Y | + |
| Metabolite - 1519 | GC | 11.2 | 1812.1 | 204.088 | Y | + |
| Metabolite - 1534 | GC | 11.3 | 1824.3 | 246.08 | Y | + |
| Metabolite - 1537 | GC | 6.14 | 1220.1 | 171.055 | Y | + |
| Metabolite - 1538 | GC | 10.6 | 1730.7 | 156.074 | Y | + |
| Metabolite - 1551 | GC | 8.73 | 1526.9 | 205.077 | Y | + |
| Metabolite - 1554 | GC | 8.88 | 1541.3 | 292.084 | Y | + |
| Metabolite - 1559 | GC | 10.2 | 1683.3 | 217.071 | Y | + |
| Metabolite - 1564 | GC | 9.4 | 1592.8 | 115.081 | Y | + |
| Metabolite - 1573 retired: glycerol-2-phosphate | LC | 1.63 | 1669 | 170.9 | 1 | − |
| Metabolite - 1574 | LC | 1.92 | 1939 | 233 | 1 | + |
| Metabolite - 1575 | LC | 2.25 | 2243.5 | 219.1 | 1 | + |
| Metabolite - 1576 | LC | 2.51 | 2530 | 247.1 | 1 | + |
| Metabolite - 1597 | LC | 3.66 | 3894 | 265.9 | 1 | + |
| Metabolite - 1608 | LC | 8.08 | 8253 | 350 | 1 | + |
| Metabolite - 1609 | LC | 8.31 | 8529 | 378 | 1 | + |
| Metabolite - 1612 | LC | 8.64 | 8850.3 | 230.9 | 1 | + |
| Metabolite - 1616 | LC | 12.7 | 12910 | 331.2 | 1 | + |
| Metabolite - 1655 | LC | 1.31 | 1374 | 107 | 1 | + |
| Metabolite - 1656 | LC | 1.46 | 1509 | 154.9 | 1 | − |
| Metabolite - 1673 | GC | 12.5 | 1982.2 | 217.019 | Y | + |
| Metabolite - 1713 retired: n-acetyl-L-aspartic acid | LC | 2.73 | 2770 | 174 | 1 | − |
| Metabolite - 1734 | LC | 8.72 | 8923 | 475 | 1 | − |
| Metabolite - 1735 | LC | 8.75 | 8929 | 644.1 | 1 | − |
| Metabolite - 1736 retired: p-hydroxybenzaldehyde | LC | 9.78 | 9961.5 | 121.1 | 1 | − |
| Metabolite - 1737 retired: 2,3-dihydroxybenzoic acid | LC | 9.84 | 10036 | 153.1 | 1 | − |
| Metabolite - 1738 | LC | 14.4 | 14574 | 277.9 | 1 | + |
| Metabolite - 1753 | GC | 8.16 | 1446.9 | 356.938 | Y | + |
| Metabolite - 1754 | GC | 12.6 | 1981.6 | 204.056 | Y | + |
| Metabolite - 1757 | GC | 11.9 | 1889.9 | 318.169 | Y | + |
| Metabolite - 1775 | GC | 11.2 | 1809.3 | 518.181 | Y | + |
| Metabolite - 1802 | LC | 8.95 | 9328 | 486.9 | 1 | + |
| Metabolite - 1814 | GC | 12.8 | 2004.7 | 290.098 | Y | + |
| Metabolite - 1815 | GC | 11.8 | 1886.8 | 289.079 | Y | + |
| Metabolite - 1817 | LC | 1.37 | 1552.3 | 252 | 1 | + |
| Metabolite - 1818 | LC | 1.43 | 1608.7 | 126.9 | 1 | − |
| Metabolite - 1819 | LC | 1.36 | 1540 | 244.8 | 1 | −i |
| Metabolite - 1820 retired: glycerol-2-phosphate | LC | 1.45 | 1626.8 | 342.8 | 1 | − |
| Metabolite - 1824 | GC | 8.55 | 1509.8 | 126.046 | Y | + |
| Metabolite - 1826 | GC | 5.5 | 1168 | 101.993 | Y | + |
| Metabolite - 1827 | GC | 11.3 | 1835.6 | 205.014 | Y | + |
| Metabolite - 1829 retired: oxalic acid | LC | 1.43 | 1600 | 135 | 1 | − |
| Metabolite - 1830 | LC | 1.49 | 1661.3 | 192.9 | 1 | − |
| Metabolite - 1831 Cl-adduct-of-citrulline | LC | 1.46 | 1638.7 | 209.9 | 1 | − |
| Metabolite - 1834 | LC | 1.64 | 1794.5 | 104 | 1 | − |
| Metabolite - 1835 | LC | 1.86 | 1999.3 | 152.1 | 1 | − |
| Metabolite - 1836 | LC | 2.1 | 2215.5 | 205.9 | 1 | − |
| Metabolite - 1839 | LC | 2.57 | 2624 | 138.1 | 1 | + |
| Metabolite - 1842 retired: 4-Guanidinobutanoic acid | LC | 3.21 | 3259 | 146.1 | 1 | + |
| Metabolite - 1843 | LC | 3.25 | 3295 | 288.7 | 1 | − |
| Metabolite - 1847 | GC | 11.6 | 1854.5 | 373.02 | Y | + |
| Metabolite - 1849 | GC | 13.1 | 2041.3 | 361.035 | Y | + |
| Metabolite - 1850 | GC | 13.7 | 2110.6 | 392.092 | Y | + |
| Metabolite - 1888 | GC | 10.1 | 1675.2 | 173.077 | Y | + |
| Metabolite - 1909 | LC | 1.66 | 1803.5 | 162.1 | 1 | + |
| Metabolite - 1910 retired: uric acid | LC | 5.85 | 6058.1 | 169.3 | 1 | + |
| Metabolite - 1911 | LC | 11.4 | 11800 | 464.1 | 1 | + |
| Metabolite - 1912 | LC | 9.22 | 9570.4 | 181.2 | 1 | + |

TABLE 19-continued

Analytical Characteristics of Isobars and Unnamed Metabolites

| Name | Platform | RT | RI | MASS | QUANT_MASS | Polarity |
|---|---|---|---|---|---|---|
| Metabolite - 1914 | LC | 10.4 | 10720 | 239.1 | 1 | + |
| Metabolite - 1915 | LC | 14.4 | 14799 | 507.2 | 1 | − |
| Metabolite - 1926 retired: trans-2,3,4-trimethoxycinnamic acid | LC | 11.5 | 11840 | 239.2 | 1 | + |
| Metabolite - 1927 retired: Metabolite - 1323 above | LC | 9.22 | 9581.5 | 186.9 | 1 | − |
| Metabolite - 1929 | LC | 1.33 | 1496.3 | 215.1 | 1 | − |
| Metabolite - 1956 | GC | 8.4 | 1482.3 | 218.037 | Y | + |
| Metabolite - 1958 | LC | 8.92 | 9282.3 | 188.2 | 1 | + |
| Metabolite - 1960 | LC | 1.42 | 1592 | 337.1 | 1 | + |
| Metabolite - 1961 retired: glycocholic acid | LC | 14 | 14431 | 466.1 | 1 | + |
| Metabolite - 1968 | GC | 10.9 | 1778.2 | 414.045 | Y | + |
| Metabolite - 1972 | LC | 9.64 | 9958.6 | 531.7 | 1 | + |
| Metabolite - 1974 | LC | 5.93 | 6077 | 160.2 | 1 | + |
| Metabolite - 1975 | LC | 5.95 | 6093 | 344 | 1 | + |
| Metabolite - 1977 5-oxoproline | LC | 3.56 | 3815 | 260.9 | 1 | + |
| Metabolite - 1979 retired: CL adduct of Isobar 19 | LC | 1.52 | 1690.3 | 199 | 1 | − |
| Metabolite - 1981 | LC | 7.94 | 8266.8 | 158.1 | 1 | + |
| Metabolite - 1988 | LC | 11.1 | 11515 | 190.1 | 1 | + |
| Metabolite - 2005 | LC | 8.62 | 9048 | 232.1 | 1 | + |
| Metabolite - 2009 | GC | 11.9 | 1905.9 | 217.024 | Y | + |
| Metabolite - 2026 | LC | 1.36 | 1556.2 | 239.2 | 1 | + |
| Metabolite - 2027 | LC | 1.56 | 1729.3 | 184.1 | 1 | + |
| Metabolite - 2033 retired: 2-isopropylmalic acid | LC | 9.03 | 9332.5 | 175 | 1 | − |
| Metabolite - 2038 | LC | 7.86 | 8139.3 | 422 | 1 | + |
| Metabolite - 2041 | LC | 13.8 | 14198 | 246.3 | 1 | + |
| Metabolite - 2045 | LC | 1.37 | 1548.9 | 148 | 1 | + |
| Metabolite - 2046 | LC | 15.8 | 16200 | 502.5 | 1 | + |
| Metabolite - 2047 retired: Metabolite - 4328 | LC | 8.82 | 9150.3 | 828.1 | 1 | + |
| Metabolite - 2051 | LC | 1.45 | 1634 | 309 | 1 | + |
| Metabolite - 2052 retired: potassium adduct of Isobar 1 | LC | 1.3 | 1429.8 | 219.1 | 1 | + |
| Metabolite - 2053 | LC | 1.35 | 1482.3 | 324.9 | 1 | − |
| Metabolite - 2055 | LC | 1.37 | 1502 | 269.9 | 1 | + |
| Metabolite - 2056 | LC | 1.37 | 1499 | 165.1 | 1 | − |
| Metabolite - 2058 | LC | 1.41 | 1538.4 | 282 | 1 | + |
| Metabolite - 2067 retired: carnitine | LC | 1.67 | 1750 | 162.1 | 1 | + |
| Metabolite - 2074 | LC | 2.24 | 2380.9 | 280.1 | 1 | + |
| Metabolite - 2100 | LC | 1.33 | 1532.9 | 499 | 1 | + |
| Metabolite - 2105 | LC | 8.15 | 8442 | 433.6 | 1 | + |
| Metabolite - 2109 | LC | 8.99 | 9266 | 321.1 | 1 | + |
| Metabolite - 2111 | LC | 9.19 | 9442.3 | 365.1 | 1 | + |
| Metabolite - 2130 | LC | 16.3 | 16626 | 792.4 | 1 | + |
| Metabolite - 2139 | LC | 8.09 | 8416.7 | 218.1 | 1 | + |
| Metabolite - 2141 | LC | 9.39 | 9605 | 409.1 | 1 | + |
| Metabolite - 2151 | LC | 14.4 | 14722 | 531.3 | 1 | + |
| Metabolite - 2168 | LC | 1.36 | 1549 | 261.1 | 1 | +i |
| Metabolite - 2173 | LC | 2.68 | 2748.2 | 230.1 | 1 | + |
| Metabolite - 2174 | LC | 2.5 | 2569 | 250.1 | 1 | + |
| Metabolite - 2175 | LC | 3.84 | 4148.4 | 144 | 1 | + |
| Metabolite - 2181 | LC | 8.37 | 8715.5 | 298 | 1 | + |
| Metabolite - 2185 | LC | 9.22 | 9499.4 | 246.2 | 1 | + |
| Metabolite - 2192 | GC | 8.88 | 1538.7 | 174.05 | Y | + |
| Metabolite - 2194 | LC | 13.7 | 13961 | 544.2 | 1 | + |
| Metabolite - 221 | GC | 11 | 1829 | 205.106 | Y | + |
| Metabolite - 2212 | LC | 16 | 16271 | 478.2 | 1 | + |
| Metabolite - 222 | GC | 11 | 1835.7 | 319.092 | Y | + |
| Metabolite - 2220 | GC | 9.75 | 1639.3 | 450.927 | Y | + |
| Metabolite - 2221 | GC | 11.6 | 1862.5 | 308.112 | Y | + |
| Metabolite - 223 | GC | 9.65 | 1677.7 | 217.137 | Y | + |
| Metabolite - 2231 | LC | 14.3 | 14629 | 278.1 | 1 | + |
| Metabolite - 2237 | LC | 10.1 | 10454 | 453.1 | 1 | + |
| Metabolite - 2238 | LC | 10.5 | 10817 | 792.2 | 1 | + |
| Metabolite - 2242 | LC | 11.6 | 11926 | 254.3 | 1 | + |
| Metabolite - 2249 | LC | 14.2 | 14571 | 267.2 | 1 | − |
| Metabolite - 2250 | LC | 14.3 | 14668 | 286.3 | 1 | + |
| Metabolite - 2254 | LC | 1.53 | 1687.6 | 217.2 | 1 | + |
| Metabolite - 2255 | LC | 9.08 | 9394 | 539.1 | 1 | + |
| Metabolite - 2256 | LC | 9.93 | 10232 | 460.8 | 1 | + |
| Metabolite - 226 | GC | 3.87 | 1011 | 200.137 | Y | + |
| Metabolite - 2266 retired 4-acetominophen sulfate | LC | 8.31 | 8713.4 | 229.9 | 1 | − |
| Metabolite - 2269 | LC | 10.4 | 10727 | 255.1 | 1 | − |
| Metabolite - 2270 | LC | 11 | 11402 | 495.2 | 1 | − |
| Metabolite - 2272 | LC | 7.96 | 8377 | 189.1 | 1 | − |
| Metabolite - 2279 | LC | 12.4 | 12781 | 490.1 | 1 | + |

TABLE 19-continued

Analytical Characteristics of Isobars and Unnamed Metabolites

| Name | Platform | RT | RI | MASS | QUANT_MASS | Polarity |
|---|---|---|---|---|---|---|
| Metabolite - 2285 | LC | 2 | 2146 | 699.6 | 1 | − |
| Metabolite - 2287 | LC | 13 | 13336 | 502.8 | 1 | + |
| Metabolite - 2292 | LC | 2.4 | 2513.6 | 343.9 | 1 | − |
| Metabolite - 2306 retired: gamma glu leu | LC | 8.89 | 9246 | 261.1 | 1 | + |
| Metabolite - 2313 | LC | 1.56 | 1685.6 | 352.9 | 1 | − |
| Metabolite - 2316 | LC | 8.82 | 9163.6 | 100.1 | 1 | + |
| Metabolite - 2319 | LC | 12.2 | 12626 | 367.2 | 1 | −i |
| Metabolite - 2321 | LC | 13.4 | 12940 | 314.3 | 1 | +i |
| Metabolite - 2329 | LC | 11.8 | 12178 | 541.2 | 1 | − |
| Metabolite - 2347 | LC | 13.7 | 14091 | 450.1 | 1 | + |
| Metabolite - 2366 | LC | 8.47 | 8870.2 | 271 | 1 | + |
| Metabolite - 2370 | LC | 16.1 | 16561 | 476.4 | 1 | − |
| Metabolite - 2386 | LC | 11.9 | 12320 | 539.2 | 1 | − |
| Metabolite - 2387 retired: gamma glu leu | LC | 8.55 | 8838.5 | 182.1 | 1 | − |
| Metabolite - 2388 | LC | 16.2 | 16567 | 259.1 | 1 | − |
| Metabolite - 2389 | LC | 1.49 | 1641.5 | 314.9 | 1 | − |
| Metabolite - 2390 | LC | 6.09 | 6144.9 | 517.4 | 1 | + |
| Metabolite - 2392 | LC | 13.1 | 13460 | 379 | 1 | − |
| Metabolite - 2395 | LC | 10.1 | 10015 | 471.9 | 1 | +i |
| Metabolite - 2407 | LC | 15.7 | 16128 | 637.3 | 1 | + |
| Metabolite - 2469 | LC | 16 | 16436 | 502.3 | 1 | + |
| Metabolite - 2486 | LC | 1.52 | 1667 | 635.7 | 1 | − |
| Metabolite - 2506 | LC | 14.1 | 14438 | 624.4 | 1 | − |
| Metabolite - 2526 | LC | 1.38 | 1516 | 215 | 1 | − |
| Metabolite - 2527 retired: citrulline | LC | 1.62 | 1742 | 175.8 | 1 | + |
| Metabolite - 2546 | LC | 1.63 | 1747.3 | 129.1 | 1 | + |
| Metabolite - 2546 | LC | 1.63 | 1747.3 | 129.1 | 1 | + |
| Metabolite - 2548 Cl-adduct-of-uric acid | LC | 5.97 | 6016 | 202.9 | 1 | − |
| Metabolite - 2550 | LC | 11.1 | 11719 | 411.1 | 1 | + |
| Metabolite - 2558 | LC | 8.14 | 8674 | 153.1 | 1 | + |
| Metabolite - 2559 | LC | 13.8 | 14151 | 539.2 | 1 | − |
| Metabolite - 2560 | LC | 14.4 | 14754 | 235.2 | 1 | + |
| Metabolite - 2561 | LC | 10.2 | 10481 | 352.1 | 1 | + |
| Metabolite - 2563 retired: lactate | LC | 2.18 | 2302 | 178.9 | 1 | − |
| Metabolite - 2564 | LC | 10.5 | 10903 | 677.1 | 1 | + |
| Metabolite - 2565 | LC | 11 | 11341 | 886.6 | 1 | + |
| Metabolite - 2567 | LC | 7.79 | 8164.7 | 247.1 | 1 | + |
| Metabolite - 2568 | LC | 8.54 | 8790.8 | 342.1 | 1 | + |
| Metabolite - 2586 retired: pieces of Isobar 1 | LC | 1.3 | 1489 | 394.3 | 1 | − |
| Metabolite - 2587 retired: p-acetaminophen-beta-d-glucuronide | LC | 8.27 | 8613.4 | 371.1 | 1 | − |
| Metabolite - 2588 | LC | 8.87 | 9108 | 608 | 1 | + |
| Metabolite - 2589 | LC | 9.04 | 9334.7 | 472.2 | 1 | + |
| Metabolite - 2591 | LC | 9.99 | 10189 | 279.3 | 1 | + |
| Metabolite - 2592 | LC | 10.6 | 10778 | 697.2 | 1 | − |
| Metabolite - 2593 | LC | 9.81 | 10139 | 627.2 | 1 | + |
| Metabolite - 2594 | LC | 9.78 | 10112 | 332.1 | 1 | +i |
| Metabolite - 2606 | LC | 1.58 | 1755.5 | 114.1 | 1 | + |
| Metabolite - 2607 | LC | 10 | 10354 | 578.2 | 1 | + |
| Metabolite - 2608 | LC | 11 | 11326 | 191.9 | 1 | + |
| Metabolite - 2627 | GC | 9.19 | 1601.6 | 334.058 | Y | + |
| Metabolite - 2628 | GC | 12.5 | 2000.2 | 308.035 | Y | + |
| Metabolite - 263 | GC | 5.35 | 1185 | 215.178 | Y | + |
| Metabolite - 264 | GC | 14.4 | 2244.3 | 299.11 | Y | + |
| Metabolite - 2646 | GC | 12.9 | 2043 | 265.127 | Y | + |
| Metabolite - 2647 | GC | 14.1 | 2190.6 | 295.028 | Y | + |
| Metabolite - 2648 | GC | 15.4 | 2351.6 | 309.096 | Y | + |
| Metabolite - 268 | GC | 8.1 | 1507.6 | 144.159 | Y | + |
| Metabolite - 2686 | LC | 1.4 | 1593 | 217 | 1 | − |
| Metabolite - 2687 retired: CL adduct of Isobar 10 | LC | 1.4 | 1593 | 181.1 | 1 | − |
| Metabolite - 2688 | LC | 1.42 | 1614 | 182.0 | 1 | −i |
| Metabolite - 2694 retired: lactate | LC | 2.23 | 2321 | 135 | 1 | − |
| Metabolite - 2696 | LC | 3.38 | 3455.5 | 105 | 1 | + |
| Metabolite - 2697 | LC | 3.77 | 4241.2 | 209.9 | 1 | + |
| Metabolite - 2698 | LC | 3.88 | 4338.5 | 157 | 1 | + |
| Metabolite - 270 | GC | 10.9 | 1834.9 | 362.22 | Y | + |
| Metabolite - 2703 | LC | 8.86 | 9054.8 | 384.1 | 1 | + |
| Metabolite - 2711 retired: pieces of lactate | LC | 2.22 | 2300 | 123 | 1 | + |
| Metabolite - 2726 | LC | 8.3 | 8550.6 | 375.2 | 1 | + |
| Metabolite - 273 | GC | 10.4 | 1781.9 | 312.126 | Y | + |
| Metabolite - 274 | GC | 11.8 | 1940.6 | 221.128 | Y | + |
| Metabolite - 2750 retired: Metabolite 3316 | LC | 2.17 | 2260 | 125.6 | 1 | − |
| Metabolite - 2752 | LC | 2.92 | 2802.3 | 189.1 | 1 | + |
| Metabolite - 2753 | LC | 3.38 | 3358 | 147 | 1 | + |
| Metabolite - 276 | GC | 4.83 | 1124.8 | 269.159 | Y | + |
| Metabolite - 2774 | LC | 3.53 | 3796 | 230.9 | 1 | + |

TABLE 19-continued

Analytical Characteristics of Isobars and Unnamed Metabolites

| Name | Platform | RT | RI | MASS | QUANT_MASS | Polarity |
|---|---|---|---|---|---|---|
| Metabolite - 278 | GC | 9.1 | 1624.2 | 117.074 | Y | + |
| Metabolite - 279 | GC | 10 | 1731.2 | 274.171 | Y | + |
| Metabolite - 2806 | LC | 1.38 | 1491 | 185.1 | 1 | + |
| Metabolite - 2821 | LC | 6.8 | 6913 | 119.1 | 1 | + |
| Metabolite - 2822 | LC | 8.65 | 8838 | 607.6 | 1 | + |
| Metabolite - 2825 | LC | 13.1 | 13155 | 235 | 1 | + |
| Metabolite - 2825 retired: Riluzole | LC | | | | | |
| Metabolite - 283 | GC | 6.13 | 1278.4 | 100.125 | Y | + |
| Metabolite - 285 | GC | 9.6 | 1681.9 | 191.07 | Y | + |
| Metabolite - 2854 | LC | 8.68 | 8933 | 767 | 1 | + |
| Metabolite - 286 | GC | 10.5 | 1789 | 217.145 | Y | + |
| Metabolite - 2866 | LC | 9.53 | 9795.3 | 231 | 1 | − |
| Metabolite - 2867 | LC | 9.65 | 9908 | 235.3 | 1 | + |
| Metabolite - 2886 retired: CL adduct of p-acetiminophen-beta-d-glucuronide | LC | 8.34 | 8637 | 361.9 | 1 | − |
| Metabolite - 289 | GC | 7.58 | 1446.1 | 540.205 | Y | + |
| Metabolite - 2890 retired: pieces of tryptophan | LC | 9.23 | 9502 | 203 | 1 | − |
| Metabolite - 2894 | LC | 9.94 | 10320 | 226.1 | 1 | − |
| Metabolite - 2898 | LC | 11.2 | 11463 | 213.1 | 1 | − |
| Metabolite - 2915 | GC | 3.77 | 1099 | 174 | Y | + |
| Metabolite - 2924 retired: 2-hydroxybutanoic acid (also called (s)-2-hydroxybutyric acid) | GC | 4.38 | 1170.7 | 130.9 | Y | + |
| Metabolite - 293 | GC | 8.64 | 1570.5 | 158.16 | Y | + |
| Metabolite - 2952 | GC | 3.15 | 1025 | 281.0 | Y | +L |
| Metabolite - 2973 | GC | 4.74 | 1213.4 | 281 | Y | + |
| Metabolite - 2981 | GC | 5.21 | 1265 | 210.9 | Y | +L |
| Metabolite - 2986 | GC | 5.56 | 1304.3 | 201.1 | Y | + |
| Metabolite - 2989 | GC | 5.87 | 1340 | 341 | Y | + |
| Metabolite - 3002 | GC | 6.74 | 1440.8 | 296.1 | Y | + |
| Metabolite - 3003 | GC | 6.79 | 1446.6 | 218.1 | Y | + |
| Metabolite - 3012 | GC | 7.17 | 1489.8 | 232 | Y | + |
| Metabolite - 3014 retired: meso-erythritol | GC | 7.43 | 1520.6 | 217.1 | Y | + |
| Metabolite - 3017 | GC | 7.61 | 1541.4 | 246.1 | Y | + |
| Metabolite - 3019 | GC | 7.74 | 1556.4 | 260.1 | Y | + |
| Metabolite - 3020 retired: threonic acid | GC | 7.81 | 1564.1 | 292 | Y | + |
| Metabolite - 3022 | GC | 7.98 | 1584.9 | 142 | Y | + |
| Metabolite - 3023 | GC | 8.04 | 1590.9 | 274.1 | Y | + |
| Metabolite - 3025 | GC | 8.11 | 1600.3 | 274.1 | Y | + |
| Metabolite - 3026 | GC | 8.17 | 1606 | 274.1 | Y | +L |
| Metabolite - 3027 retired: arginine | GC | 8.21 | 1610.6 | 142 | Y | + |
| Metabolite - 303 threonine-deriv | GC | 8.88 | 1689.4 | 116.9 | Y | + |
| Metabolite - 3030 | GC | 8.62 | 1659.7 | 320 | Y | + |
| Metabolite - 3040 | GC | 9.27 | 1735.7 | 274.1 | Y | + |
| Metabolite - 3044 | LC | 1.52 | 1615.3 | 150.1 | 1 | + |
| Metabolite - 3045 retired: Isobar 1 | LC | 1.51 | 1601.5 | 180.6 | 1 | + |
| Metabolite - 3052 | LC | 8.7 | 9035 | 426.2 | 1 | +i |
| Metabolite - 3055 | LC | 9.2 | 9443 | 196.8 | 1 | + |
| Metabolite - 3056 | LC | 9.19 | 9432 | 185.2 | 1 | + |
| Metabolite - 3058 | GC | 9.7 | 1786.9 | 335.1 | Y | + |
| Metabolite - 3065 retired 1,5-anhdro-d-glucitol | GC | 9.74 | 1790.8 | 217.1 | Y | + |
| Metabolite - 3067 | GC | 10 | 1824.2 | 132 | Y | + |
| Metabolite - 3073 | GC | 10.2 | 1838.8 | 362.1 | Y | + |
| Metabolite - 3074 | GC | 10.2 | 1844.5 | 204.1 | Y | + |
| Metabolite - 3075 | GC | 10.4 | 1857.9 | 204 | Y | + |
| Metabolite - 3077 | GC | 10.4 | 1866.2 | 308.1 | Y | + |
| Metabolite - 3078 | GC | 10.7 | 1887 | 203.1 | Y | + |
| Metabolite - 3081 | GC | 10.9 | 1911.5 | 204 | Y | + |
| Metabolite - 3085 retired inositol | GC | 11 | 1926.1 | 217 | Y | + |
| Metabolite - 3087 | GC | 11.2 | 1942 | 174.1 | Y | +L |
| Metabolite - 3088 | GC | 11.2 | 1946.1 | 372.2 | Y | + |
| Metabolite - 3090 | GC | 11.3 | 1955 | 243.1 | Y | + |
| Metabolite - 3093 | GC | 11.5 | 1975.6 | 204 | Y | + |
| Metabolite - 3094 | GC | 11.6 | 1980.6 | 299 | Y | + |
| Metabolite - 3097 | GC | 11.6 | 1990.4 | 204 | Y | + |
| Metabolite - 3098 | GC | 11.8 | 2003 | 307.8 | Y | + |
| Metabolite - 3099 | GC | 11.8 | 2005.2 | 204 | Y | + |
| Metabolite - 3100 | GC | 11.9 | 2013.2 | 204 | Y | + |
| Metabolite - 3101 | GC | 11.9 | 2022.2 | 290 | Y | + |
| Metabolite - 3102 | GC | 12 | 2028.2 | 217.1 | Y | + |
| Metabolite - 3103 | GC | 12.1 | 2039.8 | 290.1 | Y | + |
| Metabolite - 3108 | GC | 12.2 | 2056.5 | 246 | Y | + |
| Metabolite - 3109 | GC | 12.6 | 2093 | 202.1 | Y | +L |
| Metabolite - 3113 | GC | 12.7 | 2113.5 | 406.2 | Y | + |
| Metabolite - 3114 | GC | 12.8 | 2121 | 204.0 | Y | +L |
| Metabolite - 3125 | LC | 11.9 | 12095 | 187.1 | 1 | + |
| Metabolite - 3127 | LC | 8.61 | 8812 | 260.1 | 1 | − |

TABLE 19-continued

Analytical Characteristics of Isobars and Unnamed Metabolites

| Name | Platform | RT | RI | MASS | QUANT_MASS | Polarity |
|---|---|---|---|---|---|---|
| Metabolite - 3129 | LC | 8.8 | 9012 | 337.1 | 1 | + |
| Metabolite - 3130 | LC | 9.09 | 9328 | 158.2 | 1 | + |
| Metabolite - 3131 retired: NH4 adduct of indole-3-acetic acid | LC | 10.5 | 10770 | 192.9 | 1 | + |
| Metabolite - 3132 | LC | 10.1 | 10392 | 260.2 | 1 | + |
| Metabolite - 3134 | LC | 14.3 | 14487 | 483.1 | 1 | + |
| Metabolite - 3138 | LC | 8.63 | 8749 | 229.2 | 1 | + |
| Metabolite - 3139 | LC | 8.82 | 8934.5 | 176.1 | 1 | + |
| Metabolite - 3143 | LC | 9.81 | 10070 | 160.1 | 1 | + |
| Metabolite - 3160 | LC | 12.1 | 12247 | 361 | 1 | + |
| Metabolite - 3162 retired: N,N-dimethylarginine | LC | 2.41 | 2444 | 203.1 | 1 | + |
| Metabolite - 3165 | LC | 8.38 | 8472.2 | 265 | 1 | + |
| Metabolite - 3166 | LC | 8.69 | 8746.5 | 394.2 | 1 | + |
| Metabolite - 3178 retired NH3 adduct of citric acid | LC | 3.15 | 3280 | 210 | 1 | + |
| Metabolite - 3179 retired 4-guanidnobutanoic acid | LC | 3.45 | 3603 | 146.1 | 1 | + |
| Metabolite - 3180 | LC | 4.14 | 4356 | 139 | 1 | + |
| Metabolite - 3181 | LC | 8.59 | 8621.4 | 165.1 | 1 | + |
| Metabolite - 3182 | LC | 8.83 | 8971 | 332.7 | 1 | + |
| Metabolite - 3183-gamma-L-glutamyl-L-phenylalanine | LC | 9.37 | 9441 | 295.2 | 1 | + |
| Metabolite - 3218 | LC | 2.2 | 2257 | 148.1 | 1 | + |
| Metabolite - 3230 | LC | 3.1 | 3043.2 | 245 | 1 | + |
| Metabolite - 3231 | LC | 3.08 | 3026 | 104.1 | 1 | + |
| Metabolite - 3235 retired DL-indole-3-lactic acid | LC | 10.5 | 10581 | 206 | 1 | + |
| Metabolite - 3249 | LC | 3.28 | 3298.3 | 141 | 1 | + |
| Metabolite - 3305 retired: duplicate of Metabolite 1088 | LC | 13.8 | 14129 | 369.3 | 1 | − |
| Metabolite - 3313 | LC | 8.1 | 8529.6 | 196.9 | 1 | − |
| Metabolite - 3314 | LC | 8.92 | 9143.5 | 264.8 | 1 | + |
| Metabolite - 3316 retired: lacate | LC | 2.09 | 2308 | 125.1 | 1 | − |
| Metabolite - 3317 | LC | 8.42 | 8702.3 | 429.6 | 1 | + |
| Metabolite - 3320 | LC | 10.7 | 10985 | 245 | 1 | − |
| Metabolite - 3327 | LC | 11.6 | 11784 | 385.3 | 1 | − |
| Metabolite - 3331 | LC | 9.38 | 9530 | 531 | 1 | + |
| Metabolite - 3334 | LC | 3.15 | 3371.5 | 409 | 1 | + |
| Metabolite - 3365 | LC | 1.87 | 2068.3 | 115.1 | 1 | + |
| Metabolite - 3370 | LC | 8.11 | 8529.1 | 226.2 | 1 | + |
| Metabolite - 3377 | LC | 8.86 | 8964 | 270.2 | 1 | +i |
| Metabolite - 3401 | LC | 1.73 | 1863.3 | 131.1 | 1 | + |
| Metabolite - 3402 | LC | 8.9 | 9052.3 | 343.2 | 1 | + |
| Metabolite - 341 | GC | 6.57 | 1278.3 | 100.098 | Y | + |
| Metabolite - 3416 | LC | 2.25 | 2582.3 | 127 | 1 | + |
| Metabolite - 3430 | LC | 2.78 | 3319.7 | 189.1 | 1 | +i |
| Metabolite - 3441 | LC | 1.51 | 1565 | 515.0 | 1 | +i |
| Metabolite - 3450 retired: 1-methlynicotinamide | LC | 1.68 | 1767.8 | 137 | 1 | + |
| Metabolite - 3457 | LC | 3.81 | 4193.3 | 212.9 | 1 | + |
| Metabolite - 3468 retired: Metabolite 1498 | LC | 1.75 | 1813.5 | 143 | 1 | − |
| Metabolite - 3489 | LC | 3.26 | 3605 | 226 | 1 | + |
| Metabolite - 3498 | LC | 7.8 | 8368.7 | 279.1 | 1 | + |
| Metabolite - 3517 | LC | 10.3 | 10892 | 382.3 | 1 | + |
| Metabolite - 3534 | LC | 10.5 | 11174 | 426.3 | 1 | + |
| Metabolite - 3603 | LC | 8.41 | 8971 | 313.6 | 1 | +i |
| Metabolite - 3604 retired CL adduct of hippuric acid | LC | 8.99 | 9551.9 | 214.2 | 1 | − |
| Metabolite - 3615 | LC | 13.6 | 14344 | 868 | 1 | + |
| Metabolite - 3624 | LC | 10.4 | 10984 | 205.1 | 1 | + |
| Metabolite - 3653-stachydrine | LC | 4.05 | 4500 | 144.1 | 1 | + |
| Metabolite - 3668 | LC | 9.63 | 9536 | 379.1 | 1 | + |
| Metabolite - 3696 | LC | 15 | 15200 | 450.3 | 1 | + |
| Metabolite - 3698 | LC | 8.31 | 8640.2 | 273.1 | 1 | + |
| Metabolite - 3707 | LC | 13.1 | 13340 | 241 | 1 | + |
| Metabolite - 3708 | LC | 1.66 | 1625.3 | 159.9 | 1 | + |
| Metabolite - 3758 | LC | 12.4 | 12714 | 309.1 | 1 | − |
| Metabolite - 3772 | LC | 2.22 | 2274 | 109 | 1 | + |
| Metabolite - 3781 | LC | 1.45 | 1544 | 262.9 | 1 | + |
| Metabolite - 3783 | LC | 1.37 | 1464 | 271.1 | 1 | + |
| Metabolite - 3807 | LC | 3 | 3398.5 | 245 | 1 | + |
| Metabolite - 3808 | LC | 3.28 | 3719 | 288.8 | 1 | −i |
| Metabolite - 381 | GC | 4.25 | 1012 | 101.043 | Y | + |
| Metabolite - 3813 | LC | 3.81 | 4312 | 212.1 | 1 | + |
| Metabolite - 382 | GC | 5.12 | 1106.8 | 221.063 | Y | + |
| Metabolite - 383 | GC | 5.43 | 1141.4 | 198.035 | Y | + |
| Metabolite - 3830 | LC | 8.42 | 8725 | 189 | 1 | − |
| Metabolite - 3832-phenol-sulfate | LC | 8.73 | 8995.8 | 173 | 1 | − |

TABLE 19-continued

Analytical Characteristics of Isobars and Unnamed Metabolites

| Name | Platform | RT | RI | MASS | QUANT_MASS | Polarity |
|---|---|---|---|---|---|---|
| Metabolite - 3837 retired: 3-incoxylsulfate | LC | 9.26 | 9466.8 | 212.1 | 1 | − |
| Metabolite - 3843 | LC | 9.54 | 9721.9 | 263.1 | 1 | + |
| Metabolite - 386 | GC | 9.3 | 1580.1 | 142.092 | Y | + |
| Metabolite - 387 | GC | 10.7 | 1746.5 | 204.077 | Y | + |
| Metabolite - 388 | GC | 4.62 | 1052.7 | 121.065 | Y | + |
| Metabolite - 3881: retired: azelaic acid | LC | 11.1 | 11318 | 188.9 | 1 | + |
| Metabolite - 3894 retired: pyroglutamic acid (5-oxoproline) | LC | 3.39 | 3883.5 | 130.1 | 1 | + |
| Metabolite - 3896 | LC | 3.38 | 3868 | 245.2 | 1 | + |
| Metabolite - 3900 | LC | 4.53 | 4871.7 | 173.1 | 1 | − |
| Metabolite - 393 | GC | 10.7 | 1750.9 | 217.073 | Y | + |
| Metabolite - 394 | GC | 4.73 | 1065.2 | 157.087 | Y | + |
| Metabolite - 3951 | LC | 8.41 | 8705.4 | 367.1 | 1 | + |
| Metabolite - 3952 | LC | 8.7 | 8941.3 | 297.2 | 1 | + |
| Metabolite - 3972 | LC | 6.16 | 6304 | 432.6 | 1 | −i |
| Metabolite - 3977 | LC | 11 | 11312 | 187.1 | 1 | − |
| Metabolite - 398 | GC | 5.15 | 1110.7 | 103.026 | Y | + |
| Metabolite - 3992 | LC | 1.4 | 1400 | 127.2 | 1 | −i |
| Metabolite - 3994 | GC | 1.63 | 1640.4 | 427 | 1 | + |
| Metabolite - 4003 | GC | 3.94 | 4397 | 205 | 1 | + |
| Metabolite - 4012 | GC | 7.02 | 1458.2 | 357 | Y | + |
| Metabolite - 4019 | GC | 7.68 | 1534.5 | 174 | Y | + |
| Metabolite - 4020 | GC | 7.91 | 1561.5 | 220.1 | Y | + |
| Metabolite - 4031 | GC | 14.26 | 14607 | 244.2 | 1 | + |
| Metabolite - 4032 retired: lysine | GC | 8.95 | 1682.6 | 156.1 | Y | + |
| Metabolite - 404 | GC | 9.34 | 1584.2 | 227.098 | Y | + |
| Metabolite - 4044 | GC | 10.53 | 1863.1 | 149 | Y | + |
| Metabolite - 4055 | GC | 12.04 | 2022.2 | 304.1 | Y | + |
| Metabolite - 406 | GC | 11.8 | 1883.2 | 204.074 | Y | + |
| Metabolite - 407 | GC | 16.7 | 2483.2 | 283.2 | Y | + |
| Metabolite - 4077 | GC | 14 | 2266.5 | 227 | Y | + |
| Metabolite - 4080 | GC | 14.02 | 2270.2 | 299 | Y | + |
| Metabolite - 4084 | GC | 14.98 | 2393.9 | 441.3 | Y | + |
| Metabolite - 4096 | GC | 8.6 | 8763.6 | 318.2 | 1 | + |
| Metabolite - 413 | GC | 11.1 | 1806 | 342.146 | Y | + |
| Metabolite - 4133 | GC | 4.35 | 1108.9 | 198 | Y | + |
| Metabolite - 4134 | GC | 5.51 | 1239 | 60.9 | Y | + |
| Metabolite - 4147 | GC | 10.07 | 1767.1 | 290.2 | Y | + |
| Metabolite - 4148 | GC | 10.23 | 1786.3 | 249.2 | Y | + |
| Metabolite - 4167 | LC | 11 | 10920 | 286.2 | 1 | +i |
| Metabolite - 4196 | GC | 12.14 | 2000.4 | 290.2 | Y | + |
| Metabolite - 4198 | GC | 13.57 | 2173.7 | 218.2 | Y | + |
| Metabolite - 421 | GC | 9.18 | 1567.4 | 243.176 | Y | + |
| Metabolite - 423 | GC | 13 | 2031.5 | 204.087 | Y | + |
| Metabolite - 4251 | GC | 4.09 | 1130.7 | 217 | Y | + |
| Metabolite - 4252 | GC | 6.02 | 1348 | 282.1 | Y | +L |
| Metabolite - 4271 | GC | 9.69 | 1777.4 | 419.2 | Y | + |
| Metabolite - 4272 | GC | 10.28 | 1840.2 | 669.3 | Y | + |
| Metabolite - 4274 | GC | 10.37 | 1857.0 | 158.1 | Y | + |
| Metabolite - 4275 | GC | 10.68 | 1887.0 | 271.1 | Y | + |
| Metabolite - 4276 | GC | 13.92 | 2262.9 | 223.1 | Y | + |
| Metabolite - 4351 | LC | 11.8 | 11937 | 427.1 | 1 | +i |
| Metabolite - 4354 | GC | 3.90 | 1074.3 | 110 | Y | + |
| Metabolite - 4357 | GC | 8.00 | 1541.1 | 216 | Y | + |
| Metabolite - 4360 | GC | 9.15 | 1678.2 | 347.2 | Y | + |
| Metabolite - 4361 | GC | 9.40 | 1706.2 | 232.2 | Y | + |
| Metabolite - 4362 | GC | 10.02 | 1779.9 | 319.2 | Y | + |
| Metabolite - 4363 | LC | 13.7 | 13709 | 830.1 | 1 | +i |
| Metabolite - 4364 | GC | 10.66 | 1852.4 | 232 | Y | + |
| Metabolite - 4365 | GC | 11.05 | 1892.9 | 204 | Y | + |
| Metabolite - 441 | GC | 3.81 | 964.2 | 73.0775 | Y | + |
| Metabolite - 442 | GC | 4.11 | 997.9 | 176.069 | Y | + |
| Metabolite - 4428 | LC | 7.92 | 8237 | 229.2 | 1 | +i |
| Metabolite - 443 | GC | 8.66 | 1506.6 | 205.092 | Y | + |
| Metabolite - 4470 | LC | 10.8 | 11037 | 271.2 | 1 | +i |
| Metabolite - 451 | GC | 5.21 | 1118.4 | 173.075 | Y | + |
| Metabolite - 4510 | GC | 9.7 | 1740 | 254.0 | Y | +L |
| Metabolite - 4511 | GC | 10.1 | 1788 | 206.0 | Y | +L |
| Metabolite - 4522 | GC | 12.3 | 2025 | 217.1 | Y | +L |
| Metabolite - 4523 | GC | 12.5 | 2047 | 258.1 | Y | +L |
| Metabolite - 4547 | LC | 11.4 | 11464 | 310.3 | 1 | +i |
| Metabolite - 458 | GC | 11.9 | 1897 | 204.089 | Y | + |
| Metabolite - 4586 | LC | 7.14 | 7487 | 260.0 | 1 | −i |
| Metabolite - 4611 | GC | 8.07 | 1547 | 292.1 | Y | +L |
| Metabolite - 4612 | LC | 11.7 | 11784 | 453.2 | 1 | −i |
| Metabolite - 4624 | GC | 10 | 1779 | 342.2 | Y | +L |

TABLE 19-continued

Analytical Characteristics of Isobars and Unnamed Metabolites

| Name | Platform | RT | RI | MASS | QUANT_MASS | Polarity |
|---|---|---|---|---|---|---|
| Metabolite - 4627 | LC | 10.8 | 11035 | 591.3 | 1 | +i |
| Metabolite - 465 | GC | 10.8 | 1757.9 | 204.088 | Y | + |
| Metabolite - 4658 | LC | 10.1 | 10321 | 194.1 | 1 | +i |
| Metabolite - 470 | GC | 15.4 | 2329.7 | 299.05 | Y | + |
| Metabolite - 472 | GC | 3.96 | 980.2 | 160.082 | Y | + |
| Metabolite - 4732 | LC | 5.84 | 6102 | 221.2 | 1 | +i |
| Metabolite - 4767 | GC | 8.77 | 1626 | 116.9 | Y | +L |
| Metabolite - 4769 | GC | 11.3 | 1916 | 156.0 | Y | +L |
| Metabolite - 4795 | GC | 14.8 | 2350 | 309.0 | Y | +L |
| Metabolite - 4806 | GC | 4.2 | 1123 | 104.9 | Y | +L |
| Metabolite - 482 | GC | 7.71 | 1396.1 | 117.055 | Y | + |
| Metabolite - 485 | GC | 5.31 | 1128.8 | 217.029 | Y | + |
| Metabolite - 4873 | LC | 12.1 | 11838 | 288.0 | 1 | +i |
| Metabolite - 490 | GC | 4.37 | 1026.7 | 191.028 | Y | + |
| Metabolite - 4906 | LC | 10.3 | 10119 | 313.2 | 1 | +i |
| Metabolite - 4931 | LC | 1.5 | 1660 | 431.0 | 1 | +i |
| Metabolite - 4986 | GC | 11.6 | 1956 | 204.1 | Y | +L |
| Metabolite - 499 | GC | 6.64 | 1276.1 | 259.062 | Y | + |
| Metabolite - 501 | GC | 5.55 | 1155.4 | 143.084 | Y | + |
| Metabolite - 502 | GC | 13.8 | 2125.7 | 361.127 | Y | + |
| Metabolite - 504 | GC | 11.6 | 1864.2 | 156.068 | Y | + |
| Metabolite - 505 | GC | 10.6 | 1737.5 | 454.125 | Y | + |
| Metabolite - 506 | GC | 11.8 | 1885.8 | 204.075 | Y | + |
| Metabolite - 508 | GC | 7.25 | 1343.8 | 466.076 | Y | + |
| Metabolite - 5086 | LC | 9.51 | 9738 | 388.2 | 1 | +i |
| Metabolite - 511 | GC | 7.51 | 1375 | 247.045 | Y | + |
| Metabolite - 522 | GC | 6.35 | 1256.3 | 211.009 | Y | + |
| Metabolite - 523 | GC | 10.7 | 1762.7 | 265.075 | Y | + |
| Metabolite - 5231 | LC | 2.09 | 2271 | 113.2 | 1 | +i |
| Metabolite - 5233 | LC | 2.56 | 2928 | 138.1 | 1 | +i |
| Metabolite - 5234 | LC | 13.5 | 13823 | 316.4 | 1 | +i |
| Metabolite - 5247 | LC | 9.94 | 10272 | 525.3 | 1 | +i |
| Metabolite - 526 | GC | 11.7 | 1886.7 | 353.125 | Y | + |
| Metabolite - 5346 | GC | 8.33 | 1573 | 202.0 | Y | +L |
| Metabolite - 5349 | GC | 10.1 | 1782 | 312.1 | Y | +L |
| Metabolite - 5366 | GC | 12.5 | 2045 | 204.0 | Y | +L |
| Metabolite - 5403 | GC | 5.92 | 1300 | 319.0 | Y | +L |
| Metabolite - 543 | GC | 12.7 | 2006.8 | 117.082 | Y | + |
| Metabolite - 547 | GC | 5.26 | 1131.8 | 113.055 | Y | + |
| Metabolite - 549 | GC | 6.5 | 1273.6 | 189.101 | Y | + |
| Metabolite - 553 | GC | 4.16 | 1005.6 | 244.035 | Y | + |
| Metabolite - 554 | GC | 10.7 | 1771.6 | 221.093 | Y | + |
| Metabolite - 557 | GC | 10.9 | 1784.5 | 245.094 | Y | + |
| Metabolite - 562 | GC | 6.1 | 1227.1 | 102.061 | Y | + |
| Metabolite - 5673 | LC | 12.8 | 12402 | 383.3 | 1 | −i |
| Metabolite - 568 | GC | 5.82 | 1196.6 | 281.047 | Y | + |
| Metabolite - 571 | GC | 4.62 | 1057.8 | 105.063 | Y | + |
| Metabolite - 5728 | LC | 1.59 | 1733 | 148.0 | 1 | −i |
| Metabolite - 5730 | LC | 8.91 | 8739 | 290.3 | 1 | +i |
| Metabolite - 5769 | LC | 11.1 | 10753 | 485.2 | 1 | −i |
| Metabolite - 577 | GC | 11.5 | 1865.4 | 272.14 | Y | + |
| Metabolite - 578 | GC | 12.5 | 1979.2 | 498.188 | Y | + |
| Metabolite - 5788 | LC | 9.24 | 9026 | 267.1 | 1 | +i |
| Metabolite - 5791 | LC | 9.79 | 9529 | 327.1 | 1 | +i |
| Metabolite - 580 | GC | 11.6 | 1876.8 | 102.025 | Y | + |
| Metabolite - 5847 | GC | 12.4 | 2040 | 288.2 | Y | +L |
| Metabolite - 5848 | LC | 10.4 | 10571 | 601.2 | 1 | +i |
| Metabolite - 5887 | LC | 9.62 | 9786 | 547.2 | 1 | +i |
| Metabolite - 5907 | GC | 8.69 | 1643 | 229.1 | Y | +L |
| Metabolite - 591 | GC | 12.2 | 1957 | 217.117 | Y | + |
| Metabolite - 593 | GC | 10.6 | 1765.3 | 196.11 | Y | + |
| Metabolite - 594 | GC | 11.5 | 1871.3 | 205.116 | Y | + |
| Metabolite - 595 | GC | 3.8 | 968.8 | 100.003 | Y | + |
| Metabolite - 596 | GC | 11.7 | 1878.8 | 217.115 | Y | + |
| Metabolite - 597 | GC | 7.91 | 1439 | 218.11 | Y | + |
| Metabolite - 5976 | LC | 11.6 | 11366 | 671.3 | 1 | +i |
| Metabolite - 5983 | GC | 14.7 | 2309 | 207.0 | Y | +L |
| Metabolite - 601 | GC | 5.19 | 1131.3 | 201.139 | Y | + |
| Metabolite - 606 | GC | 6.16 | 1242 | 131.105 | Y | + |
| Metabolite - 609 | GC | 5.04 | 1113.3 | 190.09 | Y | + |
| Metabolite - 6126 | LC | 9.76 | 9577 | 202.9 | 1 | −i |
| Metabolite - 613 | GC | 9.25 | 1599.6 | 156.088 | Y | + |
| Metabolite - 614 | GC | 5.8 | 1196.7 | 233.092 | Y | + |
| Metabolite - 618 | GC | 8.46 | 1507.3 | 103.045 | Y | + |
| Metabolite - 621 | GC | 12.9 | 2040.3 | 217.114 | Y | + |
| Metabolite - 6226 | GC | 4.38 | 1137 | 154.0 | Y | +L |

TABLE 19-continued

Analytical Characteristics of Isobars and Unnamed Metabolites

| Name | Platform | RT | RI | MASS | QUANT_MASS | Polarity |
|---|---|---|---|---|---|---|
| Metabolite - 6227 | GC | 5 | 1211 | 196.1 | Y | +L |
| Metabolite - 6246 | GC | 6.94 | 1428 | 160.1 | Y | +L |
| Metabolite - 6269 | GC | 10.9 | 1881 | 217.1 | Y | +L |
| Metabolite - 6270 | GC | 11.4 | 1930 | 320.2 | Y | +L |
| Metabolite - 6272 | GC | 12.6 | 2070 | 131.0 | Y | +L |
| Metabolite - 6326 | GC | 7.66 | 1511 | 144.1 | Y | +L |
| Metabolite - 6346 | GC | 8 | 1551 | 263.2 | Y | +L |
| Metabolite - 6347 | GC | 8.16 | 1569 | 244.1 | Y | +L |
| Metabolite - 638 | GC | 7.86 | 1437.9 | 218.112 | Y | + |
| Metabolite - 642 | GC | 10.3 | 1724.5 | 103.045 | Y | + |
| Metabolite - 645 | GC | 11.6 | 1873.5 | 203.109 | Y | + |
| Metabolite - 6467 | GC | 11.1 | 1894 | 320.1 | Y | +L |
| Metabolite - 6488 | GC | 12.3 | 2022 | 204.1 | Y | +L |
| Metabolite - 651 | GC | 4.55 | 1059.6 | 175.108 | Y | + |
| Metabolite - 653 | GC | 6.57 | 1291 | 192.106 | Y | + |
| Metabolite - 655 | GC | 11.7 | 1912.8 | 156.085 | Y | + |
| Metabolite - 6551 | LC | 9.24 | 9020 | 492.1 | 1 | +i |
| Metabolite - 664 | GC | 12.4 | 1961.4 | 174.095 | Y | + |
| Metabolite - 669 | GC | 12.7 | 2017.7 | 361.164 | Y | + |
| Metabolite - 670 | GC | 12.9 | 2039.7 | 258.125 | Y | + |
| Metabolite - 671 | GC | 13.7 | 2144.9 | 204.123 | Y | + |
| Metabolite - 6711 | LC | 1.54 | 1647 | 381.1 | 1 | +i |
| Metabolite - 681 | GC | 12.3 | 1955.4 | 243.083 | Y | + |
| Metabolite - 6827 | LC | 4.59 | 5000 | 139.0 | 1 | −i |
| Metabolite - 683 | GC | 8.46 | 1502.7 | 188.09 | Y | + |
| Metabolite - 6869 | GC | 8 | 1546 | 257.1 | Y | +L |
| Metabolite - 687 | GC | 9.26 | 1591.8 | 210.977 | Y | + |
| Metabolite - 688 | GC | 9.96 | 1674.9 | 156.111 | Y | + |
| Metabolite - 6907 | GC | 9.22 | 1687 | 337.1 | Y | +L |
| Metabolite - 691 | GC | 10.3 | 1711 | 274.083 | Y | + |
| Metabolite - 6931 | GC | 10.4 | 1820 | 267.1 | Y | +L |
| Metabolite - 6955 | GC | 11.8 | 1979 | 306.1 | Y | +L |
| Metabolite - 6963 | GC | 11.9 | 1989 | 103.0 | Y | +L |
| Metabolite - 7008 | LC | 1.47 | 1616 | 125.1 | 1 | −i |
| Metabolite - 7009 | LC | 1.62 | 1577 | 349.9 | 1 | +i |
| Metabolite - 702 | GC | 10.8 | 1784 | 218.077 | Y | + |
| Metabolite - 704 | GC | 6.51 | 1275.1 | 171.059 | Y | + |
| Metabolite - 7050 | LC | 9.44 | 9626 | 242.9 | 1 | −i |
| Metabolite - 706 | GC | 10.6 | 1751.4 | 437.153 | Y | + |
| Metabolite - 7089 | LC | 9.23 | 9391 | 297.0 | 1 | −i |
| Metabolite - 709 | GC | 12.5 | 1979.8 | 109.065 | Y | + |
| Metabolite - 7146 | LC | 2.13 | 2248 | 229.7 | 1 | +i |
| Metabolite - 7147 | LC | 3.13 | 3467 | 245.0 | 1 | +i |
| Metabolite - 7177 | LC | 12.1 | 12101 | 405.1 | 1 | −i |
| Metabolite - 721 | GC | 7.54 | 1421.2 | 373.062 | Y | + |
| Metabolite - 7336 | LC | 8.78 | 9007 | 470.8 | 1 | +i |
| Metabolite - 734 | GC | 8.42 | 1524.1 | 232.108 | Y | + |
| Metabolite - 736 | GC | 13.5 | 2133.5 | 506.129 | Y | + |
| Metabolite - 749 | GC | 12.8 | 2030.8 | 101.143 | Y | + |
| Metabolite - 753 | GC | 7.92 | 1465.7 | 218.137 | Y | + |
| Metabolite - 760 | GC | 8.67 | 1552.4 | 220.099 | Y | + |
| Metabolite - 761 | GC | 10.6 | 1777.9 | 217.104 | Y | + |
| Metabolite - 763 | GC | 8.45 | 1528.5 | 230.135 | Y | + |
| Metabolite - 770 | GC | 6.87 | 1341.4 | 247.075 | Y | + |
| Metabolite - 7706 | LC | 2.32 | 2457 | 222.7 | 1 | +i |
| Metabolite - 7707 | LC | 2.29 | 2371 | 250.8 | 1 | +i |
| Metabolite - 771 | GC | 11.2 | 1854.4 | 246.092 | Y | + |
| Metabolite - 7762 | LC | 8.92 | 8776 | 197.0 | 1 | −i |
| Metabolite - 7765 | LC | 11.2 | 10919 | 245.0 | 1 | −i |
| Metabolite - 777 | GC | 10.3 | 1741.6 | 299.052 | Y | + |
| Metabolite - 780 | GC | 6.13 | 1233.1 | 280.996 | Y | + |
| Metabolite - 7807 | LC | 11.3 | 10966 | 256.7 | 1 | +i |
| Metabolite - 7815 | LC | 8.43 | 8450 | 381.9 | 1 | +i |
| Metabolite - 782 | GC | 10.8 | 1776 | 287.056 | Y | + |
| Metabolite - 783 | GC | 5.16 | 1121.3 | 180.969 | Y | + |
| Metabolite - 7846 | GC | 5.1 | 1208 | 145.1 | Y | +L |
| Metabolite - 7888 | GC | 16 | 2513 | 311.3 | Y | +L |
| Metabolite - 7889 | GC | 16.8 | 2629 | 311.3 | Y | +L |
| Metabolite - 7890 | GC | 17.8 | 2752 | 129.0 | Y | +L |
| Metabolite - 841 | GC | 15 | 2261.1 | 488.377 | Y | + |
| Metabolite - 861 | GC | 7.64 | 1401.8 | 247.111 | Y | + |
| Metabolite - 863 | GC | 9.98 | 1675 | 347.161 | Y | + |
| Metabolite - 941 | GC | 11.6 | 1912.5 | 204.1 | Y | + |
| Metabolite - 961 | GC | 6.31 | 1296.1 | 319.078 | Y | + |
| Metabolite - 982 | GC | 6.12 | 1274.8 | 175.039 | Y | + |
| Metabolite - 984 | GC | 8.39 | 1538.8 | 314.083 | Y | + |

TABLE 19-continued

Analytical Characteristics of Isobars and Unnamed Metabolites

| Name | Platform | RT | RI | MASS | QUANT_MASS | Polarity |
|---|---|---|---|---|---|---|
| Metabolite - 985 | GC | 6.35 | 1301.3 | 174.11 | Y | + |
| Metabolite - 987 | GC | 8.86 | 1595.2 | 244.121 | Y | + |
| Metabolite - 988 | GC | 9.77 | 1701.3 | 519.157 | Y | + |
| Metabolite - 990 | GC | 7.24 | 1404.6 | 405.107 | Y | + |
| Metabolite - 991 | GC | 4.14 | 1051.9 | 117.094 | Y | + |
| Metabolite - 992 | GC | 7.53 | 1434 | 296.155 | Y | + |
| Metabolite - 995 | GC | 11.4 | 1890.9 | 305.152 | Y | + |
| Metabolite - 996 | GC | 12.2 | 1984.3 | 357.151 | Y | + |
| Metabolite - 998 | GC | 7.36 | 1415.4 | 241.171 | Y | + |

While the invention has been described in detail and with reference to specific embodiments thereof, it will be apparent to one skilled in the art that various changes and modifications can be made without departing from the spirit and scope of the invention.

What is claimed is:

1. A method of aiding in diagnosing whether a subject has amyotrophic lateral sclerosis (ALS), comprising:
analyzing a cerebral spinal fluid, blood, or blood plasma sample from a subject to determine the levels of a plurality of biomarkers for amyotrophic lateral sclerosis in the sample, wherein the plurality of biomarkers comprise creatine-creatinine and citrulline and wherein the analysis method for the sample is mass spectrometry, and
comparing the levels of the plurality of biomarkers in the sample to ALS-positive and/or ALS-negative reference levels of the plurality of biomarkers in order to aid in diagnosing whether the subject has amyotrophic lateral sclerosis.

2. The method of claim 1, wherein the ALS-negative reference levels of the plurality of biomarkers comprise levels of the plurality of biomarkers in one or more samples from one or more subjects not having ALS and the ALS-positive reference levels of the plurality of biomarkers comprise levels of the plurality of biomarkers in one or more samples from one or more subjects diagnosed with ALS.

3. The method of claim 2, wherein differential levels of the plurality of biomarkers between the sample and the ALS-negative reference levels are indicative of a diagnosis of ALS in the subject.

4. The method of claim 2, wherein differential levels of the plurality of biomarkers between the sample and the ALS-positive reference levels are indicative of a diagnosis of no ALS in the subject.

5. The method of claim 2, wherein levels of the plurality of biomarkers in the sample corresponding to the ALS-positive reference levels are indicative of a diagnosis of ALS in the subject.

6. The method of claim 2, wherein levels of the plurality of biomarkers in the sample corresponding to the ALS-negative reference levels are indicative of a diagnosis of no ALS in the subject.

7. The method of claim 1, wherein the sample is further analyzed using one or more techniques selected from the group consisting of ELISA and antibody linkage.

8. A method of aiding in diagnosing whether a subject has amyotrophic lateral sclerosis (ALS), comprising:
analyzing a blood plasma sample from a subject to determine the levels of a plurality of biomarkers for amyotrophic lateral sclerosis in the sample, wherein the plurality of biomarkers comprise creatine-creatinine and citrulline and wherein the analysis method for the sample is mass spectrometry, and
comparing the levels of the plurality of biomarkers in the sample to ALS-positive and/or ALS-negative reference levels of the plurality of biomarkers in order to aid in diagnosing whether the subject has amyotrophic lateral sclerosis.

9. The method of claim 1, wherein elevated levels of creatine-creatinine and citrulline in the sample are indicative that the subject has amyotrophic lateral sclerosis.

10. The method of claim 8, wherein elevated levels of creatine-creatinine and citrulline in the blood plasma sample are indicative that the subject has amyotrophic lateral sclerosis.

* * * * *